(12) United States Patent
Dewdney et al.

(10) Patent No.: US 7,683,064 B2
(45) Date of Patent: Mar. 23, 2010

(54) INHIBITORS OF BRUTON'S TYROSINE KINASE

(75) Inventors: Nolan James Dewdney, Saratoga, CA (US); Joshua Kennedy-Smith, San Francisco, CA (US); Rama K. Kondru, Sunnyvale, CA (US); Bradley E. Loe, Santa Cruz, CA (US); Yan Lou, San Jose, CA (US); Joel McIntosh, Pacifica, CA (US); Timothy D. Owens, Mountain View, CA (US); Michael Soth, Milpitas, CA (US); Zachary Kevin Sweeney, Redwood City, CA (US); Joshua Paul Gergely Taygerly, San Francisco, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 0 days.

(21) Appl. No.: 12/322,870

(22) Filed: Feb. 5, 2009

(65) Prior Publication Data

US 2009/0306041 A1    Dec. 10, 2009

Related U.S. Application Data

(60) Provisional application No. 61/122,510, filed on Dec. 15, 2008, provisional application No. 61/075,277, filed on Jun. 24, 2008, provisional application No. 61/026,204, filed on Feb. 5, 2008.

(51) Int. Cl.
| | | |
|---|---|---|
| A61K 31/501 | (2006.01) | |
| A61K 31/4725 | (2006.01) | |
| C07D 401/10 | (2006.01) | |
| C07D 217/24 | (2006.01) | |

(52) U.S. Cl. .................. 514/252.01; 514/309; 544/238
(58) Field of Classification Search .................. None
See application file for complete search history.

(56) References Cited

U.S. PATENT DOCUMENTS

2008/0153834 A1    6/2008    Blomgren et al.

FOREIGN PATENT DOCUMENTS

| WO | 2006099075 | 9/2006 |
|---|---|---|
| WO | 2006124731 | 11/2006 |
| WO | 2007021795 | 2/2007 |
| WO | 2007027528 | 3/2007 |
| WO | 2007027594 | 3/2007 |
| WO | 2007027729 | 3/2007 |
| WO | 2007136465 | 11/2007 |
| WO | 2008033854 | 3/2008 |
| WO | 2008033857 | 3/2008 |
| WO | 2008033858 | 3/2008 |
| WO | 2009039397 | 3/2009 |
| WO | 2009053269 | 4/2009 |
| WO | WO 2009/053269 | * 4/2009 |

* cited by examiner

Primary Examiner—Rebecca L Anderson
Assistant Examiner—Alicia L Fierro
(74) Attorney, Agent, or Firm—George W. Johnston; Dennis P. Tramaloni; Jennifer L. Kisko

(57) ABSTRACT

This application discloses 5-phenyl-1H-pyridin-2-one and 6-phenyl-2H-pyridazin-3-one derivatives according to generic Formulae I-III:

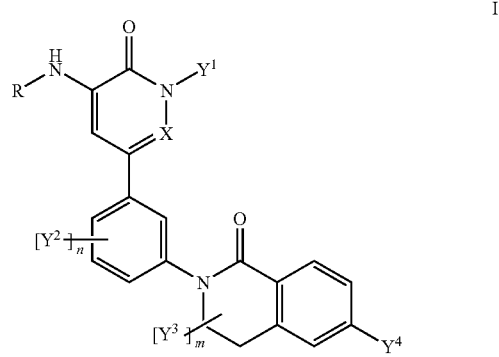

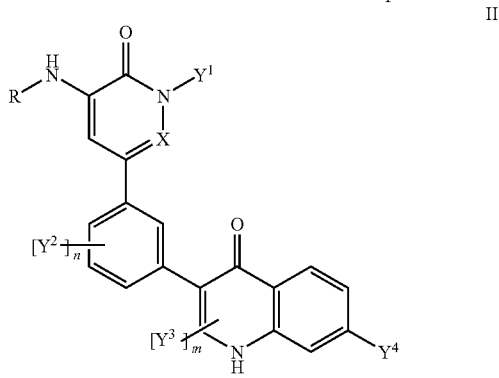

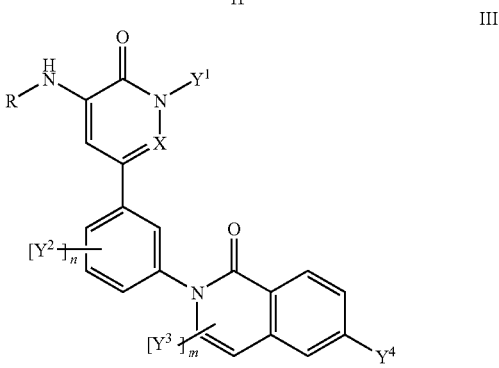

wherein, variables R, X, $Y^1$, $Y^2$, $Y^3$, $Y^4$, n and m are defined as described herein, which inhibit Btk. The compounds disclosed herein are useful to modulate the activity of Btk and treat diseases associated with excessive Btk activity. The compounds are further useful to treat inflammatory and auto immune diseases associated with aberrant B-cell proliferation such as rheumatoid arthritis. Also disclosed are compositions containing compounds of Formulae I-III and at least one carrier, diluent or excipient.

19 Claims, No Drawings

INHIBITORS OF BRUTON'S TYROSINE KINASE

CROSS-REFERENCE TO RELATED APPLICATIONS

This application is entitled to the benefit of U.S. provisional patent application Ser. No. 61/026,204 filed on Feb. 5, 2008, U.S. provisional patent application Ser. No. 61/075,277 filed on Jun. 24, 2008, and U.S. provisional patent application Ser. No. 61/122,510, filed Dec. 15, 2008, the disclosures of which are incorporated herein by reference.

FIELD OF THE INVENTION

The present invention relates to the use of novel derivatives which inhibit Btk and are useful for the treatment of autoimmune and inflammatory diseases caused by aberrant B-cell activation. The novel 5-phenyl-1H-pyridin-2-one and 6-phenyl-2H-pyridazin-3-one derivatives described herein are useful for the treatment of arthritis.

BACKGROUND OF THE INVENTION

Protein kinases constitute one of the largest families of human enzymes and regulate many different signaling processes by adding phosphate groups to proteins (T. Hunter, Cell 1987 50:823-829). Specifically, tyrosine kinases phosphorylate proteins on the phenolic moiety of tyrosine residues. The tyrosine kinase family includes members that control cell growth, migration, and differentiation. Abnormal kinase activity has been implicated in a variety of human diseases including cancers, autoimmune and inflammatory diseases. Since protein kinases are among the key regulators of cell signaling they provide a target to modulate cellular function with small molecular kinase inhibitors and thus make good drug design targets. In addition to treatment of kinase-mediated disease processes, selective and efficacious inhibitors of kinase activity are also useful for investigation of cell signaling processes and identification of other cellular targets of therapeutic interest.

There is good evidence that B-cells play a key role in the pathogenesis of autoimmune and/or inflammatory disease. Protein-based therapeutics that deplete B cells such as Rituxan are effective against autoantibody-driven inflammatory diseases such as rheumatoid arthritis (Rastetter et al. *Annu Rev Med* 2004 55:477). Therefore inhibitors of the protein kinases that play a role in B-cell activation should be useful therapeutics for B-cell mediated disease pathology such as autoantibody production.

Signaling through the B-cell receptor (BCR) controls a range of B-cell responses including proliferation and differentiation into mature antibody producing cells. The BCR is a key regulatory point for B-cell activity and aberrant signaling can cause deregulated B-cell proliferation and formation of pathogenic autoantibodies that lead to multiple autoimmune and/or inflammatory diseases. Bruton's Tyrosine Kinase (Btk) is a non-BCR associated kinase that is membrane proximal and immediately downstream from BCR. Lack of Btk has been shown to block BCR signaling and therefore inhibition of Btk could be a useful therapeutic approach to block B-cell mediated disease processes.

Btk is a member of the Tec family of tyrosine kinases, and has been shown to be a critical regulator of early B-cell development and mature B-cell activation and survival (Khan et al. *Immunity* 1995 3:283; Ellmeier et al. *J. Exp. Med.* 2000 192:1611). Mutation of Btk in humans leads to the condition X-linked agammaglobulinemia (XLA) (reviewed in Rosen et al. *New Eng. J. Med.* 1995 333:431 and Lindvall et al. Immunol. Rev. 2005 203:200). These patients are immunocompromised and show impaired maturation of B-cells, decreased immunoglobulin and peripheral B-cell levels, diminished T-cell independent immune responses as well as attenuated calcium mobilization following BCR stimulation.

Evidence for a role for Btk in autoimmune and inflammatory diseases has also been provided by Btk-deficient mouse models. In preclinical murine models of systemic lupus erythematosus (SLE), Btk-deficient mice show marked amelioration of disease progression. In addition, Btk-deficient mice are resistant to collagen-induced arthritis (Jansson and Holmdahl *Clin. Exp. Immunol.* 1993 94:459). A selective Btk inhibitor has been demonstrated dose-dependent efficacy in a mouse arthritis model (Z. Pan et al., *Chem. Med Chem.* 2007 2:58-61).

Btk is also expressed by cells other than B-cells that may be involved in disease processes. For example, Btk is expressed by mast cells and Btk-deficient bone marrow derived mast cells demonstrate impaired antigen induced degranulation (Iwaki et al. *J. Biol. Chem.* 2005 280:40261). This shows Btk could be useful to treat pathological mast cells responses such as allergy and asthma. Also monocytes from XLA patients, in which Btk activity is absent, show decreased TNF alpha production following stimulation (Horwood et al. J Exp Med 197:1603, 2003). Therefore TNF alpha mediated inflammation could be modulated by small molecular Btk inhibitors. Also, Btk has been reported to play a role in apoptosis (Islam and Smith *Immunol. Rev.* 2000 178:49,) and thus Btk inhibitors would be useful for the treatment of certain B-cell lymphomas and leukemias (Feldhahn et al. *J. Exp. Med.* 2005 201:1837,).

SUMMARY OF THE INVENTION

The present application provides the Btk inhibitor compounds of Formulae I-III, methods of use thereof, as described herein below:

The application provides a compound of Formula I,

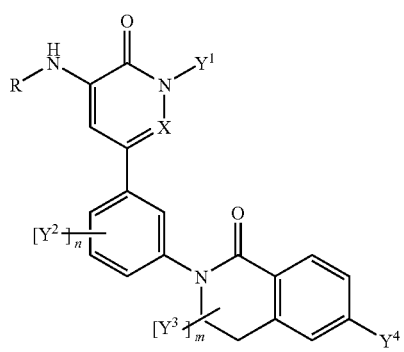

wherein:

R is H, -R$^1$, -R$^1$-R$^2$-R$^3$, or -R$^2$-R$^3$;

R$^1$ is aryl, heteroaryl, cycloalkyl, or heterocycloalkyl, and is optionally substituted with lower alkyl, hydroxy, lower alkoxy, halo, nitro, amino, cyano, or halo-lower alkyl;

R$^2$ is —C(═O), —C(═O)O, C(═O)NH, or —S(═O)$_2$;

R$^3$ is H or R$^4$;

R⁴ is lower alkyl, aryl, arylalkyl, alkylaryl, heteroaryl, alkyl heteroaryl, heteroaryl alkyl, cycloalkyl, alkyl cycloalkyl, cycloalkyl alkyl, heterocycloalkyl, alkyl heterocycloalkyl, or heterocycloalkyl alkyl, and is optionally substituted with lower alkyl, hydroxy, lower alkoxy, halo, nitro, amino, cyano, or halo-lower alkyl;

X is CH or N;

$Y^1$ is H or lower alkyl;

each $Y^2$ is independently halogen or lower alkyl, wherein lower alkyl is optionally substituted with one or more substituents selected from the group consisting of hydroxy, lower alkoxy, and halogen;

n is 0, 1, 2, or 3.

$Y^3$ is H, halogen, or lower alkyl, wherein lower alkyl is optionally substituted with one or more substituents selected from the group consisting of hydroxy, lower alkoxy, amino, and halogen;

m is 0 or 1;

$Y^4$ is $Y^{4a}$, $Y^{4b}$, $Y^{4c}$, or $Y^{4d}$;

$Y^{4a}$ is H or halogen;

$Y^{4b}$ is lower alkyl, optionally substituted with one or more substituents selected from the group consisting of lower haloalkyl, halogen, hydroxy, amino, and lower alkoxy;

$Y^{4c}$ is lower cycloalkyl, optionally substituted with one or more substituents selected from the group consisting of lower alkyl, lower haloalkyl, halogen, hydroxy, amino, and lower alkoxy; and $Y^{4d}$ is amino, optionally substituted with one or more lower alkyl;

or a pharmaceutically acceptable salt thereof.

In one variation of Formula I, $Y^1$ is methyl.

In one variation of Formula I, X is CH.

In one variation of Formula I, n is 1 and m is 0.

In one variation of Formula I, $Y^3$ is H.

In one variation of Formula I, $Y^2$ is methyl.

In one variation of Formula I, $Y^2$ is hydroxymethyl.

In one variation of Formula I, $Y^2$ is hydroxyethyl.

In one variation of Formula I, $Y^2$ is halogen.

In one variation of Formula I, $Y^2$ is

wherein, $Y^5$ is halogen, lower alkyl or lower haloalkyl.

In one variation of Formula I, wherein $Y^4$ is

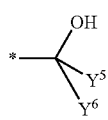

wherein, $Y^5$ and $Y^6$ are independently H, lower alkyl, or lower haloalkyl.

In one variation of Formula I, wherein $Y^4$ is

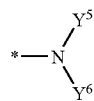

wherein, $Y^5$ and $Y^6$ are independently H or lower alkyl.

In one variation of the above compound, wherein $Y^4$ is

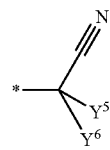

wherein, $Y^5$ and $Y^6$ are independently H, lower alkyl, or lower haloalkyl.

In one variation of Formula I,

R is -$R^1$-$R^2$-$R^3$;

$R^1$ is phenyl or pyridyl;

$R^2$ is —C(=O);

$R^3$ is $R^4$; and $R^4$ is morpholine or piperazine, optionally substituted with one or more lower alkyl.

In one variation of Formula I, R is -$R^1$-$R^2$-$R^3$;

$R^1$ is phenyl or pyridyl;

$R^2$ is —C(=O);

$R^3$ is $R^4$; and $R^4$ is morpholine or piperazine, optionally substituted with one or more lower alkyl.

In one variation of Formula I, R is -$R^1$-$R^2$-$R^3$;

$R^1$ is phenyl or pyridyl;

$R^2$ is —C(=O);

$R^3$ is $R^4$; and $R^4$ is morpholine or piperazine, optionally substituted with one or more lower alkyl.

In one variation of Formula I, R is -$R^1$-$R^2$-$R^3$;

$R^1$ is phenyl or pyridyl;

$R^2$ is —C(=O);

$R^3$ is $R^4$; and $R^4$ is morpholine or piperazine, optionally substituted with one or more lower alkyl.

In one variation, Formula I is:

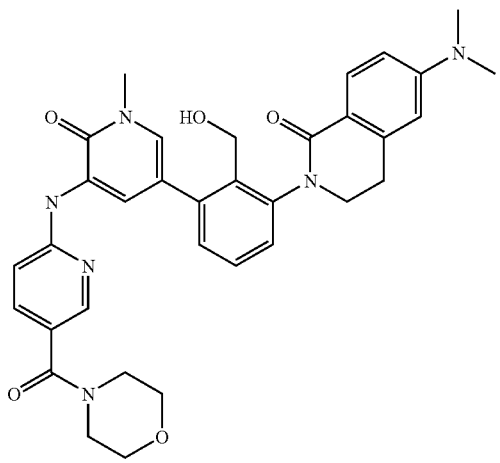

In one variation, Formula I is:

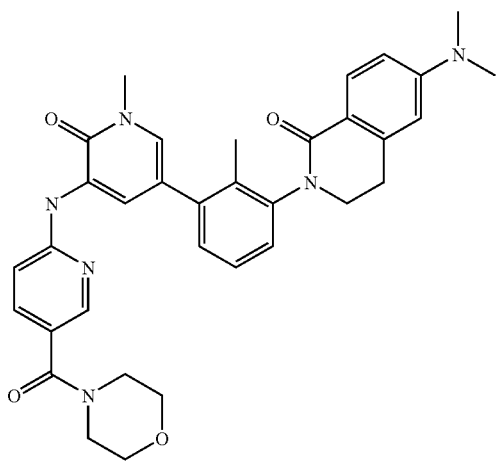

In one variation, Formula I is:

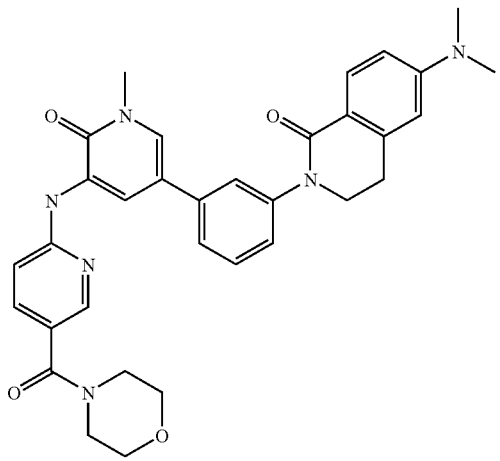

The application provides a compound of Formula II,

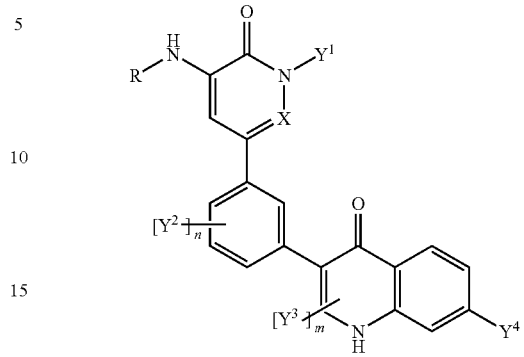

wherein:

R is H, -$R^1$, -$R^1$-$R^2$-$R^3$, or -$R^2$-$R^3$;
  $R^1$ is aryl, heteroaryl, cycloalkyl, or heterocycloalkyl, and is optionally substituted with lower alkyl, hydroxy, lower alkoxy, halo, nitro, amino, cyano, or halo-lower alkyl;
  $R^2$ is —C(=O), —C(=O)O, —C(=O)NH, or —S(=O)$_2$;
  $R^3$ is H or $R^4$;
  $R^4$ is lower alkyl, aryl, arylalkyl, alkylaryl, heteroaryl, alkyl heteroaryl, heteroaryl alkyl, cycloalkyl, alkyl cycloalkyl, cycloalkyl alkyl, heterocycloalkyl, alkyl heterocycloalkyl, or heterocycloalkyl alkyl, and is optionally substituted with lower alkyl, hydroxy, lower alkoxy, halo, nitro, amino, cyano, or halo-lower alkyl;

X is CH or N;

$Y^1$ is H or lower alkyl;

each $Y^2$ is independently halogen or lower alkyl, wherein lower alkyl is optionally substituted with one or more substituents selected from the group consisting of hydroxy, lower alkoxy, and halogen;

n is 0, 1, 2, or 3.

$Y^3$ is H, halogen, or lower alkyl, wherein lower alkyl is optionally substituted with one or more substituents selected from the group consisting of hydroxy, lower alkoxy, amino, and halogen;

m is 0 or 1;

$Y^4$ is $Y^{4a}$, $Y^{4b}$, $Y^{4c}$, or $Y^{4d}$;
  $Y^{4a}$ is H or halogen;
  $Y^{4b}$ is lower alkyl, optionally substituted with one or more substituents selected from the group consisting of lower haloalkyl, halogen, hydroxy, amino, and lower alkoxy;
  $Y^{4c}$ is lower cycloalkyl, optionally substituted with one or more substituents selected from the group consisting of lower alkyl, lower haloalkyl, halogen, hydroxy, amino, and lower alkoxy; and
  $Y^{4d}$ is amino, optionally substituted with one or more lower alkyl;

or a pharmaceutically acceptable salt thereof.

In one variation of Formula II, $Y^1$ is methyl.
In one variation of Formula II, X is CH.
In one variation of the above compound, n is 1 and m is 0.
In one variation of Formula II, $Y^3$ is H.
In one variation of Formula II, $Y^2$ is methyl.

In one variation of Formula II, $Y^2$ is hydroxymethyl.
In one variation of Formula II, $Y^2$ is hydroxyethyl.
In one variation of Formula II, $Y^2$ is halogen.
In one variation of Formula II, $Y^4$ is

wherein, $Y^5$ is halogen, lower alkyl, or lower haloalkyl.
In one variation of Formula II, $Y^4$ is

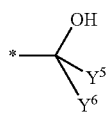

wherein, $Y^5$ and $Y^6$ are independently H, lower alkyl, or lower haloalkyl.
In one variation of Formula II, $Y^4$ is

wherein, $Y^5$ and $Y^6$ are independently H or lower alkyl.
In one variation of Formula II, $Y^4$ is

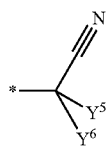

wherein, $Y^5$ and $Y^6$ are independently H, lower alkyl, or lower alkyl.
In one variation of Formula II, R is -$R^1$-$R^2$-$R^3$;

$R^1$ is phenyl or pyridyl;

R is —C(=O);

$R^3$ is $R^4$; and $R^4$ is morpholine or piperazine, optionally substituted with one or more lower alkyl.
In one variation of Formula II, R is -$R^1$-$R^2$-$R^3$;

$R^1$ is phenyl or pyridyl;

$R^2$ is —C(=O);

$R^3$ is $R^4$; and $R^4$ is morpholine or piperazine, optionally substituted with one or more lower alkyl.
In one variation of Formula II, R is -$R^1$-$R^2$-$R^3$;

$R^1$ is phenyl or pyridyl;

$R^2$ is —C(=O);

$R^3$ is $R^4$; and $R^4$ is morpholine or piperazine, optionally substituted with one or more lower alkyl.
In one variation of Formula II, R is -$R^1$-$R^2$-$R^3$;

$R^1$ is phenyl or pyridyl;

$R^2$ is —C(=O);

$R^3$ is $R^4$; and $R^4$ is morpholine or piperazine, optionally substituted with one or more lower alkyl.

In one variation, Formula II is:

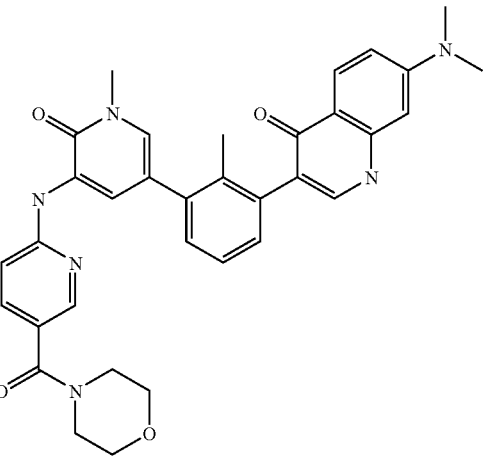

In one variation, Formula II is:

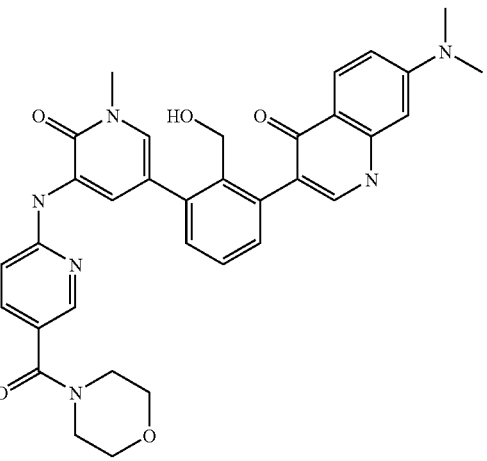

In one variation, Formula II is:

The application provides a compound of Formula III,

III wherein:

R is H, -R$^1$, -R$^1$-R$^2$-R$^3$, or -R$^2$-R$^3$;
  R$^1$ is aryl, heteroaryl, cycloalkyl, or heterocycloalkyl, and is optionally substituted with lower alkyl, hydroxy, lower alkoxy, halo, nitro, amino, cyano, or halo-lower alkyl;
  R$^2$ is —C(═O), —C(═O)O, —C(═O)NH, or —S(═O)$_2$;
  R$^3$ is H or R$^4$;
  R$^4$ is lower alkyl, aryl, arylalkyl, alkylaryl, heteroaryl, alkyl heteroaryl, heteroaryl alkyl, cycloalkyl, alkyl cycloalkyl, cycloalkyl alkyl, heterocycloalkyl, alkyl heterocycloalkyl, or heterocycloalkyl alkyl, and is optionally substituted with lower alkyl, hydroxy, lower alkoxy, halo, nitro, amino, cyano, or halo-lower alkyl;

X is CH or N;

Y$^1$ is H or lower alkyl;

each Y$^2$ is independently halogen or lower alkyl, wherein lower alkyl is optionally substituted with one or more substituents selected from the group consisting of hydroxy, lower alkoxy, and halogen;

n is 0, 1, 2, or 3.

Y$^3$ is H, halogen, or lower alkyl, wherein lower alkyl is optionally substituted with one or more substituents selected from the group consisting of hydroxy, lower alkoxy, amino, and halogen;

m is 0 or 1;

Y$^4$ is Y$^{4a}$, Y$^{4b}$, Y$^{4c}$, or Y$^{4d}$;
  Y$^{4a}$ is H or halogen;
  Y$^{4b}$ is lower alkyl, optionally substituted with one or more substituents selected from the group consisting of lower haloalkyl, halogen, hydroxy, amino, and lower alkoxy;
  Y$^{4c}$ is lower cycloalkyl, optionally substituted with one or more substituents selected from the group consisting of lower alkyl, lower haloalkyl, halogen, hydroxy, amino, and lower alkoxy; and
  Y$^{4d}$ is amino, optionally substituted with one or more lower alkyl;

or a pharmaceutically acceptable salt thereof.

In one variation of Formula III, Y$^1$ is methyl.
In one variation of Formula III, X is CH.
In one variation of Formula III, n is 1 and m is 0.
In one variation of Formula III, Y$^3$ is H.
In one variation of Formula III, Y$^2$ is methyl.
In one variation of Formula III, Y$^2$ is hydroxymethyl.
In one variation of Formula III, Y$^2$ is hydroxyethyl.
In one variation of Formula III, Y$^2$ is halogen.
In one variation of Formula III, Y$^4$ is wherein, Y$^5$ is halogen, lower alkyl, or lower haloalkyl.
In one variation of Formula III, Y$^4$ is wherein, Y$^5$ and Y$^6$ are independently H, lower alkyl, or lower haloalkyl.
In one variation of Formula III, Y$^4$ is wherein, Y$^5$ and Y$^6$ are independently H or lower alkyl.
In one variation of Formula III, Y$^4$ is wherein, Y$^5$ and Y$^6$ are independently H, lower alkyl, or lower haloalkyl.

In one variation of Formula III,

R is -R$^1$-R$^2$-R$^3$;

R$^1$ is phenyl or pyridyl;

R$^2$ is —C(=O);

R$^3$ is R$^4$; and

R$^4$ is morpholine or piperazine, optionally substituted with one or more lower alkyl.

In one variation of Formula III,

R is -R$^1$-R$^2$-R$^3$;

R$^1$ is phenyl or pyridyl;

R$^2$ is —C(=O);

R$^3$ is R$^4$; and

R$^4$ is morpholine or piperazine, optionally substituted with one or more lower alkyl.

In one variation of Formula III,

R is -R$^1$-R$^2$-R$^3$;

R$^1$ is phenyl or pyridyl;

R$^2$ is —C(=O);

R$^3$ is R$^4$; and

R$^4$ is morpholine or piperazine, optionally substituted with one or more lower alkyl.

In one variation of Formula III,

R is -R$^1$-R$^2$-R$^3$;

R$^1$ is phenyl or pyridyl;

R$^2$ is —C(=O);

R$^3$ is R$^4$; and

R$^4$ is morpholine or piperazine, optionally substituted with one or more lower alkyl.

In one variation, Formula III is:

In one variation, Formula III is:

In one variation, Formula III is:

The application provides a compound of Formula I,

I wherein:

R is H, -R$^1$, -R$^1$-R$^2$-R$^3$, or -R$^2$-R$^3$;

R$^1$ is aryl, heteroaryl, cycloalkyl, or heterocycloalkyl, and is optionally substituted with lower alkyl, hydroxy, lower alkoxy, halo, nitro, amino, cyano, or halo-lower alkyl;

$R^2$ is —C(=O), —C(=O)O, —C(=O)NH, or —S(=O)$_2$;

$R^3$ is H or $R^4$;

$R^4$ is lower alkyl, aryl, arylalkyl, alkylaryl, heteroaryl, alkyl heteroaryl, heteroaryl alkyl, cycloalkyl, alkyl cycloalkyl, cycloalkyl alkyl, heterocycloalkyl, alkyl heterocycloalkyl, or heterocycloalkyl alkyl, and is optionally substituted with lower alkyl, hydroxy, lower alkoxy, halo, nitro, amino, cyano, or halo-lower alkyl;

X is CH or N;

$Y^1$ is H or lower alkyl;

each $Y^2$ is independently halogen or lower alkyl, wherein lower alkyl is optionally substituted with one or more substituents selected from the group consisting of hydroxy, lower alkoxy, and halogen;

n is 0, 1, 2, or 3.

$Y^3$ is H, halogen, or lower alkyl, wherein lower alkyl is optionally substituted with one or more substituents selected from the group consisting of hydroxy, lower alkoxy, amino, and halogen;

m is 0 or 1;

$Y^4$ is $Y^{4a}$, $Y^{4b}$, $Y^{4c}$, or $Y^{4d}$;

$Y^{4a}$ is H or halogen;

$Y^{4b}$ is lower alkyl, optionally substituted with one or more substituents selected from the group consisting of lower haloalkyl, halogen, hydroxy, amino, and lower alkoxy;

$Y^{4c}$ is lower cycloalkyl, optionally substituted with one or more substituents selected from the group consisting of lower alkyl, lower haloalkyl, halogen, hydroxy, amino, and lower alkoxy; and $Y^{4d}$ is amino, optionally substituted with one or more lower alkyl;

or a pharmaceutically acceptable salt thereof.

The application also provides a compound of Formula I,

I wherein:

R is H, $-R^1$, $-R^1-R^2-R^3$, $-R^1-R^3$, or $-R^2-R^3$;

$R^1$ is aryl, heteroaryl, cycloalkyl, or heterocycloalkyl, and is optionally substituted with one or more lower alkyl, hydroxy, hydroxy lower alkyl, lower alkoxy, halo, nitro, amino, amido, cyano, oxo, or halo-lower alkyl;

$R^2$ is —C(=O), —C(=O)O, —C(=O)NR$^{2'}$, —NHC(=O)O, —C(=NH)NR$^{2'}$, or —S(=O)$_2$;

$R^2$ is H or lower alkyl;

$R^3$ is H or $R^4$;

$R^4$ is lower alkyl, amino, aryl, arylalkyl, alkylaryl, heteroaryl, alkyl heteroaryl, heteroaryl alkyl, cycloalkyl, alkyl cycloalkyl, cycloalkyl alkyl, heterocycloalkyl, alkyl heterocycloalkyl, or heterocycloalkyl alkyl, and is optionally substituted with one or more lower alkyl, hydroxy, lower alkoxy, hydroxy lower alkyl, hydroxy lower alkoxy, lower alkyl sulfonyl, lower alkyl sulfonamido, carbamate, carboxy, ester, amido, acyl, halo, nitro, amino, cyano, oxo, or halo-lower alkyl;

X is CH or N;

$Y^1$ is H, lower alkyl, or lower haloalkyl;

each $Y^2$ is independently halogen, oxime, or lower alkyl, wherein lower alkyl is optionally substituted with one or more substituents selected from the group consisting of hydroxy, lower alkoxy, lower haloalkoxy, lower haloalkyl, carboxy, amino, and halogen;

n is 0, 1, 2, or 3.

$Y^3$ is H, halogen, or lower alkyl, wherein lower alkyl is optionally substituted with one or more substituents selected from the group consisting of hydroxy, lower alkoxy, amino, and halogen;

m is 0 or 1;

$Y^4$ is $Y^{4a}$, $Y^{4b}$, $Y^{4c}$, or $Y^{4d}$;

$Y^{4a}$ is H or halogen;

$Y^{4b}$ is lower alkyl, optionally substituted with one or more substituents selected from the group consisting of lower haloalkyl, halogen, hydroxy, amino, cyano, and lower alkoxy;

$Y^{4c}$ is lower cycloalkyl, optionally substituted with one or more substituents selected from the group consisting of lower alkyl, lower haloalkyl, halogen, hydroxy, amino, cyano, and lower alkoxy; and $Y^{4d}$ is amino, optionally substituted with one or more lower alkyl, alkoxy lower alkyl, or hydroxy lower alkyl;

or a pharmaceutically acceptable salt thereof.

In one variation of Formula I, $Y^1$ is methyl.
In one variation of Formula I, X is CH.
In one variation of Formula I, n is 1 and m is 0.
In one variation of Formula I, $Y^3$ is H.
In one variation of Formula I, $Y^2$ is methyl.
In one variation of Formula I, $Y^1$ is hydroxymethyl.
In one variation of Formula I, $Y^2$ is hydroxyethyl.
In one variation of Formula I, $Y^2$ is halogen.
In one variation of Formula I, $Y^4$ is wherein, $Y^5$ is halogen, lower alkyl or lower haloalkyl.

In one variation of Formula I, wherein $Y^4$ is wherein, $Y^5$ and $Y^6$ are independently H, lower alkyl, or lower haloalkyl.

In one variation of Formula I, wherein $Y^4$ is

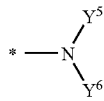

wherein, $Y^5$ and $Y^6$ are independently H or lower alkyl.

In one variation of the above compound, wherein $Y^4$ is

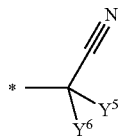

wherein, $Y^5$ and $Y^6$ are independently H, lower alkyl, or lower haloalkyl.

In one variation of Formula I,

R is -$R^1$-$R^2$-$R^3$;

$R^1$ is phenyl or pyridyl;

$R^2$ is —C(=O);

$R^3$ is $R^4$; and $R^4$ is morpholine or piperazine, optionally substituted with one or more lower alkyl.

In one variation of Formula I, R is -$R^1$-$R^2$-$R^3$;

$R^1$ is phenyl or pyridyl;

$R^2$ is —C(=O);

$R^3$ is $R^4$; and $R^4$ is morpholine or piperazine, optionally substituted with one or more lower alkyl.

In one variation of Formula I, R is -$R^1$-$R^2$-$R^3$;

$R^1$ is phenyl or pyridyl;

$R^2$ is —C(=O);

$R^3$ is $R^4$; and $R^4$ is morpholine or piperazine, optionally substituted with one or more lower alkyl.

In one variation of Formula I, R is -$R^1$-$R^2$-$R^3$;

$R^1$ is phenyl or pyridyl;

$R^2$ is —C(=O);

$R^3$ is $R^4$; and $R^4$ is morpholine or piperazine, optionally substituted with one or more lower alkyl.

In one variation, Formula I is:

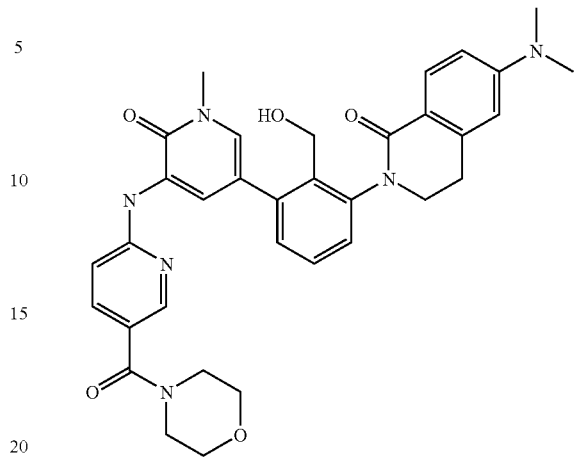

In one variation, Formula I is:

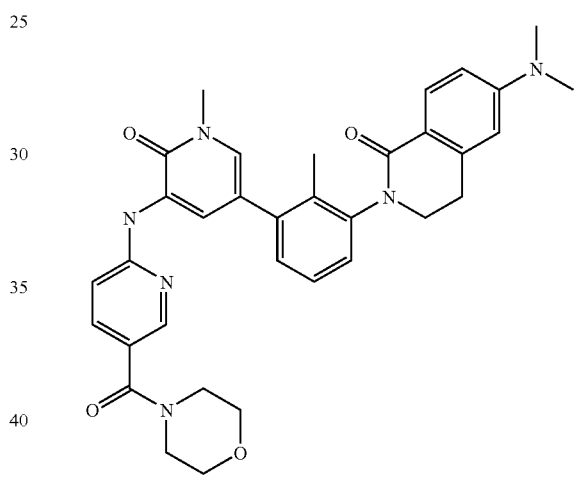

In one variation, Formula I is:

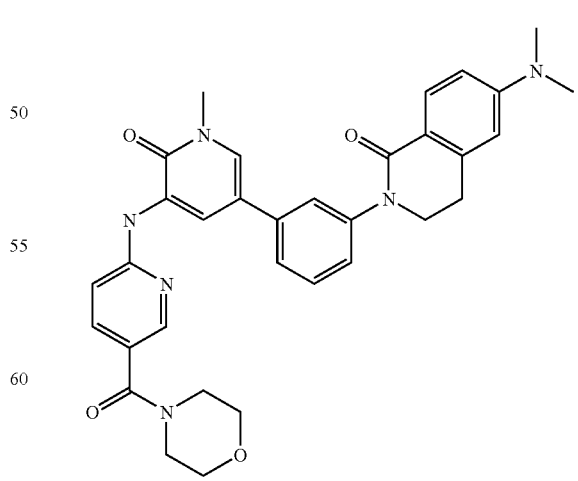

The application also provides a compound of Formula I, wherein Formula I is selected from the group consisting of:

6-Dimethylamino-2-(3-{1-methyl-5-[5-(morpholine-4-carbonyl)-pyridin-2-ylamino]-6-oxo-1,6-dihydro-pyridin-3-yl}-phenyl)-3,4-dihydro-2H-isoquinolin-1-one;

6-Dimethylamino-2-(2-hydroxymethyl-3-{1-methyl-5-[5-(morpholine-4-carbonyl)-pyridin-2-ylamino]-6-oxo-1,6-dihydro-pyridin-3-yl}-phenyl)-3,4-dihydro-2H-isoquinolin-1-one;

6-Dimethylamino-2-(2-methyl-3-{1-methyl-5-[5-(morpholine-4-carbonyl)-pyridin-2-ylamino]-6-oxo-1,6-dihydro-pyridin-3-yl}-phenyl)-3,4-dihydro-2H-isoquinolin-1-one;

1-{5-[3-(6-Dimethylamino-1-oxo-3,4-dihydro-1H-isoquinolin-2-yl)-2-hydroxymethyl-phenyl]-1-methyl-2-oxo-1,2-dihydro-pyridin-3-yl}-3-ethyl-urea;

6-Dimethylamino-2-{2-hydroxymethyl-3-[1-methyl-5-(1-methyl-1H-pyrazol-3-ylamino)-6-oxo-1,6-dihydro-pyridin-3-yl]-phenyl}-3,4-dihydro-2H-isoquinolin-1-one;

6-Cyclopropyl-2-(2-hydroxymethyl-3-{1-methyl-5-[5-(morpholine-4-carbonyl)-pyridin-2-ylamino]-6-oxo-1,6-dihydro-pyridin-3-yl}-phenyl)-3,4-dihydro-2H-isoquinolin-1-one;

2-(2-Difluoromethoxy-3-{1-methyl-5-[5-(morpholine-4-carbonyl)-pyridin-2-ylamino]-6-oxo-1,6-dihydro-pyridin-3-yl}-phenyl)-6-dimethylamino-3,4-dihydro-2H-isoquinolin-1-one;

6-Dimethylamino-2-{2-hydroxymethyl-3-[1-methyl-5-(5-morpholin-4-ylmethyl-pyridin-2-ylamino)-6-oxo-1,6-dihydro-pyridin-3-yl]-phenyl}-3,4-dihydro-2H-isoquinolin-1-one;

6-Dimethylamino-2-(2-hydroxymethyl-3-{1-methyl-5-[5-(4-methyl-piperazine-1-carbonyl)-pyridin-2-ylamino]-6-oxo-1,6-dihydro-pyridin-3-yl}-phenyl)-3,4-dihydro-2H-isoquinolin-1-one;

2-(2-Hydroxymethyl-3-{1-methyl-5-[5-(morpholine-4-carbonyl)-pyridin-2-ylamino]-6-oxo-1,6-dihydro-pyridin-3-yl}-phenyl)-6-methylamino-3,4-dihydro-2H-isoquinolin-1-one;

2-{3-[5-(1-tert-Butyl-1H-pyrazol-3-ylamino)-1-methyl-6-oxo-1,6-dihydro-pyridin-3-yl]-2-hydroxymethyl-phenyl}-6-cyclopropyl-3,4-dihydro-2H-isoquinolin-1-one;

6-Cyclopropyl-2-{3-[5-(1-ethyl-1H-pyrazol-3-ylamino)-1-methyl-6-oxo-1,6-dihydro-pyridin-3-yl]-2-hydroxymethyl-phenyl}-3,4-dihydro-2H-isoquinolin-1-one;

2-{3-[5-(1-Cyclohexyl-1H-pyrazol-3-ylamino)-1-methyl-6-oxo-1,6-dihydro-pyridin-3-yl]-2-hydroxymethyl-phenyl}-6-cyclopropyl-3,4-dihydro-2H-isoquinolin-1-one;

6-Cyclopropyl-2-(2-hydroxymethyl-3-{1-methyl-6-oxo-5-[1-(2,2,2-trifluoro-ethyl)-1H-pyrazol-3-ylamino]-1,6-dihydro-pyridin-3-yl}-phenyl)-3,4-dihydro-2H-isoquinolin-1-one;

6-Cyclopropyl-2-{3-[5-(1-cyclopropyl-1H-pyrazol-3-ylamino)-1-methyl-6-oxo-1,6-dihydro-pyridin-3-yl]-2-hydroxymethyl-phenyl}-3,4-dihydro-2H-isoquinolin-1-one;

6-Dimethylamino-2-(2-hydroxymethyl-3-{1-methyl-5-[5-(4-methyl-piperazin-1-yl)-pyridin-2-ylamino]-6-oxo-1,6-dihydro-pyridin-3-yl}-phenyl)-3,4-dihydro-2H-isoquinolin-1-one;

6-Cyclopropyl-2-{2-hydroxymethyl-3-[1-methyl-5-(1-methyl-1H-pyrazol-3-ylamino)-6-oxo-1,6-dihydro-pyridin-3-yl]-phenyl}-3,4-dihydro-2H-isoquinolin-1-one;

6-Cyclopropyl-2-{2-hydroxymethyl-3-[5-(2-isopropyl-2H-[1,2,3]triazol-4-ylamino)-1-methyl-6-oxo-1,6-dihydro-pyridin-3-yl]-phenyl}-3,4-dihydro-2H-isoquinolin-1-one;

6-Cyclopropyl-2-{2-hydroxymethyl-3-[5-(1-isopropyl-1H-pyrazol-3-ylamino)-1-methyl-6-oxo-1,6-dihydro-pyridin-3-yl]-phenyl}-3,4-dihydro-2H-isoquinolin-1-one;

6-(1-Fluoro-cyclopropyl)-2-(2-hydroxymethyl-3-{1-methyl-5-[5-(morpholine-4-carbonyl)-pyridin-2-ylamino]-6-oxo-1,6-dihydro-pyridin-3-yl}-phenyl)-3,4-dihydro-2H-isoquinolin-1-one;

6-Dimethylamino-2-{2-hydroxymethyl-3-[1-methyl-5-(5-morpholin-4-yl-pyridin-2-ylamino)-6-oxo-1,6-dihydro-pyridin-3-yl]-phenyl}-3,4-dihydro-2H-isoquinolin-1-one;

6-(Ethyl-methyl-amino)-2-(2-hydroxymethyl-3-{1-methyl-5-[5-(morpholine-4-carbonyl)-pyridin-2-ylamino]-6-oxo-1,6-dihydro-pyridin-3-yl}-phenyl)-3,4-dihydro-2H-isoquinolin-1-one;

6-tert-Butyl-2-(2-hydroxymethyl-3-{1-methyl-5-[5-(morpholine-4-carbonyl)-pyridin-2-ylamino]-6-oxo-1,6-dihydro-pyridin-3-yl}-phenyl)-3,4-dihydro-2H-isoquinolin-1-one;

6-(1-Difluoromethyl-cyclopropyl)-2-(2-hydroxymethyl-3-{1-methyl-5-[5-(morpholine-4-carbonyl)-pyridin-2-ylamino]-6-oxo-1,6-dihydro-pyridin-3-yl}-phenyl)-3,4-dihydro-2H-isoquinolin-1-one;

6-Cyclopropyl-2-(2-hydroxymethyl-3-{1-methyl-5-[5-(4-methyl-piperazin-1-yl)-pyridin-2-ylamino]-6-oxo-1,6-dihydro-pyridin-3-yl}-phenyl)-3,4-dihydro-2H-isoquinolin-1-one;

6-Fluoro-2-(2-hydroxymethyl-3-{1-methyl-5-[5-(morpholine-4-carbonyl)-pyridin-2-ylamino]-6-oxo-1,6-dihydro-pyridin-3-yl}-phenyl)-3,4-dihydro-2H-isoquinolin-1-one;

6-tert-Butyl-2-(2-hydroxymethyl-3-{1-methyl-5-[5-(4-methyl-piperazin-1-yl)-pyridin-2-ylamino]-6-oxo-1,6-dihydro-pyridin-3-yl}-phenyl)-3,4-dihydro-2H-isoquinolin-1-one;

6-Cyclopropyl-2-(2-hydroxymethyl-3-{1-methyl-5-[6-(4-methyl-piperazin-1-yl)-pyridazin-3-ylamino]-6-oxo-1,6-dihydro-pyridin-3-yl}-phenyl)-3,4-dihydro-2H-isoquinolin-1-one;

2-(3-{5-[5-(4,4-Difluoro-piperidine-1-carbonyl)-pyridin-2-ylamino]-1-methyl-6-oxo-1,6-dihydro-pyridin-3-yl}-2-hydroxymethyl-phenyl)-6-dimethylamino-3,4-dihydro-2H-isoquinolin-1-one;

6-Dimethylamino-2-{2-hydroxymethyl-3-[1-methyl-5-(1-methyl-5-oxo-4,5-dihydro-1H-[1,2,4]triazol-3-ylamino)-6-oxo-1,6-dihydro-pyridin-3-yl]-phenyl}-3,4-dihydro-2H-isoquinolin-1-one;

6-Dimethylamino-2-(2-hydroxymethyl-3-{1-methyl-5-[5-(2-oxa-6-aza-spiro[3.3]heptane-6-carbonyl)-pyridin-2-ylamino]-6-oxo-1,6-dihydro-pyridin-3-yl}-phenyl)-3,4-dihydro-2H-isoquinolin-1-one;

6-Dimethylamino-2-(2-hydroxymethyl-3-{1-methyl-5-[6-(4-methyl-piperazin-1-yl)-pyridazin-3-ylamino]-6-oxo-1,6-dihydro-pyridin-3-yl}-phenyl)-3,4-dihydro-2H-isoquinolin-1-one;

6-Dimethylamino-2-(3-{5-[5-(1,1-dioxo-1$\lambda^6$-thiomorpholine-4-carbonyl)-pyridin-2-ylamino]-1-methyl-6-oxo-1,6-dihydro-pyridin-3-yl}-2-hydroxymethyl-phenyl)-3,4-dihydro-2H-isoquinolin-1-one;

6-Cyclopropyl-2-(2-hydroxymethyl-3-{5-[1-(2-hydroxy-2-methyl-propyl)-1H-pyrazol-3-ylamino]-1-methyl-6-oxo-1,6-dihydro-pyridin-3-yl}-phenyl)-3,4-dihydro-2H-isoquinolin-1-one;

6-Dimethylamino-2-{3-[5-(5-ethoxymethyl-pyridin-2-ylamino)-1-methyl-6-oxo-1,6-dihydro-pyridin-3-yl]-2-hydroxymethyl-phenyl}-3,4-dihydro-2H-isoquinolin-1-one;

6-Dimethylamino-2-(2-hydroxymethyl-3-{5-[5-(2-methoxy-ethoxymethyl)-pyridin-2-ylamino]-1-methyl-6-oxo-1,6-dihydro-pyridin-3-yl}-phenyl)-3,4-dihydro-2H-isoquinolin-1-one;

6-Dimethylamino-2-(3-{5-[5-(2-hydroxy-ethoxymethyl)-pyridin-2-ylamino]-1-methyl-6-oxo-1,6-dihydro-pyridin-3-yl}-2-hydroxymethyl-phenyl)-3,4-dihydro-2H-isoquinolin-1-one;

6-Cyclopropyl-2-(3-{5-[1-(2-hydroxy-ethyl)-1H-pyrazol-3-ylamino]-1-methyl-6-oxo-1,6-dihydro-pyridin-3-yl}-2-hydroxymethyl-phenyl)-3,4-dihydro-2H-isoquinolin-1-one;

6-Dimethylamino-2-{2-hydroxymethyl-3-[5-(5-methanesulfonylmethyl-pyridin-2-ylamino)-1-methyl-6-oxo-1,6-dihydro-pyridin-3-yl]-phenyl}-3,4-dihydro-2H-isoquinolin-1-one;

6-Dimethylamino-2-(2-hydroxymethyl-3-{1-methyl-6-oxo-5-[5-(2-oxo-pyrrolidin-1-ylmethyl)-pyridin-2-ylamino]-1,6-dihydro-pyridin-3-yl}-phenyl)-3,4-dihydro-2H-isoquinolin-1-one;

6-{5-[3-(6-Dimethylamino-1-oxo-3,4-dihydro-1H-isoquinolin-2-yl)-2-hydroxymethyl-phenyl]-1-methyl-2-oxo-1,2-dihydro-pyridin-3-ylamino}-N-(2-methoxy-ethyl)-N-methyl-nicotinamide;

2-(3-{5-[5-(4,4-Difluoro-piperidin-1-ylmethyl)-pyridin-2-ylamino]-1-methyl-6-oxo-1,6-dihydro-pyridin-3-yl}-2-hydroxymethyl-phenyl)-6-dimethylamino-3,4-dihydro-2H-isoquinolin-1-one;

6-Cyclopropyl-2-(3-{5-[1-(2-hydroxy-3-methoxy-propyl)-1H-pyrazol-3-ylamino]-1-methyl-6-oxo-1,6-dihydro-pyridin-3-yl}-2-hydroxymethyl-phenyl)-3,4-dihydro-2H-isoquinolin-1-one;

6-Cyclopropyl-2-(2-hydroxymethyl-3-{1-methyl-5-[1-(2-morpholin-4-yl-ethyl)-1H-pyrazol-3-ylamino]-6-oxo-1,6-dihydro-pyridin-3-yl}-phenyl)-3,4-dihydro-2H-isoquinolin-1-one;

6-Dimethylamino-2-[3-(5-{5-[4-(2-hydroxy-ethyl)-piperazin-1-yl]-pyridin-2-ylamino}-1-methyl-6-oxo-1,6-dihydro-pyridin-3-yl)-2-hydroxymethyl-phenyl]-3,4-dihydro-2H-isoquinolin-1-one;

2-(2-Hydroxymethyl-3-{1-methyl-5-[5-(morpholine-4-carbonyl)-pyridin-2-ylamino]-6-oxo-1,6-dihydro-pyridin-3-yl}-phenyl)-6-(1-methyl-cyclopropyl)-3,4-dihydro-2H-isoquinolin-1-one;

6-Dimethylamino-2-(3-{5-[5-(4-ethoxy-piperidine-1-carbonyl)-pyridin-2-ylamino]-1-methyl-6-oxo-1,6-dihydro-pyridin-3-yl}-2-hydroxymethyl-phenyl)-3,4-dihydro-2H-isoquinolin-1-one;

6-Dimethylamino-2-(2-hydroxymethyl-3-{5-[5-(4-methoxymethyl-piperidine-1-carbonyl)-pyridin-2-ylamino]-1-methyl-6-oxo-1,6-dihydro-pyridin-3-yl}-phenyl)-3,4-dihydro-2H-isoquinolin-1-one;

2-(3-{5-[5-(Azetidine-1-carbonyl)-pyridin-2-ylamino]-1-methyl-6-oxo-1,6-dihydro-pyridin-3-yl}-2-hydroxymethyl-phenyl)-6-dimethylamino-3,4-dihydro-2H-isoquinolin-1-one;

2-(3-{5-[5-(3,3-Difluoro-azetidine-1-carbonyl)-pyridin-2-ylamino]-1-methyl-6-oxo-1,6-dihydro-pyridin-3-yl}-2-hydroxymethyl-phenyl)-6-dimethylamino-3,4-dihydro-2H-isoquinolin-1-one;

6-Dimethylamino-2-(3-{5-[5-(1,1-dioxo-1λ⁶-isothiazolidin-2-ylmethyl)-pyridin-2-ylamino]-1-methyl-6-oxo-1,6-dihydro-pyridin-3-yl}-2-hydroxymethyl-phenyl)-3,4-dihydro-2H-isoquinolin-1-one;

6-tert-Butyl-2-{2-hydroxymethyl-3-[1-methyl-5-(5-morpholin-4-yl-pyridin-2-ylamino)-6-oxo-1,6-dihydro-pyridin-3-yl]-phenyl}-3,4-dihydro-2H-isoquinolin-1-one;

6-tert-Butyl-2-(2-hydroxymethyl-3-{1-methyl-5-[5-(2-oxa-6-aza-spiro[3.3]heptane-6-carbonyl)-pyridin-2-ylamino]-6-oxo-1,6-dihydro-pyridin-3-yl}-phenyl)-3,4-dihydro-2H-isoquinolin-1-one;

6-Dimethylamino-2-(3-{5-[5-(4-ethyl-piperazin-1-yl)-pyridin-2-ylamino]-1-methyl-6-oxo-1,6-dihydro-pyridin-3-yl}-2-hydroxymethyl-phenyl)-3,4-dihydro-2H-isoquinolin-1-one;

6-Dimethylamino-2-(3-{5-[5-(4-ethyl-piperazin-1-yl)-pyridin-2-ylamino]-1-methyl-6-oxo-1,6-dihydro-pyridin-3-yl}-2-hydroxymethyl-phenyl)-3,4-dihydro-2H-isoquinolin-1-one;

6-Dimethylamino-2-(2-hydroxymethyl-3-{5-[5-(4-hydroxy-4-methyl-piperidine-1-carbonyl)-pyridin-2-ylamino]-1-methyl-6-oxo-1,6-dihydro-pyridin-3-yl}-phenyl)-3,4-dihydro-2H-isoquinolin-1-one;

N-(6-{5-[3-(6-Dimethylamino-1-oxo-3,4-dihydro-1H-isoquinolin-2-yl)-2-hydroxymethyl-phenyl]-1-methyl-2-oxo-1,2-dihydro-pyridin-3-ylamino}-pyridin-3-ylmethyl)-methanesulfonamide;

(6-{5-[3-(6-Dimethylamino-1-oxo-3,4-dihydro-1H-isoquinolin-2-yl)-2-hydroxymethyl-phenyl]-1-methyl-2-oxo-1,2-dihydro-pyridin-3-ylamino}-pyridin-3-ylmethyl)-carbamic acid methyl ester;

6-Cyclopropyl-2-(2-hydroxymethyl-3-{1-methyl-5-[5-(2-oxa-6-aza-spiro[3.3]heptane-6-carbonyl)-pyridin-2-ylamino]-6-oxo-1,6-dihydro-pyridin-3-yl}-phenyl)-3,4-dihydro-2H-isoquinolin-1-one;

6-Cyclopropyl-2-(3-{5-[5-(1,1-dioxo-1λ⁶-thiomorpholine-4-carbonyl)-pyridin-2-ylamino]-1-methyl-6-oxo-1,6-dihydro-pyridin-3-yl}-2-hydroxymethyl-phenyl)-3,4-dihydro-2H-isoquinolin-1-one;

6-(Ethyl-methyl-amino)-2-{2-hydroxymethyl-3-[1-methyl-5-(5-morpholin-4-yl-pyridin-2-ylamino)-6-oxo-1,6-dihydro-pyridin-3-yl]-phenyl}-3,4-dihydro-2H-isoquinolin-1-one;

6-Cyclopropyl-2-(3-{5-[1-(2-dimethylamino-ethyl)-1H-pyrazol-3-ylamino]-1-methyl-6-oxo-1,6-dihydro-pyridin-3-yl}-2-hydroxymethyl-phenyl)-3,4-dihydro-2H-isoquinolin-1-one;

6-(1-Hydroxy-1-methyl-ethyl)-2-(2-hydroxymethyl-3-{1-methyl-5-[5-(morpholine-4-carbonyl)-pyridin-2-ylamino]-6-oxo-1,6-dihydro-pyridin-3-yl}-phenyl)-3,4-dihydro-2H-isoquinolin-1-one;

6-[(2-Hydroxy-ethyl)-methyl-amino]-2-(2-hydroxymethyl-3-{1-methyl-5-[5-(morpholine-4-carbonyl)-pyridin-2-ylamino]-6-oxo-1,6-dihydro-pyridin-3-yl}-phenyl)-3,4-dihydro-2H-isoquinolin-1-one;

6-Dimethylamino-2-[3-(5-{5-[(2-hydroxy-ethyl)-methyl-amino]-pyridin-2-ylamino}-1-methyl-6-oxo-1,6-dihydro-pyridin-3-yl)-2-hydroxymethyl-phenyl]-3,4-dihydro-2H-isoquinolin-1-one;

6-Dimethylamino-2-{2-hydroxymethyl-3-[5-(4-hydroxy-3,4,5,6-tetrahydro-2H-[1,3']bipyridinyl-6'-ylamino)-1-methyl-6-oxo-1,6-dihydro-pyridin-3-yl]-phenyl}-3,4-dihydro-2H-isoquinolin-1-one;

6-Dimethylamino-2-(3-{5-[5-(1,1-dioxo-1λ⁶-thiomorpholin-4-yl)-pyridin-2-ylamino]-1-methyl-6-oxo-1,6-dihydro-pyridin-3-yl}-2-hydroxymethyl-phenyl)-3,4-dihydro-2H-isoquinolin-1-one;

2-(3-{5-[5-(3,3-Difluoro-azetidin-1-yl)-pyridin-2-ylamino]-1-methyl-6-oxo-1,6-dihydro-pyridin-3-yl}-2-hydroxymethyl-phenyl)-6-dimethylamino-3,4-dihydro-2H-isoquinolin-1-one;

6-Dimethylamino-2-(3-{5-[5-(3-hydroxy-azetidin-1-yl)-pyridin-2-ylamino]-1-methyl-6-oxo-1,6-dihydro-pyridin-3-yl}-2-hydroxymethyl-phenyl)-3,4-dihydro-2H-isoquinolin-1-one;

2-{3-[5-(5-Diethylamino-pyridin-2-ylamino)-1-methyl-6-oxo-1,6-dihydro-pyridin-3-yl]-2-hydroxymethyl-phenyl}-6-dimethylamino-3,4-dihydro-2H-isoquinolin-1-one;

2-{2-Hydroxymethyl-3-[1-methyl-5-(5-morpholin-4-yl-pyridin-2-ylamino)-6-oxo-1,6-dihydro-pyridin-3-yl]-phenyl}-6-(1-methyl-cyclopropyl)-3,4-dihydro-2H-isoquinolin-1-one;

2-{3-[5-(4,4-Difluoro-3,4,5,6-tetrahydro-2H-[1,3']bipyridinyl-6'-ylamino)-1-methyl-6-oxo-1,6-dihydro-pyridin-3-yl]-2-hydroxymethyl-phenyl}-6-dimethylamino-3,4-dihydro-2H-isoquinolin-1-one;

6-Dimethylamino-2-{2-hydroxymethyl-3-[5-(1-methanesulfonylmethyl-1H-pyrazol-3-ylamino)-1-methyl-6-oxo-1,6-dihydro-pyridin-3-yl]-phenyl}-3,4-dihydro-2H-isoquinolin-1-one;

6-Dimethylamino-2-{2-hydroxymethyl-3-[1-methyl-6-oxo-5-(2-propyl-2H-[1,2,3]triazol-4-ylamino)-1,6-dihydro-pyridin-3-yl]-phenyl}-3,4-dihydro-2H-isoquinolin-1-one;

6-Dimethylamino-2-(2-hydroxymethyl-3-{1-methyl-6-oxo-5-[5-(2-oxo-pyrrolidin-1-yl)-pyridin-2-ylamino]-1,6-dihydro-pyridin-3-yl}-phenyl)-3,4-dihydro-2H-isoquinolin-1-one;

6'-{5-[3-(6-Dimethylamino-1-oxo-3,4-dihydro-1H-isoquinolin-2-yl)-2-hydroxymethyl-phenyl]-1-methyl-2-oxo-1,2-dihydro-pyridin-3-ylamino}-3,4,5,6-tetrahydro-[1,3']bipyridinyl-2-one;

6-Dimethylamino-2-(3-{5-[5-(1,1-dioxo-1$\lambda^6$-[1,2]thiazinan-2-yl)-pyridin-2-ylamino]-1-methyl-6-oxo-1,6-dihydro-pyridin-3-yl}-2-hydroxymethyl-phenyl)-3,4-dihydro-2H-isoquinolin-1-one;

6-Dimethylamino-2-(3-{5-[5-(1,1-dioxo-1$\lambda^6$-isothiazolidin-2-yl)-pyridin-2-ylamino]-1-methyl-6-oxo-1,6-dihydro-pyridin-3-yl}-2-hydroxymethyl-phenyl)-3,4-dihydro-2H-isoquinolin-1-one;

2-(6-{5-[3-(6-Dimethylamino-1-oxo-3,4-dihydro-1H-isoquinolin-2-yl)-2-hydroxymethyl-phenyl]-1-methyl-2-oxo-1,2-dihydro-pyridin-3-ylamino}-pyridin-3-yloxy)-acetamide;

6-Cyclopropyl-2-(2-hydroxymethyl-3-{1-methyl-5-[5-(2-oxa-6-aza-spiro[3.3]hept-6-yl)-pyridin-2-ylamino]-6-oxo-1,6-dihydro-pyridin-3-yl}-phenyl)-3,4-dihydro-2H-isoquinolin-1-one;

1-(6-{5-[3-(6-Cyclopropyl-1-oxo-3,4-dihydro-1H-isoquinolin-2-yl)-2-hydroxymethyl-phenyl]-1-methyl-2-oxo-1,2-dihydro-pyridin-3-ylamino}-pyridine-3-carbonyl)-piperidine-4-carbonitrile;

6-Cyclopropyl-2-(3-{5-[5-(3-ethoxy-pyrrolidine-1-carbonyl)-pyridin-2-ylamino]-1-methyl-6-oxo-1,6-dihydro-pyridin-3-yl}-2-hydroxymethyl-phenyl)-3,4-dihydro-2H-isoquinolin-1-one;

6-Dimethylamino-2-(2-hydroxymethyl-3-{5-[5-(3-methanesulfonyl-propoxy)-pyridin-2-ylamino]-1-methyl-6-oxo-1,6-dihydro-pyridin-3-yl}-phenyl)-3,4-dihydro-2H-isoquinolin-1-one;

6-Dimethylamino-2-(3-{5-[5-(2-hydroxy-ethoxy)-pyridin-2-ylamino]-1-methyl-6-oxo-1,6-dihydro-pyridin-3-yl}-2-hydroxymethyl-phenyl)-3,4-dihydro-2H-isoquinolin-1-one;

2-(3-{5-[5-(4-Acetyl-piperazin-1-yl)-pyridin-2-ylamino]-1-methyl-6-oxo-1,6-dihydro-pyridin-3-yl}-2-hydroxymethyl-phenyl)-6-dimethylamino-3,4-dihydro-2H-isoquinolin-1-one;

1-(6-{5-[3-(6-Cyclopropyl-1-oxo-3,4-dihydro-1H-isoquinolin-2-yl)-2-hydroxymethyl-phenyl]-1-methyl-2-oxo-1,2-dihydro-pyridin-3-ylamino}-pyridine-3-carbonyl)-piperidine-3-carbonitrile;

2-(2-acetaldehyde oxime-3-{1-methyl-5-[5-(morpholine-4-carbonyl)-pyridin-2-ylamino]-6-oxo-1,6-dihydro-pyridin-3-yl}-phenyl)-6-dimethylamino-3,4-dihydro-2H-isoquinolin-1-one 2-[6-(1-Chloro-cyclopropyl)-1-oxo-3,4-dihydro-1H-isoquinolin-2-yl]-6-{1-methyl-5-[5-(morpholine-4-carbonyl)-pyridin-2-ylamino]-6-oxo-1,6-dihydro-pyridin-3-yl}-benzaldehyde;

6-(1-Chloro-cyclopropyl)-2-(2-hydroxymethyl-3-{1-methyl-5-[5-(morpholine-4-carbonyl)-pyridin-2-ylamino]-6-oxo-1,6-dihydro-pyridin-3-yl}-phenyl)-3,4-dihydro-2H-isoquinolin-1-one;

6-Dimethylamino-2-{2-hydroxymethyl-3-[5-(4-hydroxy-4-methyl-3,4,5,6-tetrahydro-2H-[1,3']bipyridinyl-6'-ylamino)-1-methyl-6-oxo-1,6-dihydro-pyridin-3-yl]-phenyl}-3,4-dihydro-2H-isoquinolin-1-one;

2-[2-(2-Hydroxymethyl-3-{1-methyl-5-[5-(morpholine-4-carbonyl)-pyridin-2-ylamino]-6-oxo-1,6-dihydro-pyridin-3-yl}-phenyl)-1-oxo-1,2,3,4-tetrahydro-isoquinolin-6-yl]-2-methyl-propionitrile;

6-(1-Chloro-cyclopropyl)-2-{2-hydroxymethyl-3-[1-methyl-5-(5-morpholin-4-yl-pyridin-2-ylamino)-6-oxo-1,6-dihydro-pyridin-3-yl]-phenyl}-3,4-dihydro-2H-isoquinolin-1-one 6-Dimethylamino-2-(2-hydroxymethyl-3-{1-methyl-5-[5-(2-oxa-6-aza-spiro[3.3]hept-6-yl)-pyridin-2-ylamino]-6-oxo-1,6-dihydro-pyridin-3-yl}-phenyl)-3,4-dihydro-2H-isoquinolin-1-one;

1-(2-{2-Hydroxymethyl-3-[1-methyl-5-(5-morpholin-4-yl-pyridin-2-ylamino)-6-oxo-1,6-dihydro-pyridin-3-yl]-phenyl}-1-oxo-1,2,3,4-tetrahydro-isoquinolin-6-yl)-cyclopropanecarbonitrile;

2-(2-{2-Hydroxymethyl-3-[1-methyl-5-(5-morpholin-4-yl-pyridin-2-ylamino)-6-oxo-1,6-dihydro-pyridin-3-yl]-phenyl}-1-oxo-1,2,3,4-tetrahydro-isoquinolin-6-yl)-2-methyl-propionitrile;

6-Dimethylamino-2-{2-hydroxymethyl-3-[1-methyl-6-oxo-5-(5-piperazin-1-yl-pyridin-2-ylamino)-1,6-dihydro-pyridin-3-yl]-phenyl}-3,4-dihydro-2H-isoquinolin-1-one;

6-Dimethylamino-2-{2-hydroxymethyl-3-[5-(5-hydroxymethyl-pyridin-2-ylamino)-1-methyl-6-oxo-1,6-dihydro-pyridin-3-yl]-phenyl}-3,4-dihydro-2H-isoquinolin-1-one;

6-Dimethylamino-2-{2-hydroxymethyl-3-[1-methyl-5-(6-morpholin-4-yl-pyrimidin-4-ylamino)-6-oxo-1,6-dihydro-pyridin-3-yl]-phenyl}-3,4-dihydro-2H-isoquinolin-1-one;

6-Dimethylamino-2-{2-hydroxymethyl-3-[1-methyl-5-(5-methyl-isoxazol-3-ylamino)-6-oxo-1,6-dihydro-pyridin-3-yl]-phenyl}-3,4-dihydro-2H-isoquinolin-1-one;

6-Dimethylamino-2-{2-hydroxymethyl-3-[5-(isoxazol-3-ylamino)-1-methyl-6-oxo-1,6-dihydro-pyridin-3-yl]-phenyl}-3,4-dihydro-2H-isoquinolin-1-one;

6-(1-Chloro-cyclopropyl)-2-[3-(5-{5-[4-(2-hydroxy-ethyl)-piperazin-1-yl]-pyridin-2-ylamino}-1-methyl-6-oxo-1,6-dihydro-pyridin-3-yl)-2-hydroxymethyl-phenyl]-3,4-dihydro-2H-isoquinolin-1-one;

1-[2-(2-Hydroxymethyl-3-{1-methyl-5-[5-(morpholine-4-carbonyl)-pyridin-2-ylamino]-6-oxo-1,6-dihydro-pyridin-3-yl}-phenyl)-1-oxo-1,2,3,4-tetrahydro-isoquinolin-6-yl]-cyclopropanecarbonitrile;

2-(6-{5-[3-(6-Dimethylamino-1-oxo-3,4-dihydro-1H-isoquinolin-2-yl)-2-hydroxymethyl-phenyl]-1-methyl-2-oxo-1,2-dihydro-pyridin-3-ylamino}-pyridin-3-yloxy)-N,N-dimethyl-acetamide;

6-(1-Hydroxy-1-methyl-ethyl)-2-{2-hydroxymethyl-3-[1-methyl-5-(5-morpholin-4-yl-pyridin-2-ylamino)-6-oxo-1,6-dihydro-pyridin-3-yl]-phenyl}-3,4-dihydro-2H-isoquinolin-1-one;

6-Dimethylamino-2-(2-hydroxymethyl-3-{5-[5-(2-hydroxy-propoxymethyl)-pyridin-2-ylamino]-1-methyl-6-oxo-1,6-dihydro-pyridin-3-yl}-phenyl)-3,4-dihydro-2H-isoquinolin-1-one;

(2-{5-[3-(6-Dimethylamino-1-oxo-3,4-dihydro-1H-isoquinolin-2-yl)-2-hydroxymethyl-phenyl]-1-methyl-2-oxo-1,2-dihydro-pyridin-3-ylamino}-pyridin-4-yl)-carbamic acid benzyl ester;

2-{3-[5-(4-Amino-pyridin-2-ylamino)-1-methyl-6-oxo-1,6-dihydro-pyridin-3-yl]-2-hydroxymethyl-phenyl}-6-dimethylamino-3,4-dihydro-2H-isoquinolin-1-one;

N-(2-{5-[3-(6-Dimethylamino-1-oxo-3,4-dihydro-1H-isoquinolin-2-yl)-2-hydroxymethyl-phenyl]-1-methyl-2-oxo-1,2-dihydro-pyridin-3-ylamino}-pyridin-4-yl)-acetamide;

6-Dimethylamino-2-(2-hydroxymethyl-3-{1-methyl-5-[6-(4-methyl-piperazin-1-yl)-pyrimidin-4-ylamino]-6-oxo-1,6-dihydro-pyridin-3-yl}-phenyl)-3,4-dihydro-2H-isoquinolin-1-one;

6-[(2-Hydroxy-ethyl)-methyl-amino]-2-{2-hydroxymethyl-3-[1-methyl-5-(5-morpholin-4-yl-pyridin-2-ylamino)-6-oxo-1,6-dihydro-pyridin-3-yl]-phenyl}-3,4-dihydro-2H-isoquinolin-1-one;

2-(3-{1-Difluoromethyl-5-[5-(morpholine-4-carbonyl)-pyridin-2-ylamino]-6-oxo-1,6-dihydro-pyridin-3-yl}-2-hydroxymethyl-phenyl)-6-dimethylamino-3,4-dihydro-2H-isoquinolin-1-one;

6-Dimethylamino-2-(2-hydroxymethyl-3-{5-[5-(2-methoxy-ethoxy)-pyridin-2-ylamino]-1-methyl-6-oxo-1,6-dihydro-pyridin-3-yl}-phenyl)-3,4-dihydro-2H-isoquinolin-1-one;

2-(3-{5-[5-(3,3-Difluoro-azetidin-1-ylmethyl)-pyridin-2-ylamino]-1-methyl-6-oxo-1,6-dihydro-pyridin-3-yl}-2-hydroxymethyl-phenyl)-6-dimethylamino-3,4-dihydro-2H-isoquinolin-1-one;

6-Dimethylamino-2-(3-{5-[5-(1,1-dioxo-1$\lambda^6$-thiomorpholin-4-ylmethyl)-pyridin-2-ylamino]-1-methyl-6-oxo-1,6-dihydro-pyridin-3-yl}-2-hydroxymethyl-phenyl)-3,4-dihydro-2H-isoquinolin-1-one;

1-(5-{3-[6-(1-Chloro-cyclopropyl)-1-oxo-3,4-dihydro-1H-isoquinolin-2-yl]-2-hydroxymethyl-phenyl}-1-methyl-2-oxo-1,2-dihydro-pyridin-3-yl)-3-ethyl-urea;

6-Dimethylamino-2-{2-hydroxymethyl-3-[1-methyl-6-oxo-5-(5-trifluoromethyl-isoxazol-3-ylamino)-1,6-dihydro-pyridin-3-yl]-phenyl}-3,4-dihydro-2H-isoquinolin-1-one;

1-{5-[3-(6-tert-Butyl-1-oxo-3,4-dihydro-1H-isoquinolin-2-yl)-2-hydroxymethyl-phenyl]-1-methyl-2-oxo-1,2-dihydro-pyridin-3-yl}-3-methyl-urea;

6-Dimethylamino-2-(2-hydroxymethyl-3-{5-[5-(3-hydroxy-3-methyl-azetidin-1-yl)-pyridin-2-ylamino]-1-methyl-6-oxo-1,6-dihydro-pyridin-3-yl}-phenyl)-3,4-dihydro-2H-isoquinolin-1-one;

6-(1-Chloro-cyclopropyl)-2-{2-hydroxymethyl-3-[5-(4-hydroxy-4-methyl-3,4,5,6-tetrahydro-2H-[1,3']bipyridinyl-6'-ylamino)-1-methyl-6-oxo-1,6-dihydro-pyridin-3-yl]-phenyl}-3,4-dihydro-2H-isoquinolin-1-one;

2-(3-{5-[5-(4-Acetyl-piperazin-1-yl)-pyridin-2-ylamino]-1-methyl-6-oxo-1,6-dihydro-pyridin-3-yl}-2-hydroxymethyl-phenyl)-6-(1-chloro-cyclopropyl)-3,4-dihydro-2H-isoquinolin-1-one;

6-(1-Chloro-cyclopropyl)-2-{2-hydroxymethyl-3-[1-methyl-6-oxo-5-(5-piperazin-1-yl-pyridin-2-ylamino)-1,6-dihydro-pyridin-3-yl]-phenyl}-3,4-dihydro-2H-isoquinolin-1-one;

1-{5-[3-(6-tert-Butyl-1-oxo-3,4-dihydro-1H-isoquinolin-2-yl)-2-hydroxymethyl-phenyl]-1-methyl-2-oxo-1,2-dihydro-pyridin-3-yl}-3-ethyl-urea;

6-[Bis-(2-hydroxy-ethyl)-amino]-2-{2-hydroxymethyl-3-[1-methyl-5-(5-morpholin-4-yl-pyridin-2-ylamino)-6-oxo-1,6-dihydro-pyridin-3-yl]-phenyl}-3,4-dihydro-2H-isoquinolin-1-one;

2-(6-Dimethylamino-1-oxo-3,4-dihydro-1H-isoquinolin-2-yl)-6-{1-methyl-5-[5-(morpholine-4-carbonyl)-pyridin-2-ylamino]-6-oxo-1,6-dihydro-pyridin-3-yl}-benzoic acid;

6-Dimethylamino-2-{5-fluoro-2-hydroxymethyl-3-[1-methyl-5-(5-morpholin-4-yl-pyridin-2-ylamino)-6-oxo-1,6-dihydro-pyridin-3-yl]-phenyl}-3,4-dihydro-2H-isoquinolin-1-one;

1-(6-{5-[3-(6-Dimethylamino-1-oxo-3,4-dihydro-1H-isoquinolin-2-yl)-2-hydroxymethyl-phenyl]-1-methyl-2-oxo-1,2-dihydro-pyridin-3-ylamino}-pyridin-3-yl)-pyrrolidine-3-carboxylic acid methyl ester;

1-(6-{5-[3-(6-Dimethylamino-1-oxo-3,4-dihydro-1H-isoquinolin-2-yl)-2-hydroxymethyl-phenyl]-1-methyl-2-oxo-1,2-dihydro-pyridin-3-ylamino}-pyridin-3-yl)-pyrrolidine-3-carboxylic acid;

6-Dimethylamino-2-(2-hydroxymethyl-3-{5-[6-(2-methoxy-1-methyl-ethylamino)-pyridin-2-ylamino]-1-methyl-6-oxo-1,6-dihydro-pyridin-3-yl}-phenyl)-3,4-dihydro-2H-isoquinolin-1-one;

6-Dimethylamino-2-{2-hydroxymethyl-3-[5-(1H-imidazol-2-ylamino)-1-methyl-6-oxo-1,6-dihydro-pyridin-3-yl]-phenyl}-3,4-dihydro-2H-isoquinolin-1-one;

N-{5-[3-(6-Dimethylamino-1-oxo-3,4-dihydro-1H-isoquinolin-2-yl)-2-hydroxymethyl-phenyl]-1-methyl-2-oxo-1,2-dihydro-pyridin-3-yl}-N'-carboxylic acid butyl ester-guanidine N-{5-[3-(6-Dimethylamino-1-oxo-3,4-dihydro-1H-isoquinolin-2-yl)-2-hydroxymethyl-phenyl]-1-methyl-2-oxo-1,2-dihydro-pyridin-3-yl}-guanidine;

2-(2-Aminomethyl-3-{1-methyl-5-[5-(morpholine-4-carbonyl)-pyridin-2-ylamino]-6-oxo-1,6-dihydro-pyridin-3-yl}-phenyl)-6-dimethylamino-3,4-dihydro-2H-isoquinolin-1-one;

6-Dimethylamino-2-(2-dimethylaminomethyl-3-{1-methyl-5-[5-(morpholine-4-carbonyl)-pyridin-2-ylamino]-6-oxo-1,6-dihydro-pyridin-3-yl}-phenyl)-3,4-dihydro-2H-isoquinolin-1-one;

1-(5-{2-Hydroxymethyl-3-[6-(1-hydroxy-1-methyl-ethyl)-1-oxo-3,4-dihydro-1H-isoquinolin-2-yl]-phenyl}-1-methyl-2-oxo-1,2-dihydro-pyridin-3-yl)-3-methyl-urea;

1-(5-{3-[6-(2-Cyano-1,1-dimethyl-ethyl)-1-oxo-3,4-dihydro-1H-isoquinolin-2-yl]-2-hydroxymethyl-phenyl}-1-methyl-2-oxo-1,2-dihydro-pyridin-3-yl)-3-methyl-urea;

2-[2-Hydroxymethyl-3-(5-{5-[4-(2-methoxy-ethyl)-piperazin-1-yl]-pyridin-2-ylamino}-1-methyl-6-oxo-1,6-dihydro-pyridin-3-yl)-phenyl]-6-(1-methyl-cyclopropyl)-3,4-dihydro-2H-isoquinolin-1-one;

6-Dimethylamino-2-(2-hydroxymethyl-3-{5-[6-((R)-3-hydroxy-pyrrolidin-1-yl)-pyridin-2-ylamino]-1-methyl-6-oxo-1,6-dihydro-pyridin-3-yl}-phenyl)-3,4-dihydro-2H-isoquinolin-1-one;

6-Dimethylamino-2-{3-[5-(5-ethyl-isoxazol-3-ylamino)-1-methyl-6-oxo-1,6-dihydro-pyridin-3-yl]-2-hydroxymethyl-phenyl}-3,4-dihydro-2H-isoquinolin-1-one;

6-Cyclopropyl-2-{2-hydroxymethyl-3-[1-methyl-5-(5-morpholin-4-yl-pyridin-2-ylamino)-6-oxo-1,6-dihydro-pyridin-3-yl]-phenyl}-3,4-dihydro-2H-isoquinolin-1-one;

6-Azetidin-1-yl-2-(2-hydroxymethyl-3-{1-methyl-5-[5-(morpholine-4-carbonyl)-pyridin-2-ylamino]-6-oxo-1,6-dihydro-pyridin-3-yl}-phenyl)-3,4-dihydro-2H-isoquinolin-1-one;

1-{5-[3-(6-Dimethylamino-1-oxo-3,4-dihydro-1H-isoquinolin-2-yl)-4-fluoro-2-hydroxymethyl-phenyl]-1-methyl-2-oxo-1,2-dihydro-pyridin-3-yl}-3-methyl-urea;

6-tert-Butyl-2-{2-hydroxymethyl-3-[1-methyl-6-oxo-5-(5-piperazin-1-yl-pyridin-2-ylamino)-1,6-dihydro-pyridin-3-yl]-phenyl}-3,4-dihydro-2H-isoquinolin-1-one;

2-Cyano-N-{5-[3-(6-dimethylamino-1-oxo-3,4-dihydro-1H-isoquinolin-2-yl)-2-hydroxymethyl-phenyl]-1-methyl-2-oxo-1,2-dihydro-pyridin-3-yl}-acetamide;

6-[2-(2-Hydroxy-ethoxy)-1,1-dimethyl-ethyl]-2-{2-hydroxymethyl-3-[1-methyl-5-(5-morpholin-4-yl-pyridin-2-ylamino)-6-oxo-1,6-dihydro-pyridin-3-yl]-phenyl}-3,4-dihydro-2H-isoquinolin-1-one;

6-(1-Chloro-cyclopropyl)-2-(2-hydroxymethyl-3-{1-methyl-5-[5-(4-methyl-piperazin-1-yl)-pyridin-2-ylamino]-6-oxo-1,6-dihydro-pyridin-3-yl}-phenyl)-3,4-dihydro-2H-isoquinolin-1-one 6-(1-Hydroxy-1-methyl-ethyl)-2-(2-hydroxymethyl-3-{1-methyl-5-[5-(4-methyl-piperazin-1-yl)-pyridin-2-ylamino]-6-oxo-1,6-dihydro-pyridin-3-yl}-phenyl)-3,4-dihydro-2H-isoquinolin-1-one;

6-(2-Hydroxy-1,1-dimethyl-ethyl)-2-(2-hydroxymethyl-3-{1-methyl-5-[5-(morpholine-4-carbonyl)-pyridin-2-ylamino]-6-oxo-1,6-dihydro-pyridin-3-yl}-phenyl)-3,4-dihydro-2H-isoquinolin-1-one;

2-[2-(2-Hydroxymethyl-3-{1-methyl-5-[5-(4-methyl-piperazin-1-yl)-pyridin-2-ylamino]-6-oxo-1,6-dihydro-pyridin-3-yl}-phenyl)-1-oxo-1,2,3,4-tetrahydro-isoquinolin-6-yl]-2-methyl-propionitrile N-{5-[3-(6-Dimethylamino-1-oxo-3,4-dihydro-1H-isoquinolin-2-yl)-2-hydroxymethyl-phenyl]-1-methyl-2-oxo-1,2-dihydro-pyridin-3-yl}-3-oxo-butyramide;

6-Dimethylamino-2-[2-hydroxymethyl-3-(5-{5-[(2-methoxy-ethylamino)-methyl]-pyridin-2-ylamino}-1-methyl-6-oxo-1,6-dihydro-pyridin-3-yl)-phenyl]-3,4-dihydro-2H-isoquinolin-1-one;

6-Dimethylamino-2-{3-[5-(5-ethyl-4-oxo-4,5-dihydro-1H-imidazol-2-ylamino)-1-methyl-6-oxo-1,6-dihydro-pyridin-3-yl]-2-hydroxymethyl-phenyl}-3,4-dihydro-2H-isoquinolin-1-one;

1-{5-[3-(6-tert-Butyl-1-oxo-3,4-dihydro-1H-isoquinolin-2-yl)-2-hydroxymethyl-phenyl]-1-methyl-2-oxo-1,2-dihydro-pyridin-3-yl}-3-(3-dimethylamino-propyl)-urea;

6-Dimethylamino-2-{3-[5-(5-ethyl-1H-imidazol-2-ylamino)-1-methyl-6-oxo-1,6-dihydro-pyridin-3-yl]-2-hydroxymethyl-phenyl}-3,4-dihydro-2H-isoquinolin-1-one;

6-Cyclopropyl-2-(2-hydroxymethyl-3-{1-methyl-5-[5-(morpholine-4-carbonyl)-pyridin-2-ylamino]-6-oxo-1,6-dihydro-pyridazin-3-yl}-phenyl)-3,4-dihydro-2H-isoquinolin-1-one; and 6-Cyclopropyl-2-{2-hydroxymethyl-3-[1-methyl-5-(1-methyl-1H-pyrazol-3-ylamino)-6-oxo-1,6-dihydro-pyridazin-3-yl]-phenyl}-3,4-dihydro-2H-isoquinolin-1-one.

The application provides a compound of Formula II,

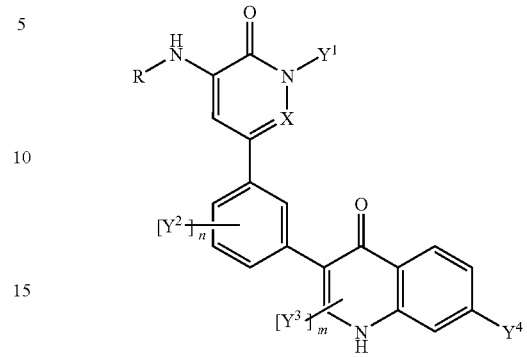

II wherein:

R is H, -R$^1$, -R$^1$-R$^2$-R$^3$, or -R$^2$-R$^3$;

R$^1$ is aryl, heteroaryl, cycloalkyl, or heterocycloalkyl, and is optionally substituted with lower alkyl, hydroxy, lower alkoxy, halo, nitro, amino, cyano, or halo-lower alkyl;

R$^2$ is —C(=O), —C(=O)O, —C(=O)NH, or —S(=O)$_2$;

R$^3$ is H or R$^4$;

R$^4$ is lower alkyl, aryl, arylalkyl, alkylaryl, heteroaryl, alkyl heteroaryl, heteroaryl alkyl, cycloalkyl, alkyl cycloalkyl, cycloalkyl alkyl, heterocycloalkyl, alkyl heterocycloalkyl, or heterocycloalkyl alkyl, and is optionally substituted with lower alkyl, hydroxy, lower alkoxy, halo, nitro, amino, cyano, or halo-lower alkyl;

X is CH or N;

Y$^1$ is H or lower alkyl;

each Y$^2$ is independently halogen or lower alkyl, wherein lower alkyl is optionally substituted with one or more substituents selected from the group consisting of hydroxy, lower alkoxy, and halogen;

n is 0, 1, 2, or 3.

Y$^3$ is H, halogen, or lower alkyl, wherein lower alkyl is optionally substituted with one or more substituents selected from the group consisting of hydroxy, lower alkoxy, amino, and halogen;

m is 0 or 1;

Y$^4$ is Y$^{4a}$, Y$^{4b}$, Y$^{4c}$, or Y$^{4d}$;

Y$^{4a}$ is H or halogen;

Y$^{4b}$ is lower alkyl, optionally substituted with one or more substituents selected from the group consisting of lower haloalkyl, halogen, hydroxy, amino, and lower alkoxy;

Y$^{4c}$ is lower cycloalkyl, optionally substituted with one or more substituents selected from the group consisting of lower alkyl, lower haloalkyl, halogen, hydroxy, amino, and lower alkoxy; and Y$^{4d}$ is amino, optionally substituted with one or more lower alkyl;

or a pharmaceutically acceptable salt thereof.

The application also provides a compound of Formula II,

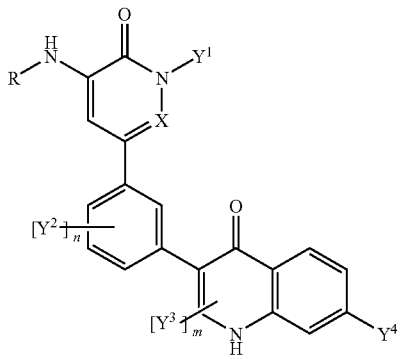

wherein:

R is H, -R¹, -R¹-R²-R³, -R¹-R³, or -R²-R³;
  R¹ is aryl, heteroaryl, cycloalkyl, or heterocycloalkyl, and is optionally substituted with one or more lower alkyl, hydroxy, hydroxy lower alkyl, lower alkoxy, halo, nitro, amino, amido, cyano, oxo, or halo-lower alkyl;
  R² is —C(=O), —C(=O)O, —C(=O)NR²', or —S(=O)₂;
  R²' is H or lower alkyl;
  R³ is H or R⁴;
  R⁴ is lower alkyl, amino, aryl, arylalkyl, alkylaryl, heteroaryl, alkyl heteroaryl, heteroaryl alkyl, cycloalkyl, alkyl cycloalkyl, cycloalkyl alkyl, heterocycloalkyl, alkyl heterocycloalkyl, or heterocycloalkyl alkyl, and is optionally substituted with one or more lower alkyl, hydroxy, hydroxy lower alkyl, lower alkoxy, halo, nitro, amino, cyano, or halo-lower alkyl;

X is CH or N;

Y¹ is H, lower alkyl, or lower haloalkyl;

each Y² is independently halogen or lower alkyl, wherein lower alkyl is optionally substituted with one or more substituents selected from the group consisting of hydroxy, lower alkoxy, lower haloalkoxy, lower haloalkyl, carboxy, amino, and halogen;

n is 0, 1, 2, or 3.

Y³ is H, halogen, or lower alkyl, wherein lower alkyl is optionally substituted with one or more substituents selected from the group consisting of hydroxy, lower alkoxy, amino, and halogen;

m is 0 or 1;

Y⁴ is Y⁴ᵃ, Y⁴ᵇ, Y⁴ᶜ or Y⁴ᵈ;
  Y⁴ᵃ is H or halogen;
  Y⁴ᵇ is lower alkyl, optionally substituted with one or more substituents selected from the group consisting of lower haloalkyl, halogen, hydroxy, amino, cyano, and lower alkoxy;
  Y⁴ᶜ is lower cycloalkyl, optionally substituted with one or more substituents selected from the group consisting of lower alkyl, lower haloalkyl, halogen, hydroxy, amino, cyano, and lower alkoxy; and
  Y⁴ᵈ is amino, optionally susbstituted with one or more lower alkyl, alkoxy lower alkyl, or hydroxy lower alkyl;

or a pharmaceutically acceptable salt thereof.

In one variation of Formula II, Y¹ is methyl.
In one variation of Formula II, X is CH.
In one variation of the above compound, n is 1 and m is 0.
In one variation of Formula II, Y³ is H.
In one variation of Formula II, Y² is methyl.
In one variation of Formula II, Y² is hydroxymethyl.
In one variation of Formula II, Y² is hydroxyethyl.
In one variation of Formula II, Y² is halogen.
In one variation of Formula II, Y⁴ is

wherein, Y⁵ is halogen, lower alkyl, or lower haloalkyl.
In one variation of Formula II, Y⁴ is

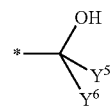

wherein, Y⁵ and Y⁶ are independently H, lower alkyl, or lower haloalkyl.
In one variation of Formula II, Y⁴ is

wherein, Y⁵ and Y⁶ are independently H or lower alkyl.
In one variation of Formula II, Y⁴ is

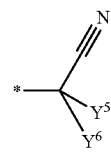

wherein, Y⁵ and Y⁶ are independently H, lower alkyl, or lower alkyl.
In one variation of Formula II, R is -R¹-R²-R³;

R¹ is phenyl or pyridyl;

R² is —C(=O);

R³ is R⁴; and

R⁴ is morpholine or piperazine, optionally substituted with one or more lower alkyl.
In one variation of Formula II, R is -R¹-R²-R³;

R¹ is phenyl or pyridyl;

R² is —C(=O);

R³ is R⁴; and

R⁴ is morpholine or piperazine, optionally substituted with one or more lower alkyl.

In one variation of Formula II,

R is -R¹-R²-R³;

R¹ is phenyl or pyridyl;

R² is —C(=O);

R³ is R⁴; and

R⁴ is morpholine or piperazine, optionally substituted with one or more lower alkyl.

In one variation of Formula II,

R is -R¹-R²-R³;

R¹ is phenyl or pyridyl;

R² is —C(=O);

R³ is R⁴; and

R⁴ is morpholine or piperazine, optionally substituted with one or more lower alkyl.

In one variation, Formula II is:

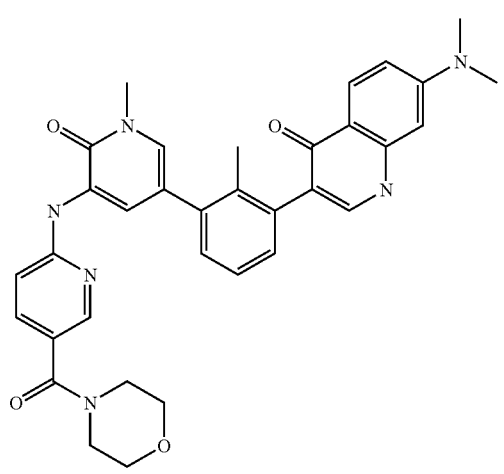

In one variation, Formula II is:

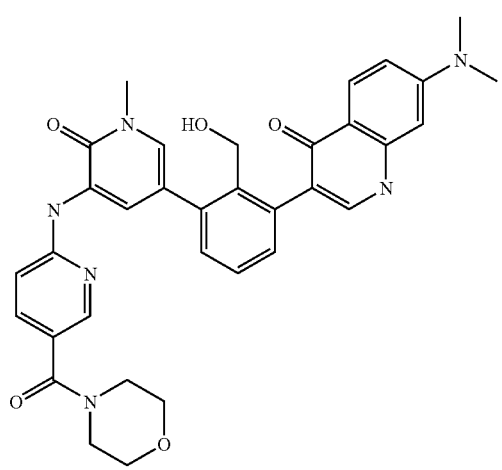

In one variation, Formula II is:

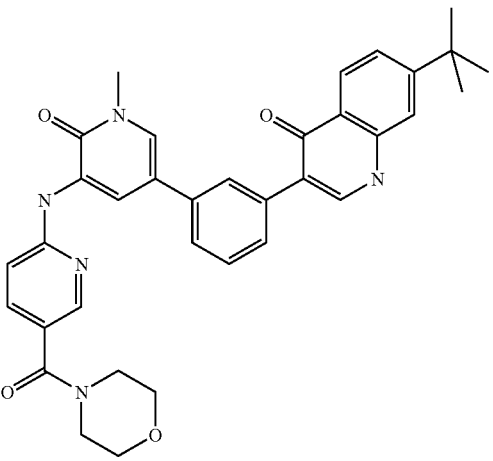

The application also provides a compound of Formula II, wherein Formula II is selected from the group consisting of:
7-tert-Butyl-3-(3-{1-methyl-5-[5-(morpholine-4-carbonyl)-pyridin-2-ylamino]-6-oxo-1,6-dihydro-pyridin-3-yl}-phenyl)-1H-quinolin-4-one; and
7-Dimethylamino-3-(2-methyl-3-{1-methyl-5-[5-(morpholine-4-carbonyl)-pyridin-2-ylamino]-6-oxo-1,6-dihydro-pyridin-3-yl}-phenyl)-1H-quinolin-4-one.

The application provides a compound of Formula III,

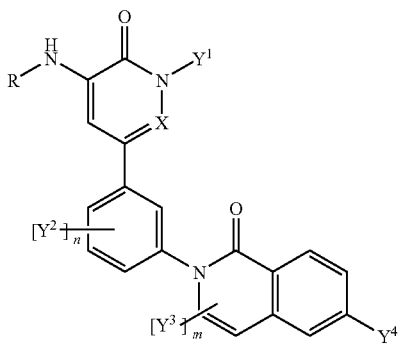

III wherein:

R is H, -R¹, -R¹-R²-R³, or -R²-R³;
  R¹ is aryl, heteroaryl, cycloalkyl, or heterocycloalkyl, and is optionally substituted with lower alkyl, hydroxy, lower alkoxy, halo, nitro, amino, cyano, or halo-lower alkyl;
  R² is —C(=O), —C(=O)O, —C(=O)NH, or —S(=O)₂;
  R³ is H or R⁴;
  R⁴ is lower alkyl, aryl, arylalkyl, alkylaryl, heteroaryl, alkyl heteroaryl, heteroaryl alkyl, cycloalkyl, alkyl cycloalkyl, cycloalkyl alkyl, heterocycloalkyl, alkyl heterocycloalkyl, or heterocycloalkyl alkyl, and is optionally substituted with lower alkyl, hydroxy, lower alkoxy, halo, nitro, amino, cyano, or halo-lower alkyl;

X is CH or N;

Y¹ is H or lower alkyl;

each $Y^2$ is independently halogen or lower alkyl, wherein lower alkyl is optionally substituted with one or more substituents selected from the group consisting of hydroxy, lower alkoxy, and halogen;

n is 0, 1, 2, or 3.

$Y^3$ is H, halogen, or lower alkyl, wherein lower alkyl is optionally substituted with one or more substituents selected from the group consisting of hydroxy, lower alkoxy, amino, and halogen;

m is 0 or 1;

$Y^4$ is $Y^{4a}$, $Y^{4b}$, $Y^{4c}$, or $Y^{4d}$;
 $Y^{4a}$ is H or halogen;
 $Y^{4b}$ is lower alkyl, optionally substituted with one or more substituents selected from the group consisting of lower haloalkyl, halogen, hydroxy, amino, and lower alkoxy;
 $Y^{4c}$ is lower cycloalkyl, optionally substituted with one or more substituents selected from the group consisting of lower alkyl, lower haloalkyl, halogen, hydroxy, amino, and lower alkoxy; and $Y^{4d}$ is amino, optionally substituted with one or more lower alkyl;

or a pharmaceutically acceptable salt thereof.

The application also provides a compound of Formula III,

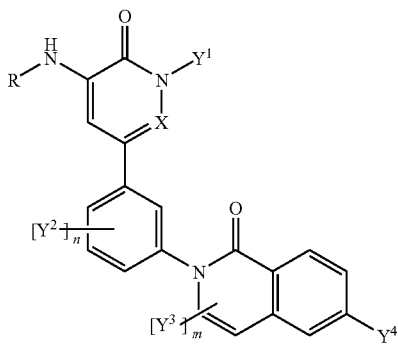

III wherein:

R is H, $-R^1$, $-R^1-R^2-R^3$, $-R^1-R^3$, or $-R^2-R^3$;
 $R^1$ is aryl, heteroaryl, cycloalkyl, or heterocycloalkyl, and is optionally substituted with one or more lower alkyl, hydroxy, hydroxy lower alkyl, lower alkoxy, halo, nitro, amino, amido, cyano, oxo, or halo-lower alkyl;
 $R^2$ is $-C(=O)$, $-O$, $-C(=O)O$, $-C(=O)NR^{2'}$, or $-S(=O)_2$;
 $R^{2'}$ is H or lower alkyl;
 $R^3$ is H or $R^4$;
 $R^4$ is lower alkyl, amino, aryl, arylalkyl, alkylaryl, heteroaryl, alkyl heteroaryl, heteroaryl alkyl, cycloalkyl, alkyl cycloalkyl, cycloalkyl alkyl, heterocycloalkyl, alkyl heterocycloalkyl, or heterocycloalkyl alkyl, and is optionally substituted with one or more lower alkyl, hydroxy, hydroxy lower alkyl, lower alkoxy, halo, nitro, amino, amido, acyl, cyano, or halo-lower alkyl;

X is CH or N;

$Y^1$ is H, lower alkyl, or lower haloalkyl;

each $Y^2$ is independently halogen or lower alkyl, wherein lower alkyl is optionally substituted with one or more substituents selected from the group consisting of hydroxy, lower alkoxy, lower haloalkoxy, lower haloalkyl, carboxy, amino, and halogen;

n is 0, 1, 2, or 3.

$Y^3$ is H, halogen, or lower alkyl, wherein lower alkyl is optionally substituted with one or more substituents selected from the group consisting of hydroxy, lower alkoxy, amino, and halogen;

m is 0 or 1;

$Y^4$ is $Y^{4a}$, $Y^{4b}$, $Y^{4c}$, or $Y^{4d}$;
 $Y^{4a}$ is H or halogen;
 $Y^{4b}$ is lower alkyl, optionally substituted with one or more substituents selected from the group consisting of haloalkyl, halogen, hydroxy, amino, cyano, and lower alkoxy;
 $Y^{4c}$ is lower cycloalkyl, optionally substituted with one or more substituents selected from the group consisting of lower alkyl, lower haloalkyl, halogen, hydroxy, hydroxy lower alkyl, amino, cyano, and lower alkoxy; and
 $Y^{4d}$ is amino, optionally substituted with one or more lower alkyl, alkoxy lower alkyl, or hydroxy lower alkyl;

or a pharmaceutically acceptable salt thereof.

In one variation of Formula III, $Y^1$ is methyl.
In one variation of Formula III, X is CH.
In one variation of Formula III, n is 1 and m is 0.
In one variation of Formula III, $Y^3$ is H.
In one variation of Formula III, $Y^2$ is methyl.
In one variation of Formula III, $Y^2$ is hydroxymethyl.
In one variation of Formula III, $Y^2$ is hydroxyethyl.
In one variation of Formula III, $Y^2$ is halogen.
In one variation of Formula III, $Y^4$ is

wherein, $Y^5$ is halogen, lower alkyl, or lower haloalkyl.
In one variation of Formula III, $Y^4$ is

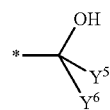

wherein, $Y^5$ and $Y^6$ are independently H, lower alkyl, or lower haloalkyl.
In one variation of Formula III, $Y^4$ is

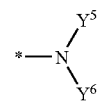

wherein, $Y^5$ and $Y^6$ are independently H or lower alkyl.

In one variation of Formula III, $Y^4$ is

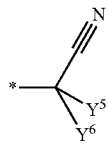

wherein, $Y^5$ and $Y^6$ are independently H, lower alkyl, or lower haloalkyl.

In one variation of Formula III,

R is $-R^1-R^2-R^3$;

$R^1$ is phenyl or pyridyl;

$R^2$ is $-C(=O)$;

$R^3$ is $R^4$; and $R^4$ is morpholine or piperazine, optionally substituted with one or more lower alkyl.

In one variation of Formula III,

R is $-R^1-R^2-R^3$;

$R^1$ is phenyl or pyridyl;

$R^2$ is $-C(=O)$;

$R^3$ is $R^4$; and $R^4$ is morpholine or piperazine, optionally substituted with one or more lower alkyl.

In one variation of Formula III,

R is $-R^1-R^2-R^3$;

$R^1$ is phenyl or pyridyl;

$R^2$ is $-C(=O)$;

$R^3$ is $R^4$; and $R^4$ is morpholine or piperazine, optionally substituted with one or more lower alkyl.

In one variation of Formula III,

R is $-R^1-R^2-R^3$;

$R^1$ is phenyl or pyridyl;

$R^2$ is $-C(=O)$;

$R^3$ is $R^4$; and $R^4$ is morpholine or piperazine, optionally substituted with one or more lower alkyl In one variation, Formula III is:

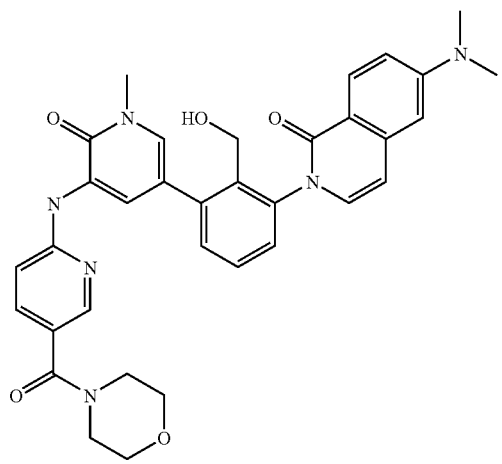

In one variation, Formula III is:

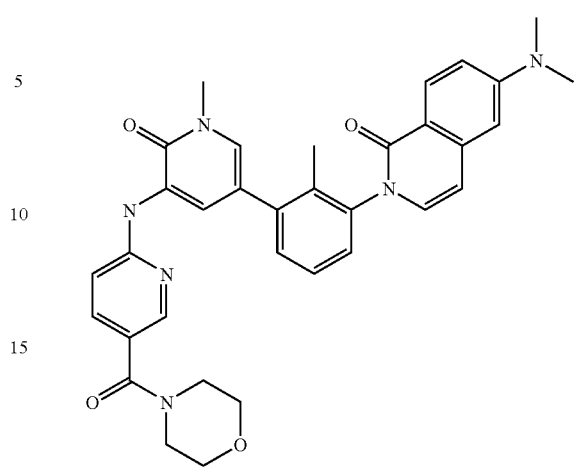

In one variation, Formula III is:

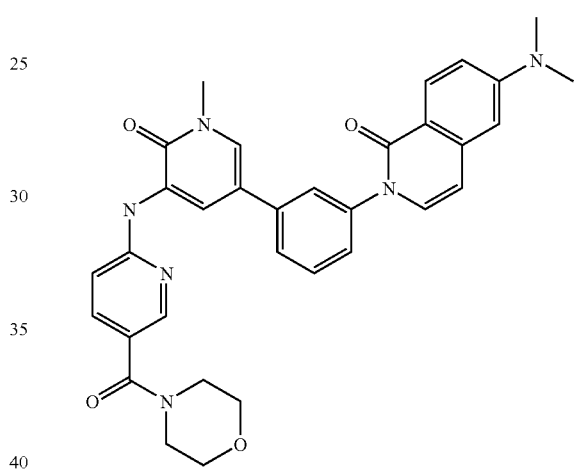

The application also provides a compound of Formula III, wherein Formula III is selected from the group consisting of:

6-Dimethylamino-2-(3-{1-methyl-5-[5-(morpholine-4-carbonyl)-pyridin-2-ylamino]-6-oxo-1,6-dihydro-pyridin-3-yl}-phenyl)-2H-isoquinolin-1-one;

6-Dimethylamino-2-(2-methyl-3-{1-methyl-5-[5-(morpholine-4-carbonyl)-pyridin-2-ylamino]-6-oxo-1,6-dihydro-pyridin-3-yl}-phenyl)-2H-isoquinolin-1-one;

6-Dimethylamino-2-(2-hydroxymethyl-3-{1-methyl-5-[5-(morpholine-4-carbonyl)-pyridin-2-ylamino]-6-oxo-1,6-dihydro-pyridin-3-yl}-phenyl)-2H-isoquinolin-1-one;

6-Dimethylamino-2-{2-hydroxymethyl-3-[1-methyl-5-(1-methyl-1H-pyrazol-3-ylamino)-6-oxo-1,6-dihydro-pyridin-3-yl]-phenyl}-2H-isoquinolin-1-one;

1-{5-[3-(6-Dimethylamino-1-oxo-1H-isoquinolin-2-yl)-2-hydroxymethyl-phenyl]-1-methyl-2-oxo-1,2-dihydro-pyridin-3-yl}-3-ethyl-urea;

2-(2-Hydroxymethyl-3-{1-methyl-5-[5-(morpholine-4-carbonyl)-pyridin-2-ylamino]-6-oxo-1,6-dihydro-pyridin-3-yl}-phenyl)-6-(1-methyl-cyclopropyl)-2H-isoquinolin-1-one;

2-{2-Hydroxymethyl-3-[1-methyl-5-(5-morpholin-4-ylmethyl-pyridin-2-ylamino)-6-oxo-1,6-dihydro-pyridin-3-yl]-phenyl}-6-(1-methyl-cyclopropyl)-2H-isoquinolin-1-one;

2-(2-Hydroxymethyl-3-{1-methyl-5-[5-(4-methyl-piperazine-1-carbonyl)-pyridin-2-ylamino]-6-oxo-1,6-dihydro-pyridin-3-yl}-phenyl)-6-(1-methyl-cyclopropyl)-2H-isoquinolin-1-one;

6-Cyclopropyl-2-{2-hydroxymethyl-3-[1-methyl-5-(5-morpholin-4-ylmethyl-pyridin-2-ylamino)-6-oxo-1,6-dihydro-pyridin-3-yl]-phenyl}-2H-isoquinolin-1-one;

6-Cyclopropyl-2-(2-hydroxymethyl-3-{1-methyl-5-[5-(4-methyl-piperazine-1-carbonyl)-pyridin-2-ylamino]-6-oxo-1,6-dihydro-pyridin-3-yl}-phenyl)-2H-isoquinolin-1-one;

6-Cyclopropyl-2-(2-hydroxymethyl-3-{1-methyl-5-[5-(morpholine-4-carbonyl)-pyridin-2-ylamino]-6-oxo-1,6-dihydro-pyridin-3-yl}-phenyl)-2H-isoquinolin-1-one;

6-Cyclopropyl-2-{2-hydroxymethyl-3-[1-methyl-5-(5-morpholin-4-yl-pyridin-2-ylamino)-6-oxo-1,6-dihydro-pyridin-3-yl]-phenyl}-2H-isoquinolin-1-one;

6-Cyclopropyl-2-(2-hydroxymethyl-3-{1-methyl-5-[5-(morpholine-4-carbonyl)-pyridin-2-ylamino]-6-oxo-1,6-dihydro-pyridin-3-yl}-phenyl)-3-methyl-2H-isoquinolin-1-one;

2-{2-Hydroxymethyl-3-[1-methyl-5-(5-morpholin-4-yl-pyridin-2-ylamino)-6-oxo-1,6-dihydro-pyridin-3-yl]-phenyl}-6-(1-methyl-cyclopropyl)-2H-isoquinolin-1-one;

6-Dimethylamino-2-{2-hydroxymethyl-3-[1-methyl-5-(5-morpholin-4-yl-pyridin-2-ylamino)-6-oxo-1,6-dihydro-pyridin-3-yl]-phenyl}-2H-isoquinolin-1-one;

6-tert-Butyl-2-(2-hydroxymethyl-3-{1-methyl-5-[5-(morpholine-4-carbonyl)-pyridin-2-ylamino]-6-oxo-1,6-dihydro-pyridin-3-yl}-phenyl)-2H-isoquinolin-1-one;

6-Cyclopropyl-3-hydroxymethyl-2-(2-hydroxymethyl-3-{1-methyl-5-[5-(morpholine-4-carbonyl)-pyridin-2-ylamino]-6-oxo-1,6-dihydro-pyridin-3-yl}-phenyl)-2H-isoquinolin-1-one;

6-Cyclopropyl-3-hydroxymethyl-2-{2-hydroxymethyl-3-[1-methyl-5-(5-morpholin-4-yl-pyridin-2-ylamino)-6-oxo-1,6-dihydro-pyridin-3-yl]-phenyl}-2H-isoquinolin-1-one;

6-Cyclopropyl-3-dimethylaminomethyl-2-{2-hydroxymethyl-3-[1-methyl-5-(5-morpholin-4-yl-pyridin-2-ylamino)-6-oxo-1,6-dihydro-pyridin-3-yl]-phenyl}-2H-isoquinolin-1-one;

3-tert-Butoxymethyl-6-cyclopropyl-2-{3-[5-(6-fluoro-pyridin-2-ylamino)-1-methyl-6-oxo-1,6-dihydro-pyridin-3-yl]-2-hydroxymethyl-phenyl}-2H-isoquinolin-1-one;

6-Dimethylamino-2-{2-hydroxymethyl-3-[1-methyl-5-(6-methylamino-pyridin-2-ylamino)-6-oxo-1,6-dihydro-pyridin-3-yl]-phenyl}-2H-isoquinolin-1-one;

6-Dimethylamino-2-(2-hydroxymethyl-3-{1-methyl-5-[6-(4-methyl-piperazin-1-yl)-pyridin-2-ylamino]-6-oxo-1,6-dihydro-pyridin-3-yl}-phenyl)-2H-isoquinolin-1-one;

2-{3-[5-(6-Amino-pyridin-2-ylamino)-1-methyl-6-oxo-1,6-dihydro-pyridin-3-yl]-2-hydroxymethyl-phenyl}-6-dimethylamino-2H-isoquinolin-1-one;

2-(6-{5-[3-(6-Dimethylamino-1-oxo-1H-isoquinolin-2-yl)-2-hydroxymethyl-phenyl]-1-methyl-2-oxo-1,2-dihydro-pyridin-3-ylamino}-pyridin-3-yloxy)-N-methyl-acetamide;

2-{3-[5-(5,6-Dimethoxy-pyridin-2-ylamino)-1-methyl-6-oxo-1,6-dihydro-pyridin-3-yl]-2-hydroxymethyl-phenyl}-6-dimethylamino-2H-isoquinolin-1-one;

6-Dimethylamino-2-(2-hydroxymethyl-3-{5-[5-methoxy-6-(2-methoxy-ethoxy)-pyridin-2-ylamino]-1-methyl-6-oxo-1,6-dihydro-pyridin-3-yl}-phenyl)-2H-isoquinolin-1-one;

6-Dimethylamino-2-(2-hydroxymethyl-3-{5-[6-methoxy-5-(2-methoxy-ethoxy)-pyridin-2-ylamino]-1-methyl-6-oxo-1,6-dihydro-pyridin-3-yl}-phenyl)-2H-isoquinolin-1-one;

2-(3-{5-[5,6-Bis-(2-methoxy-ethoxy)-pyridin-2-ylamino]-1-methyl-6-oxo-1,6-dihydro-pyridin-3-yl}-2-hydroxymethyl-phenyl)-6-dimethylamino-2H-isoquinolin-1-one;

6-Dimethylamino-2-{2-hydroxymethyl-3-[1-methyl-5-(2-morpholin-4-yl-pyrimidin-4-ylamino)-6-oxo-1,6-dihydro-pyridin-3-yl]-phenyl}-2H-isoquinolin-1-one;

6-Dimethylamino-2-(2-hydroxymethyl-3-{1-methyl-5-[2-(4-methyl-piperazin-1-yl)-pyrimidin-4-ylamino]-6-oxo-1,6-dihydro-pyridin-3-yl}-phenyl)-2H-isoquinolin-1-one;

2-[4-(6-{5-[3-(6-Dimethylamino-1-oxo-1H-isoquinolin-2-yl)-2-hydroxymethyl-phenyl]-1-methyl-2-oxo-1,2-dihydro-pyridin-3-ylamino}-pyridin-3-yl)-piperazin-1-yl]-isobutyramide;

2-(3-{5-[6-(4-Acetyl-piperazin-1-yl)-pyridin-2-ylamino]-1-methyl-6-oxo-1,6-dihydro-pyridin-3-yl}-2-hydroxymethyl-phenyl)-6-dimethylamino-2H-isoquinolin-1-one;

6-Dimethylamino-2-{3-[5-(5-ethyl-1H-pyrazol-3-ylamino)-1-methyl-6-oxo-1,6-dihydro-pyridin-3-yl]-2-hydroxymethyl-phenyl}-2H-isoquinolin-1-one;

6-Dimethylamino-2-(3-{5-[5-(2-hydroxy-ethoxy)-6-(2-methoxy-ethoxy)-pyridin-2-ylamino]-1-methyl-6-oxo-1,6-dihydro-pyridin-3-yl}-2-hydroxymethyl-phenyl)-2H-isoquinolin-1-one;

6-Cyclopropyl-2-(2-hydroxymethyl-3-{1-methyl-5-[5-(morpholine-4-carbonyl)-pyridin-2-ylamino]-6-oxo-1,6-dihydro-pyridazin-3-yl}-phenyl)-2H-isoquinolin-1-one; and 2-(2-Hydroxymethyl-3-{1-methyl-5-[5-(morpholine-4-carbonyl)-pyridin-2-ylamino]-6-oxo-1,6-dihydro-pyridazin-3-yl}-phenyl)-6-(1-methyl-cyclopropyl)-2H-isoquinolin-1-one.

The application provides a method for treating an inflammatory and/or autoimmune condition comprising administering to a patient in need thereof a therapeutically effective amount of the Btk inhibitor compound of any one of the above Formulae or variations thereof.

The application provides a method for treating an arthritis comprising administering to a patient in need thereof a therapeutically effective amount of the Btk inhibitor compound of any one of the above Formulae or variations thereof.

The application provides a method of inhibiting B-cell proliferation comprising administering to a patient in need thereof a therapeutically effective amount of the Btk inhibitor compound of any one of the above Formulae or variations thereof.

The application provides a method for inhibiting Btk activity comprising administering the Btk inhibitor compound of any one of the above Formulae or variations thereof, wherein the Btk inhibitor compound exhibits an $IC_{50}$ of 50 micromolar or less in an in vitro biochemical assay of Btk activity.

In one variation of the above method, the Btk inhibitor compound exhibits an $IC_{50}$ of 100 nanomolar or less in an in vitro biochemical assay of Btk activity.

In one variation of the above method, the compound exhibits an $IC_{50}$ of 10 nanomolar or less in an in vitro biochemical assay of Btk activity.

The application provides a method for treating an inflammatory condition comprising co-administering to a patient in need thereof a therapeutically effective amount of an anti-inflammatory compound in combination with the Btk inhibitor compound of any one of the above Formulae or variations thereof.

The application provides a method for treating arthritis comprising co-administering to a patient in need thereof a therapeutically effective amount of an anti-inflammatory compound in combination with the Btk inhibitor compound of any one of the above Formulae or variations thereof.

The application provides a method for treating a lymphoma or a BCR-ABL1+ leukemia cells by administering to a patient in need thereof a therapeutically effective amount of the Btk inhibitor compound of any one of the above Formulae or variations thereof.

The application provides a pharmaceutical composition comprising the Btk inhibitor compound of any one of the above Formulae or variations thereof, admixed with at least one pharmaceutically acceptable carrier, excipient or diluent.

DETAILED DESCRIPTION OF THE INVENTION

The present application provides compounds of generic Formulae I-III, wherein variables R, X, $Y^1$, $Y^2$, $Y^3$, $Y^4$, n, and m are as defined herein above.

In one embodiment of the present invention, there is provided a compound according to generic Formula I which comprises the exemplified Btk inhibitor compounds of Formulae I-1 to I-155. In one embodiment of the present invention, there is provided a compound according to generic Formula II which comprises the exemplified Btk inhibitor compounds of Formulae II-1 and II-2. In one embodiment of the present invention, there is provided a compound according to generic Formula III which comprises the exemplified Btk inhibitor compounds of Formulae III-1 to III-36.

The present application discloses 5-phenyl-1H-pyridin-2-one and 6-phenyl-2H-pyridazin-3-one derivatives according to generic Formulae I-III:

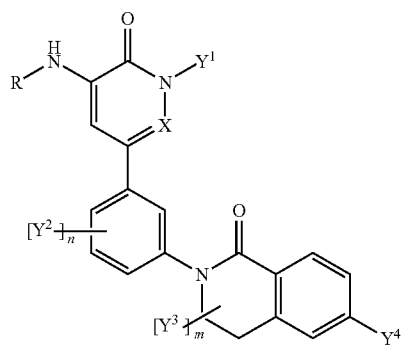

I

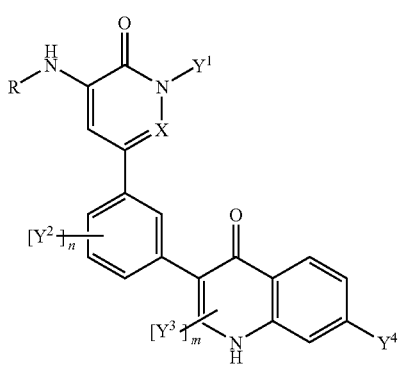

II

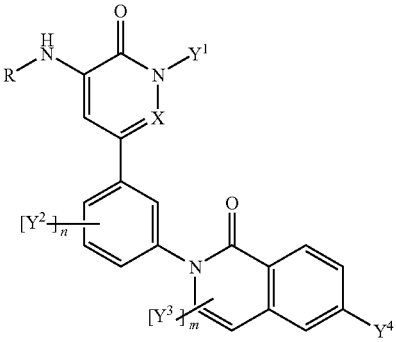

III

The phrase "as defined herein above" refers to the broadest definition for each group as provided in the Summary of the Invention or the broadest claim. In all other aspects, variations and embodiments provided, substituents which can be present in each embodiment and which are not explicitly defined retain the broadest definition provided in the Summary of the Invention.

The compounds of generic Formulae I-III inhibit Bruton's tyrosine kinase (Btk). Activation of Btk by upstream kinases results in activation of phospholipase-Cγ which, in turn, stimulates release of pro-inflammatory mediators. The compounds of generic Formulae I-III, incorporating side chains of 1H-quinolin-4-one, 3,4-dihydro-2H-isoquinolin-1-one, and 2H-isoquinolin-1-one on the 5-phenyl-1H-pyridin-2-one and 6-phenyl-2H-pyridazin-3-one ring systems, exhibit unexpectedly enhanced inhibitory activity compared to analogues with other side chains. Compounds of Formulae I-III are useful in the treatment of arthritis and other anti-inflammatory and auto-immune diseases. Compounds according to Formulae I-III are, accordingly, useful for the treatment of arthritis. Compounds of Formulae I-III are useful for inhibiting Btk in cells and for modulating B-cell development. The present invention further comprises pharmaceutical compositions containing compounds of Formulae I-III admixed with pharmaceutically acceptable carrier, excipients or diluents.

DEFINITIONS

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein above" refers to the broadest definition for each group as provided in the Summary of the Invention or the broadest claim. In all other embodiments provided below, substituents which can be present in each embodiment and which are not explicitly defined retain the broadest definition provided in the Summary of the Invention.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

As used herein, unless specifically indicated otherwise, the word "or" is used in the "inclusive" sense of "and/or" and not the "exclusive" sense of "either/or".

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

The symbols "*" at the end of a bond or "------" drawn through a bond each refer to the point of attachment of a functional group or other chemical moiety to the rest of the molecule of which it is a part. Thus, for example:

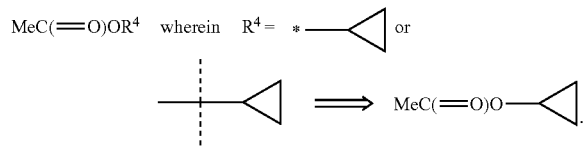

A bond drawn into ring system (as opposed to connected at a distinct vertex) indicates that the bond may be attached to any of the suitable ring atoms The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen or a substituent.

The phrase "optional bond" means that the bond may or may not be present, and that the description includes single, double, or triple bonds. If a substituent is designated to be a "bond" or "absent", the atoms linked to the substituents are then directly connected.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

Certain compounds of formulae I-III may exhibit tautomerism. Tautomeric compounds can exist as two or more interconvertable species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH— ⇌ —C(—OH)=CH—), amide/imidic acid (—C(=O)—NH— ⇌ —C(—OH)=N—) and amidine (—C(=NR)—NH— ⇌ —C(—NHR)=N—) tautomers. The latter two are particularly common in heteroaryl and heterocyclic rings and the present invention encompasses all tautomeric forms of the compounds.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics*, 10$^{th}$ Ed., McGraw Hill Companies Inc., New York (2001). Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

The definitions described herein may be appended to form chemically-relevant combinations, such as "heteroalkylaryl," "haloalkylheteroaryl," "arylalkylheterocyclyl," "alkylcarbonyl," "alkoxyalkyl," and the like. When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" refers to an alkyl group having one to two phenyl substituents, and thus includes benzyl, phenylethyl, and biphenyl. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below. The term -(ar)alkyl refers to either an unsubstituted alkyl or an aralkyl group. The term (hetero)aryl or (het)aryl refers to either an aryl or a heteroaryl group.

The term "acyl" as used herein denotes a group of formula —C(=O)R wherein R is hydrogen or lower alkyl as defined herein. The term or "alkylcarbonyl" as used herein denotes a group of formula C(=O)R wherein R is alkyl as defined herein. The term $C_{1-6}$ acyl refers to a group —C(=O)R contain 6 carbon atoms. The term "arylcarbonyl" as used herein means a group of formula C(=O)R wherein R is an aryl group; the term "benzoyl" as used herein an "arylcarbonyl" group wherein R is phenyl.

The term "alkyl" as used herein denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-10}$ alkyl" as used herein refers to an alkyl composed of 1 to 10 carbons. Examples of alkyl groups include, but are not limited to, lower alkyl groups include methyl, ethyl, propyl, i-propyl, n-butyl, i-butyl, t-butyl or pentyl, isopentyl, neopentyl, hexyl, heptyl, and octyl.

When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" denotes the radical R'R"—, wherein R' is a phenyl radical, and R" is an alkylene radical as defined herein with the understanding that the attachment point of the phenylalkyl moiety will be on the alkylene radical. Examples of arylalkyl radicals include, but are not limited to, benzyl, phenylethyl, 3-phenylpropyl. The terms "arylalkyl" or "aralkyl" are interpreted similarly except R' is an aryl radical. The terms "(het)aryla- lkyl" or "(het)aralkyl" are interpreted similarly except R' is optionally an aryl or a heteroaryl radical.

The terms "haloalkyl" or "halo-lower alkyl" or "lower haloalkyl" refers to a straight or branched chain hydrocarbon residue containing 1 to 6 carbon atoms wherein one or more carbon atoms are substituted with one or more halogen atoms.

The term "alkylene" or "alkylenyl" as used herein denotes a divalent saturated linear hydrocarbon radical of 1 to 10 carbon atoms (e.g., $(CH_2)_n$) or a branched saturated divalent hydrocarbon radical of 2 to 10 carbon atoms (e.g., —CHMe— or —$CH_2CH(i-Pr)CH_2$—), unless otherwise indicated. Except in the case of methylene, the open valences of an alkylene group are not attached to the same atom. Examples of alkylene radicals include, but are not limited to, methylene, ethylene, propylene, 2-methyl-propylene, 1,1-dimethyl-ethylene, butylene, 2-ethylbutylene.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an-O-alkyl wherein alkyl is $C_{1-10}$.

The term "hydroxyalkyl" as used herein denotes an alkyl radical as herein defined wherein one to three hydrogen atoms on different carbon atoms is/are replaced by hydroxyl groups.

The terms "alkylsulfonyl" and "arylsulfonyl" as used herein refers to a group of formula —S(=O)$_2$R wherein R is alkyl or aryl respectively and alkyl and aryl are as defined herein. The term "heteroalkylsulfonyl" as used herein refers herein denotes a group of formula —S(=O)$_2$R wherein R is "heteroalkyl" as defined herein.

The terms "alkylsulfonylamino" and "arylsulfonylamino" as used herein refers to a group of formula —NR'S(=O)$_2$R wherein R is alkyl or aryl respectively, R' is hydrogen or $C_{1-3}$ alkyl, and alkyl and aryl are as defined herein.

The term "cycloalkyl" as used herein refers to a saturated carbocyclic ring containing 3 to 8 carbon atoms, i.e. cyclopropyl, cyclobutyl, cyclopentyl, cyclohexyl, cycloheptyl or cyclooctyl. "$C_{3-7}$ cycloalkyl" as used herein refers to an cycloalkyl composed of 3 to 7 carbons in the carbocyclic ring.

The term carboxy-alkyl as used herein refers to an alkyl moiety wherein one, hydrogen atom has been replaced with a carboxyl with the understanding that the point of attachment of the heteroalkyl radical is through a carbon atom. The term "carboxy" or "carboxyl" refers to a —$CO_2H$ moiety.

The term "heteroaryl" or "heteroaromatic" as used herein means a monocyclic or bicyclic radical of 5 to 12 ring atoms having at least one aromatic ring containing four to eight atoms per ring, incorporating one or more N, O, or S heteroatoms, the remaining ring atoms being carbon, with the understanding that the attachment point of the heteroaryl radical will be on an aromatic ring. As well known to those skilled in the art, heteroaryl rings have less aromatic character than their all-carbon counter parts. Thus, for the purposes of the invention, a heteroaryl group need only have some degree of aromatic character. Examples of heteroaryl moieties include monocyclic aromatic heterocycles having 5 to 6 ring atoms and 1 to 3 heteroatoms include, but is not limited to, pyridinyl, pyrimidinyl, pyrazinyl, pyrrolyl, pyrazolyl, imidazolyl, oxazol, isoxazole, thiazole, isothiazole, triazolole, thiadiazole and oxadiaxoline which can optionally be substituted with one or more, preferably one or two substituents selected from hydroxy, cyano, alkyl, alkoxy, thio, lower haloalkoxy, alkylthio, halo, lower haloalkyl, alkylsulfinyl, alkylsulfonyl, halogen, amino, alkylamino, dialkylamino, aminoalkyl, alkylaminoalkyl, and dialkylaminoalkyl, nitro, alkoxycarbonyl and carbamoyl, alkylcarbamoyl, dialkylcarbamoyl, arylcarbamoyl, alkylcarbonylamino and arylcarbonylamino. Examples of bicyclic moieties include, but are not limited to, quinolinyl, isoquinolinyl, benzofuryl, benzothiophenyl, benzoxazole, benzisoxazole, benzothiazole and benzisothiazole. Bicyclic moieties can be optionally substituted on either ring; however the point of attachment is on a ring containing a heteroatom.

The term "heterocyclyl", "heterocycloalkyl" or "heterocycle" as used herein denotes a monovalent saturated cyclic radical, consisting of one or more rings, preferably one to two rings, including spirocyclic ring systems, of three to eight atoms per ring, incorporating one or more ring heteroatoms (chosen from N, O or S(O)$_{0-2}$), and which can optionally be independently substituted with one or more, preferably one or two substituents selected from hydroxy, oxo, cyano, lower alkyl, lower alkoxy, lower haloalkoxy, alkylthio, halo, lower haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, arylcarbonylamino, unless otherwise indicated. Examples of heterocyclic radicals include, but are not limited to, azetidinyl, pyrrolidinyl, hexahydroazepinyl, oxetanyl, tetrahydrofuranyl, tetrahydrothiophenyl, oxazolidinyl, thiazolidinyl, isoxazolidinyl, morpholinyl, piperazinyl, piperidinyl, tetrahydropyranyl, thiomorpholinyl, quinuclidinyl and imidazolinyl.

Commonly used abbreviations include: acetyl (Ac), azobis-isobutyrylnitrile (AIBN), atmospheres (Atm), 9-borabicyclo[3.3.1]nonane (9-BBN or BBN), tert-butoxycarbonyl (Boc), di-tert-butyl pyrocarbonate or boc anhydride (BOC$_2$O), benzyl (Bn), butyl (Bu), Chemical Abstracts Registration Number (CASRN), benzyloxycarbonyl (CBZ or Z), carbonyl diimidazole (CDI), 1,4-diazabicyclo[2.2.2]octane (DABCO), diethylaminosulfur trifluoride (DAST), dibenzylideneacetone (dba), 1,5-diazabicyclo[4.3.0]non-5-ene (DBN), 1,8-diazabicyclo[5.4.0]undec-7-ene (DBU), N,N'-dicyclohexylcarbodiimide (DCC), 1,2-dichloroethane (DCE), dichloromethane (DCM), diethyl azodicarboxylate (DEAD), di-iso-propylazodicarboxylate (DLAD), di-iso-butylaluminumhydride (DIBAL or DIBAL-H), di-iso-propylethylamine (DIPEA), N,N-dimethyl acetamide (DMA), 4-N,N-dimethylaminopyridine (DMAP), N,N-dimethylformamide (DMF), dimethyl sulfoxide (DMSO), 1,1'-bis-(diphenylphosphino)ethane (dppe), 1,1'-bis-(diphenylphosphino)ferrocene (dppf), 1-(3-dimethylaminopropyl)-3-ethylcarbodiimide hydrochloride (EDCI), ethyl (Et), ethyl acetate (EtOAc), ethanol (EtOH), 2-ethoxy-2H-quinoline-1-carboxylic acid ethyl ester (EEDQ), diethyl ether (Et$_2$O), O-(7-azabenzotriazole-1-yl)-N,N,N'N'-tetramethyluronium hexafluorophosphate acetic acid (HATU), acetic acid (HOAc), 1-N-hydroxybenzotriazole (HOBt), high pressure liquid chromatography (HPLC), iso-propanol (IPA), lithium hexamethyl disilazane (LiHMDS), methanol (MeOH), melting point (mp), MeSO$_2$— (mesyl or Ms), methyl (Me), acetonitrile (MeCN), m-chloroperbenzoic acid (MCPBA), mass spectrum (ms), methyl t-butyl ether (MTBE), N-bromosuccinimide (NBS), N-carboxyanhydride (NCA), N-chlorosuccinimide (NCS), N-methylmorpholine (NMM), N-methylpyrrolidone (NMP), pyridinium chlorochromate (PCC), pyridinium dichromate (PDC), phenyl (Ph), propyl (Pr), iso-propyl (i-Pr), pounds per square inch (psi), pyridine (pyr), room temperature (rt or RT), tert-butyldimethylsilyl or t-BuMe₂Si (TBDMS), triethylamine (TEA or Et₃N), 2,2,6,6-tetramethylpiperidine 1-oxyl (TEMPO), triflate or CF₃SO₂— (Tf), trifluoroacetic acid (TFA), 1,1'-bis-2,2,6,6-tetramethyl-heptane-2,6-dione (TMHD), O-benzotriazol-1-yl-N,N,N',N'-tetramethyluronium tetrafluoroborate (TBTU), thin layer chromatography (TLC), tetrahydrofuran (THF), trimethylsilyl or Me₃Si (TMS), p-toluenesulfonic acid monohydrate (TsOH or pTsOH), 4-Me-C₆H₄SO₂— or tosyl (Ts), N-urethane-N-carboxyanhydride (UNCA). Conventional nomenclature including the prefixes normal (n), iso (i-), secondary (sec-), tertiary (tert-) and neo have their customary meaning when used with an alkyl moiety. (J. Rigaudy and D. P. Klesney, *Nomenclature in Organic Chemistry*, IUPAC 1979 Pergamon Press, Oxford.).

Compounds and Preparation

Examples of representative compounds encompassed by the present invention and within the scope of the invention are provided in the following Table. These examples and preparations which follow are provided to enable those skilled in the art to more clearly understand and to practice the present invention. They should not be considered as limiting the scope of the invention, but merely as being illustrative and representative thereof.

In general, the nomenclature used in this Application is based on AUTONOM™ v.4.0, a Beilstein Institute computerized system for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

TABLE I depicts examples of pyridinone compounds according to generic Formulae I-III wherein X either is CH or N.

TABLE I

| Compound | Structure | Nomenclature | (M + H)⁺ |
|---|---|---|---|
| I-1 | 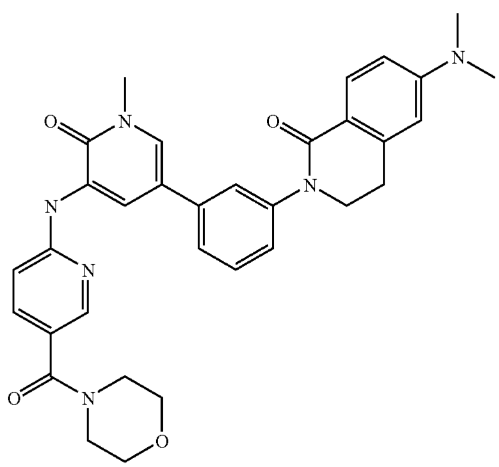 | 6-Dimethylamino-2-(3-{1-methyl-5-[5-(morpholine-4-carbonyl)-pyridin-2-ylamino]-6-oxo-1,6-dihydro-pyridin-3-yl}-phenyl)-3,4-dihydro-2H-isoquinolin-1-one | 579.2 |
| I-2 | 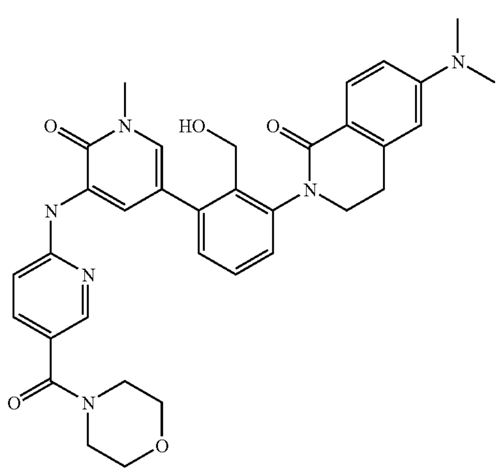 | 6-Dimethylamino-2-(2-hydroxymethyl-3-{1-methyl-5-[5-(morpholine-4-carbonyl)-pyridin-2-ylamino]-6-oxo-1,6-dihydro-pyridin-3-yl}-phenyl)-3,4-dihydro-2H-isoquinolin-1-one | 609.1 |

TABLE I-continued

| Compound | Structure | Nomenclature | (M + H)+ |
|---|---|---|---|
| I-3 | 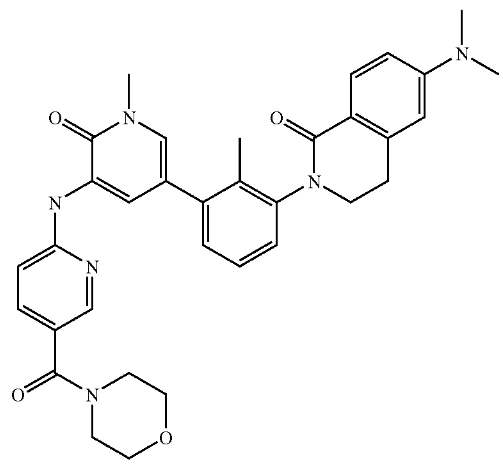 | 6-Dimethylamino-2-(2-methyl-3-{1-methyl-5-[5-(morpholine-4-carbonyl)-pyridin-2-ylamino]-6-oxo-1,6-dihydro-pyridin-3-yl}-phenyl)-3,4-dihydro-2H-isoquinolin-1-one | 593.3 |
| II-1 | 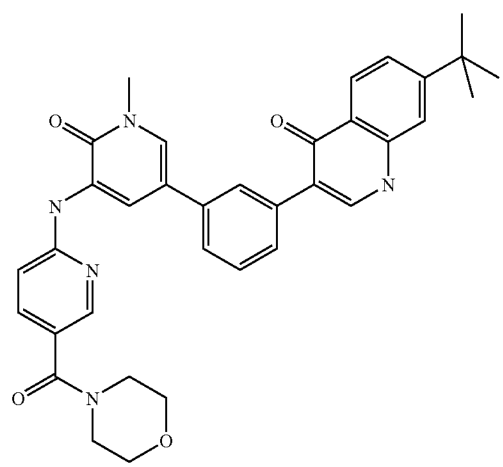 | 7-tert-Butyl-3-(3-{1-methyl-5-[5-(morpholine-4-carbonyl)-pyridin-2-ylamino]-6-oxo-1,6-dihydro-pyridin-3-yl}-phenyl)-1H-quinolin-4-one | 590.1 |
| II-2 | 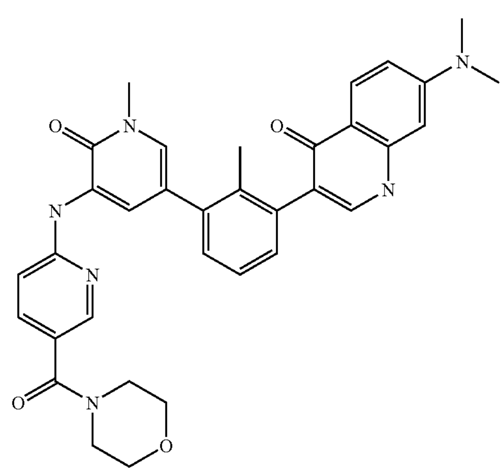 | 7-Dimethylamino-3-(2-methyl-3-{1-methyl-5-[5-(morpholine-4-carbonyl)-pyridin-2-ylamino]-6-oxo-1,6-dihydro-pyridin-3-yl}-phenyl)-1H-quinolin-4-one | 591.1 |

TABLE I-continued

| Compound | Structure | Nomenclature | (M + H)+ |
|---|---|---|---|
| III-1 | 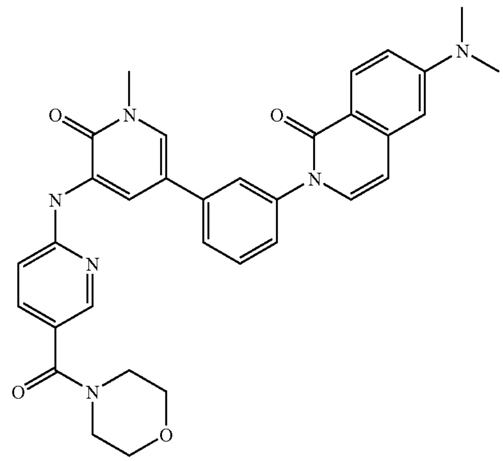 | 6-Dimethylamino-2-(3-{1-methyl-5-[5-(morpholine-4-carbonyl)-pyridin-2-ylamino]-6-oxo-1,6-dihydro-pyridin-3-yl}-phenyl)-2H-isoquinolin-1-one | 577.1 |
| III-2 | 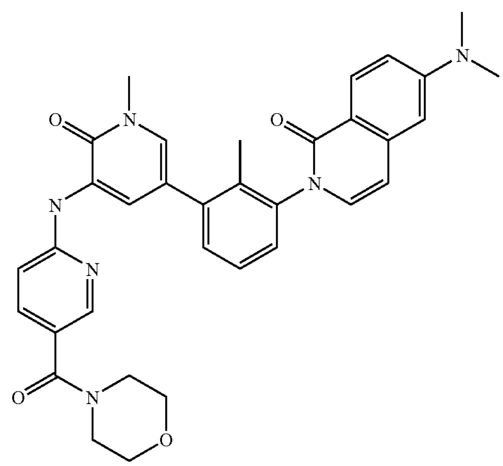 | 6-Dimethylamino-2-(2-methyl-3-{1-methyl-5-[5-(morpholine-4-carbonyl)-pyridin-2-ylamino]-6-oxo-1,6-dihydro-pyridin-3-yl}-phenyl)-2H-isoquinolin-1-one | 591.1 |
| III-3 | 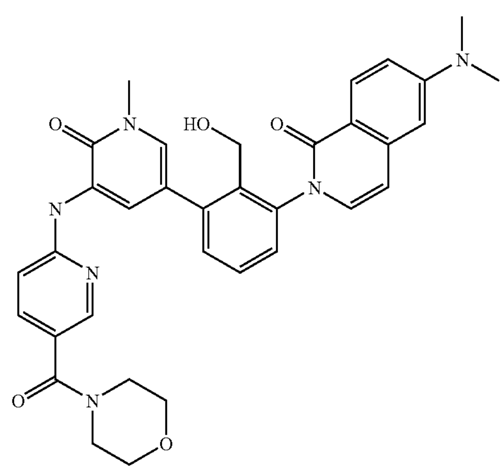 | 6-Dimethylamino-2-(2-hydroxymethyl-3-{1-methyl-5-[5-(morpholine-4-carbonyl)-pyridin-2-ylamino]-6-oxo-1,6-dihydro-pyridin-3-yl}-phenyl)-2H-isoquinolin-1-one | 607.2 |

TABLE I-continued

| Compound | Structure | Nomenclature | (M + H)+ |
|---|---|---|---|
| I-4 | 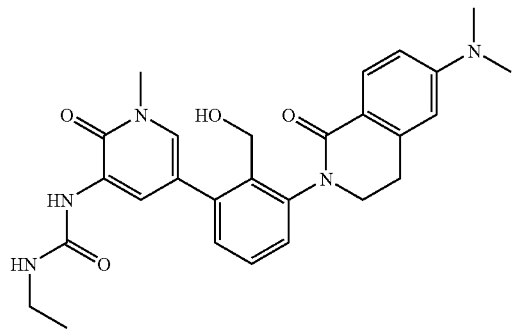 | 1-{5-[3-(6-Dimethylamino-1-oxo-3,4-dihydro-1H-isoquinolin-2-yl)-2-hydroxymethyl-phenyl]-1-methyl-2-oxo-1,2-dihydro-pyridin-3-yl}-3-ethyl-urea | |
| I-5 | 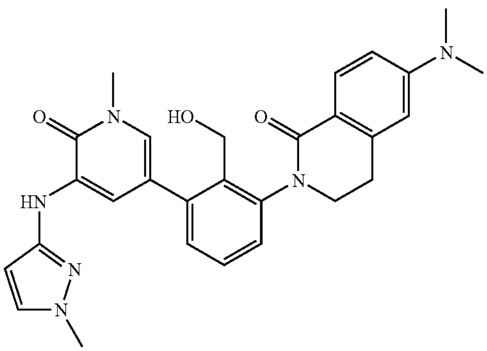 | 6-Dimethylamino-2-{2-hydroxymethyl-3-[1-methyl-5-(1-methyl-1H-pyrazol-3-ylamino)-6-oxo-1,6-dihydro-pyridin-3-yl]-phenyl}-3,4-dihydro-2H-isoquinolin-1-one | |
| I-6 | 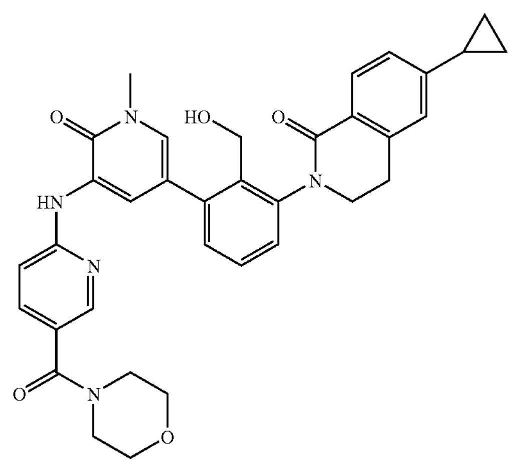 | 6-Cyclopropyl-2-(2-hydroxymethyl-3-{1-methyl-5-[5-(morpholine-4-carbonyl)-pyridin-2-ylamino]-6-oxo-1,6-dihydro-pyridin-3-yl}-phenyl)-3,4-dihydro-2H-isoquinolin-1-one | |
| I-7 | 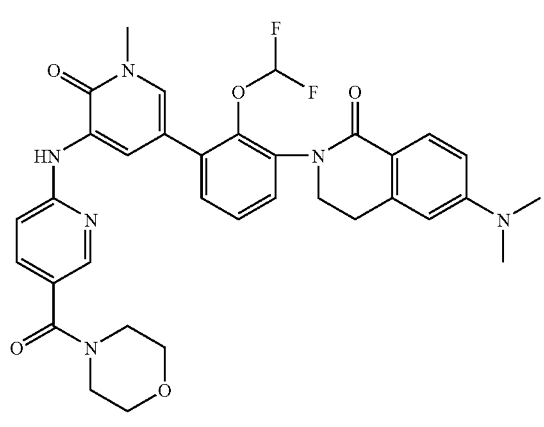 | 2-(2-Difluoromethoxy-3-{1-methyl-5-[5-(morpholine-4-carbonyl)-pyridin-2-ylamino]-6-oxo-1,6-dihydro-pyridin-3-yl}-phenyl)-6-dimethylamino-3,4-dihydro-2H-isoquinolin-1-one | |

TABLE I-continued

| Compound | Structure | Nomenclature | (M + H)+ |
|---|---|---|---|
| I-8 | 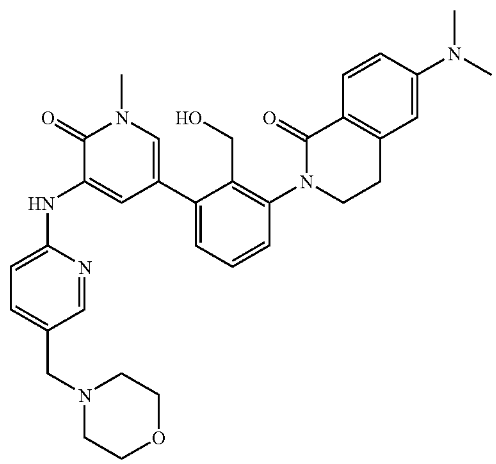 | 6-Dimethylamino-2-{2-hydroxymethyl-3-[1-methyl-5-(5-morpholin-4-ylmethyl-pyridin-2-ylamino)-6-oxo-1,6-dihydro-pyridin-3-yl]-phenyl}-3,4-dihydro-2H-isoquinolin-1-one | |
| I-9 | 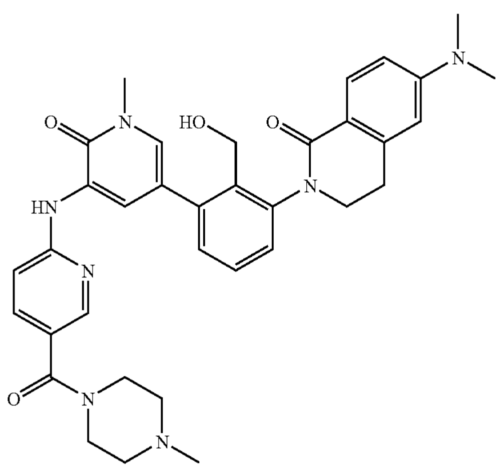 | 6-Dimethylamino-2-(2-hydroxymethyl-3-{1-methyl-5-[5-(4-methyl-piperazine-1-carbonyl)-pyridin-2-ylamino]-6-oxo-1,6-dihydro-pyridin-3-yl}-phenyl)-3,4-dihydro-2H-isoquinolin-1-one | |
| I-10 | 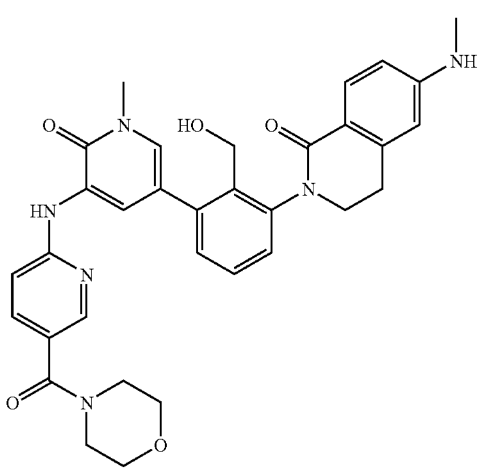 | 2-(2-Hydroxymethyl-3-{1-methyl-5-[5-(morpholine-4-carbonyl)-pyridin-2-ylamino]-6-oxo-1,6-dihydro-pyridin-3-yl}-phenyl)-6-methylamino-3,4-dihydro-2H-isoquinolin-1-one | |

TABLE I-continued

| Compound | Structure | Nomenclature | (M + H)+ |
|---|---|---|---|
| I-11 | 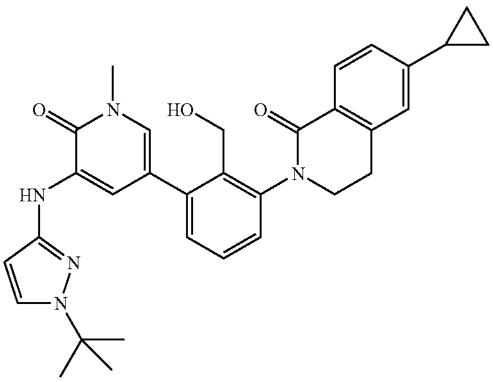 | 2-{3-[5-(1-tert-Butyl-1H-pyrazol-3-ylamino)-1-methyl-6-oxo-1,6-dihydro-pyridin-3-yl]-2-hydroxymethyl-phenyl}-6-cyclopropyl-3,4-dihydro-2H-isoquinolin-1-one | |
| I-12 | 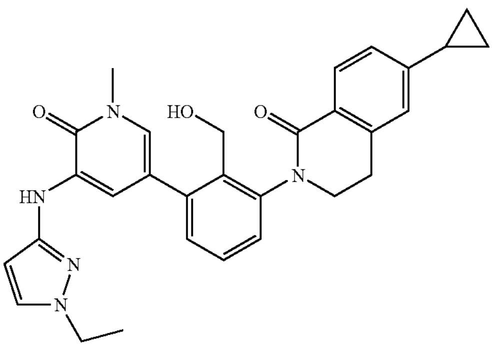 | 6-Cyclopropyl-2-{3-[5-(1-ethyl-1H-pyrazol-3-ylamino)-1-methyl-6-oxo-1,6-dihydro-pyridin-3-yl]-2-hydroxymethyl-phenyl}-3,4-dihydro-2H-isoquinolin-1-one | |
| I-13 | 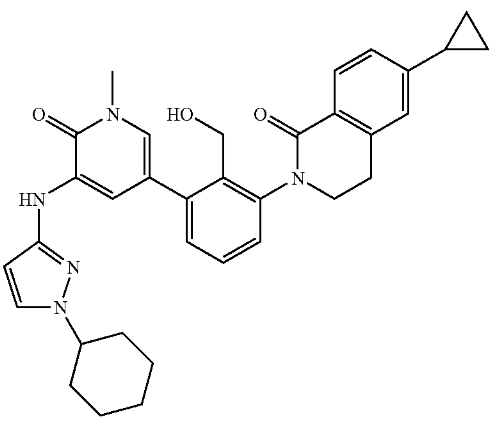 | 2-{3-[5-(1-Cyclohexyl-1H-pyrazol-3-ylamino)-1-methyl-6-oxo-1,6-dihydro-pyridin-3-yl]-2-hydroxymethyl-phenyl}-6-cyclopropyl-3,4-dihydro-2H-isoquinolin-1-one | |
| I-14 | 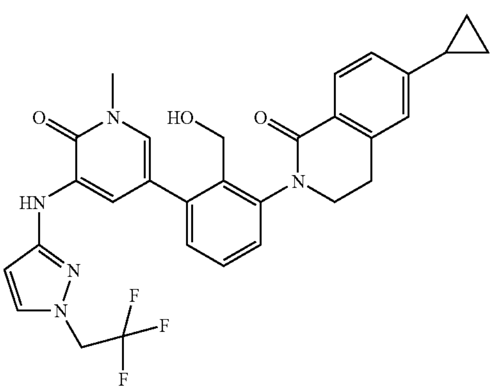 | 6-Cyclopropyl-2-(2-hydroxymethyl-3-{1-methyl-6-oxo-5-[1-(2,2,2-trifluoro-ethyl)-1H-pyrazol-3-ylamino]-1,6-dihydro-pyridin-3-yl}-phenyl)-3,4-dihydro-2H-isoquinolin-1-one | |

TABLE I-continued

| Compound | Structure | Nomenclature | (M + H)+ |
|---|---|---|---|
| I-15 | 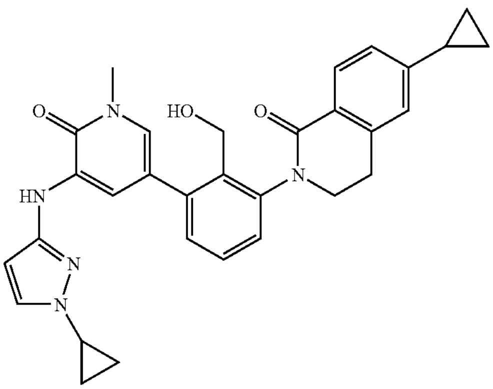 | 6-Cyclopropyl-2-{3-[5-(1-cyclopropyl-1H-pyrazol-3-ylamino)-1-methyl-6-oxo-1,6-dihydro-pyridin-3-yl]-2-hydroxymethyl-phenyl}-3,4-dihydro-2H-isoquinolin-1-one | |
| I-16 | 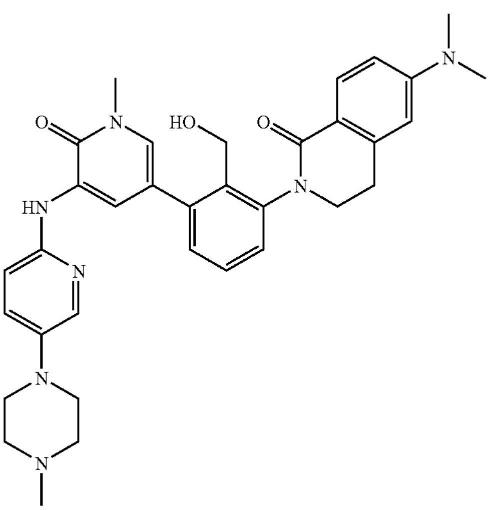 | 6-Dimethylamino-2-(2-hydroxymethyl-3-{1-methyl-5-[5-(4-methyl-piperazin-1-yl)-pyridin-2-ylamino]-6-oxo-1,6-dihydro-pyridin-3-yl}-phenyl)-3,4-dihydro-2H-isoquinolin-1-one | |
| I-17 | 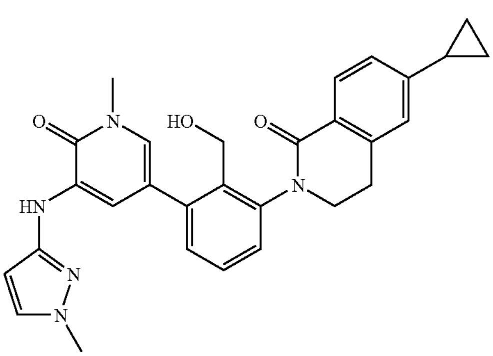 | 6-Cyclopropyl-2-{2-hydroxymethyl-3-[1-methyl-5-(1-methyl-1H-pyrazol-3-ylamino)-6-oxo-1,6-dihydro-pyridin-3-yl]-phenyl}-3,4-dihydro-2H-isoquinolin-1-one | |

TABLE I-continued

| Compound | Structure | Nomenclature | (M + H)+ |
|---|---|---|---|
| I-18 | 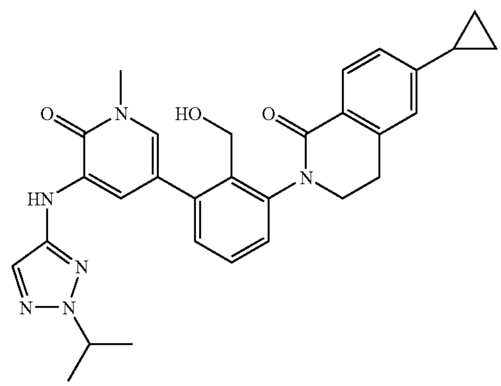 | 6-Cyclopropyl-2-{2-hydroxymethyl-3-[5-(2-isopropyl-2H-[1,2,3]triazol-4-ylamino)-1-methyl-6-oxo-1,6-dihydro-pyridin-3-yl]-phenyl}-3,4-dihydro-2H-isoquinolin-1-one | |
| I-19 | 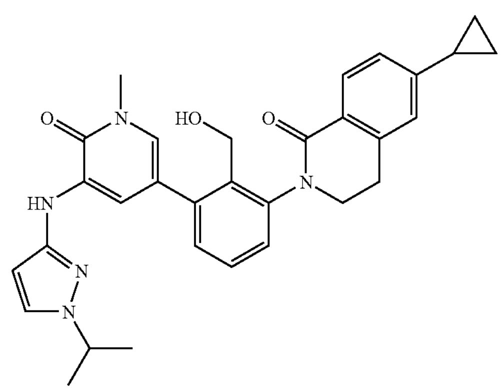 | 6-Cyclopropyl-2-{2-hydroxymethyl-3-[5-(1-isopropyl-1H-pyrazol-3-ylamino)-1-methyl-6-oxo-1,6-dihydro-pyridin-3-yl]-phenyl}-3,4-dihydro-2H-isoquinolin-1-one | |
| I-20 | 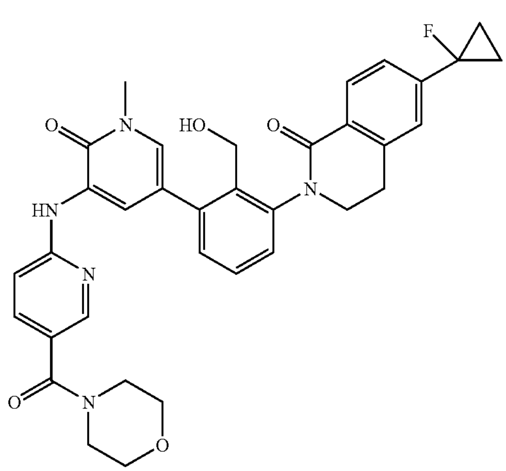 | 6-(1-Fluoro-cyclopropyl)-2-(2-hydroxymethyl-3-{1-methyl-5-[5-(morpholine-4-carbonyl)-pyridin-2-ylamino]-6-oxo-1,6-dihydro-pyridin-3-yl}-phenyl)-3,4-dihydro-2H-isoquinolin-1-one | |

TABLE I-continued

| Compound | Structure | Nomenclature | (M + H)+ |
|---|---|---|---|
| I-21 | 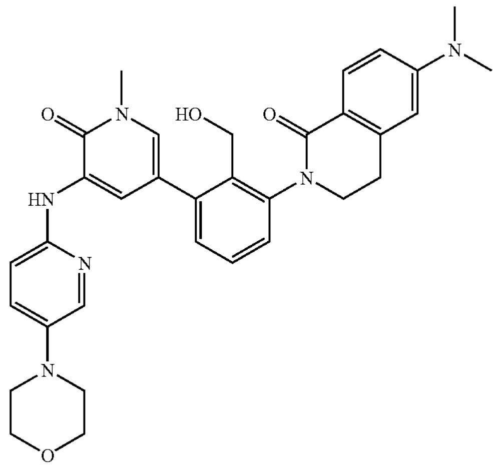 | 6-Dimethylamino-2-{2-hydroxymethyl-3-[1-methyl-5-(5-morpholin-4-yl-pyridin-2-ylamino)-6-oxo-1,6-dihydro-pyridin-3-yl]-phenyl}-3,4-dihydro-2H-isoquinolin-1-one | |
| I-22 | 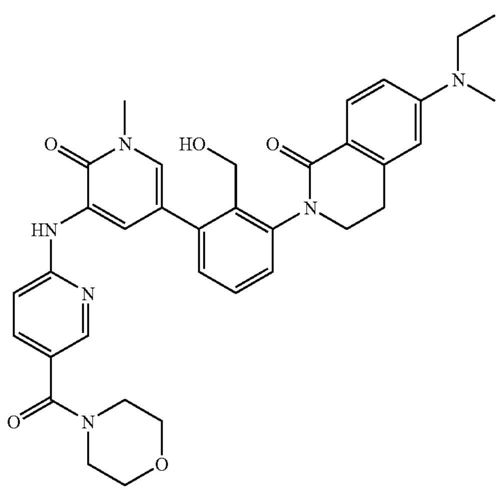 | 6-(Ethyl-methyl-amino)-2-(2-hydroxymethyl-3-{1-methyl-5-[5-(morpholine-4-carbonyl)-pyridin-2-ylamino]-6-oxo-1,6-dihydro-pyridin-3-yl}-phenyl)-3,4-dihydro-2H-isoquinolin-1-one | |
| I-23 | 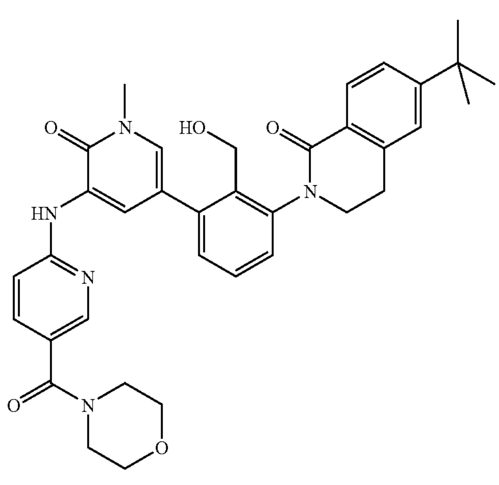 | 6-tert-Butyl-2-(2-hydroxymethyl-3-{1-methyl-5-[5-(morpholine-4-carbonyl)-pyridin-2-ylamino]-6-oxo-1,6-dihydro-pyridin-3-yl}-phenyl)-3,4-dihydro-2H-isoquinolin-1-one | |

TABLE I-continued

| Compound | Structure | Nomenclature | (M + H)+ |
|---|---|---|---|
| I-24 | 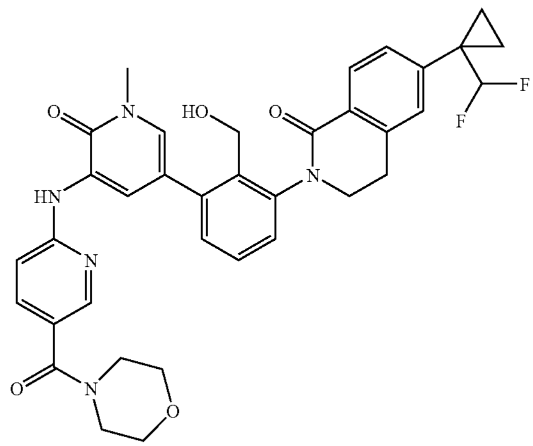 | 6-(1-Difluoromethyl-cyclopropyl)-2-(2-hydroxymethyl-3-{1-methyl-5-[5-(morpholine-4-carbonyl)-pyridin-2-ylamino]-6-oxo-1,6-dihydro-pyridin-3-yl}-phenyl)-3,4-dihydro-2H-isoquinolin-1-one | |
| I-25 | 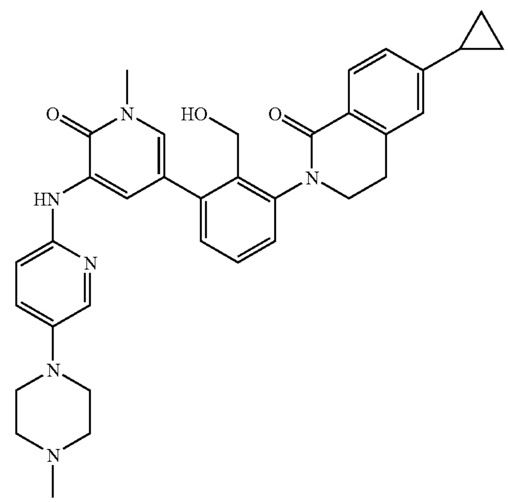 | 6-Cyclopropyl-2-(2-hydroxymethyl-3-{1-methyl-5-[5-(4-methyl-piperazin-1-yl)-pyridin-2-ylamino]-6-oxo-1,6-dihydro-pyridin-3-yl}-phenyl)-3,4-dihydro-2H-isoquinolin-1-one | |
| I-26 | 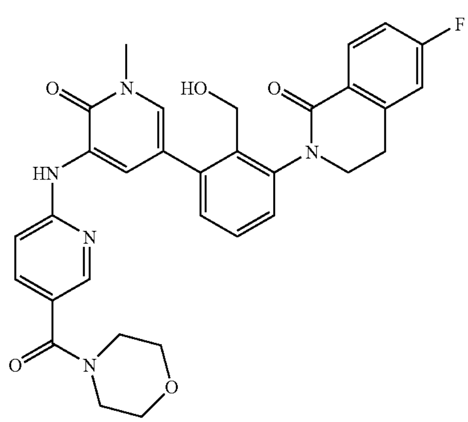 | 6-Fluoro-2-(2-hydroxymethyl-3-{1-methyl-5-[5-(morpholine-4-carbonyl)-pyridin-2-ylamino]-6-oxo-1,6-dihydro-pyridin-3-yl}-phenyl)-3,4-dihydro-2H-isoquinolin-1-one | |

TABLE I-continued

| Compound | Structure | Nomenclature | (M + H)+ |
|---|---|---|---|
| I-27 | 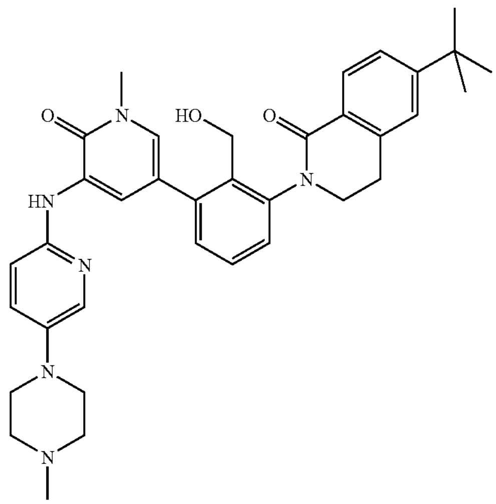 | 6-tert-Butyl-2-(2-hydroxymethyl-3-{1-methyl-5-[5-(4-methyl-piperazin-1-yl)-pyridin-2-ylamino]-6-oxo-1,6-dihydro-pyridin-3-yl}-phenyl)-3,4-dihydro-2H-isoquinolin-1-one | |
| I-28 | 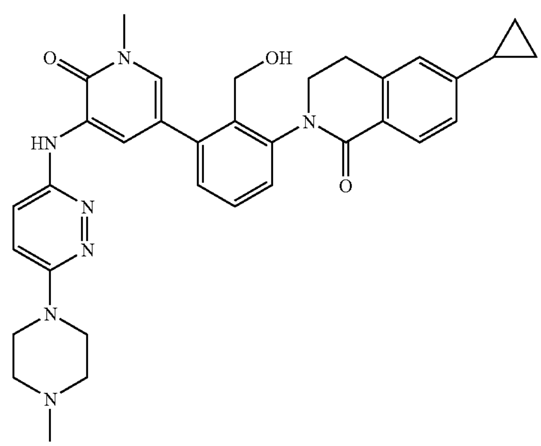 | 6-Cyclopropyl-2-(2-hydroxymethyl-3-{1-methyl-5-[6-(4-methyl-piperazin-1-yl)-pyridazin-3-ylamino]-6-oxo-1,6-dihydro-pyridin-3-yl}-phenyl)-3,4-dihydro-2H-isoquinolin-1-one | |
| I-29 | 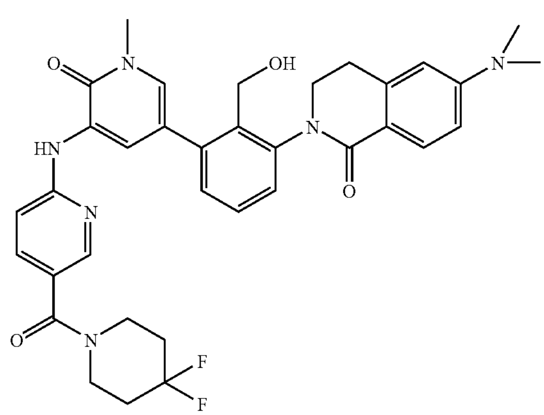 | 2-(3-{5-[5-(4,4-Difluoro-piperidine-1-carbonyl)-pyridin-2-ylamino]-1-methyl-6-oxo-1,6-dihydro-pyridin-3-yl}-2-hydroxymethyl-phenyl)-6-dimethylamino-3,4-dihydro-2H-isoquinolin-1-one | |

TABLE I-continued

| Compound | Structure | Nomenclature | (M + H)+ |
|---|---|---|---|
| I-30 | 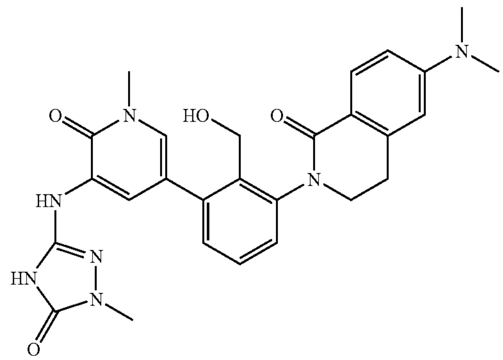 | 6-Dimethylamino-2-{2-hydroxymethyl-3-[1-methyl-5-(1-methyl-5-oxo-4,5-dihydro-1H-[1,2,4]triazol-3-ylamino)-6-oxo-1,6-dihydro-pyridin-3-yl]-phenyl}-3,4-dihydro-2H-isoquinolin-1-one | |
| I-31 | 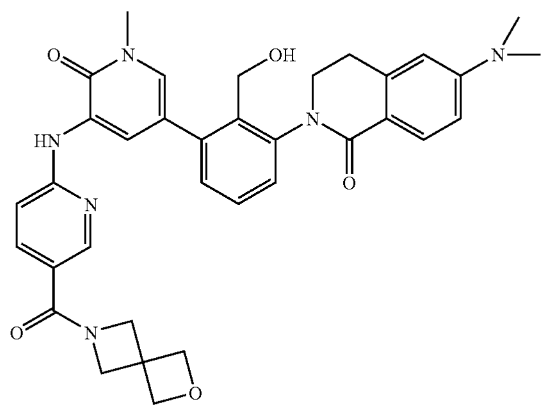 | 6-Dimethylamino-2-(2-hydroxymethyl-3-{1-methyl-5-[5-(2-oxa-6-aza-spiro[3.3]heptane-6-carbonyl)-pyridin-2-ylamino]-6-oxo-1,6-dihydro-pyridin-3-yl}-phenyl)-3,4-dihydro-2H-isoquinolin-1-one | |
| I-32 | 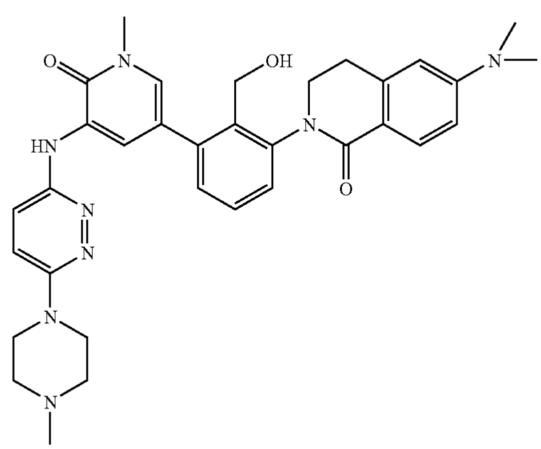 | 6-Dimethylamino-2-(2-hydroxymethyl-3-{1-methyl-5-[6-(4-methyl-piperazin-1-yl)-pyridazin-3-ylamino]-6-oxo-1,6-dihydro-pyridin-3-yl}-phenyl)-3,4-dihydro-2H-isoquinolin-1-one | |

TABLE I-continued

| Compound | Structure | Nomenclature | (M + H)+ |
|---|---|---|---|
| I-33 | 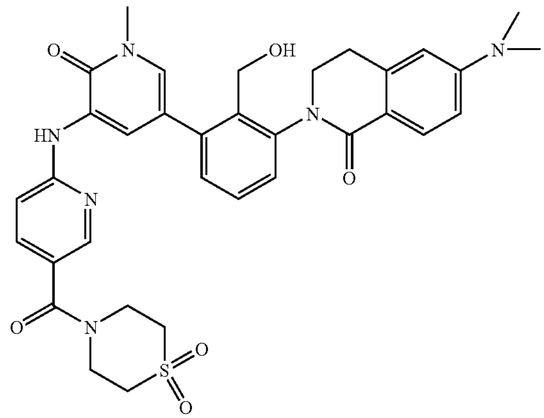 | 6-Dimethylamino-2-(3-{5-[5-(1,1-dioxo-1λ⁶-thiomorpholine-4-carbonyl)-pyridin-2-ylamino]-1-methyl-6-oxo-1,6-dihydro-pyridin-3-yl}-2-hydroxymethyl-phenyl)-3,4-dihydro-2H-isoquinolin-1-one | |
| I-34 | 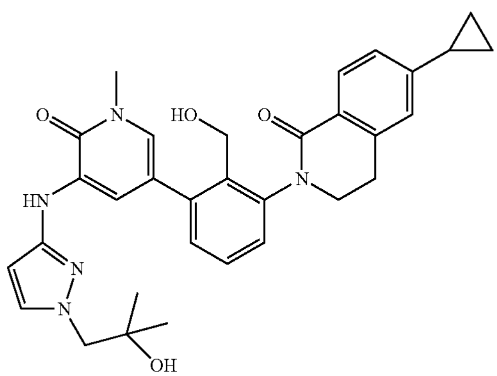 | 6-Cyclopropyl-2-(2-hydroxymethyl-3-{5-[1-(2-hydroxy-2-methyl-propyl)-1H-pyrazol-3-ylamino]-1-methyl-6-oxo-1,6-dihydro-pyridin-3-yl}-phenyl)-3,4-dihydro-2H-isoquinolin-1-one | |
| I-35 | 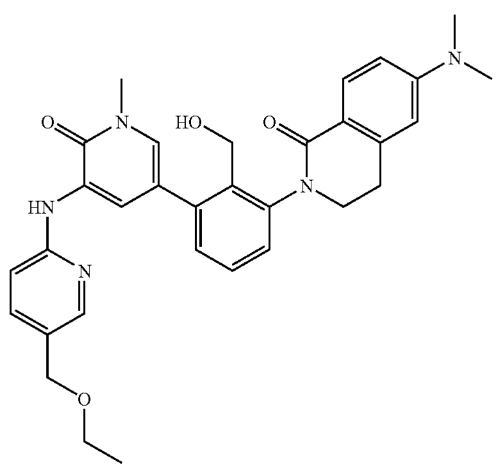 | 6-Dimethylamino-2-{3-[5-(5-ethoxymethyl-pyridin-2-ylamino)-1-methyl-6-oxo-1,6-dihydro-pyridin-3-yl]-2-hydroxymethyl-phenyl}-3,4-dihydro-2H-isoquinolin-1-one | |

| Compound | Structure | Nomenclature | (M + H)+ |
|---|---|---|---|
| I-36 | 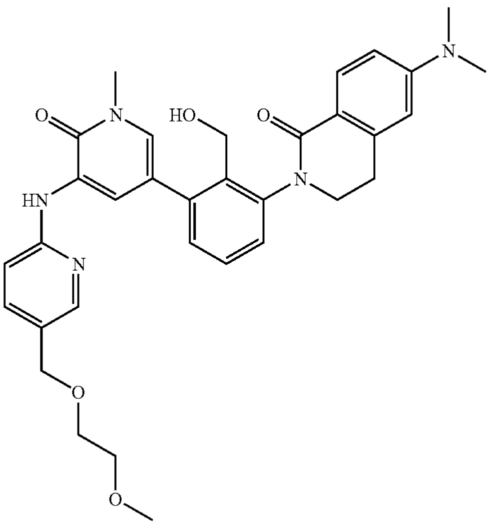 | 6-Dimethylamino-2-(2-hydroxymethyl-3-{5-[5-(2-methoxy-ethoxymethyl)-pyridin-2-ylamino]-1-methyl-6-oxo-1,6-dihydro-pyridin-3-yl}-phenyl)-3,4-dihydro-2H-isoquinolin-1-one | |
| I-37 | 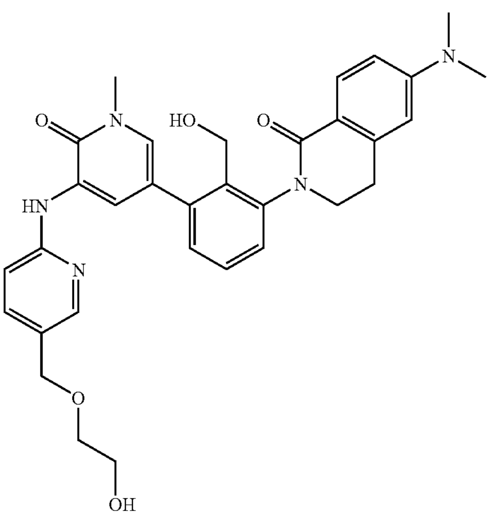 | 6-Dimethylamino-2-(3-{5-[5-(2-hydroxy-ethoxymethyl)-pyridin-2-ylamino]-1-methyl-6-oxo-1,6-dihydro-pyridin-3-yl}-2-hydroxymethyl-phenyl)-3,4-dihydro-2H-isoquinolin-1-one | |
| I-38 | 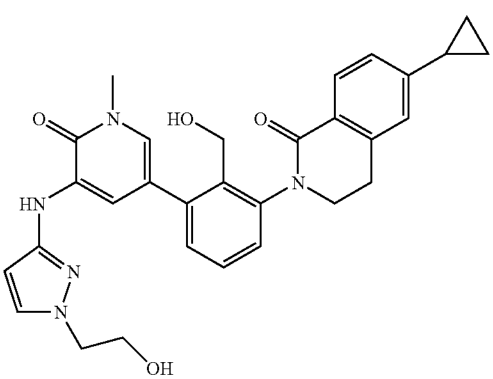 | 6-Cyclopropyl-2-(3-{5-[1-(2-hydroxy-ethyl)-1H-pyrazol-3-ylamino]-1-methyl-6-oxo-1,6-dihydro-pyridin-3-yl}-2-hydroxymethyl-phenyl)-3,4-dihydro-2H-isoquinolin-1-one | |

TABLE I-continued

| Compound | Structure | Nomenclature | (M + H)⁺ |
|---|---|---|---|
| I-39 | 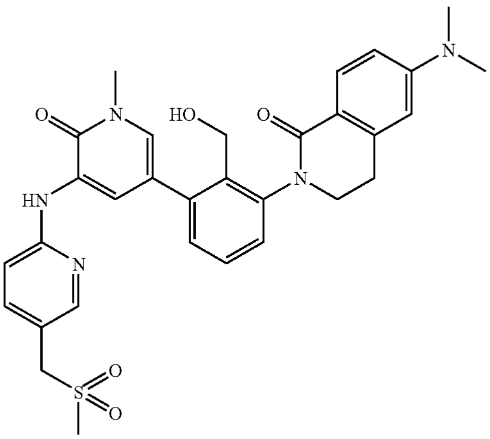 | 6-Dimethylamino-2-{2-hydroxymethyl-3-[5-(5-methanesulfonylmethyl-pyridin-2-ylamino)-1-methyl-6-oxo-1,6-dihydro-pyridin-3-yl]-phenyl}-3,4-dihydro-2H-isoquinolin-1-one | |
| I-40 | 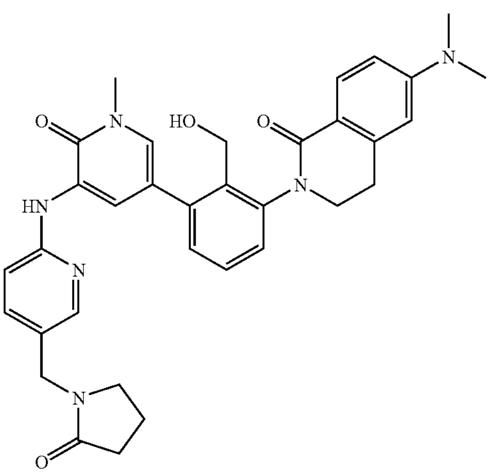 | 6-Dimethylamino-2-(2-hydroxymethyl-3-{1-methyl-6-oxo-5-[5-(2-oxo-pyrrolidin-1-ylmethyl)-pyridin-2-ylamino]-1,6-dihydro-pyridin-3-yl}-phenyl)-3,4-dihydro-2H-isoquinolin-1-one | |
| I-41 | 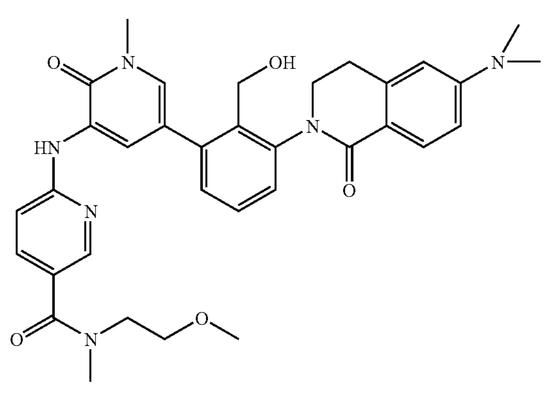 | 6-{5-[3-(6-Dimethylamino-1-oxo-3,4-dihydro-1H-isoquinolin-2-yl)-2-hydroxymethyl-phenyl]-1-methyl-2-oxo-1,2-dihydro-pyridin-3-ylamino}-N-(2-methoxy-ethyl)-N-methyl-nicotinamide | |

TABLE I-continued

| Compound | Structure | Nomenclature | (M + H)+ |
|---|---|---|---|
| I-42 | 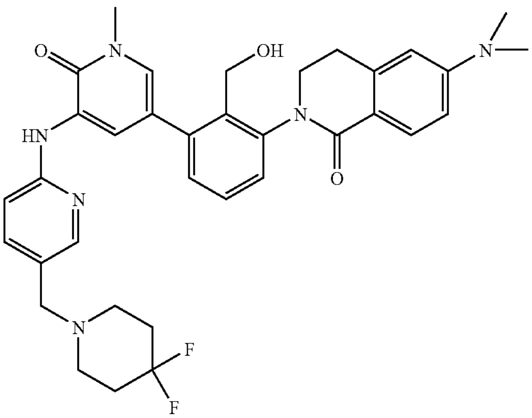 | 2-(3-{5-[5-(4,4-Difluoro-piperidin-1-ylmethyl)-pyridin-2-ylamino]-1-methyl-6-oxo-1,6-dihydro-pyridin-3-yl}-2-hydroxymethyl-phenyl)-6-dimethylamino-3,4-dihydro-2H-isoquinolin-1-one | |
| I-43 | 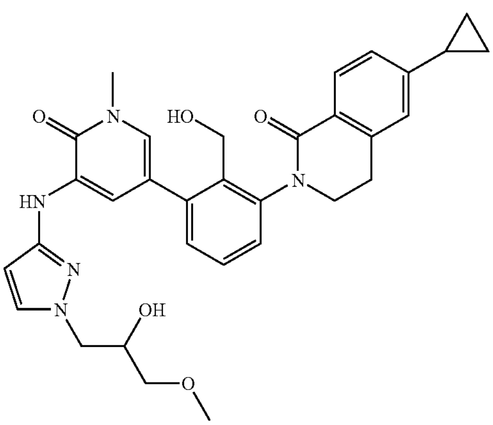 | 6-Cyclopropyl-2-(3-{5-[1-(2-hydroxy-3-methoxy-propyl)-1H-pyrazol-3-ylamino]-1-methyl-6-oxo-1,6-dihydro-pyridin-3-yl}-2-hydroxymethyl-phenyl)-3,4-dihydro-2H-isoquinolin-1-one | |
| I-44 | 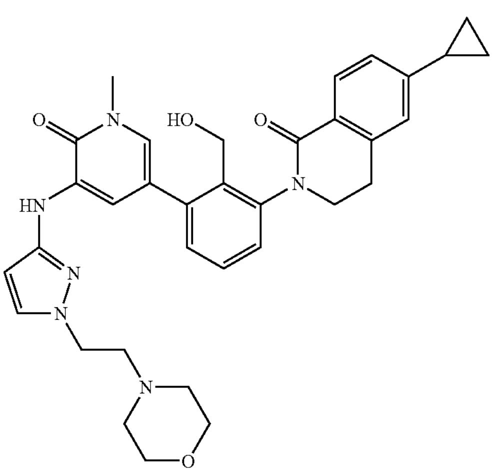 | 6-Cyclopropyl-2-(2-hydroxymethyl-3-{1-methyl-5-[1-(2-morpholin-4-yl-ethyl)-1H-pyrazol-3-ylamino]-6-oxo-1,6-dihydro-pyridin-3-yl}-phenyl)-3,4-dihydro-2H-isoquinolin-1-one | |

TABLE I-continued

| Compound | Structure | Nomenclature | (M + H)+ |
|---|---|---|---|
| I-45 | 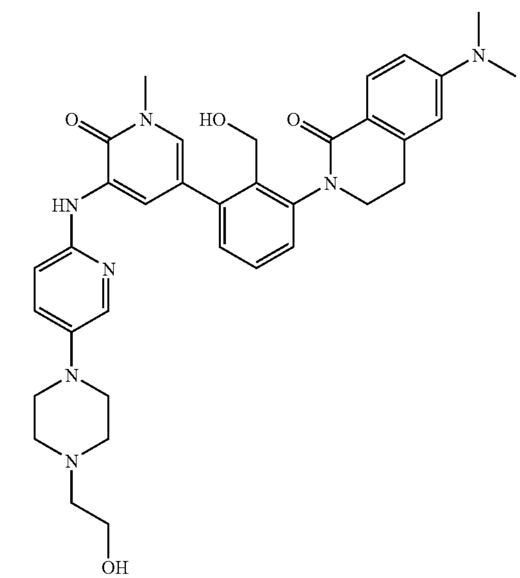 | 6-Dimethylamino-2-[3-(5-{5-[4-(2-hydroxy-ethyl)-piperazin-1-yl]-pyridin-2-ylamino}-1-methyl-6-oxo-1,6-dihydro-pyridin-3-yl)-2-hydroxymethyl-phenyl]-3,4-dihydro-2H-isoquinolin-1-one | |
| I-46 | 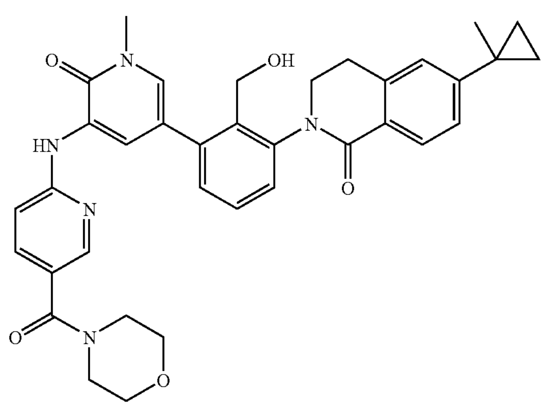 | 2-(2-Hydroxymethyl-3-{1-methyl-5-[5-(morpholine-4-carbonyl)-pyridin-2-ylamino]-6-oxo-1,6-dihydro-pyridin-3-yl}-phenyl)-6-(1-methyl-cyclopropyl)-3,4-dihydro-2H-isoquinolin-1-one | |
| I-47 | 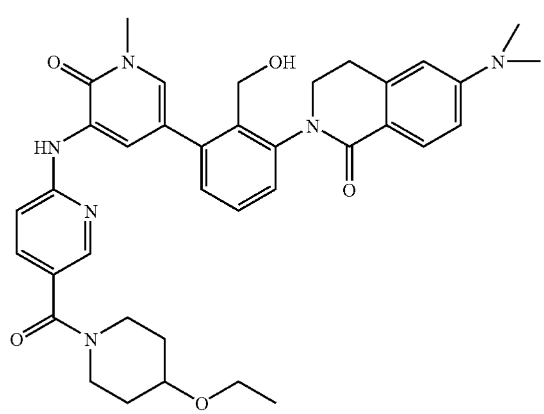 | 6-Dimethylamino-2-(3-{5-[5-(4-ethoxy-piperidine-1-carbonyl)-pyridin-2-ylamino]-1-methyl-6-oxo-1,6-dihydro-pyridin-3-yl}-2-hydroxymethyl-phenyl)-3,4-dihydro-2H-isoquinolin-1-one | |

TABLE I-continued

| Compound | Structure | Nomenclature | (M + H)+ |
|---|---|---|---|
| I-48 | 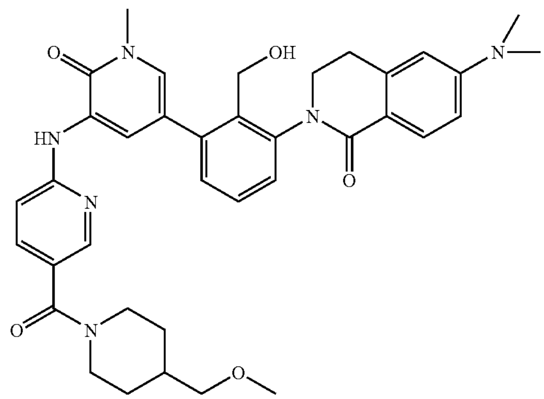 | 6-Dimethylamino-2-(2-hydroxymethyl-3-{5-[5-(4-methoxymethyl-piperidine-1-carbonyl)-pyridin-2-ylamino]-1-methyl-6-oxo-1,6-dihydro-pyridin-3-yl}-phenyl)-3,4-dihydro-2H-isoquinolin-1-one | |
| I-49 | 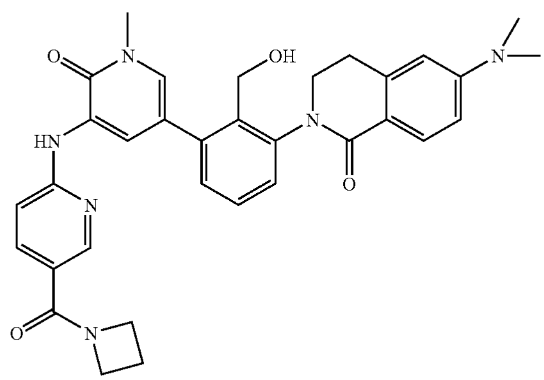 | 2-(3-{5-[5-(Azetidine-1-carbonyl)-pyridin-2-ylamino]-1-methyl-6-oxo-1,6-dihydro-pyridin-3-yl}-2-hydroxymethyl-phenyl)-6-dimethylamino-3,4-dihydro-2H-isoquinolin-1-one | |
| I-50 | 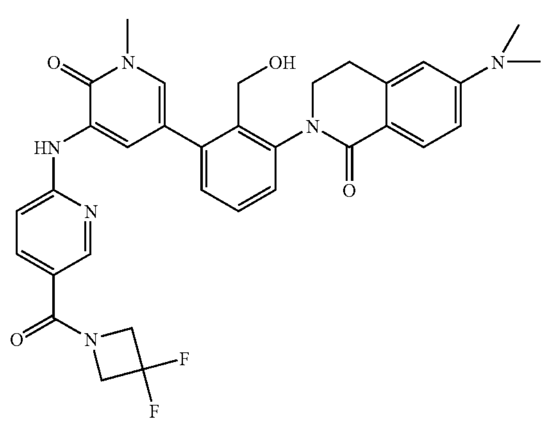 | 2-(3-{5-[5-(3,3-Difluoro-azetidine-1-carbonyl)-pyridin-2-ylamino]-1-methyl-6-oxo-1,6-dihydro-pyridin-3-yl}-2-hydroxymethyl-phenyl)-6-dimethylamino-3,4-dihydro-2H-isoquinolin-1-one | |

TABLE I-continued

| Compound | Structure | Nomenclature | (M + H)+ |
|---|---|---|---|
| I-51 | 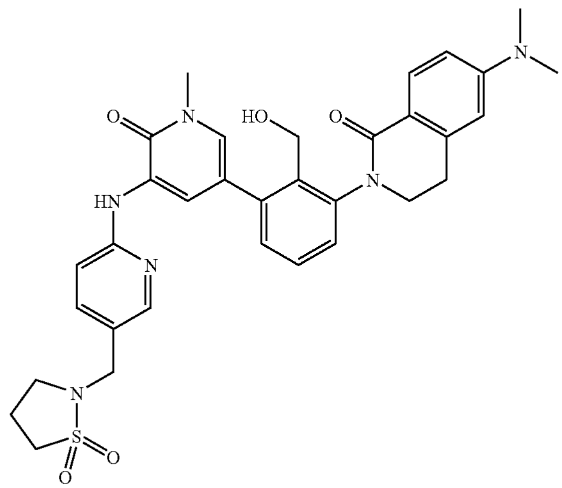 | 6-Dimethylamino-2-(3-{5-[5-(1,1-dioxo-1λ$^6$-isothiazolidin-2-ylmethyl)-pyridin-2-ylamino]-1-methyl-6-oxo-1,6-dihydro-pyridin-3-yl}-2-hydroxymethyl-phenyl)-3,4-dihydro-2H-isoquinolin-1-one | |
| I-52 | 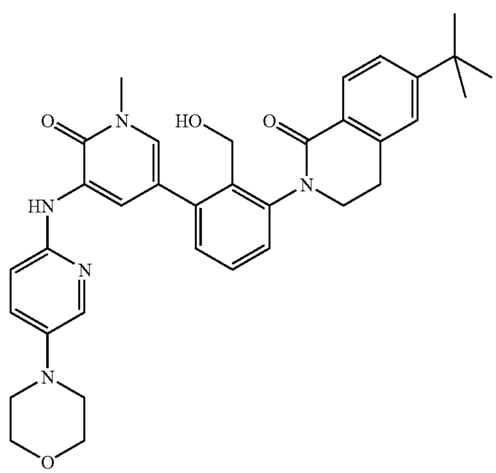 | 6-tert-Butyl-2-{2-hydroxymethyl-3-[1-methyl-5-(5-morpholin-4-yl-pyridin-2-ylamino)-6-oxo-1,6-dihydro-pyridin-3-yl]-phenyl}-3,4-dihydro-2H-isoquinolin-1-one | |
| I-53 | 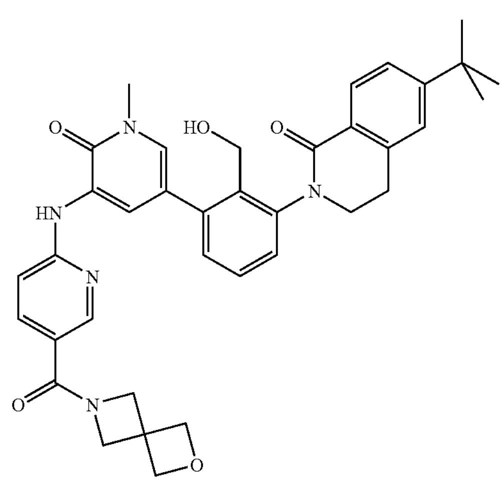 | 6-tert-Butyl-2-(2-hydroxymethyl-3-{1-methyl-5-[5-(2-oxa-6-aza-spiro[3.3]heptane-6-carbonyl)-pyridin-2-ylamino]-6-oxo-1,6-dihydro-pyridin-3-yl}-phenyl)-3,4-dihydro-2H-isoquinolin-1-one | |

TABLE I-continued

| Compound | Structure | Nomenclature | (M + H)+ |
|---|---|---|---|
| I-54 | 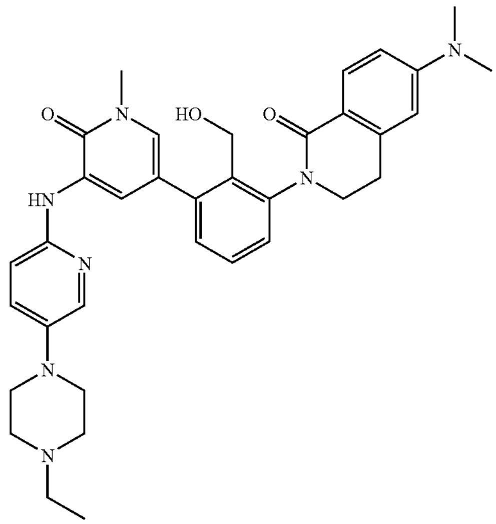 | 6-Dimethylamino-2-(3-{5-[5-(4-ethyl-piperazin-1-yl)-pyridin-2-ylamino]-1-methyl-6-oxo-1,6-dihydro-pyridin-3-yl}-2-hydroxymethyl-phenyl)-3,4-dihydro-2H-isoquinolin-1-one | |
| I-55 | 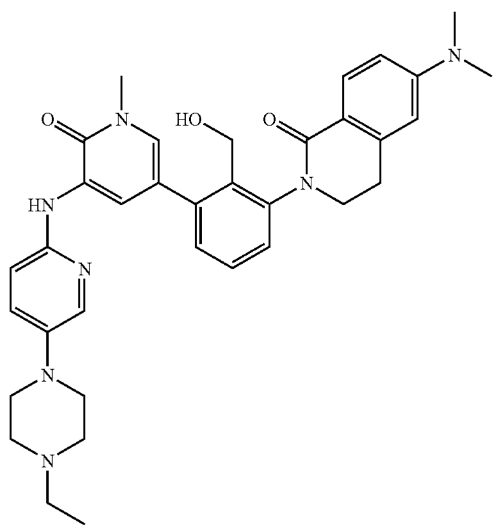 | 6-Dimethylamino-2-(3-{5-[5-(4-ethyl-piperazin-1-yl)-pyridin-2-ylamino]-1-methyl-6-oxo-1,6-dihydro-pyridin-3-yl}-2-hydroxymethyl-phenyl)-3,4-dihydro-2H-isoquinolin-1-one | |
| I-56 | 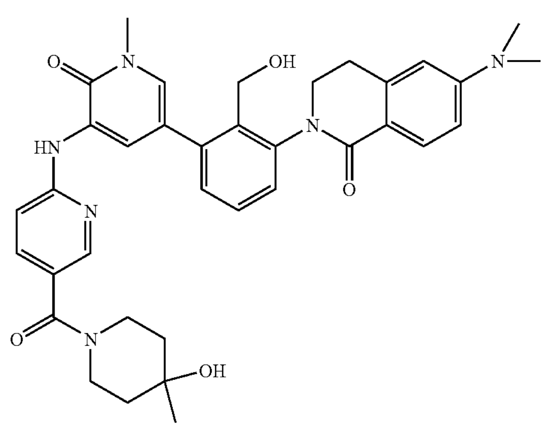 | 6-Dimethylamino-2-(2-hydroxymethyl-3-{5-[5-(4-hydroxy-4-methyl-piperidine-1-carbonyl)-pyridin-2-ylamino]-1-methyl-6-oxo-1,6-dihydro-pyridin-3-yl}-phenyl)-3,4-dihydro-2H-isoquinolin-1-one | |

TABLE I-continued

| Compound | Structure | Nomenclature | (M + H)+ |
|---|---|---|---|
| I-57 | 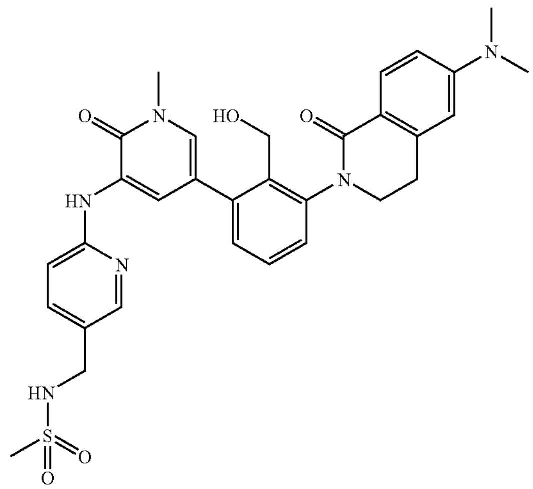 | N-(6-{5-[3-(6-Dimethylamino-1-oxo-3,4-dihydro-1H-isoquinolin-2-yl)-2-hydroxymethyl-phenyl]-1-methyl-2-oxo-1,2-dihydro-pyridin-3-ylamino}-pyridin-3-ylmethyl)-methanesulfonamide | |
| I-58 | 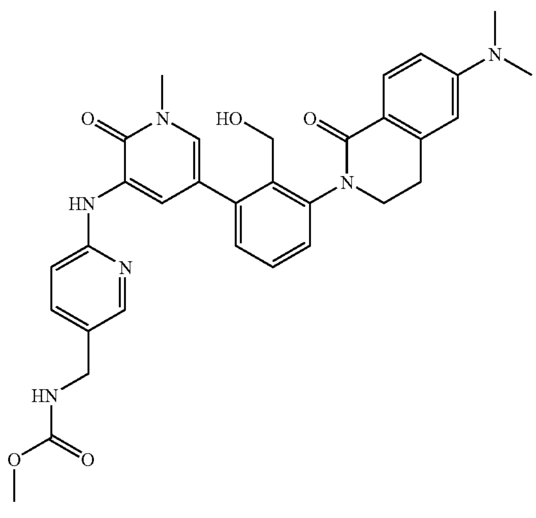 | (6-{5-[3-(6-Dimethylamino-1-oxo-3,4-dihydro-1H-isoquinolin-2-yl)-2-hydroxymethyl-phenyl]-1-methyl-2-oxo-1,2-dihydro-pyridin-3-ylamino}-pyridin-3-ylmethyl)-carbamic acid methyl ester | |
| I-59 | 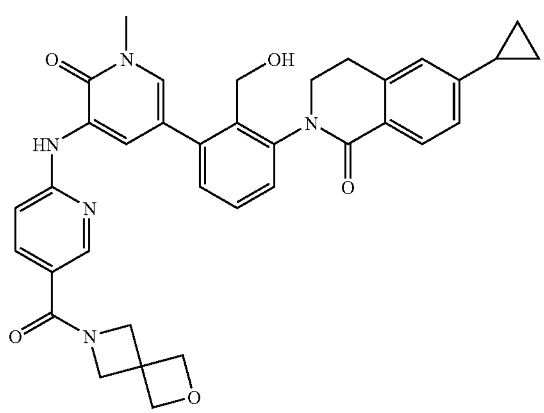 | 6-Cyclopropyl-2-(2-hydroxymethyl-3-{1-methyl-5-[5-(2-oxa-6-aza-spiro[3.3]heptane-6-carbonyl)-pyridin-2-ylamino]-6-oxo-1,6-dihydro-pyridin-3-yl}-phenyl)-3,4-dihydro-2H-isoquinolin-1-one | |

TABLE I-continued

| Compound | Structure | Nomenclature | (M + H)+ |
|---|---|---|---|
| I-60 | 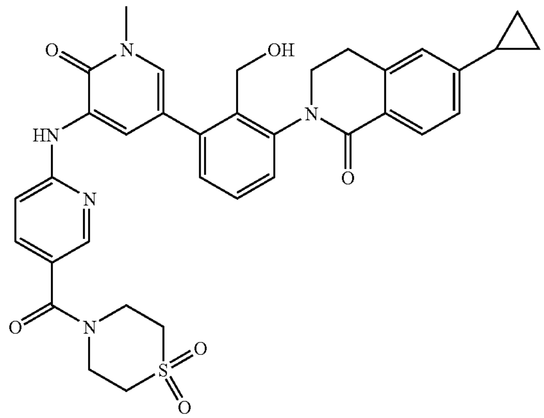 | 6-Cyclopropyl-2-(3-{5-[5-(1,1-dioxo-1λ6-thiomorpholine-4-carbonyl)-pyridin-2-ylamino]-1-methyl-6-oxo-1,6-dihydro-pyridin-3-yl}-2-hydroxymethyl-phenyl)-3,4-dihydro-2H-isoquinolin-1-one | |
| I-61 | 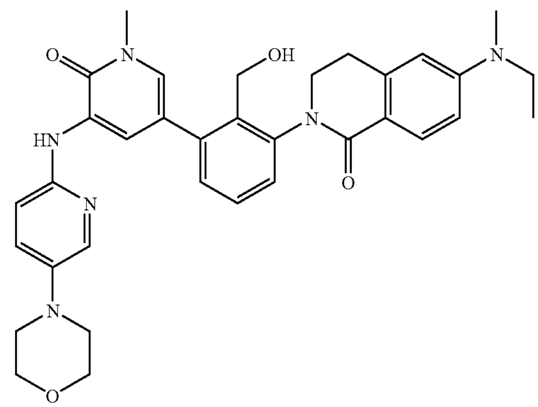 | 6-(Ethyl-methyl-amino)-2-{2-hydroxymethyl-3-[1-methyl-5-(5-morpholin-4-yl-pyridin-2-ylamino)-6-oxo-1,6-dihydro-pyridin-3-yl]-phenyl}-3,4-dihydro-2H-isoquinolin-1-one | |
| I-62 | 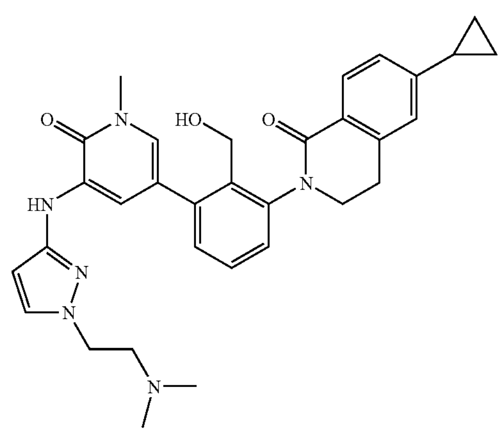 | 6-Cyclopropyl-2-(3-{5-[1-(2-dimethylamino-ethyl)-1H-pyrazol-3-ylamino]-1-methyl-6-oxo-1,6-dihydro-pyridin-3-yl}-2-hydroxymethyl-phenyl)-3,4-dihydro-2H-isoquinolin-1-one | |

TABLE I-continued

| Compound | Structure | Nomenclature | (M + H)+ |
|---|---|---|---|
| I-63 | 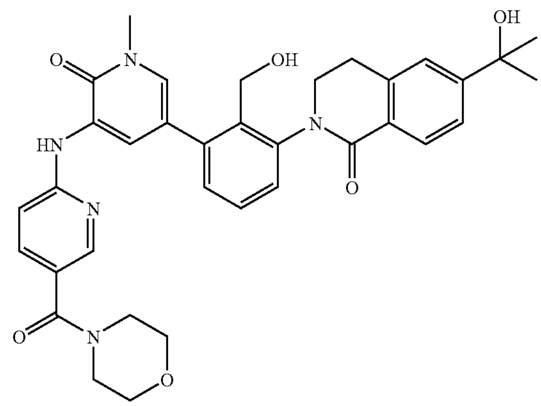 | 6-(1-Hydroxy-1-methyl-ethyl)-2-(2-hydroxymethyl-3-{1-methyl-5-[5-(morpholine-4-carbonyl)-pyridin-2-ylamino]-6-oxo-1,6-dihydro-pyridin-3-yl}-phenyl)-3,4-dihydro-2H-isoquinolin-1-one | |
| I-64 | 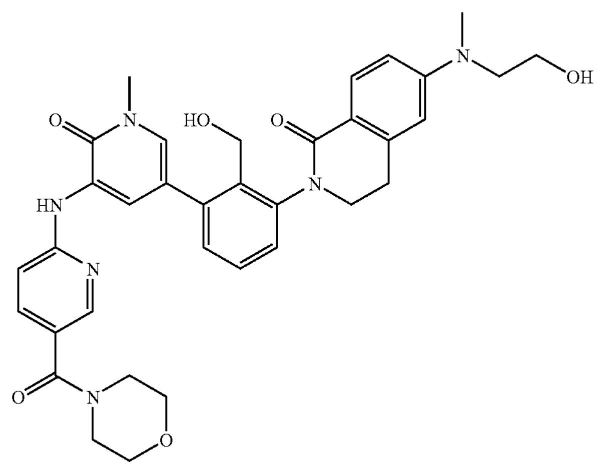 | 6-[(2-Hydroxy-ethyl)-methyl-amino]-2-(2-hydroxymethyl-3-{1-methyl-5-[5-(morpholine-4-carbonyl)-pyridin-2-ylamino]-6-oxo-1,6-dihydro-pyridin-3-yl}-phenyl)-3,4-dihydro-2H-isoquinolin-1-one | |
| I-65 | 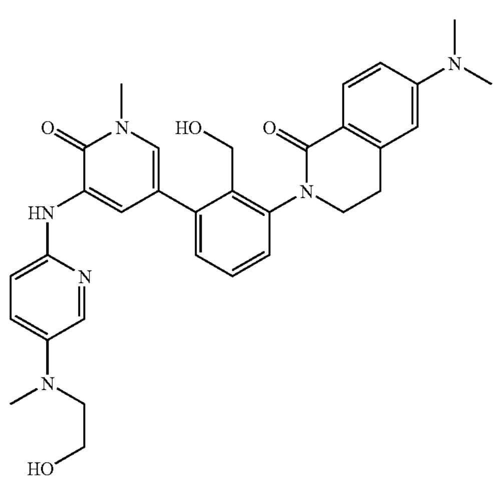 | 6-Dimethylamino-2-[3-(5-{5-[(2-hydroxy-ethyl)-methyl-amino]-pyridin-2-ylamino}-1-methyl-6-oxo-1,6-dihydro-pyridin-3-yl)-2-hydroxymethyl-phenyl]-3,4-dihydro-2H-isoquinolin-1-one | |

TABLE I-continued

| Compound | Structure | Nomenclature | (M + H)+ |
|---|---|---|---|
| I-66 | 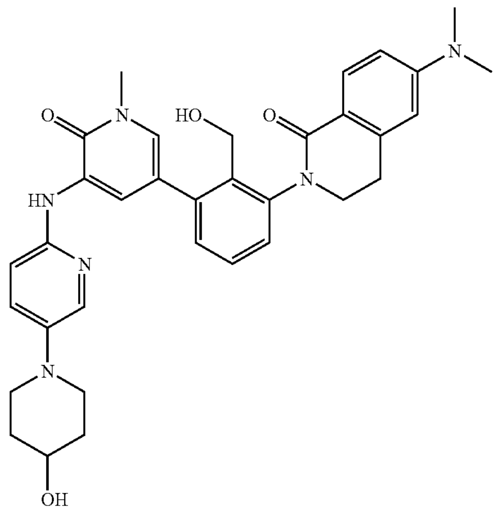 | 6-Dimethylamino-2-{2-hydroxymethyl-3-[5-(4-hydroxy-3,4,5,6-tetrahydro-2H-[1,3']bipyridinyl-6'-ylamino)-1-methyl-6-oxo-1,6-dihydro-pyridin-3-yl]-phenyl}-3,4-dihydro-2H-isoquinolin-1-one | |
| I-67 | 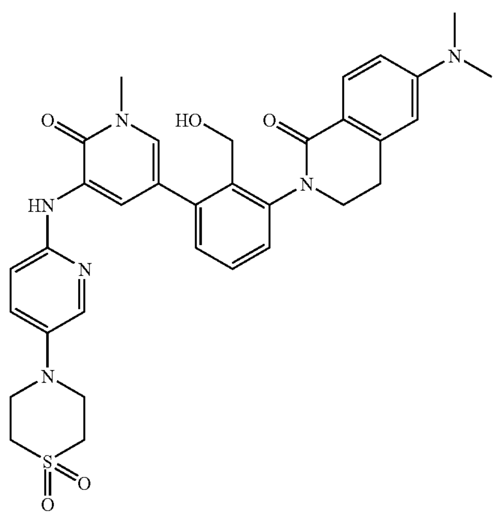 | 6-Dimethylamino-2-(3-{5-[5-(1,1-dioxo-1$\lambda^6$-thiomorpholin-4-yl)-pyridin-2-ylamino]-1-methyl-6-oxo-1,6-dihydro-pyridin-3-yl}-2-hydroxymethyl-phenyl)-3,4-dihydro-2H-isoquinolin-1-one | |
| I-68 | 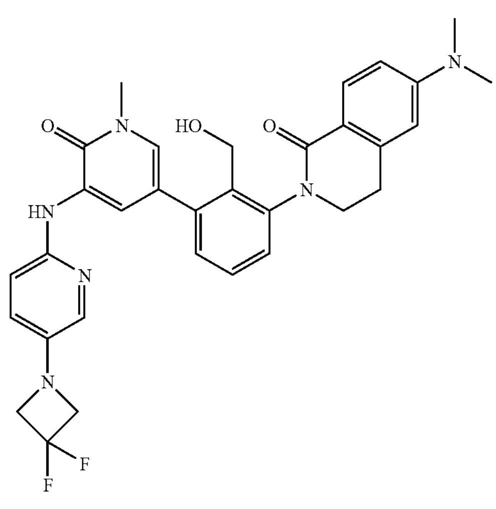 | 2-(3-{5-[5-(3,3-Difluoro-azetidin-1-yl)-pyridin-2-ylamino]-1-methyl-6-oxo-1,6-dihydro-pyridin-3-yl}-2-hydroxymethyl-phenyl)-6-dimethylamino-3,4-dihydro-2H-isoquinolin-1-one | |

TABLE I-continued

| Compound | Structure | Nomenclature | (M + H)⁺ |
|---|---|---|---|
| I-69 | 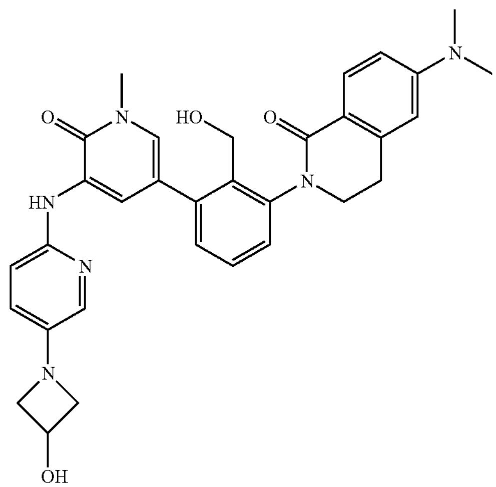 | 6-Dimethylamino-2-(3-{5-[5-(3-hydroxy-azetidin-1-yl)-pyridin-2-ylamino]-1-methyl-6-oxo-1,6-dihydro-pyridin-3-yl}-2-hydroxymethyl-phenyl)-3,4-dihydro-2H-isoquinolin-1-one | |
| I-70 | 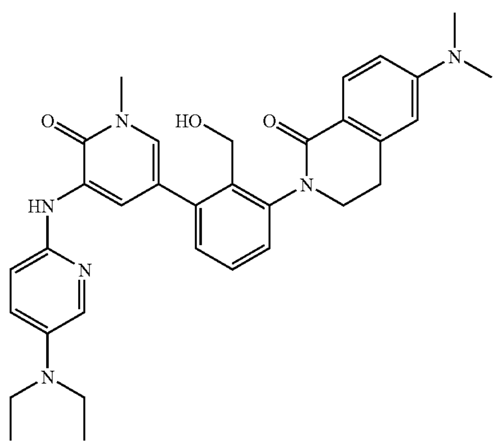 | 2-{3-[5-(5-Diethylamino-pyridin-2-ylamino)-1-methyl-6-oxo-1,6-dihydro-pyridin-3-yl]-2-hydroxymethyl-phenyl}-6-dimethylamino-3,4-dihydro-2H-isoquinolin-1-one | |
| I-71 | 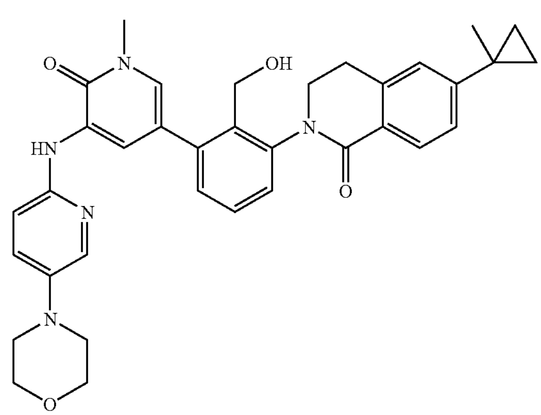 | 2-{2-Hydroxymethyl-3-[1-methyl-5-(5-morpholin-4-yl-pyridin-2-ylamino)-6-oxo-1,6-dihydro-pyridin-3-yl]-phenyl}-6-(1-methyl-cyclopropyl)-3,4-dihydro-2H-isoquinolin-1-one | |

TABLE I-continued

| Compound | Structure | Nomenclature | (M + H)+ |
|---|---|---|---|
| I-72 | 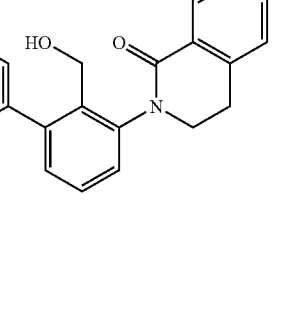 | 2-{3-[5-(4,4-Difluoro-3,4,5,6-tetrahydro-2H-[1,3']bipyridinyl-6'-3,4,5,6-tetrahydro-2H-ylamino)-1-methyl-6-oxo-1,6-dihydro-pyridin-3-yl]-2-hydroxymethyl-phenyl}-6-dimethylamino-3,4-dihydro-2H-isoquinolin-1-one | |
| I-73 | 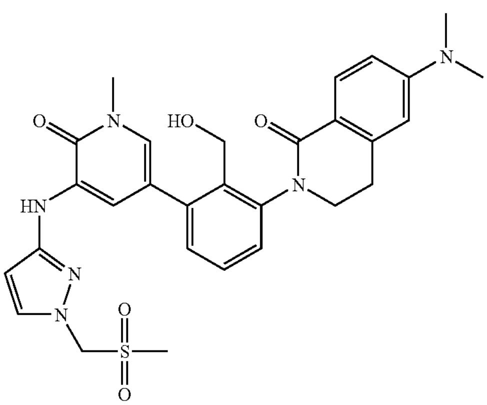 | 6-Dimethylamino-2-{2-hydroxymethyl-3-[5-(1-methanesulfonylmethyl-1H-pyrazol-3-ylamino)-1-methyl-6-oxo-1,6-dihydro-pyridin-3-yl]-phenyl}-3,4-dihydro-2H-isoquinolin-1-one | |
| I-74 | 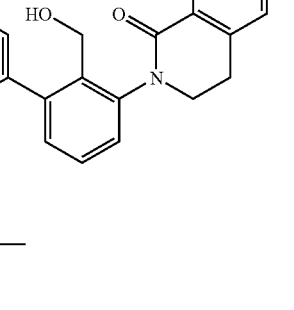 | 6-Dimethylamino-2-{2-hydroxymethyl-3-[1-methyl-6-oxo-5-(2-propyl-2H-[1,2,3]triazol-4-ylamino)-1,6-dihydro-pyridin-3-yl]-phenyl}-3,4-dihydro-2H-isoquinolin-1-one | |

TABLE I-continued

| Compound | Structure | Nomenclature | (M + H)+ |
|---|---|---|---|
| I-75 | 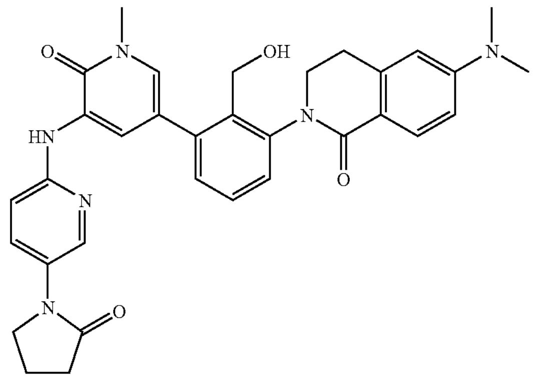 | 6-Dimethylamino-2-(2-hydroxymethyl-3-{1-methyl-6-oxo-5-[5-(2-oxo-pyrrolidin-1-yl)-pyridin-2-ylamino]-1,6-dihydro-pyridin-3-yl}-phenyl)-3,4-dihydro-2H-isoquinolin-1-one | |
| I-76 | 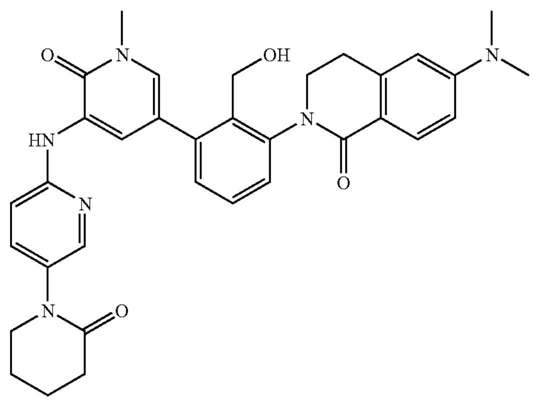 | 6'-{5-[3-(6-Dimethylamino-1-oxo-3,4-dihydro-1H-isoquinolin-2-yl)-2-hydroxymethyl-phenyl]-1-methyl-2-oxo-1,2-dihydro-pyridin-3-ylamino}-3,4,5,6-tetrahydro-[1,3']bipyridinyl-2-one | |
| I-77 | 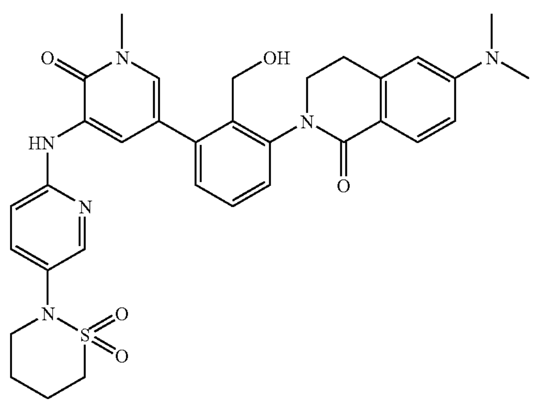 | 6-Dimethylamino-2-(3-{5-[5-(1,1-dioxo-1λ6-[1,2]thiazinan-2-yl)-pyridin-2-ylamino]-1-methyl-6-oxo-1,6-dihydro-pyridin-3-yl}-2-hydroxymethyl-phenyl)-3,4-dihydro-2H-isoquinolin-1-one | |
| I-78 | 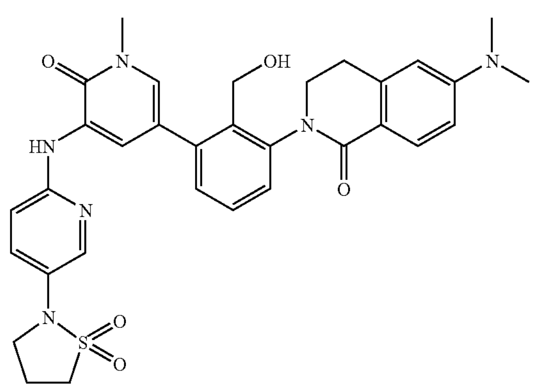 | 6-Dimethylamino-2-(3-{5-[5-(1,1-dioxo-1λ6-isothiazolidin-2-yl)-pyridin-2-ylamino]-1-methyl-6-oxo-1,6-dihydro-pyridin-3-yl}-2-hydroxymethyl-phenyl)-3,4-dihydro-2H-isoquinolin-1-one | |

TABLE I-continued

| Compound | Structure | Nomenclature | (M + H)+ |
|---|---|---|---|
| I-79 | 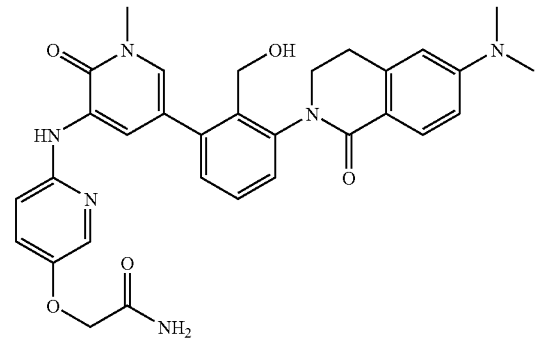 | 2-(6-{5-[3-(6-Dimethylamino-1-oxo-3,4-dihydro-1H-isoquinolin-2-yl)-2-hydroxymethyl-phenyl]-1-methyl-2-oxo-1,2-dihydro-pyridin-3-ylamino}-pyridin-3-yloxy)-acetamide | |
| I-80 | 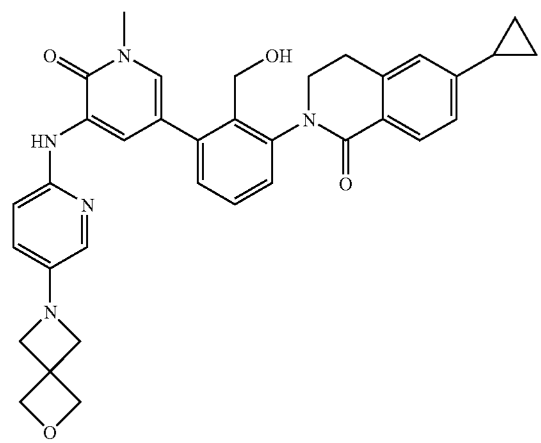 | 6-Cyclopropyl-2-(2-hydroxymethyl-3-{1-methyl-5-[2-(2-oxa-6-aza-spiro[3.3]hept-6-yl)-pyridin-2-ylamino]-6-oxo-1,6-dihydro-pyridin-3-yl}-phenyl)-3,4-dihydro-2H-isoquinolin-1-one | |
| I-81 | 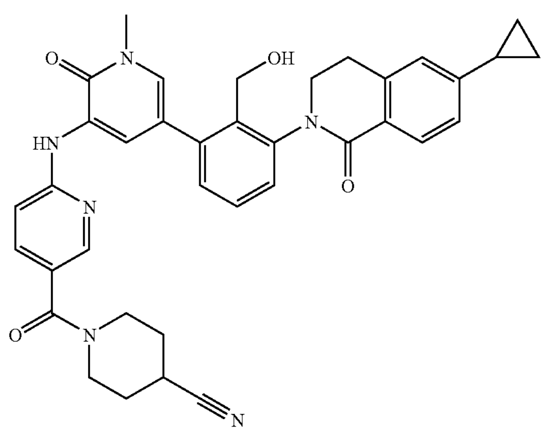 | 1-(6-{5-[3-(6-Cyclopropyl-1-oxo-3,4-dihydro-1H-isoquinolin-2-yl)-2-hydroxymethyl-phenyl]-1-methyl-2-oxo-1,2-dihydro-pyridin-3-ylamino}-pyridine-3-carbonyl)-piperidine-4-carbonitrile | |

TABLE I-continued

| Compound | Structure | Nomenclature | (M + H)+ |
|---|---|---|---|
| I-82 | 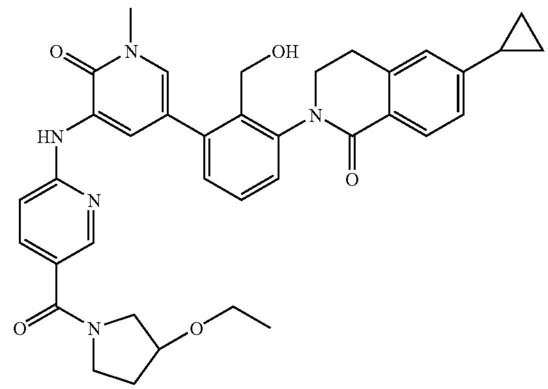 | 6-Cyclopropyl-2-(3-{5-[5-(3-ethoxy-pyrrolidine-1-carbonyl)-pyridin-2-ylamino]-1-methyl-6-oxo-1,6-dihydro-pyridin-3-yl}-2-hydroxymethyl-phenyl)-3,4-dihydro-2H-isoquinolin-1-one | |
| I-83 | 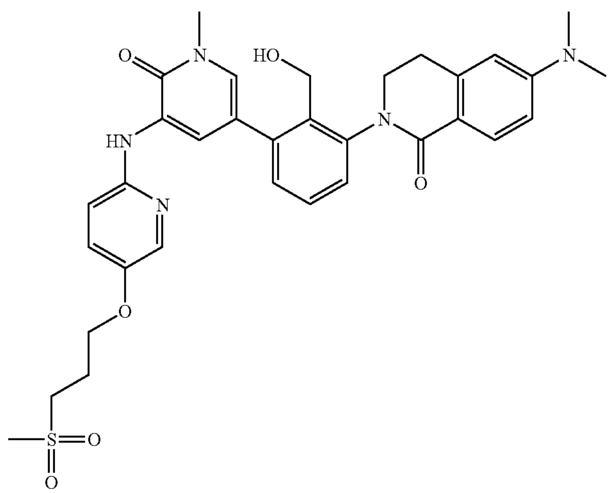 | 6-Dimethylamino-2-(2-hydroxymethyl-3-{5-[5-(3-methanesulfonyl-propoxy)-pyridin-2-ylamino]-1-methyl-6-oxo-1,6-dihydro-pyridin-3-yl}-phenyl)-3,4-dihydro-2H-isoquinolin-1-one | |
| I-84 | 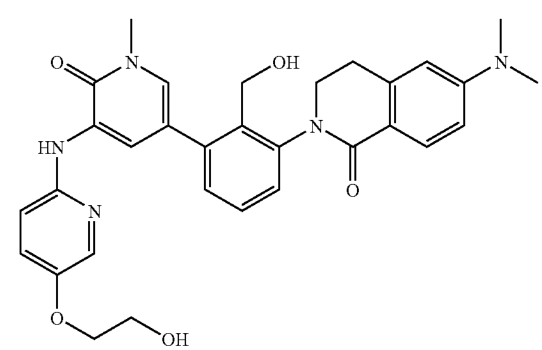 | 6-Dimethylamino-2-(3-{5-[5-(2-hydroxy-ethoxy)-pyridin-2-ylamino]-1-methyl-6-oxo-1,6-dihydro-pyridin-3-yl}-2-hydroxymethyl-phenyl)-3,4-dihydro-2H-isoquinolin-1-one | |

TABLE I-continued

| Compound | Structure | Nomenclature | (M + H)+ |
|---|---|---|---|
| I-85 | 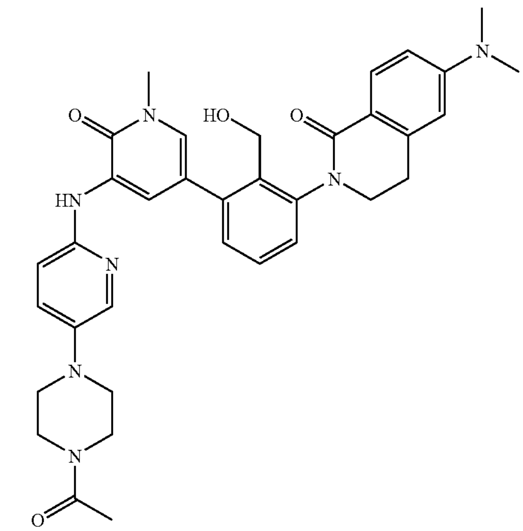 | 2-(3-{5-[5-(4-Acetyl-piperazin-1-yl)-pyridin-2-ylamino]-1-methyl-6-oxo-1,6-dihydro-pyridin-3-yl}-2-hydroxymethyl-phenyl)-6-dimethylamino-3,4-dihydro-2H-isoquinolin-1-one | |
| I-86 | 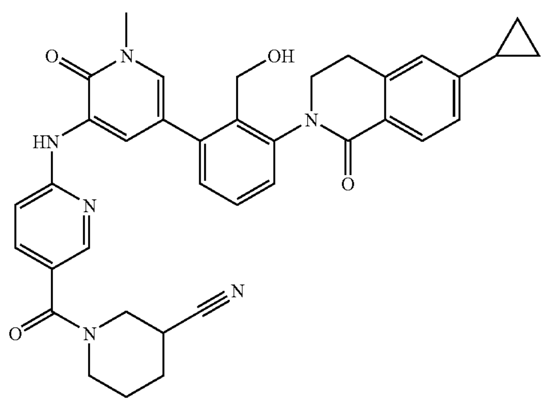 | 1-(6-{5-[3-(6-Cyclopropyl-1-oxo-3,4-dihydro-1H-isoquinolin-2-yl)-2-hydroxymethyl-phenyl]-1-methyl-2-oxo-1,2-dihydro-pyridin-3-ylamino}-pyridine-3-carbonyl)-piperidine-3-carbonitrile | |
| I-87 | 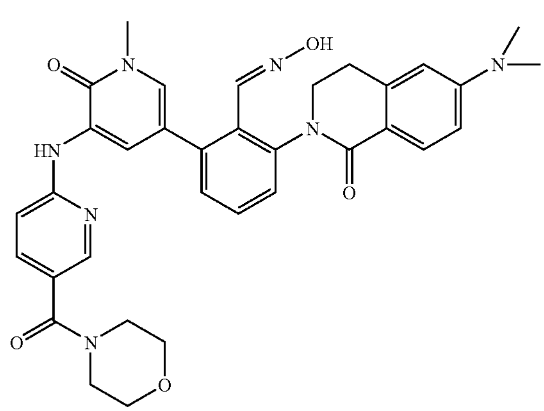 | 2-(2-acetaldehyde oxime-3-{1-methyl-5-[5-(morpholine-4-carbonyl)-pyridin-2-ylamino]-6-oxo-1,6-dihydro-pyridin-3-yl}-phenyl)-6-dimethylamino-3,4-dihydro-2H-isoquinolin-1-one | |

TABLE I-continued

| Compound | Structure | Nomenclature | (M + H)+ |
|---|---|---|---|
| I-88 | 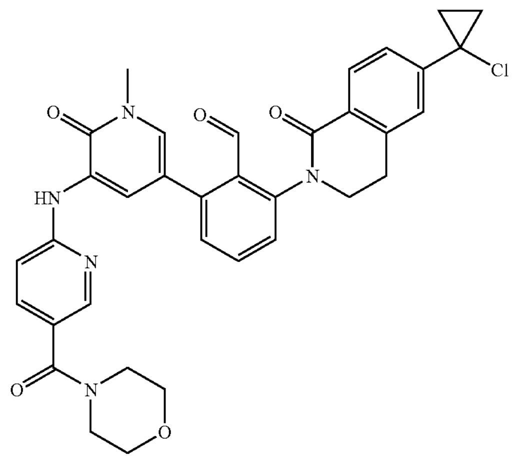 | 2-[6-(1-Chloro-cyclopropyl)-1-oxo-3,4-dihydro-1H-isoquinolin-2-yl]-6-{1-methyl-5-[5-(morpholine-4-carbonyl)-pyridin-2-ylamino]-6-oxo-1,6-dihydro-pyridin-3-yl}-benzaldehyde | |
| I-89 | 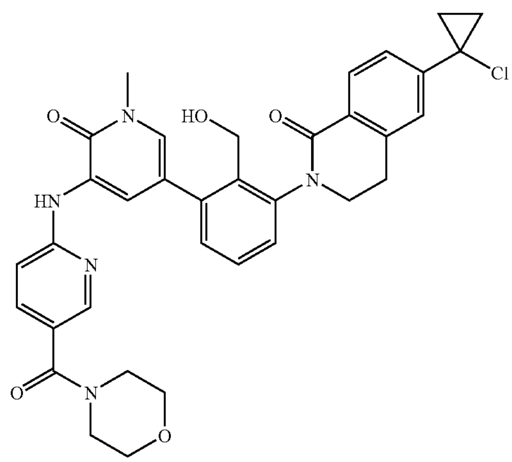 | 6-(1-Chloro-cyclopropyl)-2-(2-hydroxymethyl-3-{1-methyl-5-[5-(morpholine-4-carbonyl)-pyridin-2-ylamino]-6-oxo-1,6-dihydro-pyridin-3-yl}-phenyl)-3,4-dihydro-2H-isoquinolin-1-one | |
| I-90 | 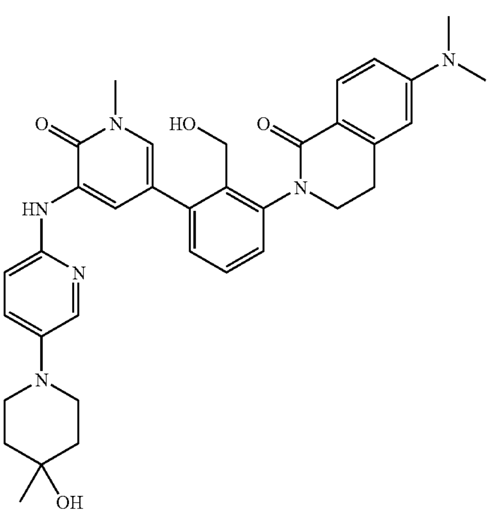 | 6-Dimethylamino-2-{2-hydroxymethyl-3-[5-(4-hydroxy-4-methyl-3,4,5,6-tetrahydro-2H-[1,3']bipyridinyl-6'-ylamino)-1-methyl-6-oxo-1,6-dihydro-pyridin-3-yl]-phenyl}-3,4-dihydro-2H-isoquinolin-1-one | |

TABLE I-continued

| Compound | Structure | Nomenclature | (M + H)+ |
|---|---|---|---|
| I-91 | 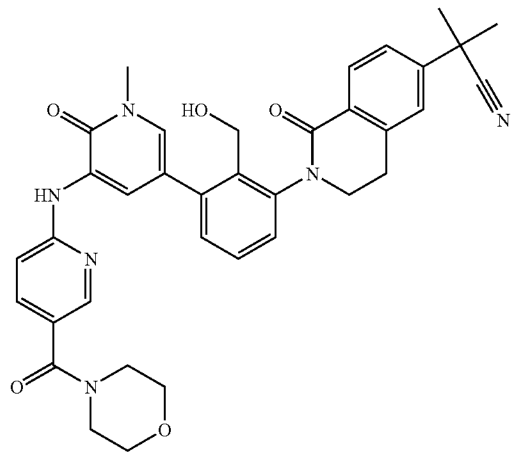 | 2-[2-(2-Hydroxymethyl-3-{1-methyl-5-[5-(morpholine-4-carbonyl)-pyridin-2-ylamino]-6-oxo-1,6-dihydro-pyridin-3-yl}-phenyl)-1-oxo-1,2,3,4-tetrahydro-isoquinolin-6-yl]-2-methyl-propionitrile | |
| I-92 | 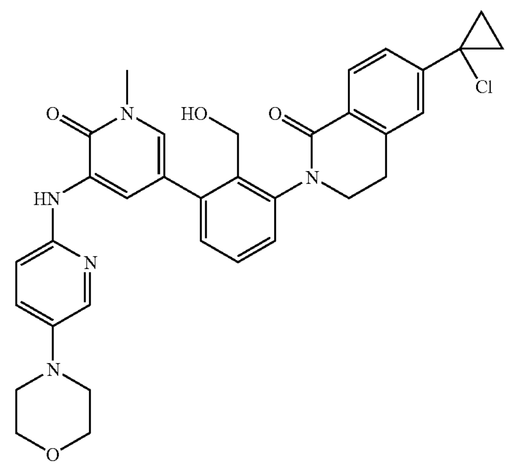 | 6-(1-Chloro-cyclopropyl)-2-{2-hydroxymethyl-3-[1-methyl-5-(5-morpholin-4-yl-pyridin-2-ylamino)-6-oxo-1,6-dihydro-pyridin-3-yl]-phenyl}-3,4-dihydro-2H-isoquinolin-1-one | |
| I-93 | 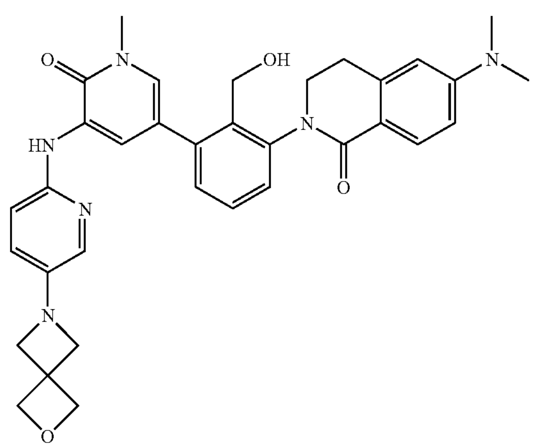 | 6-Dimethylamino-2-(2-hydroxymethyl-3-{1-methyl-5-[5-(2-oxa-6-aza-spiro[3.3]hept-6-yl)-pyridin-3-ylamino]-6-oxo-1,6-dihydro-pyridin-3-yl}-phenyl)-3,4-dihydro-2H-isoquinolin-1-one | |

TABLE I-continued

| Compound | Structure | Nomenclature | (M + H)+ |
|---|---|---|---|
| I-94 | 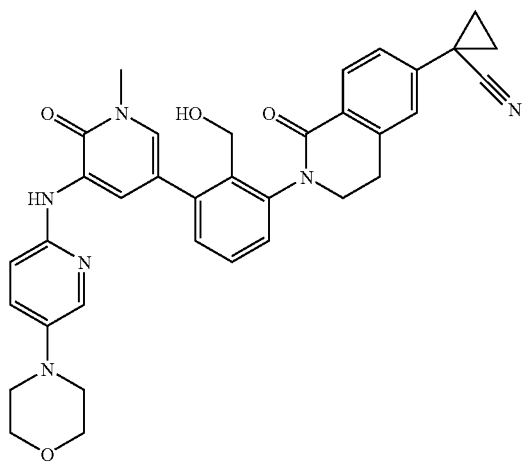 | 1-(2-{2-Hydroxymethyl-3-[1-methyl-5-(5-morpholin-4-yl-pyridin-2-ylamino)-6-oxo-1,6-dihydro-pyridin-3-yl]-phenyl}-1-oxo-1,2,3,4-tetrahydro-isoquinolin-6-yl)-cyclopropanecarbonitrile | |
| I-95 | 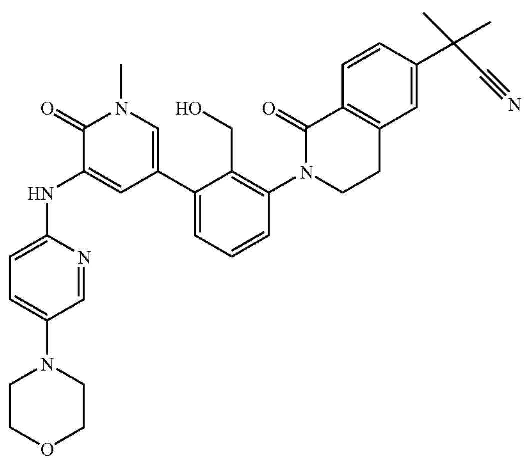 | 2-(2-{2-Hydroxymethyl-3-[1-methyl-5-(5-morpholin-4-yl-pyridin-2-ylamino)-6-oxo-1,6-dihydro-pyridin-3-yl]-phenyl}-1-oxo-1,2,3,4-tetrahydro-isoquinolin-6-yl)-2-methyl-propionitrile | |
| I-96 | 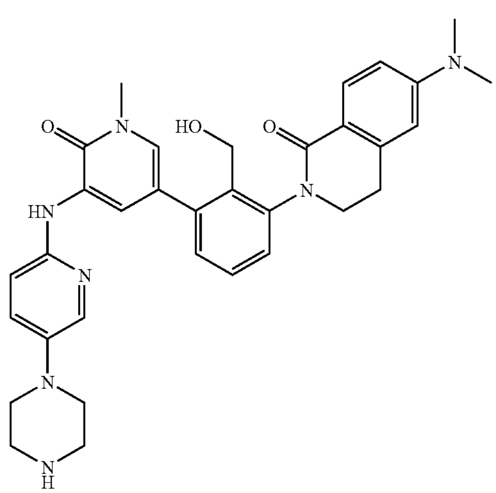 | 6-Dimethylamino-2-{2-hydroxymethyl-3-[1-methyl-6-oxo-5-(5-piperazin-1-yl-pyridin-2-ylamino)-1,6-dihydro-pyridin-3-yl]-phenyl}-3,4-dihydro-2H-isoquinolin-1-one | |

TABLE I-continued

| Compound | Structure | Nomenclature | (M + H)+ |
|---|---|---|---|
| I-97 | 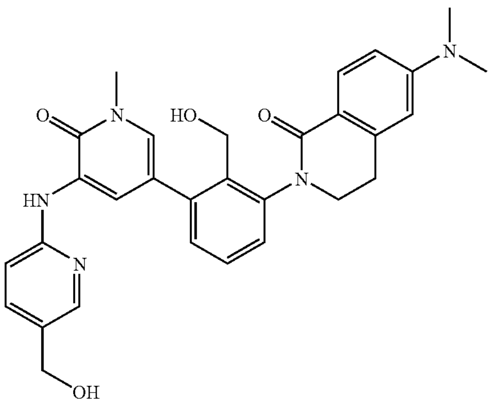 | 6-Dimethylamino-2-{2-hydroxymethyl-3-[5-(5-hydroxymethyl-pyridin-2-ylamino)-1-methyl-6-oxo-1,6-dihydro-pyridin-3-yl]-phenyl}-3,4-dihydro-2H-isoquinolin-1-one | |
| I-98 | 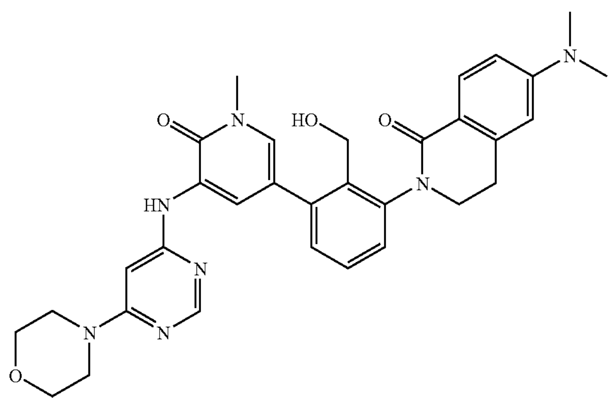 | 6-Dimethylamino-2-{2-hydroxymethyl-3-[1-methyl-5-(6-morpholin-4-yl-pyrimidin-4-ylamino)-6-oxo-1,6-dihydro-pyridin-3-yl]-phenyl}-3,4-dihydro-2H-isoquinolin-1-one | |
| I-99 | 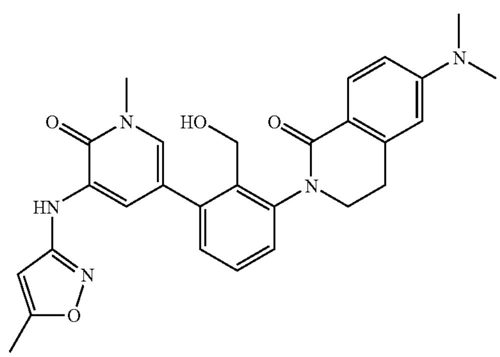 | 6-Dimethylamino-2-{2-hydroxymethyl-3-[1-methyl-5-(5-methyl-isoxazol-3-ylamino)-6-oxo-1,6-dihydro-pyridin-3-yl]-phenyl}-3,4-dihydro-2H-isoquinolin-1-one | |
| I-100 | 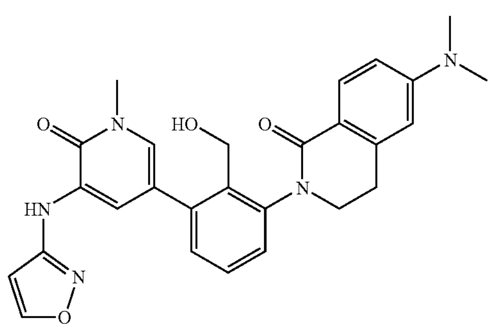 | 6-Dimethylamino-2-{2-hydroxymethyl-3-[5-(isoxazol-3-ylamino)-1-methyl-6-oxo-1,6-dihydro-pyridin-3-yl]-phenyl}-3,4-dihydro-2H-isoquinolin-1-one | |

TABLE I-continued

| Compound | Structure | Nomenclature | (M + H)+ |
|---|---|---|---|
| I-101 | 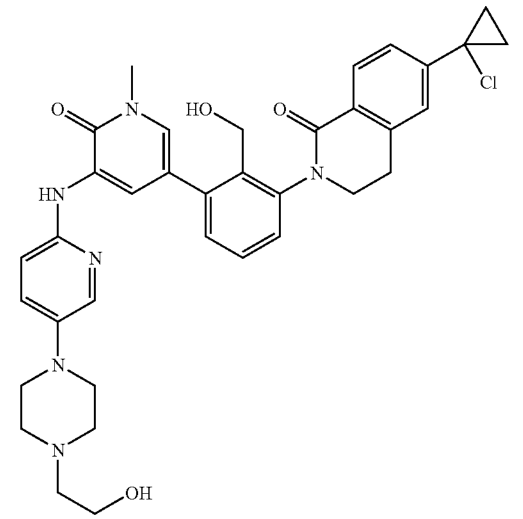 | 6-(1-Chloro-cyclopropyl)-2-[3-(5-{5-[4-(2-hydroxy-ethyl)-piperazin-1-yl]-pyridin-2-ylamino}-1-methyl-6-oxo-1,6-dihydro-pyridin-3-yl)-2-hydroxymethyl-phenyl]-3,4-dihydro-2H-isoquinolin-1-one | |
| I-102 | 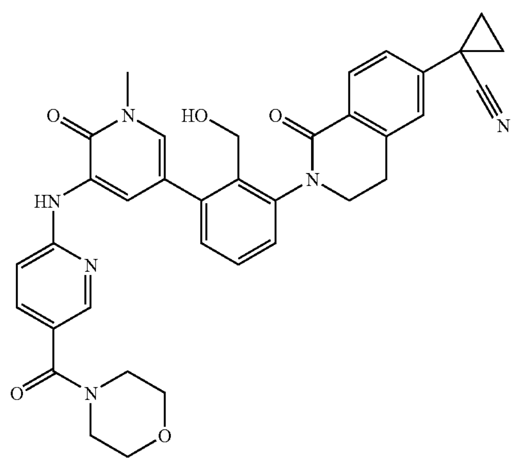 | 1-[2-(2-Hydroxymethyl-3-{1-methyl-5-[5-(morpholine-4-carbonyl)-pyridin-2-ylamino]-6-oxo-1,6-dihydro-pyridin-3-yl}-phenyl)-1-oxo-1,2,3,4-tetrahydro-isoquinolin-6-yl]-cyclopropanecarbonitrile | |
| I-103 | 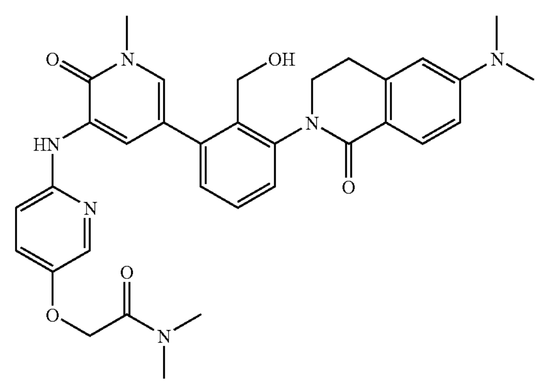 | 2-(6-{5-[3-(6-Dimethylamino-1-oxo-3,4-dihydro-1H-isoquinolin-2-yl)-2-hydroxymethyl-phenyl]-1-methyl-2-oxo-1,2-dihydro-pyridin-3-ylamino}-pyridin-3-yloxy)-N,N-dimethyl-acetamide | |

TABLE I-continued

| Compound | Structure | Nomenclature | (M + H)+ |
|---|---|---|---|
| I-104 | 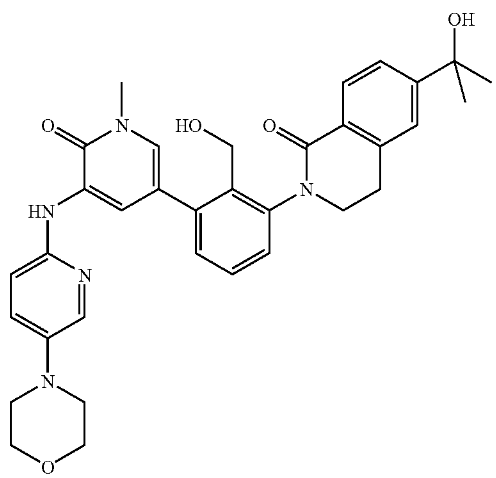 | 6-(1-Hydroxy-1-methyl-ethyl)-2-{2-hydroxymethyl-3-[1-methyl-5-(5-morpholin-4-yl-pyridin-2-ylamino)-6-oxo-1,6-dihydro-pyridin-3-yl]-phenyl}-3,4-dihydro-2H-isoquinolin-1-one | |
| I-105 | 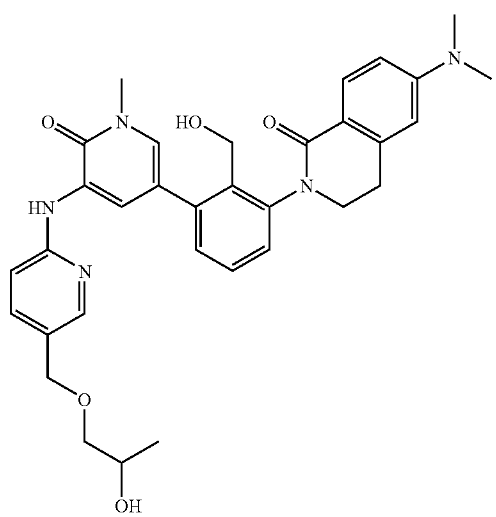 | 6-Dimethylamino-2-(2-hydroxymethyl-3-{5-[5-(2-hydroxy-propoxymethyl)-pyridin-2-ylamino]-1-methyl-6-oxo-1,6-dihydro-pyridin-3-yl}-phenyl)-3,4-dihydro-2H-isoquinolin-1-one | |
| I-106 | 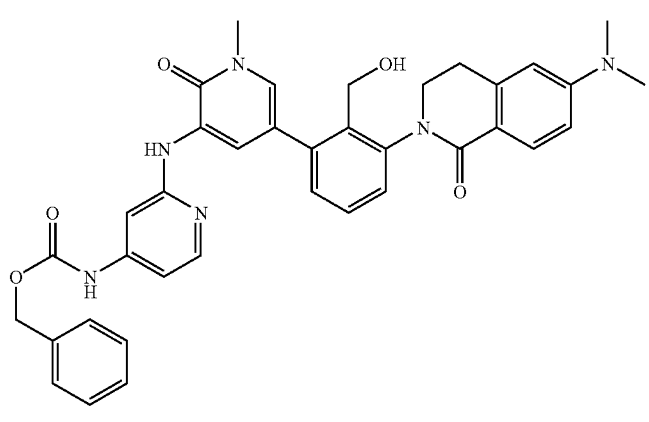 | (2-{5-[3-(6-Dimethylamino-1-oxo-3,4-dihydro-1H-isoquinolin-2-yl)-2-hydroxymethyl-phenyl]-1-methyl-2-oxo-1,2-dihydro-pyridin-3-ylamino}-pyridin-4-yl)-carbamic acid benzyl ester | |

TABLE I-continued

| Compound | Structure | Nomenclature | (M + H)+ |
|---|---|---|---|
| I-107 | 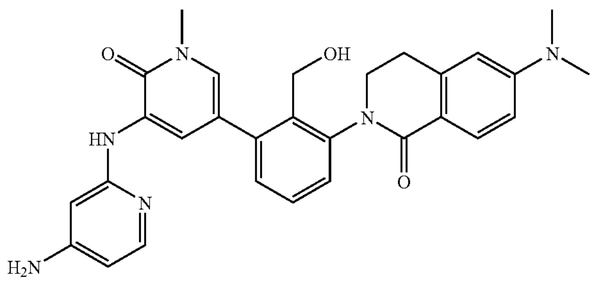 | 2-{3-[5-(4-Amino-pyridin-2-ylamino)-1-methyl-6-oxo-1,6-dihydro-pyridin-3-yl]-2-hydroxymethyl-phenyl}-6-dimethylamino-3,4-dihydro-2H-isoquinolin-1-one | |
| I-108 | 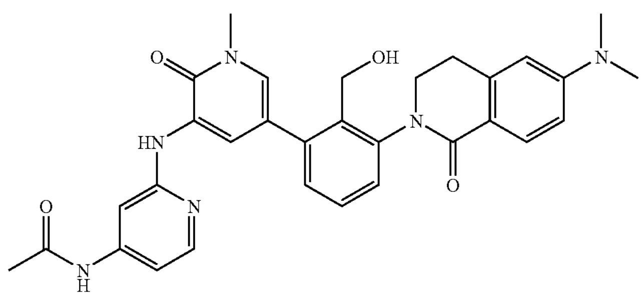 | N-(2-{5-[3-(6-Dimethylamino-1-oxo-3,4-dihydro-1H-isoquinolin-2-yl)-2-hydroxymethyl-phenyl]-1-methyl-2-oxo-1,2-dihydro-pyridin-3-ylamino}-pyridin-4-yl)-acetamide | |
| I-109 | 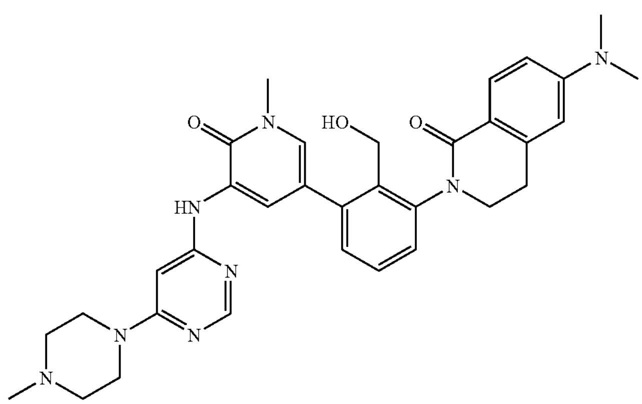 | 6-Dimethylamino-2-(2-hydroxymethyl-3-{1-methyl-5-[6-(4-methyl-piperazin-1-yl)-pyrimidin-4-ylamino]-6-oxo-1,6-dihydro-pyridin-3-yl}-phenyl)-3,4-dihydro-2H-isoquinolin-1-one | |
| I-110 | 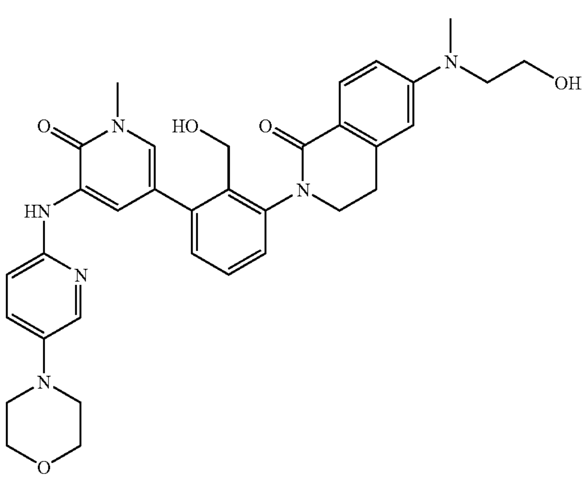 | 6-[(2-Hydroxy-ethyl)-methyl-amino]-2-{2-hydroxymethyl-3-[1-methyl-5-(5-morpholin-4-yl-pyridin-2-ylamino)-6-oxo-1,6-dihydro-pyridin-3-yl]-phenyl}-3,4-dihydro-2H-isoquinolin-1-one | |

TABLE I-continued

| Compound | Structure | Nomenclature | (M + H)+ |
|---|---|---|---|
| I-111 | 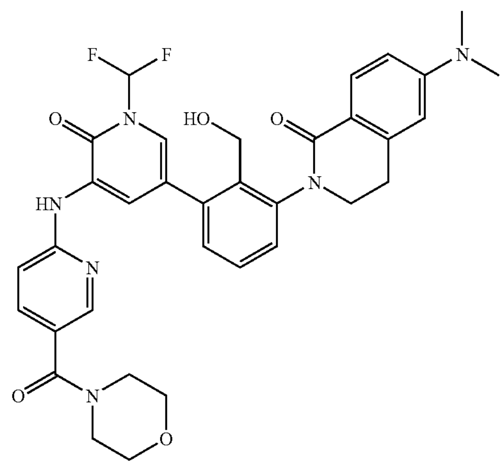 | 2-(3-{1-Difluoromethyl-5-[5-(morpholine-4-carbonyl)-pyridin-2-ylamino]-6-oxo-1,6-dihydro-pyridin-3-yl}-2-hydroxymethyl-phenyl)-6-dimethylamino-3,4-dihydro-2H-isoquinolin-1-one | |
| I-112 | 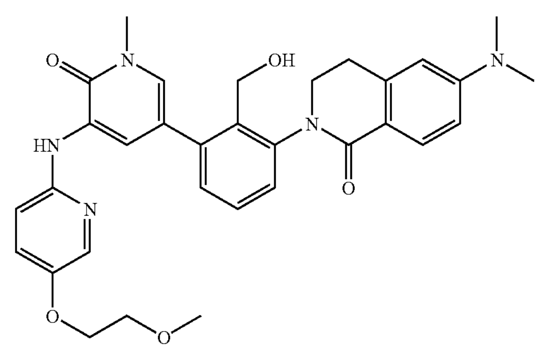 | 6-Dimethylamino-2-(2-hydroxymethyl-3-{5-[5-(2-methoxy-ethoxy)-pyridin-2-ylamino]-1-methyl-6-oxo-1,6-dihydro-pyridin-3-yl}-phenyl)-3,4-dihydro-2H-isoquinolin-1-one | |
| I-113 | 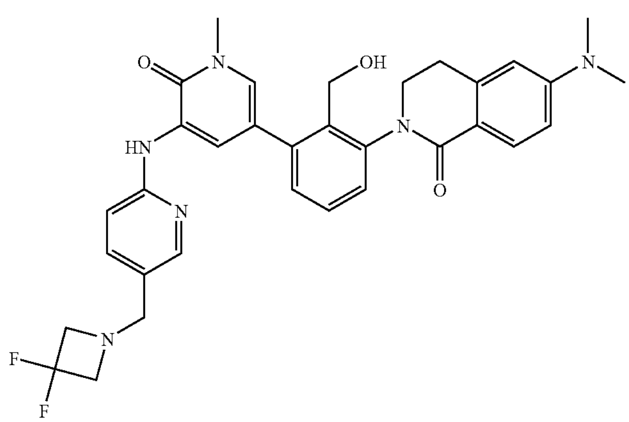 | 2-(3-{5-[5-(3,3-Difluoro-azetidin-1-ylmethyl)-pyridin-2-ylamino]-1-methyl-6-oxo-1,6-dihydro-pyridin-3-yl}-2-hydroxymethyl-phenyl)-6-dimethylamino-3,4-dihydro-2H-isoquinolin-1-one | |

TABLE I-continued

| Compound | Structure | Nomenclature | (M + H)+ |
|---|---|---|---|
| I-114 | 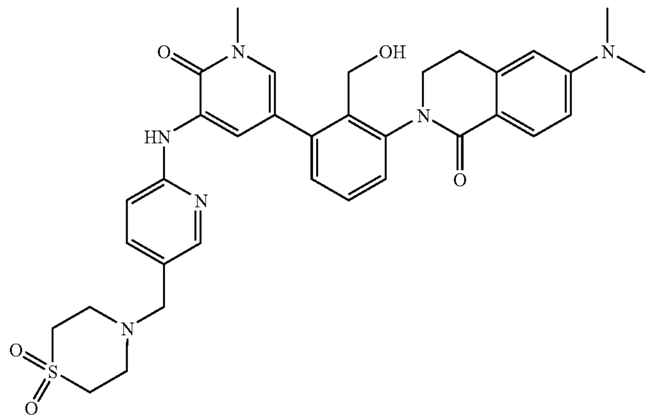 | 6-Dimethylamino-2-(3-{5-[5-(1,1-dioxo-1$\lambda^6$-thiomorpholin-4-ylmethyl)-pyridin-2-ylamino]-1-methyl-6-oxo-1,6-dihydro-pyridin-3-yl}-2-hydroxymethyl-phenyl)-3,4-dihydro-2H-isoquinolin-1-one | |
| I-115 | 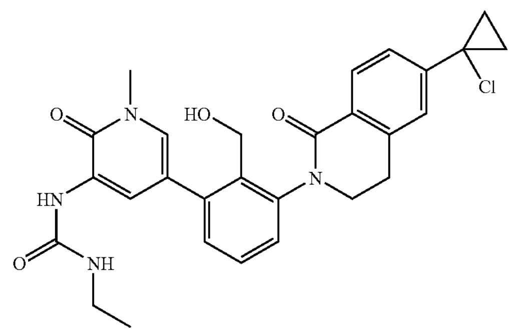 | 1-(5-{3-[6-(1-Chloro-cyclopropyl)-1-oxo-3,4-dihydro-1H-isoquinolin-2-yl]-2-hydroxymethyl-phenyl}-1-methyl-2-oxo-1,2-dihydro-pyridin-3-yl)-3-ethyl-urea | |
| I-116 | 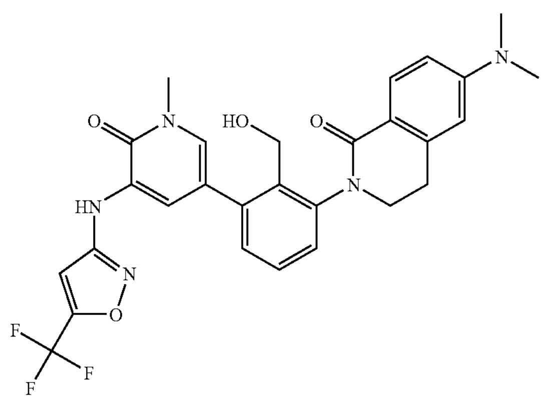 | 6-Dimethylamino-2-{2-hydroxymethyl-3-[1-methyl-6-oxo-5-(5-trifluoromethyl-isoxazol-3-ylamino)-1,6-dihydro-pyridin-3-yl]-phenyl}-3,4-dihydro-2H-isoquinolin-1-one | |
| I-117 | 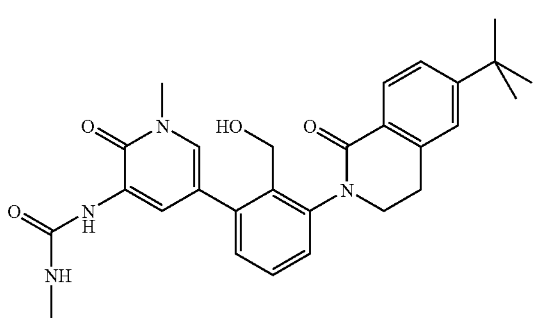 | 1-{5-[3-(6-tert-Butyl-1-oxo-3,4-dihydro-1H-isoquinolin-2-yl)-2-hydroxymethyl-phenyl]-1-methyl-2-oxo-1,2-dihydro-pyrindin-3-yl}-3-methyl-urea | |

TABLE I-continued

| Compound | Structure | Nomenclature | (M + H)+ |
|---|---|---|---|
| I-118 | 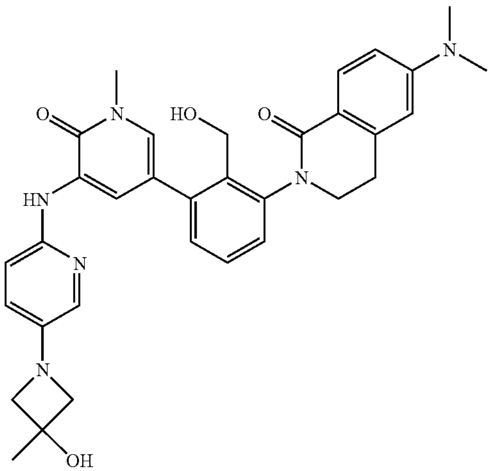 | 6-Dimethylamino-2-(2-hydroxymethyl-3-{5-[5-(3-hydroxy-3-methyl-azetidin-1-yl)-pyridin-2-ylamino]-1-methyl-6-oxo-1,6-dihydro-pyridin-3-yl}-phenyl)-3,4-dihydro-2H-isoquinolin-1-one | |
| I-119 | 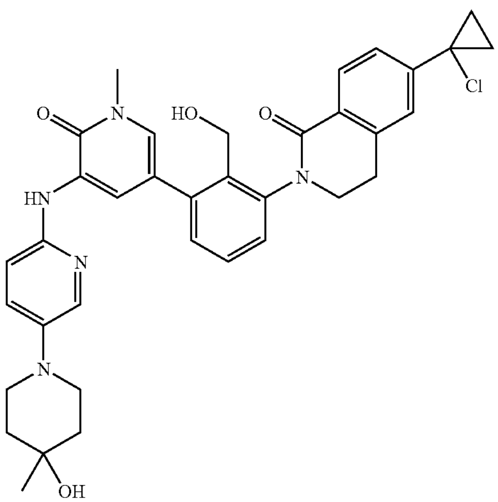 | 6-(1-Chloro-cyclopropyl)-2-{2-hydroxymethyl-3-[5-(4-hydroxy-4-methyl-3,4,5,6-tetrahydro-2H-[1,3']bipyridinyl-6'-ylamino)-1-methyl-6-oxo-1,6-dihydro-pyridin-3-yl]-phenyl}-3,4-dihydro-2H-isoquinolin-1-one | |
| I-120 | 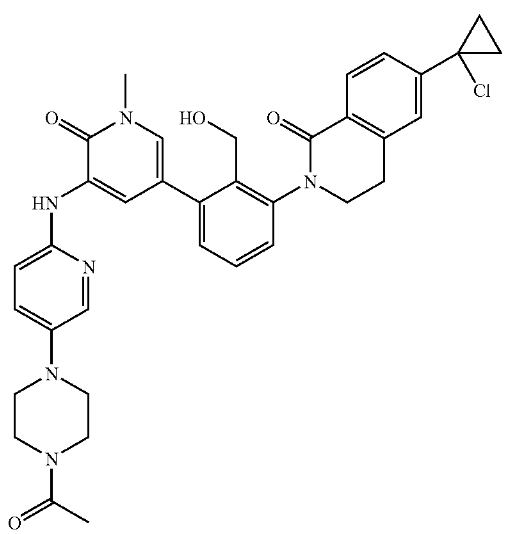 | 2-(3-{5-[5-(4-Acetyl-piperazin-1-yl)-pyridin-2-ylamino]-1-methyl-6-oxo-1,6-dihydro-pyridin-3-yl}-2-hydroxymethyl-phenyl)-6-(1-chloro-cyclopropyl)-3,4-dihydro-2H-isoquinolin-1-one | |

TABLE I-continued

| Compound | Structure | Nomenclature | (M + H)+ |
|---|---|---|---|
| I-121 | 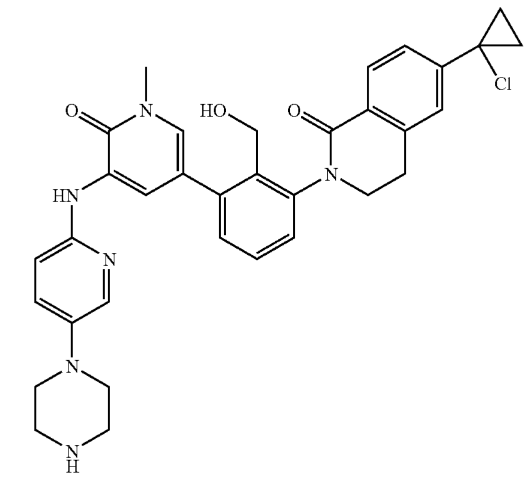 | 6-(1-Chlorocyclopropyl)-2-{2-hydroxymethyl-3-[1-methyl-6-oxo-5-(5-piperazin-1-yl-pyridin-2-ylamino)-1,6-dihydro-pyridin-3-yl]-phenyl}-3,4-dihydro-2H-isoquinolin-1-one | |
| I-122 | 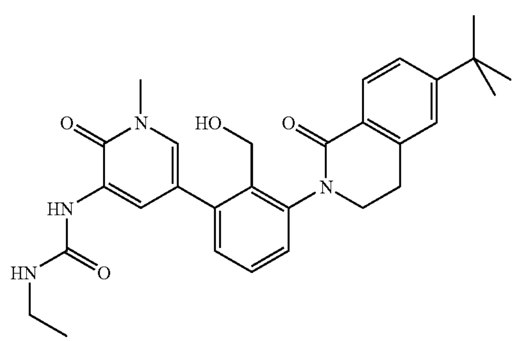 | 1-{5-[3-(6-tert-Butyl-1-oxo-3,4-dihydro-1H-isoquinolin-2-yl)-2-hydroxymethyl-phenyl]-1-methyl-2-oxo-1,2-dihydro-pyridin-3-yl}-3-ethyl-urea | |
| I-123 | 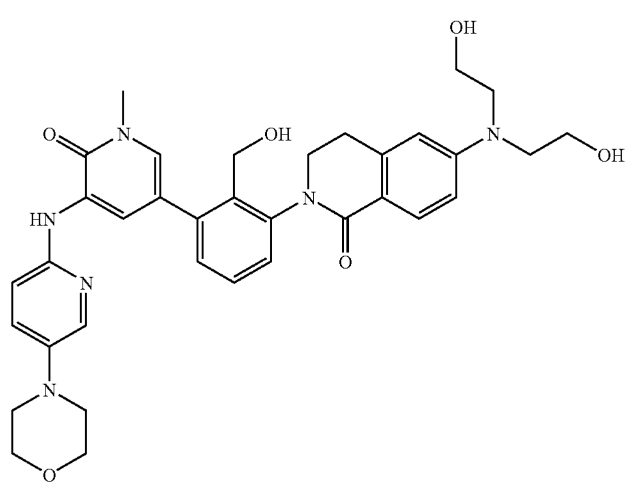 | 6-[Bis-(2-hydroxyethyl)-amino]-2-{2-hydroxymethyl-3-[1-methyl-5-(5-morpholin-4-yl-pyridin-2-ylamino)-6-oxo-1,6-dihydro-pyridin-3-yl]-phenyl}-3,4-dihydro-2H-isoquinolin-1-one | |

TABLE I-continued

| Compound | Structure | Nomenclature | (M + H)+ |
|---|---|---|---|
| I-124 | 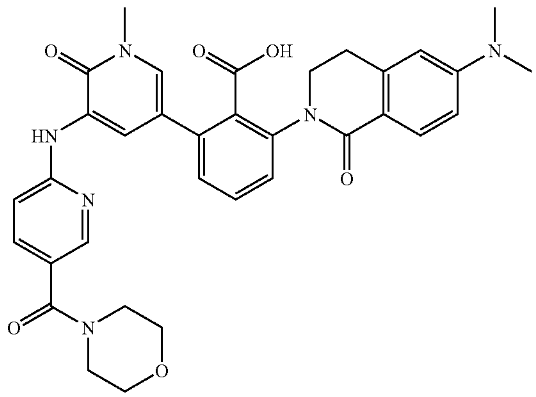 | 2-(6-Dimethylamino-1-oxo-3,4-dihydro-1H-isoquinolin-2-yl)-6-{1-methyl-5-[5-(morpholine-4-carbonyl)-pyridin-2-ylamino]-6-oxo-1,6-dihydro-pyridin-3-yl}-benzoic acid | |
| I-125 | 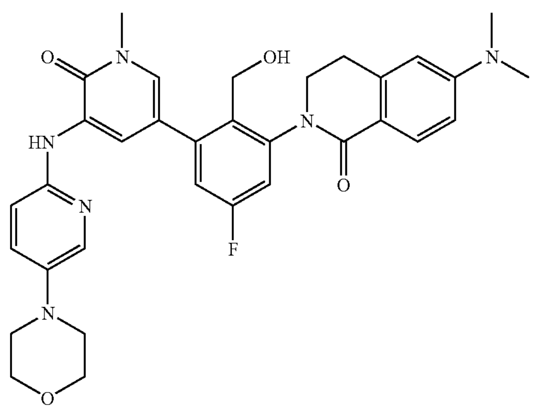 | 6-Dimethylamino-2-{5-fluoro-2-hydroxymethyl-3-[1-methyl-5-(5-morpholin-4-yl-pyridin-2-ylamino)-6-oxo-1,6-dihydro-pyridin-3-yl]-phenyl}-3,4-dihydro-2H-isoquinolin-1-one | |
| I-126 | 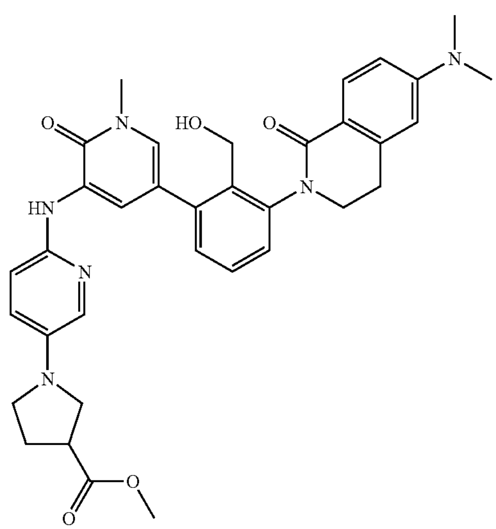 | 1-(6-{5-[3-(6-Dimethylamino-1-oxo-3,4-dihydro-1H-isoquinolin-2-yl)-2-hydroxymethyl-phenyl]-1-methyl-2-oxo-1,2-dihydro-pyridin-3-ylamino}-pyridin-3-yl)-pyrrolidine-3-carboxylic acid methyl ester | |

TABLE I-continued

| Compound | Structure | Nomenclature | (M + H)+ |
|---|---|---|---|
| I-127 | 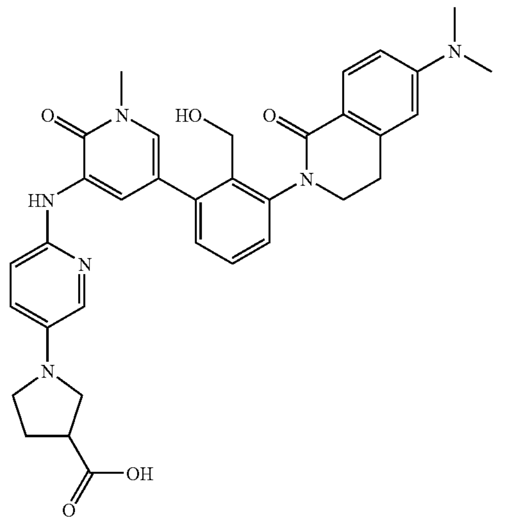 | 1-(6-{5-[3-(6-Dimethylamino-1-oxo-3,4-dihydro-1H-isoquinolin-2-yl)-2-hydroxymethyl-phenyl]-1-methyl-2-oxo-1,2-dihydro-pyridin-3-ylamino}-pyridin-3-yl)-pyrrolidine-3-carboxylic acid | |
| I-128 | 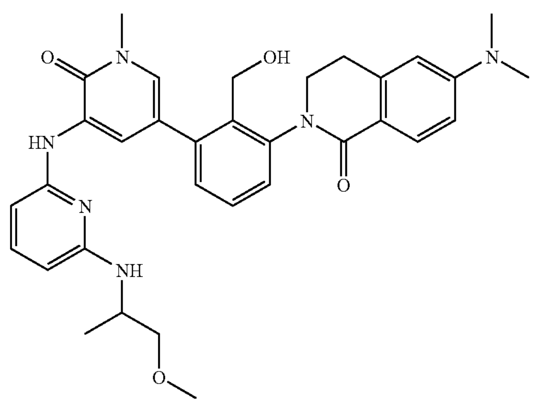 | 6-Dimethylamino-2-(2-hydroxymethyl-3-{5-[6-(2-methoxy-1-methyl-ethylamino)-pyridin-2-ylamino]-1-methyl-6-oxo-1,6-dihydro-pyridin-3-yl}-phenyl)-3,4-dihydro-2H-isoquinolin-1-one | |
| I-129 | 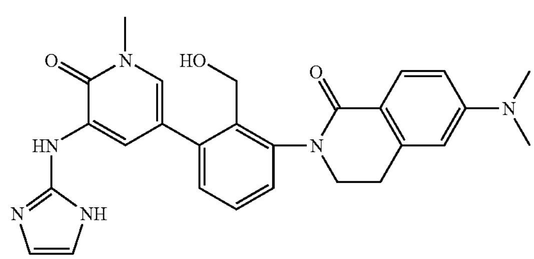 | 6-Dimethylamino-2-{2-hydroxymethyl-3-[5-(1H-imidazol-2-ylamino)-1-methyl-6-oxo-1,6-dihydro-pyridin-3-yl]-phenyl}-3,4-dihydro-2H-isoquinolin-1-one | |
| I-130 | 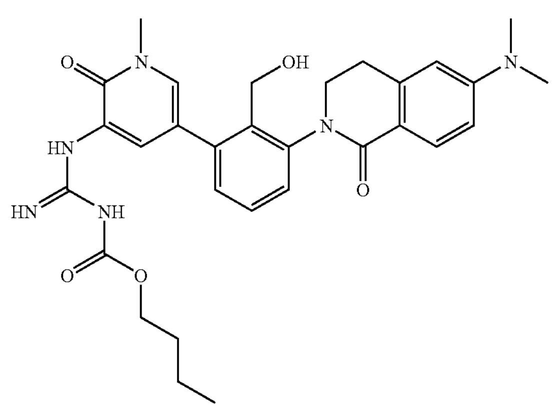 | N-{5-[3-(6-Dimethylamino-1-oxo-3,4-dihydro-1H-isoquinolin-2-yl)-2-hydroxy-methyl-phenyl]-1-methyl-2-oxo-1,2-dihydro-pyridin-3-yl}-N'-carboxylic acid butyl ester-quanidine | |

TABLE I-continued

| Compound | Structure | Nomenclature | (M + H)+ |
|---|---|---|---|
| I-131 | 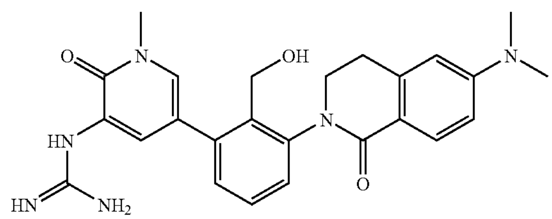 | N-{5-[3-(6-Dimethylamino-1-oxo-3,4-dihydro-1H-isoquinolin-2-yl)-2-hydroxymethyl-phenyl]-1-methyl-2-oxo-1,2-dihydro-pyridin-3-yl}-quanidine | |
| I-132 | 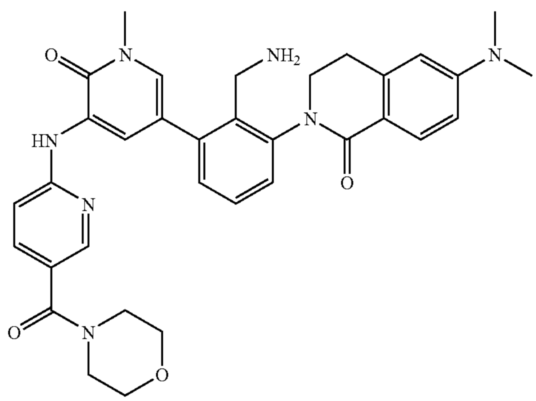 | 2-(2-Aminomethyl-3-{1-methyl-5-[5-(morpholine-4-carbonyl)-pyridin-2-ylamino]-6-oxo-1,6-dihydro-pyridin-3-yl}-phenyl)-6-dimethylamino-3,4-dihydro-2H-isoquinolin-1-one | |
| I-133 | 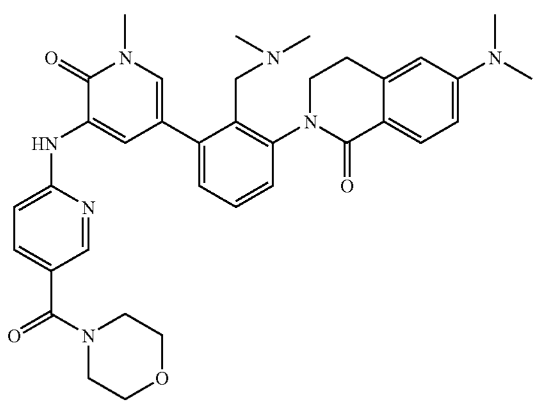 | 6-Dimethylamino-2-(2-dimethylaminomethyl-3-{1-methyl-5-[5-(morpholine-4-carbonyl)-pyridin-2-ylamino]-6-oxo-1,6-dihydro-pyridin-3-yl}-phenyl)-3,4-dihydro-2H-isoquinolin-1-one | |
| I-134 | 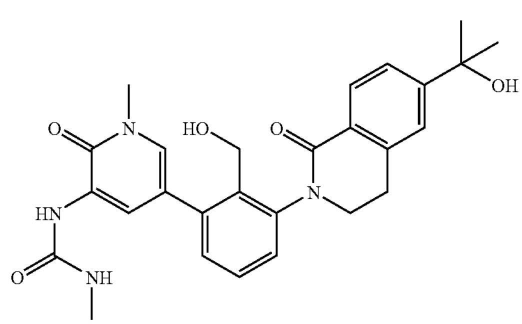 | 1-(5-{2-Hydroxymethyl-3-[6-(1-hydroxy-1-methyl-ethyl)-1-oxo-3,4-dihydro-1H-isoquinolin-2-yl]-phenyl}-1-methyl-2-oxo-1,2-dihydro-pyridin-3-yl)-3-methyl-urea | |

TABLE I-continued

| Compound | Structure | Nomenclature | (M + H)+ |
|---|---|---|---|
| I-135 | 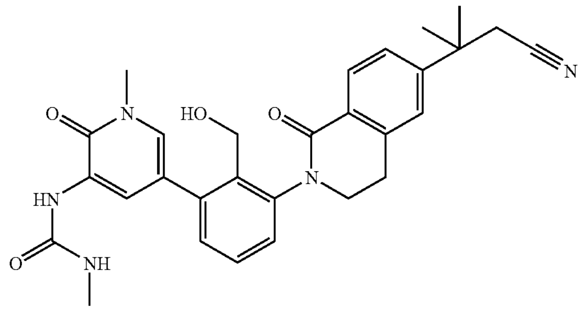 | 1-(5-{3-[6-(2-Cyano-1,1-dimethyl-ethyl)-1-oxo-3,4-dihydro-1H-isoquinolin-2-yl]-2-hydroxymethyl-phenyl}-1-methyl-2-oxo-1,2-dihydro-pyridin-3-yl)-3-methyl-urea | |
| I-136 | 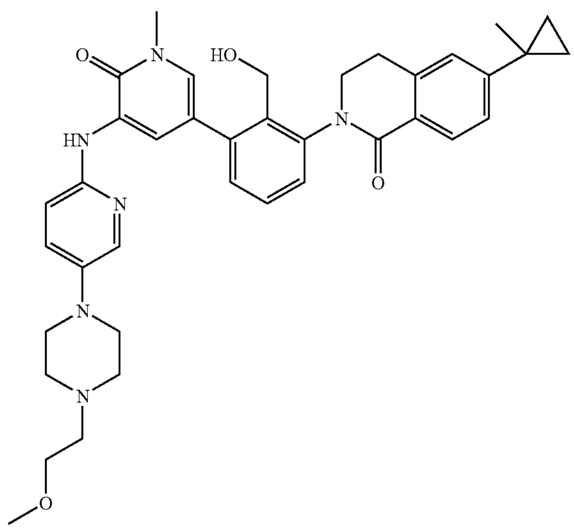 | 2-[2-Hydroxymethyl-3-(5-{5-[4-(2-methoxy-ethyl)-piperazin-1-yl]-pyridin-2-ylamino}-1-methyl-6-oxo-1,6-dihydro-pyridin-3-yl)-phenyl]-6-(1-methyl-cyclopropyl)-3,4-dihydro-2H-isoquinolin-1-one | |
| I-137 | 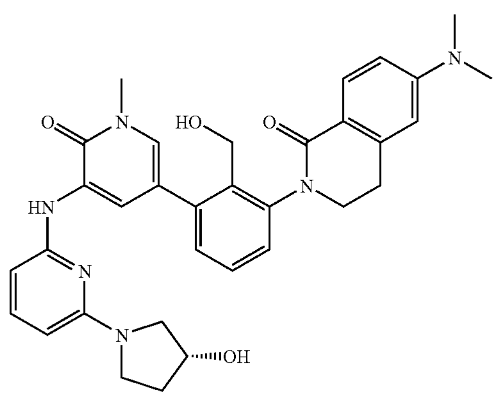 | 6-Dimethylamino-2-(2-hydroxymethyl-3-{5-[6-((R)-3-hydroxy-pyrrolidin-1-yl)-pyridin-2-ylamino]-1-methyl-6-oxo-1,6-dihydro-pyridin-3-yl}-phenyl)-3,4-dihydro-2H-isoquinolin-1-one | |
| I-138 | 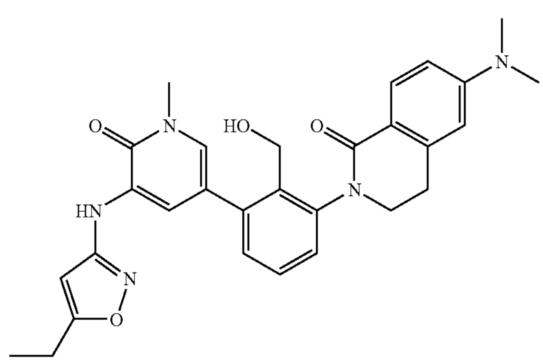 | 6-Dimethylamino-2-{3-[5-(5-ethyl-isoxazol-3-ylamino)-1-methyl-6-oxo-1,6-dihydro-pyridin-3-yl]-2-hydroxymethyl-phenyl}-3,4-dihydro-2H-isoquinolin-1-one | |

TABLE I-continued

| Compound | Structure | Nomenclature | (M + H)+ |
|---|---|---|---|
| I-139 | 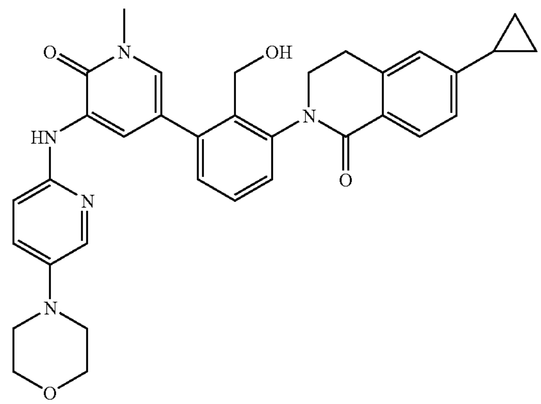 | 6-Cyclopropyl-2-{2-hydroxymethyl-3-[1-methyl-5-(5-morpholin-4-yl-pyridin-2-ylamino)-6-oxo-1,6-dihydro-pyridin-3-yl]-phenyl}-3,4-dihydro-2H-isoquinolin-1-one | |
| I-140 | 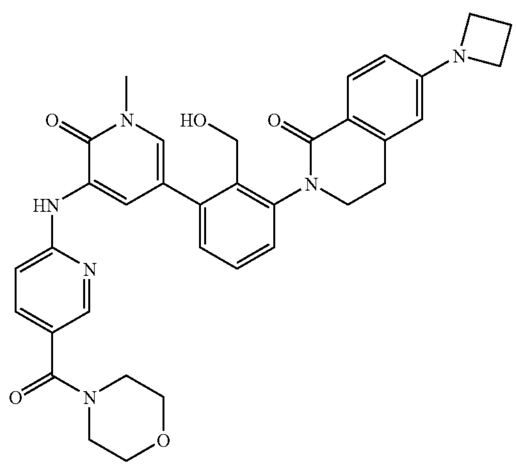 | 6-Azetidin-1-yl-2-(2-hydroxymethyl-3-{1-methyl-5-[5-(morpholine-4-carbonyl)-pyridin-2-ylamino]-6-oxo-1,6-dihydro-pyridin-3-yl}-phenyl)-3,4-dihydro-2H-isoquinolin-1-one | |
| I-141 | 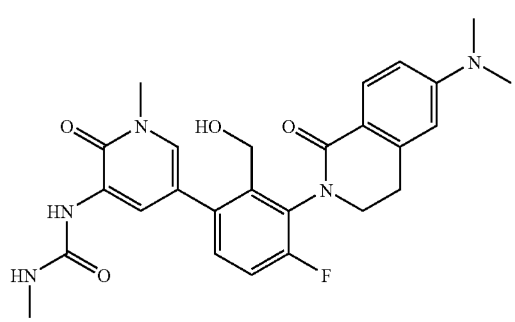 | 1-{5-[3-(6-Dimethylamino-1-oxo-3,4-dihydro-1H-isoquinolin-2-yl)-4-fluoro-2-hydroxymethyl-phenyl]-1-methyl-2-oxo-1,2-dihydro-pyridin-3-yl}-3-methyl-urea | |

TABLE I-continued

| Compound | Structure | Nomenclature | (M + H)+ |
|---|---|---|---|
| I-142 | 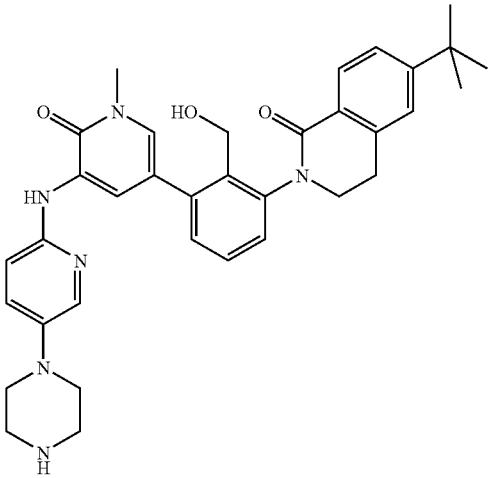 | 6-tert-Butyl-2-{2-hydroxymethyl-3-[1-methyl-6-oxo-5-(5-piperazin-1-yl-pyridin-2-ylamino)-1,6-dihydro-pyridin-3-yl]-phenyl}-3,4-dihydro-2H-isoquinolin-1-one | |
| I-143 | 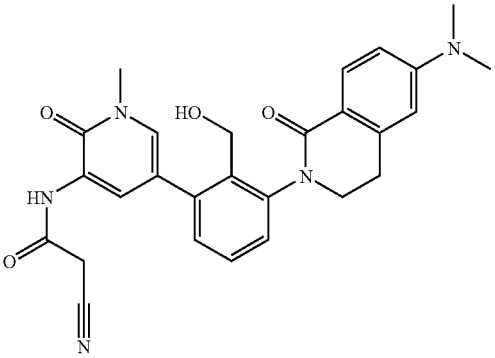 | 2-Cyano-N-{5-[3-(6-dimethylamino-1-oxo-3,4-dihydro-1H-isoquinolin-2-yl)-2-hydroxymethyl-phenyl]-1-methyl-2-oxo-1,2-dihydro-pyridin-3-yl}-acetamide | |
| I-144 | 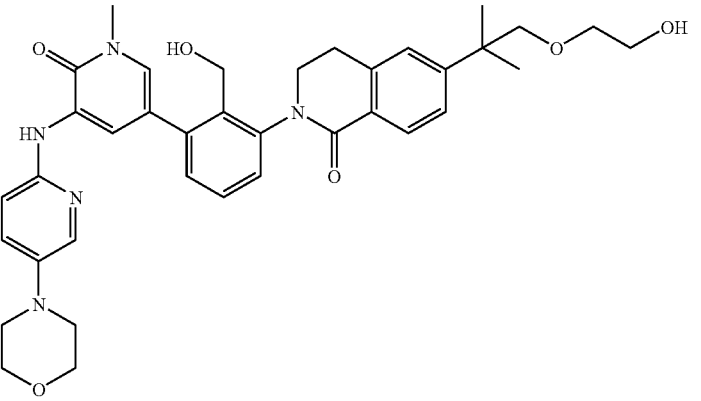 | 6-[2-(2-Hydroxy-ethoxy)-1,1-dimethyl-ethyl]-2-{2-hydroxymethyl-3-[1-methyl-5-(5-morpholin-4-yl-pyridin-2-ylamino)-6-oxo-1,6-dihydro-pyridin-3-yl]-phenyl}-3,4-dihydro-2H-isoquinolin-1-one | |

TABLE I-continued

| Compound | Structure | Nomenclature | (M + H)+ |
|---|---|---|---|
| I-145 | 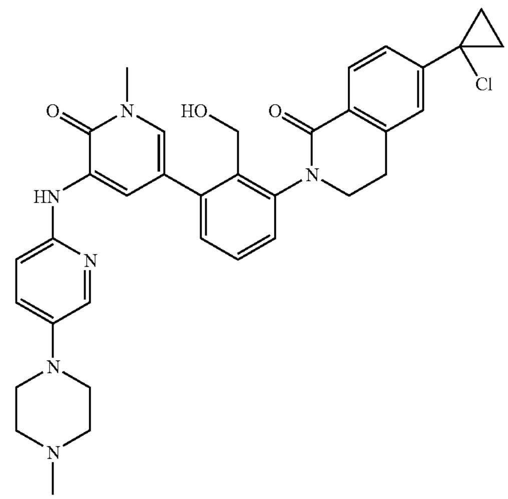 | 6-(1-Chloro-cyclopropyl)-2-(2-hydroxymethyl-3-{1-methyl-5-[5-(4-methyl-piperazin-1-yl)-pyridin-2-ylamino]-6-oxo-1,6-dihydro-pyridin-3-yl}-phenyl)-3,4-dihydro-2H-isoquinolin-1-one | |
| I-146 | 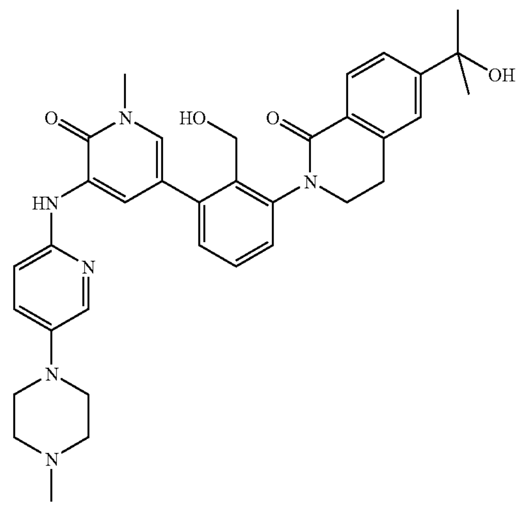 | 6-(1-Hydroxy-1-methyl-ethyl)-2-(2-hydroxymethyl-3-{1-methyl-5-[5-(4-methyl-piperazin-1-yl)-pyridin-2-ylamino]-6-oxo-1,6-dihydro-pyridin-3-yl}-phenyl)-3,4-dihydro-2H-isoquinolin-1-one | |
| I-147 | 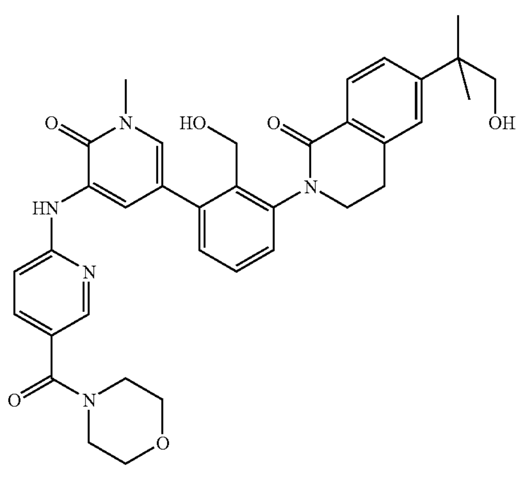 | 6-(2-Hydroxy-1,1-dimethyl-ethyl)-2-(2-hydroxymethyl-3-{1-methyl-5-[5-(morpholine-4-carbonyl)-pyridin-2-ylamino]-6-oxo-1,6-dihydro-pyridin-3-yl}-phenyl)-3,4-dihydro-2H-isoquinolin-1-one | |

TABLE I-continued

| Compound | Structure | Nomenclature | (M + H)+ |
|---|---|---|---|
| I-148 | 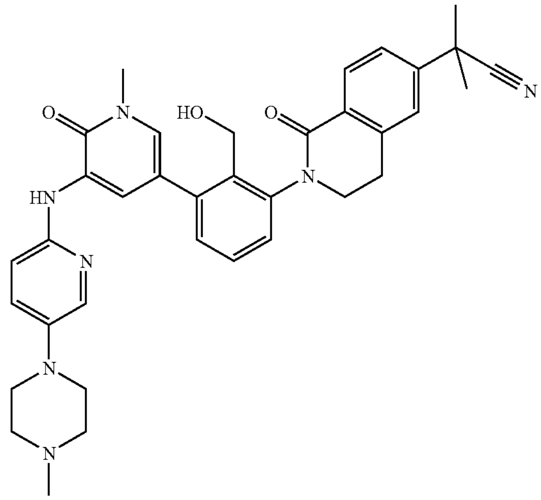 | 2-[2-(2-Hydroxymethyl-3-{1-methyl-5-[5-(4-methyl-piperazin-1-yl)-pyridin-2-ylamino]-6-oxo-1,6-dihydro-pyridin-3-yl}-phenyl)-1-oxo-1,2,3,4-tetrahydro-isoquinolin-6-yl]-2-methyl-propionitrile | |
| I-149 | 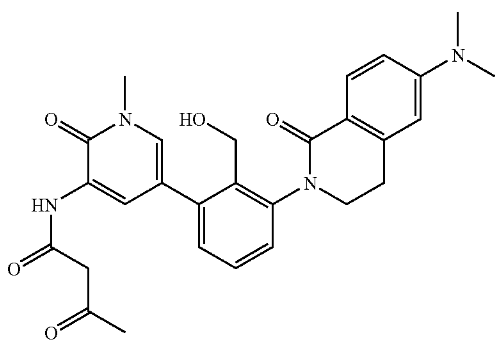 | N-{5-[3-(6-Dimethylamino-1-oxo-3,4-dihydro-1H-isoquinolin-2-yl)-2-hydroxymethyl-phenyl]-1-methyl-2-oxo-1,2-dihydro-pyridin-3-yl}-3-oxo-butyramide | |
| I-150 | 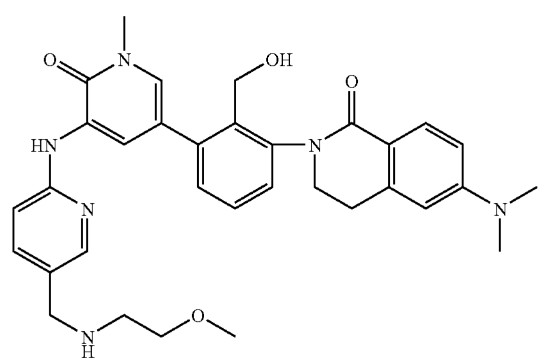 | 6-Dimethylamino-2-[2-hydroxymethyl-3-(5-{5-[(2-methoxy-ethylamino)-methyl]-pyridin-2-ylamino}-1-methyl-6-oxo-1,6-dihydro-pyridin-3-yl)-phenyl]-3,4-dihydro-2H-isoquinolin-1-one | |
| I-151 | 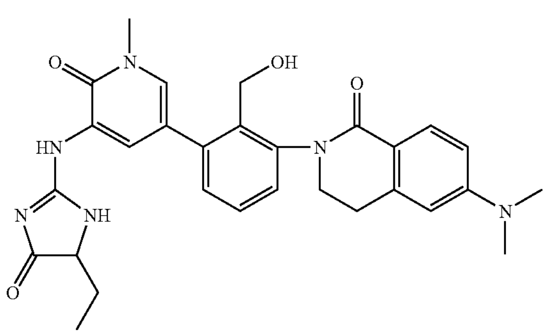 | 6-Dimethylamino-2-{3-[5-(5-ethyl-4-oxo-4,5-dihydro-1H-imidazol-2-ylamino)-1-methyl-6-oxo-1,6-dihydro-pyridin-3-yl]-2-hydroxymethyl-phenyl}-3,4-dihydro-2H-isoquinolin-1-one | |

TABLE I-continued

| Compound | Structure | Nomenclature | (M + H)+ |
|---|---|---|---|
| I-152 | 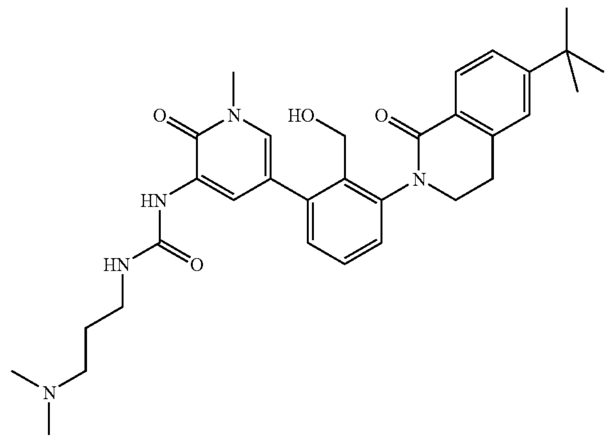 | 1-{5-[3-(6-tert-Butyl-1-oxo-3,4-dihydro-1H-isoquinolin-2-yl)-2-hydroxymethyl-phenyl]-1-methyl-2-oxo-1,2-dihydro-pyridin-3-yl}-3-(3-dimethylamino-propyl)-urea | |
| I-153 | 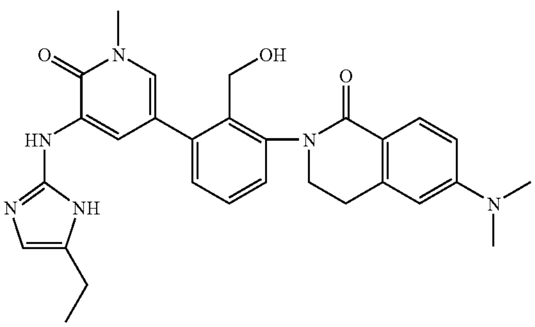 | 6-Dimethylamino-2-{3-[5-(5-ethyl-1H-imidazol-2-ylamino)-1-methyl-6-oxo-1,6-dihydro-pyridin-3-yl]-2-hydroxymethyl-phenyl}-3,4-dihydro-2H-isoquinolin-1-one | |
| I-154 | 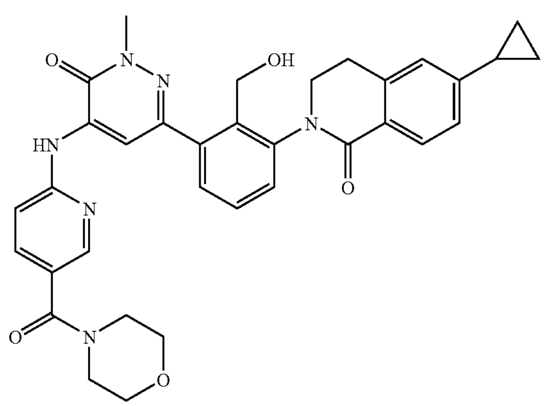 | 6-Cyclopropyl-2-(2-hydroxymethyl-3-{1-methyl-5-[5-(morpholine-4-carbonyl)-pyridin-2-ylamino]-6-oxo-1,6-dihydro-pyridazin-3-yl}-phenyl)-3,4-dihydro-2H-isoquinolin-1-one | |
| I-155 | 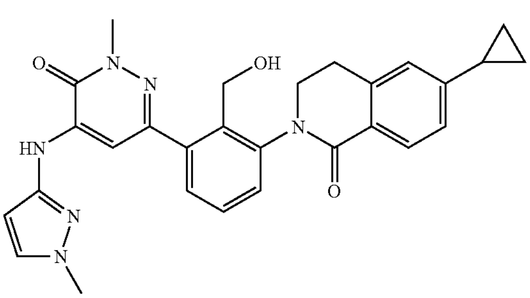 | 6-Cyclopropyl-2-{2-hydroxymethyl-3-[1-methyl-5-(1-methyl-1H-pyrazol-3-ylamino)-6-oxo-1,6-dihydro-pyridazin-3-yl]-phenyl}-3,4-dihydro-2H-isoquinolin-1-one | |

TABLE I-continued

| Compound | Structure | Nomenclature | (M + H)+ |
|---|---|---|---|
| III-4 | 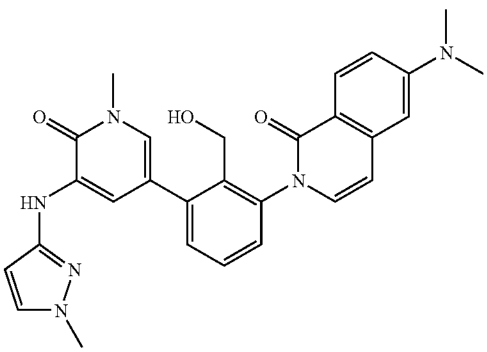 | 6-Dimethylamino-2-{2-hydroxymethyl-3-[1-methyl-5-(1-methyl-1H-pyrazol-3-ylamino)-6-oxo-1,6-dihydro-pyridin-3-yl]-phenyl}-2H-isoquinolin-1-one | |
| III-5 | 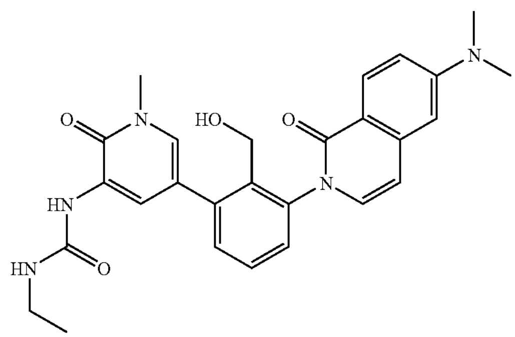 | 1-{5-[3-(6-Dimethylamino-1-oxo-1H-isoquinolin-2-yl)-2-hydroxymethyl-phenyl]-1-methyl-2-oxo-1,2-dihydro-pyridin-3-yl}-3-ethyl-urea | |
| III-6 | 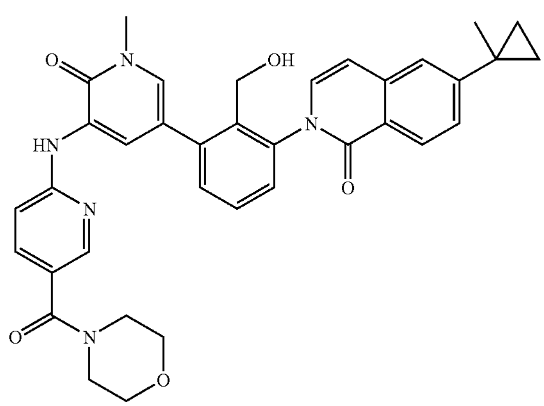 | 2-(2-Hydroxymethyl-3-{1-methyl-5-[5-(morpholine-4-carbonyl)-pyridin-2-ylamino]-6-oxo-1,6-dihydro-pyridin-3-yl}-phenyl)-6-(1-methyl-cyclopropyl)-2H-isoquinolin-1-one | |
| III-7 | 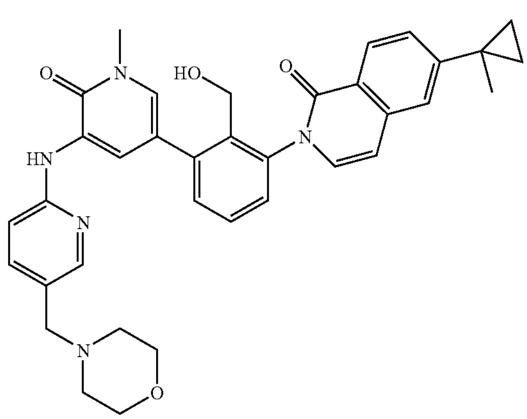 | 2-{2-Hydroxymethyl-3-[1-methyl-5-(5-morpholin-4-ylmethyl-pyridin-2-ylamino)-6-oxo-1,6-dihydro-pyridin-3-yl]-phenyl}-6-(1-methyl-cyclopropyl)-2H-isoquinolin-1-one | |

TABLE I-continued

| Compound | Structure | Nomenclature | (M + H)+ |
| --- | --- | --- | --- |
| III-8 | 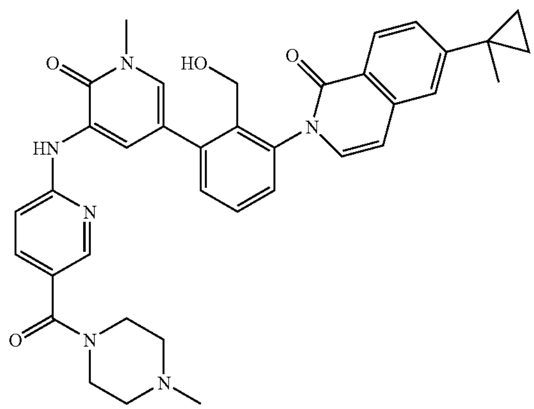 | 2-(2-Hydroxymethyl-3-{1-methyl-5-[5-(4-methyl-piperazine-1-carbonyl)-pyridin-2-ylamino]-6-oxo-1,6-dihydro-pyridin-3-yl}-phenyl)-6-(1-methyl-cyclopropyl)-2H-isoquinolin-1-one | |
| III-9 | 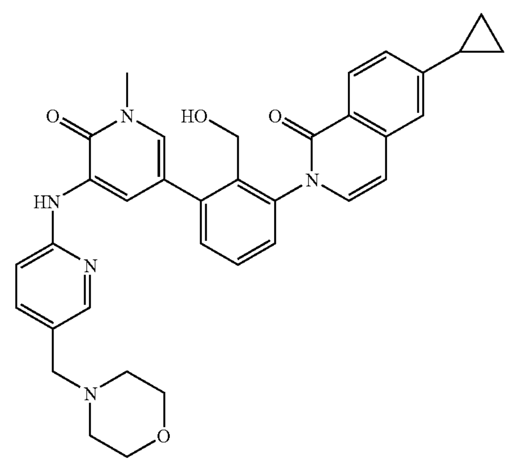 | 6-Cyclopropyl-2-{2-hydroxymethyl-3-[1-methyl-5-(5-morpholin-4-ylmethyl-pyridin-2-ylamino)-6-oxo-1,6-dihydro-pyridin-3-yl]-phenyl}-2H-isoquinolin-1-one | |
| III-10 | 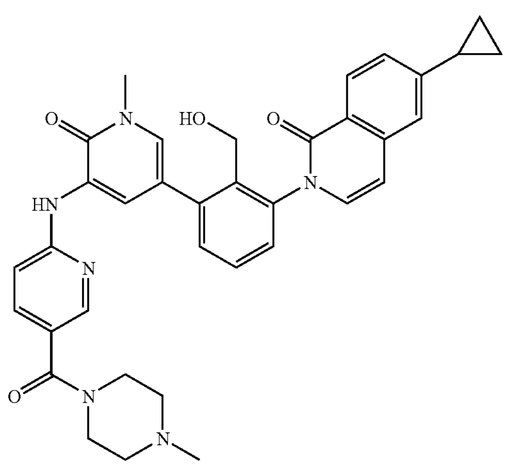 | 6-Cyclopropyl-2-(2-hydroxymethyl-3-{1-methyl-5-[5-(4-methyl-piperazine-1-carbonyl)-pyridin-2-ylamino]-6-oxo-1,6-dihydro-pyridin-3-yl}-phenyl)-2H-isoquinolin-1-one | |

TABLE I-continued

| Compound | Structure | Nomenclature | (M + H)+ |
|---|---|---|---|
| III-11 | 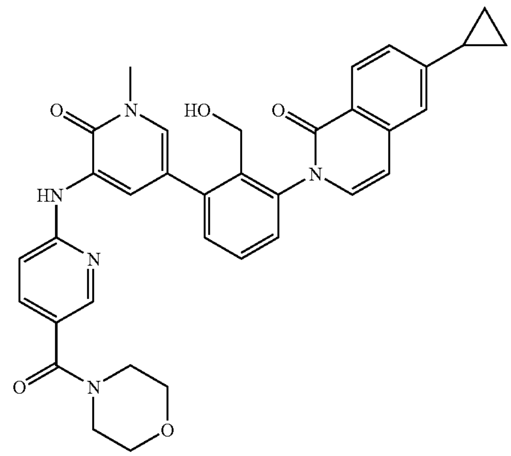 | 6-Cyclopropyl-2-(2-hydroxymethyl-3-{1-methyl-5-[5-(morpholine-4-carbonyl)-pyridin-2-ylamino]-6-oxo-1,6-dihydro-pyridin-3-yl}-phenyl)-2H-isoquinolin-1-one | |
| III-12 | 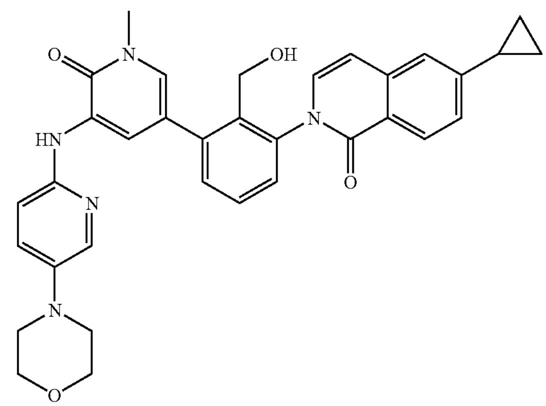 | 6-Cyclopropyl-2-{2-hydroxymethyl-3-[1-methyl-5-(5-morpholin-4-yl-pyridin-2-ylamino)-6-oxo-1,6-dihydro-pyridin-3-yl]-phenyl}-2H-isoquinolin-1-one | |
| III-13 | 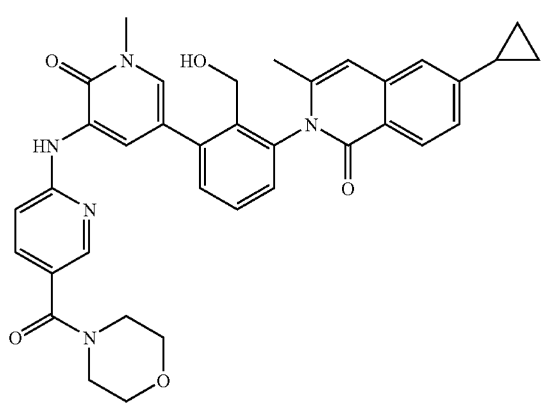 | 6-Cyclopropyl-2-(2-hydroxymethyl-3-{1-methyl-5-[5-(morpholine-4-carbonyl)-pyridin-2-ylamino]-6-oxo-1,6-dihydro-pyridin-3-yl}-phenyl)-3-methyl-2H-isoquinolin-1-one | |

TABLE I-continued

| Compound | Structure | Nomenclature | (M + H)+ |
|---|---|---|---|
| III-14 | 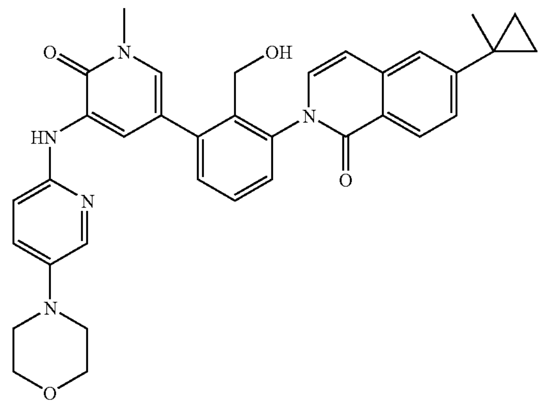 | 2-{2-Hydroxymethyl-3-[1-methyl-5-(5-morpholin-4-yl-pyridin-2-ylamino)-6-oxo-1,6-dihydro-pyridin-3-yl]-phenyl}-6-(1-methyl-cyclopropyl)-2H-isoquinolin-1-one | |
| III-15 | 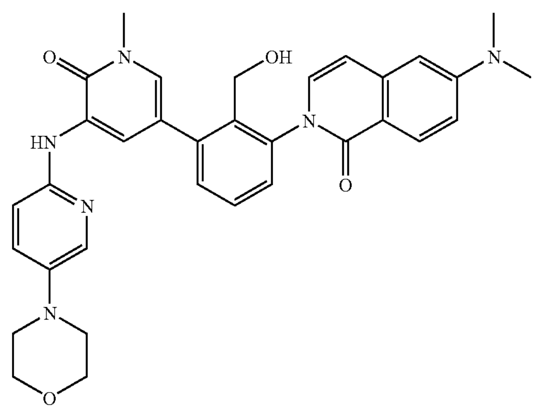 | 6-Dimethylamino-2-{2-hydroxymethyl-3-[1-methyl-5-(5-morpholin-4-yl-pyridin-2-ylamino)-6-oxo-1,6-dihydro-pyridin-3-yl]-phenyl}-2H-isoquinolin-1-one | |
| III-16 | 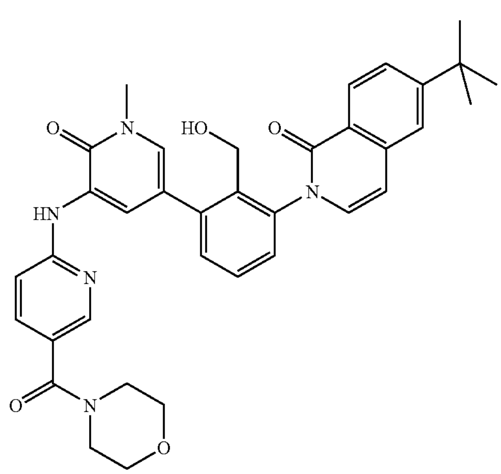 | 6-tert-Butyl-2-(2-hydroxymethyl-3-{1-methyl-5-[5-(morpholine-4-carbonyl)-pyridin-2-ylamino]-6-oxo-1,6-dihydro-pyridin-3-yl}-phenyl)-2H-isoquinolin-1-one | |

TABLE I-continued

| Compound | Structure | Nomenclature | (M + H)+ |
|---|---|---|---|
| III-17 | 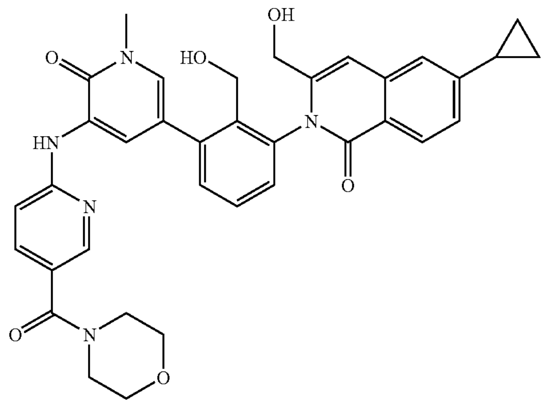 | 6-Cyclopropyl-3-hydroxymethyl-2-(2-hydroxymethyl-3-{1-methyl-5-[5-(morpholine-4-carbonyl)-pyridin-2-ylamino]-6-oxo-1,6-dihydro-pyridin-3-yl}-phenyl)-2H-isoquinolin-1-one | |
| III-18 | 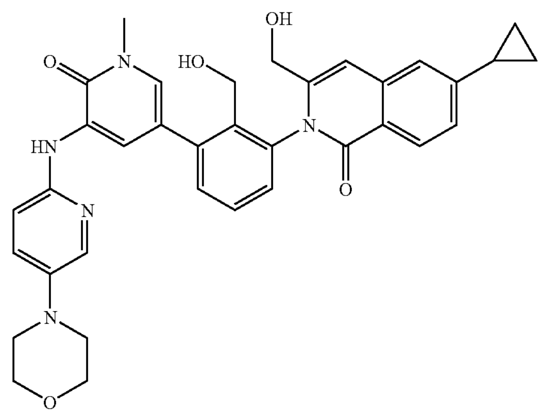 | 6-Cyclopropyl-3-hydroxymethyl-2-{2-hydroxymethyl-3-[1-methyl-5-(5-morpholin-4-yl-pyridin-2-ylamino)-6-oxo-1,6-dihydro-pyridin-3-yl]-phenyl}-2H-isoquinolin-1-one | |
| III-19 | 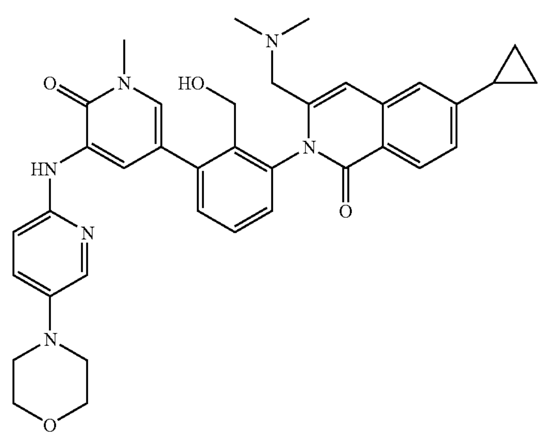 | 6-Cyclopropyl-3-dimethylaminomethyl-2-{2-hydroxymethyl-3-[1-methyl-5-(5-morpholin-4-yl-pyridin-2-ylamino)-6-oxo-1,6-dihydro-pyridin-3-yl]-phenyl}-2H-isoquinolin-1-one | |

TABLE I-continued

| Compound | Structure | Nomenclature | (M + H)+ |
|---|---|---|---|
| III-20 | 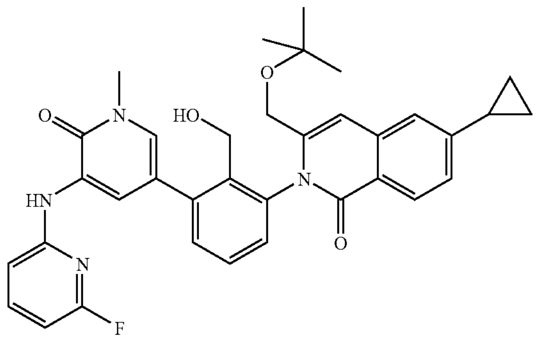 | 3-tert-Butoxymethyl-6-cyclopropyl-2-{3-[5-(6-fluoro-pyridin-2-ylamino)-1-methyl-6-oxo-1,6-dihydro-pyridin-3-yl]-2-hydroxymethyl-phenyl}-2H-isoquinolin-1-one | |
| III-21 | 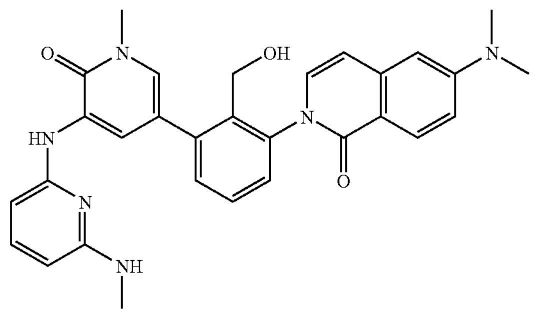 | 6-Dimethylamino-2-{2-hydroxymethyl-3-[1-methyl-5-(6-methylamino-pyridin-2-ylamino)-6-oxo-1,6-dihydro-pyridin-3-yl]-phenyl}-2H-isoquinolin-1-one | |
| III-22 | 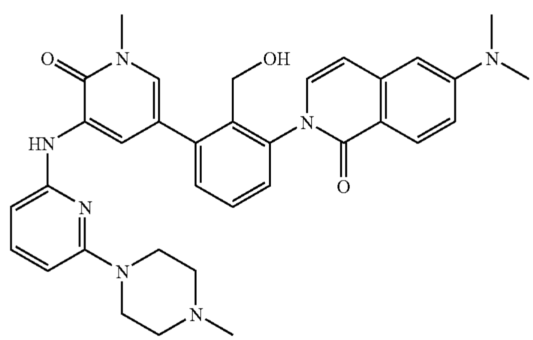 | 6-Dimethylamino-2-(2-hydroxymethyl-3-{1-methyl-5-[6-(4-methyl-piperazin-1-yl)-pyridin-2-ylamino]-6-oxo-1,6-dihydro-pyridin-3-yl}-phenyl)-2H-isoquinolin-1-one | |
| III-23 | 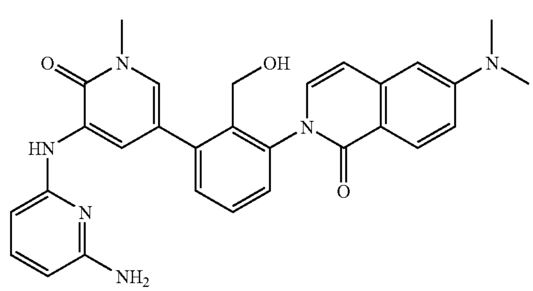 | 2-{3-[5-(6-Amino-pyridin-2-ylamino)-1-methyl-6-oxo-1,6-dihydro-pyridin-3-yl]-2-hydroxymethyl-phenyl}-6-dimethylamino-2H-isoquinolin-1-one | |

TABLE I-continued

| Compound | Structure | Nomenclature | (M + H)+ |
|---|---|---|---|
| III-24 | 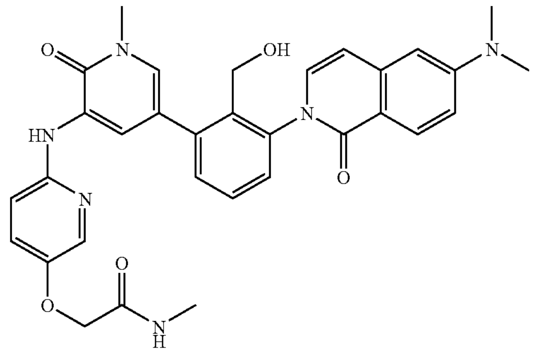 | 2-(6-{5-[3-(6-Dimethylamino-1-oxo-1H-isoquinolin-2-yl)-2-hydroxymethyl-phenyl]-1-methyl-2-oxo-1,2-dihydro-pyridin-3-ylamino}-pyridin-3-yloxy)-N-methyl-acetamide | |
| III-25 | 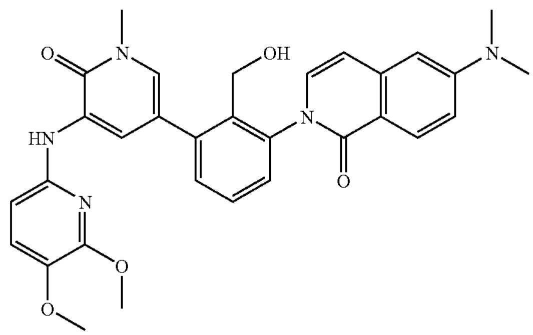 | 2-{3-[5-(5,6-Dimethoxy-pyridin-2-ylamino)-1-methyl-6-oxo-1,6-dihydro-pyridin-3-yl]-2-hydroxymethyl-phenyl}-6-dimethylamino-2H-isoquinolin-1-one | |
| III-26 | 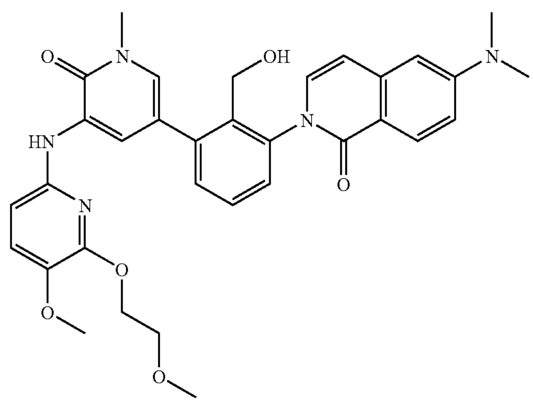 | 6-Dimethylamino-2-(2-hydroxymethyl-3-{5-[5-methoxy-6-(2-methoxy-ethoxy)-pyridin-2-ylamino]-1-methyl-6-oxo-1,6-dihydro-pyridin-3-yl}-phenyl)-2H-isoquinolin-1-one | |
| III-27 | 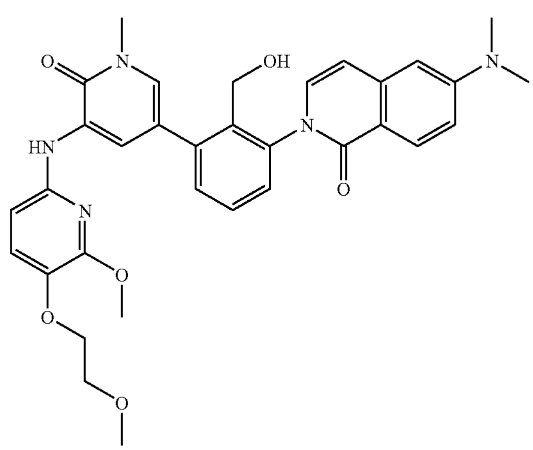 | 6-Dimethylamino-2-(2-hydroxymethyl-3-{5-[6-methoxy-5-(2-methoxy-ethoxy)-pyridin-2-ylamino]-1-methyl-6-oxo-1,6-dihydro-pyridin-3-yl}-phenyl)-2H-isoquinolin-1-one | |

TABLE I-continued

| Compound | Structure | Nomenclature | (M + H)+ |
| --- | --- | --- | --- |
| III-28 | 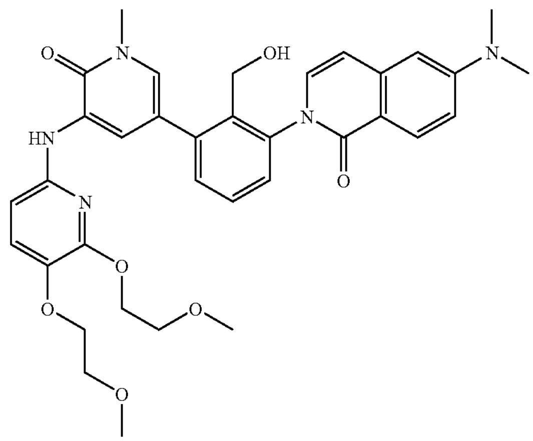 | 2-(3-{5-[5,6-Bis-(2-methoxy-ethoxy)-pyridin-2-ylamino]-1-methyl-6-oxo-1,6-dihydro-pyridin-3-yl}-2-hydroxymethyl-phenyl)-6-dimethylamino-2H-isoquinolin-1-one | |
| III-29 | 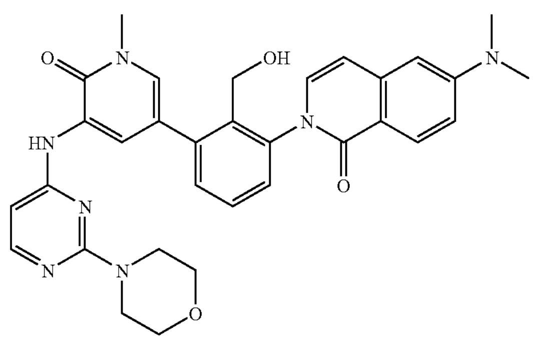 | 6-Dimethylamino-2-{2-hydroxymethyl-3-[1-methyl-5-(2-morpholin-4-yl-pyrimidin-4-ylamino)-6-oxo-1,6-dihydro-pyridin-3-yl]-phenyl}-2H-isoquinolin-1-one | |
| III-30 | 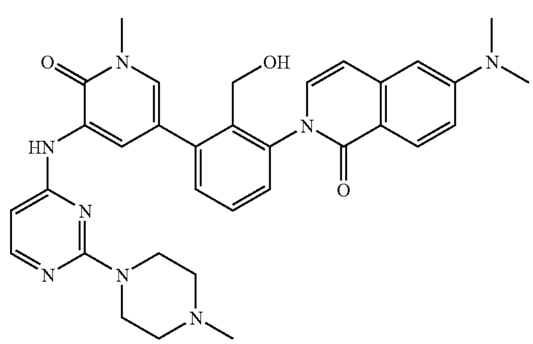 | 6-Dimethylamino-2-(2-hydroxymethyl-3-{1-methyl-5-[2-(4-methyl-piperazin-1-yl)-pyrimidin-4-ylamino]-6-oxo-1,6-dihydro-pyridin-3-yl}-phenyl)-2H-isoquinolin-1-one | |

TABLE I-continued

| Compound | Structure | Nomenclature | (M + H)+ |
|---|---|---|---|
| III-31 | 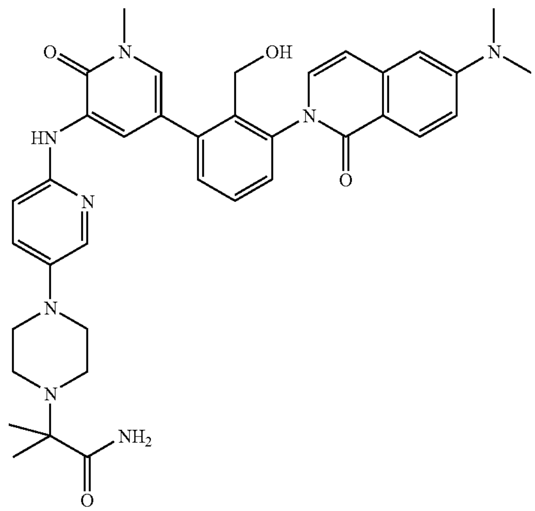 | 2-[4-(6-{5-[3-(6-Dimethylamino-1-oxo-1H-isoquinolin-2-yl)-2-hydroxymethyl-phenyl]-1-methyl-2-oxo-1,2-dihydro-pyridin-3-ylamino}-pyridin-3-yl)-piperazin-1-yl]-isobutyramide | |
| III-32 | 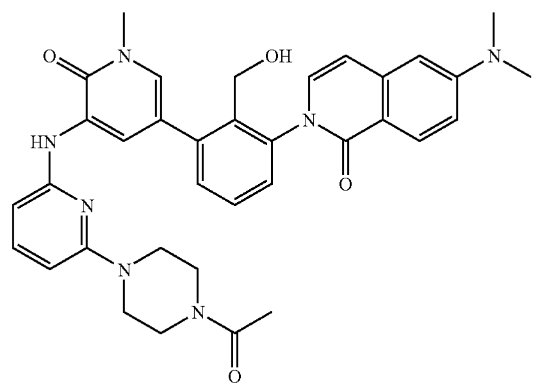 | 2-(3-{5-[6-(4-Acetyl-piperazin-1-yl)-pyridin-2-ylamino]-1-methyl-6-oxo-1,6-dihydro-pyridin-3-yl}-2-hydroxymethyl-phenyl)-6-dimethylamino-2H-isoquinolin-1-one | |
| III-33 | 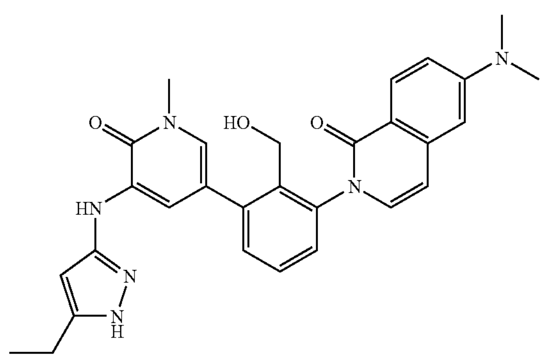 | 6-Dimethylamino-2-{3-[5-(5-ethyl-1H-pyrazol-3-ylamino)-1-methyl-6-oxo-1,6-dihydro-pyridin-3-yl]-2-hydroxymethyl-phenyl}-2H-isoquinolin-1-one | |

TABLE I-continued

| Compound | Structure | Nomenclature | (M + H)+ |
|---|---|---|---|
| III-34 | 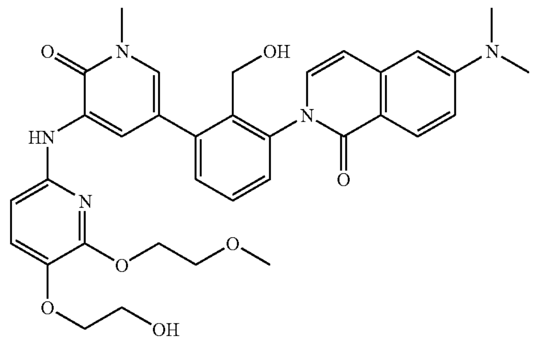 | 6-Dimethylamino-2-(3-{5-[5-(2-hydroxy-ethoxy)-6-(2-methoxy-ethoxy)-pyridin-2-ylamino]-1-methyl-6-oxo-1,6-dihydro-pyridin-3-yl}-2-hydroxymethyl-phenyl)-2H-isoquinolin-1-one | |
| III-35 | 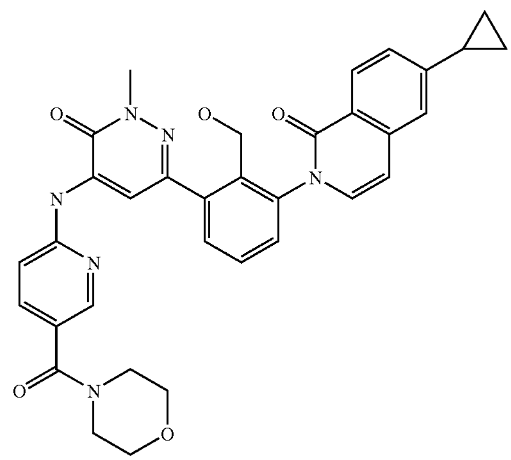 | 6-Cyclopropyl-2-(2-hydroxymethyl-3-{1-methyl-5-[5-(morpholine-4-carbonyl)-pyridin-2-ylamino]-6-oxo-1,6-dihydro-pyridazin-3-yl}-phenyl)-2H-isoquinolin-1-one | |
| III-36 | 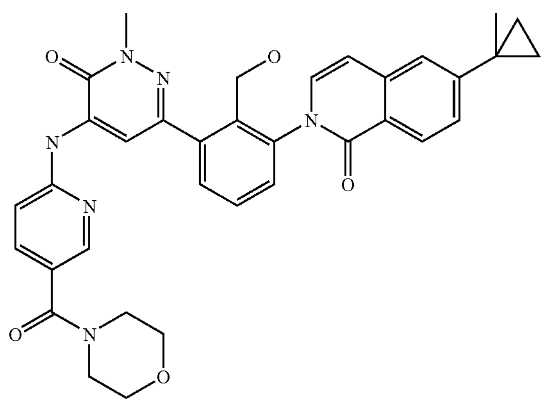 | 2-(2-Hydroxymethyl-3-{1-methyl-5-[5-(morpholine-4-carbonyl)-pyridin-2-ylamino]-6-oxo-1,6-dihydro-pyridazin-3-yl}-phenyl)-6-(1-methyl-cyclopropyl)-2H-isoquinolin-1-one | |

Pharmacological Activity

The pyridinone and pyridazinone derivatives described herein are kinase inhibitors, in particular Btk inhibitors. These inhibitors can be useful for treating one or more diseases responsive to kinase inhibition, including diseases responsive to Btk inhibition and/or inhibition of B-cell proliferation, in mammals. Without wishing to be bound to any particular theory, it is believed that the interaction of the compounds of the invention with Btk results in the inhibition of Btk activity and thus in the pharmaceutical utility of these compounds. Accordingly, the invention includes a method of treating a mammal, for instance a human, having a disease responsive to inhibition of Btk activity, and/or inhibiting B-cell proliferation, comprising administrating to the mammal having such a disease, an effective amount of at least one chemical entity provided herein. An effective concentration may be ascertained experimentally, for example by assaying blood concentration of the compound, or theoretically, by calculating bioavailability. Other kinases that may be affected in addition to Btk include, but are not limited to, other tyrosine kinases and serine/threonine kinases.

Kinases play notable roles in signaling pathways controlling fundamental cellular processes such as proliferation, differentiation, and death (apoptosis). Abnormal kinase activity has been implicated in a wide range of diseases, including multiple cancers, autoimmune and/or inflammatory diseases, and acute inflammatory reactions. The multifaceted role of kinases in key cell signaling pathways provides a significant opportunity to identify novel drugs targeting kinases and signaling pathways.

An embodiment includes a method of treating a patient having an autoimmune and/or inflammatory disease, or an acute inflammatory reaction responsive to inhibition of Btk activity and/or B-cell proliferation.

Autoimmune and/or inflammatory diseases that can be affected using compounds and compositions according to the invention include, but are not limited to: psoriasis, allergy, Crohn's disease, irritable bowel syndrome, Sjogren's disease, tissue graft rejection, and hyperacute rejection of transplanted organs, asthma, systemic lupus erythematosus (and associated glomerulonephritis), dermatomyositis, multiple sclerosis, scleroderma, vasculitis (ANCA-associated and other vasculitides), autoimmune hemolytic and thrombocytopenic states, Goodpasture's syndrome (and associated glomerulonephritis and pulmonary hemorrhage), atherosclerosis, rheumatoid arthritis, chronic Idiopathic thrombocytopenic purpura (ITP), Addison's disease, Parkinson's disease, Alzheimer's disease, diabetes, septic shock, and myasthenia gravis, Included herein are methods of treatment in which at least one chemical entity provided herein is administered in combination with an anti-inflammatory agent. Anti-inflammatory agents include but are not limited to NSAIDs, non-specific and COX-2 specific cyclooxygenase enzyme inhibitors, gold compounds, corticosteroids, methotrexate, tumor necrosis factor receptor (TNF) receptors antagonists, immunosuppressants and methotrexate.

Examples of NSAIDs include, but are not limited to, ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Examples of NSAIDs also include COX-2 specific inhibitors such as celecoxib, valdecoxib, lumiracoxib and/or etoricoxib.

In some embodiments, the anti-inflammatory agent is a salicylate. Salicylates include by are not limited to acetylsalicylic acid or aspirin, sodium salicylate, and choline and magnesium salicylates.

The anti-inflammatory agent may also be a corticosteroid. For example, the corticosteroid may be cortisone, dexamethasone, methylprednisolone, prednisolone, prednisolone sodium phosphate, or prednisone.

In additional embodiments the anti-inflammatory agent is a gold compound such as gold sodium thiomalate or auranofin.

The invention also includes embodiments in which the anti-inflammatory agent is a metabolic inhibitor such as a dihydrofolate reductase inhibitor, such as methotrexate or a dihydroorotate dehydrogenase inhibitor, such as leflunomide.

Other embodiments of the invention pertain to combinations in which at least one anti-inflammatory compound is an anti-C5 monoclonal antibody (such as eculizumab or pexelizumab), a TNF antagonist, such as entanercept, or infliximab, which is an anti-TNF alpha monoclonal antibody.

Still other embodiments of the invention pertain to combinations in which at least one active agent is an immunosuppressant compound such as an immunosuppressant compound chosen from methotrexate, leflunomide, cyclosporine, tacrolimus, azathioprine, and mycophenolate mofetil.

B-cells and B-cell precursors expressing BTK have been implicated in the pathology of B-cell malignancies, including, but not limited to, B-cell lymphoma, lymphoma (including Hodgkin's and non-Hodgkin's lymphoma), hairy cell lymphoma, multiple myeloma, chronic and acute myelogenous leukemia and chronic and acute lymphocytic leukemia.

BTK has been shown to be an inhibitor of the Fas/APO-1 (CD-95) death inducing signaling complex (DISC) in B-lineage lymphoid cells. The fate of leukemia/lymphoma cells may reside in the balance between the opposing proapoptotic effects of caspases activated by DISC and an upstream anti-apoptotic regulatory mechanism involving BTK and/or its substrates (Vassilev et al., J. Biol. Chem. 1998, 274, 1646-1656).

It has also been discovered that BTK inhibitors are useful as chemosensitizing agents, and, thus, are useful in combination with other chemotherapeutic drugs, in particular, drugs that induce apoptosis. Examples of other chemotherapeutic drugs that can be used in combination with chemosensitizing BTK inhibitors include topoisomerase I inhibitors (camptothecin or topotecan), topoisomerase II inhibitors (e.g. daunomycin and etoposide), alkylating agents (e.g. cyclophosphamide, melphalan and BCNU), tubulin directed agents (e.g. taxol and vinblastine), and biological agents (e.g. antibodies such as anti CD20 antibody, IDEC 8, immunotoxins, and cytokines).

Btk activity has also be associated with some leukemias expressing the bcr-abl fusion gene resulting from translocation of parts of chromosome 9 and 22. This abnormality is commonly observed in chronic myelogenous leukemia. Btk is constitutively phosphorylated by the bcr-abl kinase which initiates downstream survival signals which circumvents apoptosis in bcr-abl cells. (N. Feldhahn et al. J. Exp. Med. 2005 201(11):1837-1852)

Dosage and Administration

The compounds of the present invention may be formulated in a wide variety of oral administration dosage forms and carriers. Oral administration can be in the form of tablets, coated tablets, dragées, hard and soft gelatine capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The compounds of this invention can be administered alone but will generally be administered in admixture with one or more suitable pharmaceutical excipients, diluents or carriers selected with regard to the intended route of administration and standard pharmaceutical practice.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

A "pharmaceutically acceptable salt" form of an active ingredient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polyactic acid.

Suitable formulations along with pharmaceutical carriers, diluents and expcipients are described in *Remington: The Science and Practice of Pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

EXAMPLES

Example 1

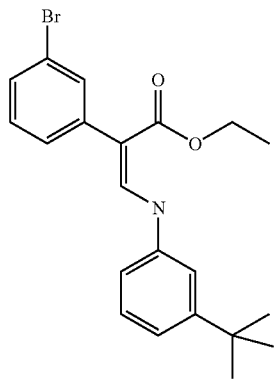

2-(3-Bromo-phenyl)-3-(3-t-butyl-phenylamino)-acrylic Acid Ethyl Ester (3-Bromo-phenyl)-acetic acid benzyl ester (1 g, 4.12 mmol) was dissolved in ethyl formate (8 mL, 99 mmol).

Sodium hydride (60%, 660 mg, 16.5 mmol) was added. After stirring overnight, this was quenched with 2 M aq. HCl. This was partitioned between ethyl acetate and water. The ethyl acetate layer was washed with water, washed with brine, dried over anhydrous magnesium sulfate, and concentrated in vacuo.

This material (0.65 g) and 3-t-butyl-aniline (0.37 mL, 2.48 mmol) were stirred in 1 mL ethanol for 18 hours. This was concentrated in vacuo and purified by flash chromatography (gradient elution 5 to 20% ethyl acetate/hexanes) to yield 2-(3-Bromo-phenyl)-3-(3-t-butyl-phenylamino)-acrylic acid ethyl ester (0.5 mg). MS (ESI) 402 (M+H)+.

Example 2

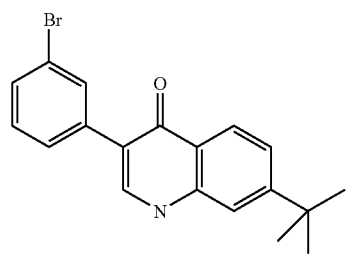

3-(3-Bromo-phenyl)-7-tert-butyl-1H-quinolin-4-one

To 2-(3-Bromo-phenyl)-3-(3-tert-butyl-phenylamino)-acrylic acid ethyl ester (151 mg, 0.388 mmol) was added 10 g of polyphosphoric acid. The resulting mixture was heated at 140° C. for 90 minutes. 80 mL of water was added. The mixture was stirred for 40 minutes. The resulting precipitate was filtered, washed with water, and air dried for 3 days to yield 3-(3-Bromo-phenyl)-7-tert-butyl-1H-quinolin-4-one (123 mg. 0.345 mmol). MS (ESI) 356 (M+H)+.

Example 3

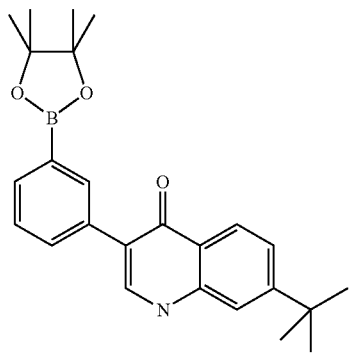

7-tert-Butyl-3-[3-(4,4,5,5-tetramethyl-[1,3,2]dioxaborolan-2-yl)-phenyl]-1H-quinolin-4-one 3-(3-Bromo-phenyl)-7-tert-butyl-1H-quinolin-4-one (119 mg, 0.334 mmol), bis(pinacolato)diboron (102 mg, 0.401 mmol), and potassium acetate (98 mg, 1.0 mmol) were deposited in a sealed vessel with 2 mL of DMSO. Argon was bubbled through the mixture for 1 minute. [1,1'-Bis(diphenylphosphino)ferrocene]dichloropalladium(II) complex with dichloromethane (8.0 mg, 0.0098 mmol) was added. Argon was bubbled through the mixture for one minute and the lid was tightly sealed. The resulting mixture was heated at 80° C. for 18 hours prior to being partitioned between ethylacetate and water. The ethylacetate layer was washed with brine, dried over anhydrous magnesium sulfate, concentrated in vacuo, and purified by flash chromatography (gradient elution 25 to 50% ethylacetate/hexanes) to yield 7-tert-Butyl-3-[3-(4,4,5,5-tetramethyl-[1,3,2]dioxaborolan-2-yl)-phenyl]-1H-quinolin-4-one (77 mg, 0.19 mmol). MS (ESI) 404.1 (M+H)+.

Example 4

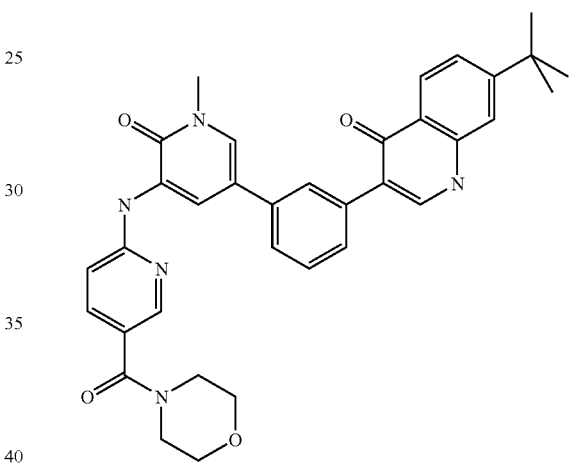

7-tert-Butyl-3-(3-{1-methyl-5-[5-(morpholine-4-carbonyl)-pyridin-2-ylamino]-6-oxo-1,6-dihydro-pyridin-3-yl}-phenyl)-1H-quinolin-4-one A solution of 5-Bromo-1-methyl-3-[5-(morpholine-4-carbonyl)-pyridin-2-ylamino]-1H-pyridin-2-one (19 mg, 0.050 mmol), 7-tert-Butyl-3-[3-(4,4,5,5-tetramethyl-[1,3,2]dioxaborolan-2-yl)-phenyl]-1H-quinolin-4-one (20 mg, 0.05 mmol), tetrakis(triphenylphosphine)palladium(0) (6.0 mg, 0.0052 mmol), and sodium carbonate (16 mg, 0.15 mmol) in 2 mL 1,2-dimethoxyethane and 1 mL water was microwaved at 170° C. for 12.5 minutes. The resulting mixture was partitioned between ethyl acetate and water. The ethyl acetate layer was washed with brine, dried over anhydrous magnesium sulfate, concentrated in vacuo, and purified by preparative TLC (5% methanol/dichloromethane) to yield 7-tert-Butyl-3-(3-{1-methyl-5-[5-(morpholine-4-carbonyl)-pyridin-2-ylamino]-6-oxo-1,6-dihydro-pyridin-3-yl}-phenyl)-1H-quinolin-4-one (5.7 mg, 0.0085 mmol). MS (ESI) 590.1 (M+H)+.

Example 5

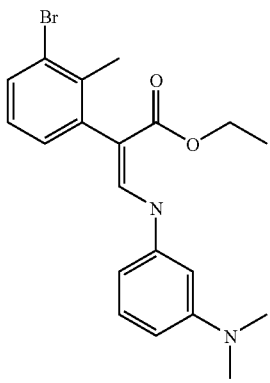

2-(3-Bromo-2-methyl-phenyl)-3-(3-dimethylamino-phenylamino)-acrylic Acid Ethyl Ester (3-Bromo-2-methyl-phenyl)-acetic acid benzyl ester (421 mg, 1.32 mmol) was dissolved in ethyl formate (2.5 mL, 31 mmol). Sodium hydride (95%, 67 mg, 2.6 mmol) was added. After stirring for 30 minutes, this was quenched with 1M aq. HCl. This was partitioned between ethyl acetate and water. The ethyl acetate layer was washed with water, washed with brine, dried over anhydrous magnesium sulfate, and concentrated in vacuo.

A portion of this material and N,N-Dimethyl-benzene-1,3-diamine (96 mg, 0.70 mmol) were stirred in 1 mL ethanol for 18 hours. This was concentrated in vacuo and purified by flash chromatography (gradient elution 5 to 20% ethyl acetate/hexanes) to yield 2-(3-Bromo-2-methyl-phenyl)-3-(3-dimethylamino-phenylamino)-acrylic acid ethyl ester (164 mg, 0.407 mmol). MS (ESI) 405.0 (M+H)$^+$.

Example 6

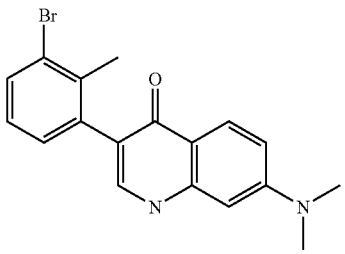

3-(3-Bromo-2-methyl-phenyl)-7-dimethylamino-1H-quinolin-4-one

To 2-(3-Bromo-2-methyl-phenyl)-3-(3-dimethylamino-phenylamino)-acrylic acid ethyl ester (100 mg, 0.248 mmol) was added 4 g polyphosphoric acid. This stirred at 140° C. for 10 minutes. 50 ml water was added and the mixture was stirred. The resulting precipitate was filtered and washed with water. The filtrate was extracted with 10% methanol/dichloromethane solution. The organic layer was dried over anhydrous magnesium sulfate and concentrated in vacuo. The resulting residue was combined with the precipitate and purified by flash chromatography (gradient elution 2 to 5% methanol/dichloromethane) to yield 3-(3-Bromo-2-methyl-phenyl)-7-dimethylamino-1H-quinolin-4-one (22 mg, 0.062 mmol). MS (ESI) 357.0 (M+H)$^+$.

Example 7

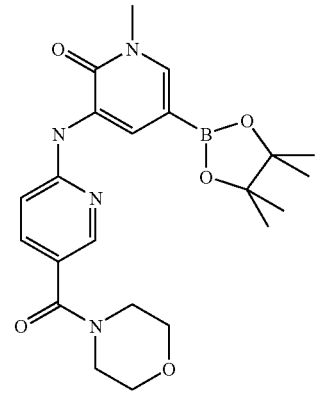

1-Methyl-3-[5-(morpholine-4-carbonyl)-pyridin-2-ylamino]-5-(4,4,5,5-tetramethyl-[1,3,2]dioxaborolan-2-yl)-1H-pyridin-2-one 5-Bromo-1-methyl-3-[5-(morpholine-4-carbonyl)-pyridin-2-ylamino]-1H-pyridin-2-one (1.00 g, 2.55 mmol), bis(pinacolato)diboron (1.94 g, 7.64 mmol), potassium acetate (750 mg, 7.64 mmol), 2-(dicyclohexylphoshphino)-2',4',6'-tri-1-propyl-1,1'-biphenyl (121 mg, 0.254 mmol), and bis(dibenzylidineacetone)palladium(0) (73 mg, 0.13 mmol) were dissolved in 15 ml degassed 1,4-dioxane. The headspace of the vessel was evacuated and backfilled with argon 5 times. This was heated at 110° C. for 3 hours. This was partitioned between ethyl acetate and water. The ethyl acetate layer was washed with brine, dried over anhydrous magnesium sulfate, concentrated in vacuo, and purified by flash chromatography (gradient elution 2 to 8% methanol/dichloromethane) to yield 1-Methyl-3-[5-(morpholine-4-carbonyl)-pyridin-2-ylamino]-5-(4,4,5,5-tetramethyl-[1,3,2]dioxaborolan-2-yl)-1H-pyridin-2-one (0.798 g, 1.81 mmol). MS (ESI) 441.2 (M+H)$^+$.

Example 8

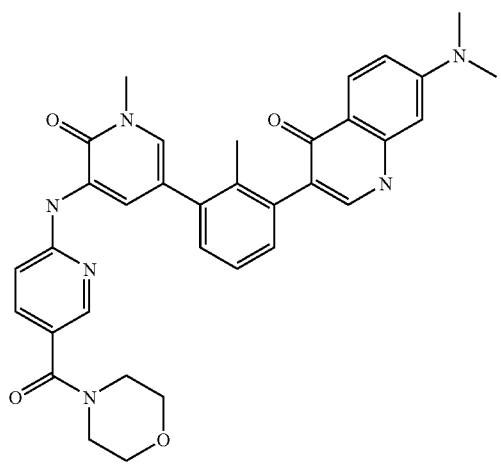

7-Dimethylamino-3-(2-methyl-3-{1-methyl-5-[5-(morpholine-4-carbonyl)-pyridin-2-ylamino]-6-oxo-1,6-dihydro-pyridin-3-yl}-phenyl)-1H-quinolin-4-one To Methyl-3-[5-(morpholine-4-carbonyl)-pyridin-2-ylamino]-5-(4,4,5,5-tetramethyl-[1,3,2]dioxaborolan-2-yl)-1H-pyridin-2-one (27 mg, 0.062 mmol), 3-(3-Bromo-2-methyl-phenyl)-7-dimethylamino-1H-quinolin-4-one (22 mg, 0.062 mmol), potassium phosphate (26 mg, 0.12 mmol), 2-(dicyclohexylphoshphino)-2',4',6'-tri-i-propyl-1,1'-biphenyl (1.7 mg, 0.0036 mmol), and bis(dibenzylidineacetone) palladium(0) (1.0 mg, 0.0018 mmol) was added 4 mL of degassed 1:3 water/n-butanol. The headspace of the vessel was evacuated and backfilled with argon 4 times. This was heated at 100° C. for 1 hour. This was partitioned between ethyl acetate and water. The ethyl acetate layer was washed with brine, dried over anhydrous magnesium sulfate, concentrated in vacuo, and purified by preparative TLC (5% methanol/dichloromethane) to yield 7-Dimethylamino-3-(2-methyl-3-{1-methyl-5-[5-(morpholine-4-carbonyl)-pyridin-2-ylamino]-6-oxo-1,6-dihydro-pyridin-3-yl}-phenyl)-1H-quinolin-4-one (14 mg, 0.024 mmol). MS (ESI) 591.1 (M+H)$^+$.

Example 9

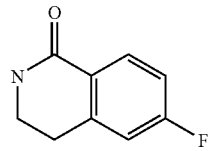

6-Fluoro-3,4-dihydro-2H-isoquinolin-1-one

5-Fluoro-indan-1-one (4.00 g, 26.6 mmol) was dissolved in 40 mL dichloromethane and 40 mL methanesulfonic acid. This was cooled to 0° C. and sodium azide (3.46 g, 53.2 mmol) was added. After 2 hours, the solution was made basic by slowly adding 20% aq. sodium hydroxide. The resulting mixture was partitioned between dichloromethane and water. The dichloromethane layer was dried over anhydrous magnesium sulfate, concentrated in vacuo, and purified by flash chromatography (gradient elution 50 to 100% ethyl acetate/hexanes) to yield 6-Fluoro-3,4-dihydro-2H-isoquinolin-1-one (2.72 g, 16.5 mmol). MS (ESI) 166.1 (M+H)$^+$.

Example 10

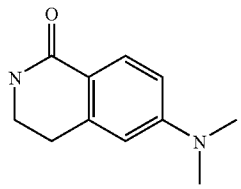

6-Dimethylamino-3,4-dihydro-2H-isoquinolin-1-one

6-Fluoro-3,4-dihydro-2H-isoquinolin-1-one (1.56 g, 9.45 mmol) was deposited in a sealed vessel with 25 mL 33% dimethylamine in ethanol. This was heated at 150° C. for 7 hours. The resulting solution was partitioned between ethyl acetate and water. The ethyl acetate layer was washed with brine, dried over anhydrous magnesium sulfate, concentrated in vacuo, and purified by flash chromatography (elution with ethyl acetate) to yield 6-Dimethylamino-3,4-dihydro-2H-isoquinolin-1-one (787 mg, 4.14 mmol). MS (ESI) 191.1 (M+H)$^+$.

Example 11

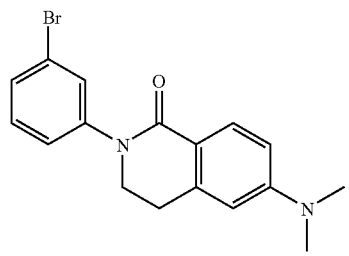

2-(3-Bromo-phenyl)-6-dimethylamino-3,4-dihydro-2H-isoquinolin-1-one

6-Dimethylamino-3,4-dihydro-2H-isoquinolin-1-one (762 mg, 4.01 mmol), cuprous iodide (153 mg, 0.802 mmol) and potassium carbonate (554 mg, 4.01 mmol) were deposited in a sealed type vessel. 6 mL DMSO and 1,3-dibromobenzene (1.89 g, 8.02 mmol) were added. Argon was bubbled through the mixture for 2 minutes and the lid was tightly closed. This was heated at 150° C. for 24 hours. Cuprous iodide (153 mg, 0.802 mmol) was added and the mixture was heated at 150° C. for an additional 24 hours. This was diluted with dichloromethane and filtered through a pad of celite. The filtrate was partitioned between dichloromethane and 5% aq. ammonium hydroxide. The dichloromethane layer was dried over anhydrous magnesium sulfate, concentrated in vacuo, and purified by flash chromatography (gradient elution 25 to 100% ethyl acetate/hexanes) to yield 2-(3-Bromo-phenyl)-6-dimethylamino-3,4-dihydro-2H-isoquinolin-1-one (939 mg, 2.72 mmol). MS (ESI) 345.0 (M+H)$^+$.

Example 12

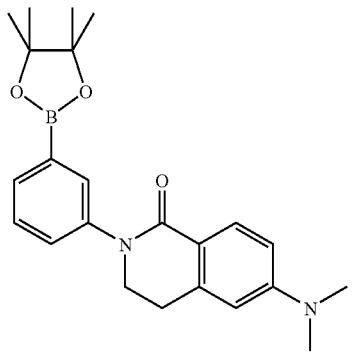

6-Dimethylamino-2-[3-(4,4,5,5-tetramethyl-[1,3,2]dioxaborolan-2-yl)-phenyl]-3,4-dihydro-2H-isoquinolin-1-one 2-(3-Bromo-phenyl)-6-dimethylamino-3,4-dihydro-2H-isoquinolin-1-one (163 mg, 0.472 mmol), bis(pinacolato)diboron (144 mg, 0.567 mmol), and potassium acetate (138 mg, 1.42 mmol) were deposited in a sealed vessel with 2 mL DMSO. Argon was bubbled through the mixture for 1 minute. [1,1'-Bis(diphenylphosphino)ferrocene]dichloropalladium(II) complex with dichloromethane (12 mg, 0.015 mmol) was added. Argon was continuted to bubble through the mixture for one more minute and the lid was tightly closed. This was heated at 80° C. for 18 hours. This was partitioned between ethyl acetate and water. The ethyl acetate layer was washed with brine, dried over anhydrous magnesium sulfate, concentrated in vacuo, and purified by flash chromatography (30% ethyl acetate/hexanes) to yield 6-Dimethylamino-2-[3-(4,4,5,5-tetramethyl-[1,3,2]dioxaborolan-2-yl)-phenyl]-3,4-dihydro-2H-isoquinolin-1-one (137 mg, 0.349 mmol). MS (ESI) 393.2 (M+H)$^+$.

Example 13

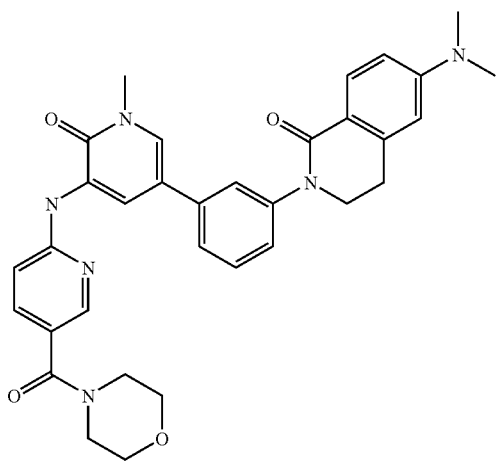

6-Dimethylamino-2-(3-{1-methyl-5-[5-(morpholine-4-carbonyl)-pyridin-2-ylamino]-6-oxo-1,6-dihydro-pyridin-3-yl}-phenyl)-3,4-dihydro-2H-isoquinolin-1-one 5-Bromo-1-methyl-3-[5-(morpholine-4-carbonyl)-pyridin-2-ylamino]-1H-pyridin-2-one (67 mg, 0.17 mmol), 6-Dimethylamino-2-[3-(4,4,5,5-tetramethyl-[1,3,2]dioxaborolan-2-yl)-phenyl]-3,4-dihydro-2H-isoquinolin-1-one (67 mg, 0.17 mmol), tetrakis(triphenylphosphine)palladium(0) (20 mg, 0.017 mmol), and sodium carbonate (54 mg, 0.51 mmol) in 2 mL 1,2-dimethoxyethane and 1 mL water was heated to 170° C. for 12.5 minutes in the microwave. The resulting mixture was partitioned between ethyl acetate and water. The ethyl acetate layer was washed with brine, dried over anhydrous magnesium sulfate, concentrated in vacuo, and purified by flash chromatography (gradient elution 2 to 5% methanol/dichloromethane) to yield 6-Dimethylamino-2-(3-{1-methyl-5-[5-(morpholine-4-carbonyl)-pyridin-2-ylamino]-6-oxo-1,6-dihydro-pyridin-3-yl}-phenyl)-3,4-dihydro-2H-isoquinolin-1-one (40 mg, 0.069 mmol). MS (ESI) 579.2 (M+H)$^+$.

Example 14

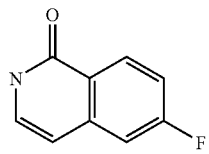

6-Fluoro-2H-isoquinolin-1-one

6-Fluoro-3,4-dihydro-2H-isoquinolin-1-one (149 mg, 0.903 mmol) was dissolved in 3 mL 1,4-dioxane. Argon was bubbled through this solution for 1 minute and 2,3-dichloro-5,6-dicyano-p-benzoquinone (205 mg, 0.903 mmol) was added. This was heated at 100° C. for 24 hours. The resulting mixture was partitioned between ethyl acetate and 1M aq. sodium hydroxide. The ethyl acetate layer was washed with brine, dried over anhydrous magnesium sulfate, concentrated in vacuo, and purified by flash chromatography (50% ethyl acetate/hexanes) to yield 6-Fluoro-2H-isoquinolin-1-one (54 mg, 0.33 mmol). MS (ESI) 164.1 (M+H)$^+$.

Example 15

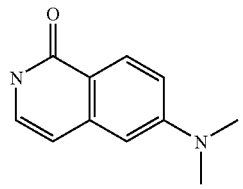

6-Dimethylamino-2H-isoquinolin-1-one

6-Fluoro-2H-isoquinolin-1-one (54 mg, 0.33 mmol) was deposited in a sealed tube with 5 mL 33% dimethylamine in ethanol. This was heated at 150° C. for 3.5 hours. This was concentrated in vacuo and purified by flash chromatography (gradient elution 50 to 100% ethyl acetate/hexanes) to yield 6-Dimethylamino-2H-isoquinolin-1-one (39 mg, 0.21 mmol). MS (ESI) 189.1 (M+H)$^+$.

Example 16

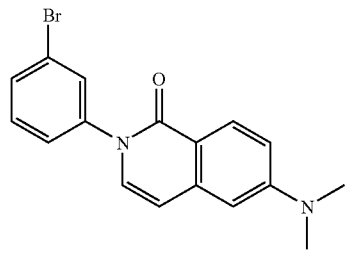

2-(3-Bromo-phenyl)-6-dimethylamino-2H-isoquinolin-1-one

6-Dimethylamino-2H-isoquinolin-1-one (39 mg, 0.21 mmol), cuprous iodide (8.0 mg, 0.041 mmol), and potassium carbonate (29 mg, 0.21 mmol) were deposited in sealed vessel. 3 mL DMSO and 1,3-dibromobenzene (98 mg, 0.42 mmol) were added. Argon was bubbled through the mixture for 2 minutes and the lid was tightly closed. This was heated at 150° C. for 5 hours. The resulting mixture was partitioned between ethyl acetate and water. The organic layer was washed with brine, dried over anhydrous magnesium sulfate, concentrated in vacuo, and purified by flash chromatography (25% ethyl acetate/hexanes) to yield 2-(3-Bromo-phenyl)-6-dimethylamino-2H-isoquinolin-1-one (45 mg, 0.13 mmol). MS (ESI) 345.0 (M+H)+.

Example 17

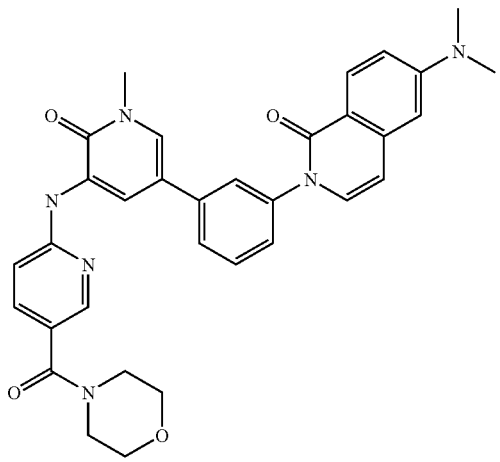

6-Dimethylamino-2-(3-{1-methyl-5-[5-(morpholine-4-carbonyl)-pyridin-2-ylamino]-6-oxo-1,6-dihydro-pyridin-3-yl}-phenyl)-2H-isoquinolin-1-one To 1-Methyl-3-[5-(morpholine-4-carbonyl)-pyridin-2-ylamino]-5-(4,4,5,5-tetramethyl-[1,3,2]dioxaborolan-2-yl)-1H-pyridin-2-one (58 mg, 0.13 mmol), 2-(3-Bromo-phenyl)-6-dimethylamino-2H-isoquinolin-1-one (45 mg, 0.13 mmol), potassium phosphate (56 mg, 0.26 mmol), 2-(dicyclohexylphoshphino)-2′,4′,6′-tri-i-propyl-1,1′-biphenyl (3.7 mg, 0.0078 mmol), and bis(dibenzylidineacetone)palladium (0) (2.2 mg, 0.0038 mmol) was added 4 mL of degassed 1:3 water/n-butanol. The headspace of the vessel was evacuated and backfilled with argon 4 times. This was heated at 100° C. for 2 hours. This was partitioned between ethyl acetate and water. The ethyl acetate layer was washed with brine, dried over anhydrous magnesium sulfate, concentrated in vacuo, and purified by preparative TLC (5% methanol/dichloromethane) to yield 6-Dimethylamino-2-(3-{1-methyl-5-[5-(morpholine-4-carbonyl)-pyridin-2-ylamino]-6-oxo-1,6-dihydro-pyridin-3-yl}-phenyl)-2H-isoquinolin-1-one (45 mg, 0.078 mmol). MS (ESI) 577.1 (M+H)+.

Example 18

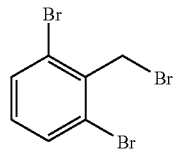

1,3-Dibromo-2-bromomethyl-benzene 2,6-dibromotoluene (2.50 g, 10.0 mmol) was dissolved in 20 mL carbontetrachloride. N-bromosuccinimide (1.87 g, 10.5 mmol) was added followed by benzoyl peroxide (73 mg, 0.30 mmol). The resulting mixture was heated at reflux for 90 minutes. 50 mL petroleum ether was added. This was filtered and concentrated in vacuo to yield 1,3-Dibromo-2-bromomethyl-benzene (3.52 g, 10.7 mmol). ¹HNMR (300 MHz, CDCl₃) δ 4.83 (s, 3H), 7.02 (t, J=8 Hz, 1H), and 7.55 (d, J=8 Hz, 2H).

Example 19

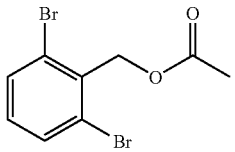

Acetic Acid 2,6-dibromo-benzyl Ester

To 1,3-Dibromo-2-bromomethyl-benzene (3.35 g, 10.2 mmol) was added potassium acetate (4.00 g, 40.8 mmol) and 25 mL N,N-dimethylformamide. This was heated at 70° C. for 20 minutes. The resulting mixture was partitioned between water and ethyl acetate. The ethyl acetate layer was washed with water, washed with brine, dried over anhydrous magnesium sulfate, concentrated in vacuo, and purified by flash chromatography (gradient elution 0 to 5% ethyl acetate hexanes) to yield Acetic acid 2,6-dibromo-benzyl ester (1.92 g, 6.23 mmol). ¹HNMR (300 MHz, CDCl₃) δ 2.12 (s, 3H), 5.42 (s, 2H), 7.08 (t, J=8 Hz, 1H), and 7.58 (d, J=8 Hz, 2H).

Example 20

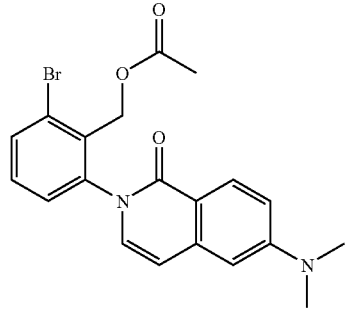

Acetic Acid 2-bromo-6-(6-dimethylamino-1-oxo-1H-isoquinolin-2-yl)-benzyl Ester

6-Dimethylamino-2H-isoquinolin-1-one (50 mg, 0.27 mmol), Acetic acid 2,6-dibromo-benzyl ester (164 mg, 532 mmol), cuprous iodide (10 mg, 0.053 mmol), and potassium carbonate (37 mg, 0.27 mmol) were deposited in sealed vessel. 3 mL DMSO was added. Argon was bubbled through the mixture for 2 minutes and the lid was tightly closed. This was heated at 150° C. for 5 hours. The resulting mixture was partitioned between ethyl acetate and water. The organic layer was washed with brine, dried over anhydrous magnesium sulfate, concentrated in vacuo, and purified by flash chromatography (gradient elution 30 to 40% ethylacetate/hexanes) to yield Acetic acid 2-bromo-6-(6-dimethylamino-1-oxo-1H-isoquinolin-2-yl)-benzyl ester (48 mg, 0.12 mmol). MS (ESI) 417.0 (M+H)$^+$.

Example 21

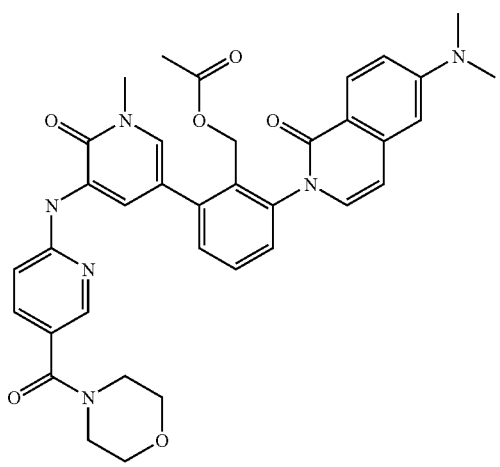

Acetic Acid 2-(6-dimethylamino-1-oxo-1H-isoquinolin-2-yl)-6-{1-methyl-5-[5-(morpholine-4-carbonyl)-pyridin-2-ylamino]-6-oxo-1,6-dihydro-pyridin-3-yl}-benzyl Ester To 1-Methyl-3-[5-(morpholine-4-carbonyl)-pyridin-2-ylamino]-5-(4,4,5,5-tetramethyl-[1,3,2]dioxaborolan-2-yl)-1H-pyridin-2-one (43 mg, 0.097 mmol), Acetic acid 2-bromo-6-(6-dimethylamino-1-oxo-1H-isoquinolin-2-yl)-benzyl ester (40 mg, 0.097 mmol), potassium phosphate (41 mg, 0.19 mmol), 2-(dicyclohexylphoshphino)-2',4',6'-tri-i-propyl-1,1'-biphenyl (2.7 mg, 0.0057 mmol), and bis(dibenzylidineacetone)palladium(0) (1.6 mg, 0.0028 mmol) was added 4 mL of degassed 1:3 water/n-butanol. The headspace of the vessel was evacuated and backfilled with argon 4 times. This was heated at 100° C. for 110 minutes. This was partitioned between ethyl acetate and water. The ethyl acetate layer was washed with brine, dried over anhydrous magnesium sulfate, concentrated in vacuo, and purified by flash chromatography (gradient elution 2 to 5% methanol/dichloromethane) to yield Acetic acid 2-(6-dimethylamino-1-oxo-1H-isoquinolin-2-yl)-6-{1-methyl-5-[5-(morpholine-4-carbonyl)-pyridin-2-ylamino]-6-oxo-1,6-dihydro-pyridin-3-yl}-benzyl ester (33 mg, 0.051 mmol). MS (ESI) 649.2 (M+H)$^+$.

Example 22

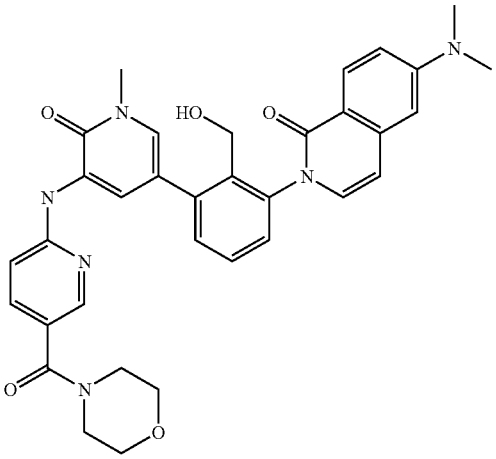

6-Dimethylamino-2-(2-hydroxymethyl-3-{1-methyl-5-[5-(morpholine-4-carbonyl)-pyridin-2-ylamino]-6-oxo-1,6-dihydro-pyridin-3-yl}-phenyl)-2H-isoquinolin-1-one To Acetic acid 2-(6-dimethylamino-1-oxo-1H-isoquinolin-2-yl)-6-1{-methyl-5-[5-(morpholine-4-carbonyl)-pyridin-2-ylamino]-6-oxo-1,6-dihydro-pyridin-3-yl}-benzyl ester (29 mg, 0.045 mmol) in 2 ml tetrahydrofuran, 1 ml methanol, and 1 ml water was added 1M aq. lithium hydroxide solution (0.13 mL, 0.13 mmol). After stirring for 18 hours, this was partitioned between ethyl acetate and water. The ethyl acetate layer was washed with brine, dried over anhydrous magnesium sulfate, concentrated in vacuo, and purified by preparative TLC (5% methanol/dichloromethane) to yield 6-Dimethylamino-2-(2-hydroxymethyl-3-{1-methyl-5-[5-(morpholine-4-carbonyl)-pyridin-2-ylamino]-6-oxo-1,6-dihydro-pyridin-3-yl}-phenyl)-2H-isoquinolin-1-one (20 mg, 0.033 mmol). MS (ESI) 607.2 (M+H)$^+$.

Example 23

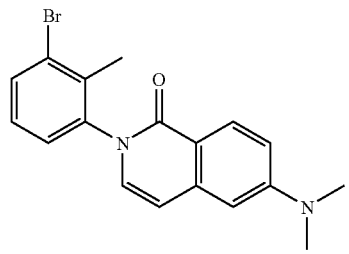

2-(3-Bromo-2-methyl-phenyl)-6-dimethylamino-2H-isoquinolin-1-one

6-Dimethylamino-2H-isoquinolin-1-one (50 mg, 0.27 mmol), cuprous iodide (10 mg, 0.053 mmol), and potassium carbonate (37 mg, 0.27 mmol) were deposited in sealed vessel. 3 mL DMSO and 2,6-dibromotoluene (133 mg, 0.532 mmol) were added. Argon was bubbled through the mixture for 2 minutes and the lid was tightly closed. This was heated at 150° C. for 5 hours. The resulting mixture was partitioned between ethyl acetate and water. The organic layer was washed with brine, dried over anhydrous magnesium sulfate, concentrated in vacuo, and purified by flash chromatography (30% ethyl acetate/hexanes) to yield 2-(3-Bromo-2-methyl-phenyl)-6-dimethylamino-2H-isoquinolin-1-one (43 mg, 0.12 mmol). MS (ESI) 357 (M+H)+.

Example 24

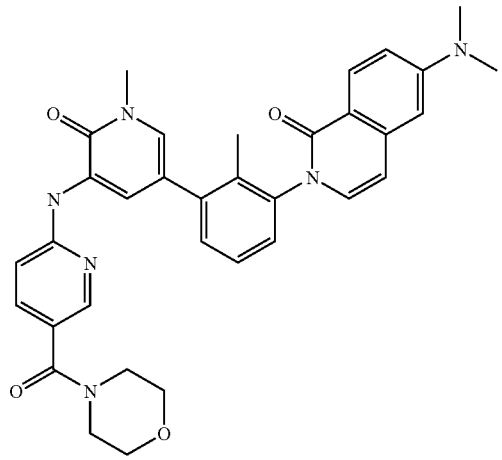

6-Dimethylamino-2-(2-methyl-3-{1-methyl-5-[5-(morpholine-4-carbonyl)-pyridin-2-ylamino]-6-oxo-1,6-dihydro-pyridin-3-yl}-phenyl)-2H-isoquinolin-1-one To 1-Methyl-3-[5-(morpholine-4-carbonyl)-pyridin-2-ylamino]-5-(4,4,5,5-tetramethyl-[1,3,2]dioxaborolan-2-yl)-1H-pyridin-2-one (69 mg, 0.16 mmol), 2-(3-Bromo-2-methyl-phenyl)-6-dimethylamino-2H-isoquinolin-1-one (36 mg, 0.10 mmol), potassium phosphate (43 mg, 0.20 mmol), 2-(dicyclohexylphoshphino)-2',4',6'-tri-i-propyl-1,1'-biphenyl (2.9 mg, 0.0061 mmol), and bis(dibenzylidineacetone)palladium(0) (1.7 mg, 0.0030 mmol) was added 4 mL of degassed 1:3 water/n-butanol. The headspace of the vessel was evacuated and backfilled with argon 4 times. This was heated at 100° C. for 110 minutes. This was partitioned between ethyl acetate and water. The ethyl acetate layer was washed with brine, dried over anhydrous magnesium sulfate, concentrated in vacuo, and purified by flash chromatography (gradient elution 2 to 10% methanol/dichloromethane) to yield 6-Dimethylamino-2-(2-methyl-3-{1-methyl-5-[5-(morpholine-4-carbonyl)-pyridin-2-ylamino]-6-oxo-1,6-dihydro-pyridin-3-yl}-phenyl)-2H-isoquinolin-1-one (46 mg, 0.078 mmol). MS (ESI) 591.1 (M+H)+.

Example 25

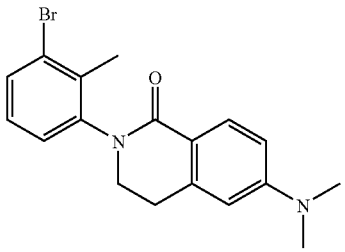

2-(3-Bromo-2-methyl-phenyl)-6-dimethylamino-3,4-dihydro-2H-isoquinolin-1-one

6-Dimethylamino-3,4-dihydro-2H-isoquinolin-1-one (150 mg, 0.789 mmol), cuprous iodide (30 mg, 0.16 mmol) and potassium carbonate (109 mg, 0.789 mmol) were deposited in a sealed vessel. 3 mL DMSO and 2,6-dibromotoluene (395 mg, 1.58 mmol) were added. Argon was bubbled through the mixture for 2 minutes and the lid was tightly closed. This was heated at 150° C. for 24 hours. Cuprous iodide (30 mg, 0.16 mmol) was added and the mixture was heated at 150° C. for an additional 24 hours. This was diluted with dichoromethane and filtered through a pad of celite. The filtrate was partitioned between dichloromethane and 5% aq. ammonium hydroxide. The dichloromethane layer was washed with brine. The combined aqueous layers were washed with dichloromethane. The combined dichloromethane layers were dried over anhydrous magnesium sulfate, concentrated in vacuo, and purified by flash chromatography (gradient elution 25 to 50% ethyl acetate/hexanes) to yield 2-(3-Bromo-2-methyl-phenyl)-6-dimethylamino-3,4-dihydro-2H-isoquinolin-1-one (181 mg, 0.504 mmol). MS (ESI) 361.1 (M+H)+.

Example 26

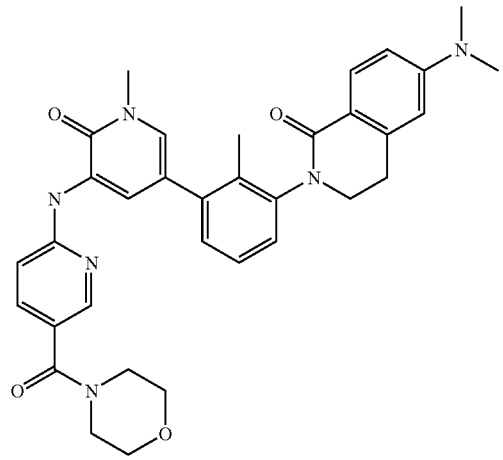

6-Dimethylamino-2-(2-methyl-3-{1-methyl-5-[5-(morpholine-4-carbonyl)-pyridin-2-ylamino]-6-oxo-1,6-dihydro-pyridin-3-yl}-phenyl)-3,4-dihydro-2H-isoquinolin-1-one To 1-Methyl-3-[5-(morpholine-4-carbonyl)-pyridin-2-ylamino]-5-(4,4,5,5-tetramethyl-[1,3,2]dioxaborolan-2-yl)-1H-pyridin-2-one (77 mg, 0.18 mmol), 2-(3-Bromo-2-methyl-phenyl)-6-dimethylamino-3,4-dihydro-2H-isoquinolin-1-one (63 mg, 0.18 mmol), potassium phosphate (74 mg, 0.35 mmol), 2-(dicyclohexylphoshphino)-2',4',6'-tri-i-propyl-1,1'-biphenyl (5.0 mg, 0.010 mmol), and bis(dibenzylidineacetone)palladium(0) (3.0 mg, 0.0052 mmol) was added 4 mL of degassed 1:3 water/n-butanol. The headspace of the vessel was evacuated and backfilled with argon 4 times. This was heated at 100° C. for 110 minutes. This was partitioned between ethyl acetate and water. The ethyl acetate layer was washed with brine, dried over anhydrous magnesium sulfate, concentrated in vacuo, and purified by flash chromatography (gradient elution 2 to 5% methanol/dichloromethane) to yield 6-Dimethylamino-2-(2-methyl-3-{1-methyl-5-[5-(morpholine-4-carbonyl)-pyridin-2-ylamino]-6-oxo-1,6-dihydro-pyridin-3-yl}-phenyl)-3,4-dihydro-2H-isoquinolin-1-one (33 mg, 0.056 mmol). MS (ESI) 593.3 (M+H)$^+$.

Example 27

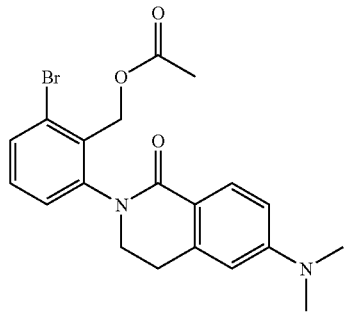

Acetic Acid 2-bromo-6-(6-dimethylamino-1-oxo-3,4-dihydro-1H-isoquinolin-2-yl)-benzyl Ester 6-Dimethylamino-3,4-dihydro-2H-isoquinolin-1-one (150 mg, 0.789 mmol), Acetic acid 2,6-dibromo-benzyl ester (487 mg, 1.58 mmol), cuprous iodide (30 mg, 0.16 mmol) and potassium carbonate (109 mg, 0.789 mmol) were deposited in a sealed vessel. 3 mL DMSO was added. Argon was bubbled through the mixture for 2 minutes and the lid was tightly closed. This was heated at 150° C. for 24 hours. Cuprous iodide (30 mg, 0.16 mmol) was added and the mixture was heated at 15° C. for an additional 24 hours. This was diluted with dichoromethane and filtered through a pad of celite. The filtrate was partitioned between dichloromethane and 5% aq. ammonium hydroxide. The dichloromethane layer was dried over anhydrous magnesium sulfate, concentrated in vacuo, and purified by flash chromatography (gradient elution 25 to 50% ethyl acetate/hexanes) to yield Acetic acid 2-bromo-6-(6-dimethylamino-1-oxo-3,4-dihydro-1H-isoquinolin-2-yl)-benzyl ester (93 mg, 0.22 mmol). MS (ESI) 417.1 (M+H)$^+$.

Example 28

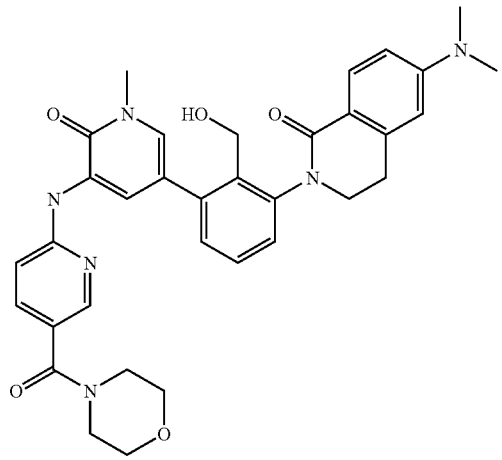

6-Dimethylamino-2-(2-hydroxymethyl-3-{1-methyl-5-[5-(morpholine-4-carbonyl)-pyridin-2-ylamino]-6-oxo-1,6-dihydro-pyridin-3-yl}-phenyl)-3,4-dihydro-2H-isoquinolin-1-one To 1-Methyl-3-[5-(morpholine-4-carbonyl)-pyridin-2-ylamino]-5-(4,4,5,5-tetramethyl-[1,3,2]dioxaborolan-2-yl)-1H-pyridin-2-one (60 mg, 0.14 mmol), Acetic acid 2-bromo-6-(6-dimethylamino-1-oxo-3,4-dihydro-1H-isoquinolin-2-yl)-benzyl ester (46 mg, 0.1 mmol), potassium phosphate (47 mg, 0.22 mmol), 2-(dicyclohexylphoshphino)-2',4',6'-tri-i-propyl-1,1'-biphenyl (3.1 mg, 0.0065 mmol), and bis(dibenzylidineacetone)palladium(0) (1.9 mg, 0033 mmol) was added 4 mL of degassed 1:3 water/n-butanol. The headspace of the vessel was evacuated and backfilled with argon 4 times. This was heated at 100° C. for 110 minutes. This was partitioned between ethyl acetate and water. The ethyl acetate layer was washed with brine, dried over anhydrous magnesium sulfate, and concentrated in vacuo. This was dissolved in 2 mL tetrahydrofuran, 1 mL methanol, and 1 mL water. 1M aq. lithium hydroxide solution (0.33 mL, 0.33 mmol) was added. After stirring for 18 hours, the resulting mixture was partitioned between ethyl acetate and water. The ethyl acetate layer was washed with brine, dried over anhydrous magnesium sulfate, concentrated in vacuo, and purified by flash chromatography (gradient elution 2 to 5% methanol/dichloromethane) to yield 6-Dimethylamino-2-(2-hydroxymethyl-3-{1-methyl-5-[5-(morpholine-4-carbonyl)-pyridin-2-ylamino]-6-oxo-1,6-dihydro-pyridin-3-yl}-phenyl)-3,4-dihydro-2H-isoquinolin-1-one (36 mg, 0.059 mmol). MS (ESI) 609.1 (M+H)$^+$.

Example 29

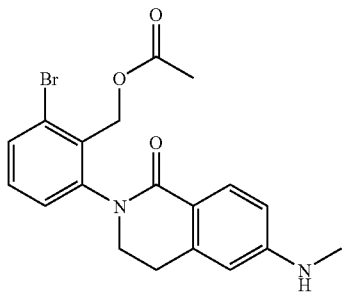

Acetic Acid 2-bromo-6-(6-methylamino-1-oxo-3,4-dihydro-1H-isoquinolin-2-yl)-benzyl Ester To a solution of acetic acid 2-bromo-6-(6-dimethylamino-1-oxo-3,4-dihydro-1H-isoquinolin-2-yl)-benzyl ester (224 mg, 0.482 mmol) in 5 mL 1,4-dioxane was added 2,3-dichloro-5,6-dicyano-p-benzoquinone (109 mg, 0.48 mmol). After stirring for 4 hours, this was partitioned between ethylacetate and 1M aq. NaOH. The organic layer was washed with water, washed with brine, dried over anhydrous magnesium sulfate, concentrated in vacuo, and purified by flash chromatography (gradient elution 40 to 50% ethylacetate/hexanes) to yield acetic acid 2-bromo-6-(6-methylamino-1-oxo-3,4-dihydro-1H-isoquinolin-2-yl)-benzyl ester (93 mg, 0.23 mmol). MS (ESI) 404.8 (M+H)$^+$.

Example 30

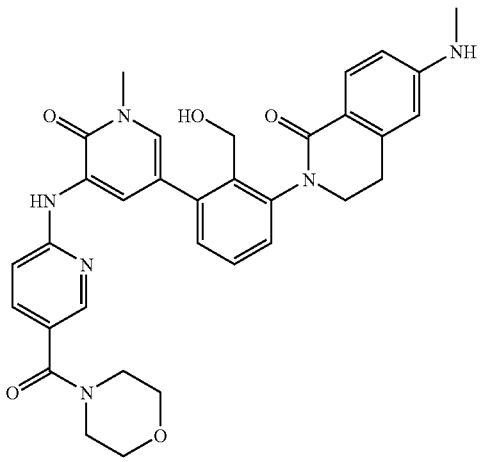

2-(2-Hydroxymethyl-3-{1-methyl-5-[5-(morpholine-4-carbonyl)-pyridin-2-ylamino]-6-oxo-1,6-dihydro-pyridin-3-yl}-phenyl)-6-methylamino-3,4-dihydro-2H-isoquinolin-1-one To 1-Methyl-3-[5-(morpholine-4-carbonyl)-pyridin-2-ylamino]-5-(4,4,5,5-tetramethyl-[1,3,2]dioxaborolan-2-yl)-1H-pyridin-2-one (96 mg, 0.22 mmol), acetic acid 2-bromo-6-(6-methylamino-1-oxo-3,4-dihydro-1H-isoquinolin-2-yl)-benzyl ester (88 mg, 0.22 mmol), potassium phosphate (46 mg, 0.22 mmol), 2-(dicyclohexylphoshphino)-2',4',6'-tri-i-propyl-1,1'-biphenyl (6.2 mg, 0.013 mmol), and bis(dibenzylidineacetone)palladium(0) (3.7 mg, 0064 mmol) was added 4 mL of degassed 1:3 water/n-butanol. The headspace of the vessel was evacuated and backfilled with argon 4 times. This was heated at 100° C. for 2 hours. This was partitioned between ethyl acetate and water. The ethyl acetate layer was washed with brine, dried over anhydrous magnesium sulfate, and concentrated in vacuo. This was dissolved in 2 mL tetrahydrofuran, 1 mL methanol, and 1 mL water. 1M aq. lithium hydroxide solution (0.65 mL, 0.65 mmol) was added. After stirring for 18 hours, the resulting mixture was partitioned between ethyl acetate and water. The ethyl acetate layer was washed with brine, dried over anhydrous magnesium sulfate, concentrated in vacuo, and purified by preparative TLC (5% methanol/dichloromethane) to yield 2-(2-Hydroxymethyl-3-{1-methyl-5-[5-(morpholine-4-carbonyl)-pyridin-2-ylamino]-6-oxo-1,6-dihydro-pyridin-3-yl}-phenyl)-6-methylamino-3,4-dihydro-2H-isoquinolin-1-one (43 mg, 0.072 mmol). MS (ESI) 595 (M+H)$^+$.

Example 31

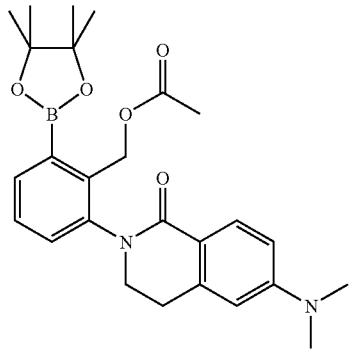

Acetic Acid 2-(6-dimethylamino-1-oxo-3,4-dihydro-1H-isoquinolin-2-yl)-6-(4,4,5,5-tetramethyl-[1,3,2]dioxaborolan-2-yl)-benzyl Ester To acetic acid 2-bromo-6-(6-dimethylamino-1-oxo-3,4-dihydro-1H-isoquinolin-2-yl)-benzyl ester (422 mg, 1.01 mmol), bis(pinacolato)diboron (308 mg, 1.21 mmol), and potassium acetate (298 mg, 3.03 mmol) in a sealed tube was added 5 mL dimethylsulfoxide. Argon was bubbled through this mixture for 3 minutes. [1,1'-Bis(diphenylphosphino)ferrocene]dichloropalladium(II) complex with dichloromethane (25 mg, 0.030 mmol) was added. Argon was continued to bubble through the mixture for one more minute and the lid was tightly closed. This was heated at 80° C. for 18 hours. This was partitioned between ethyl acetate and water. The ethyl acetate layer was washed with brine, dried over anhydrous magnesium sulfate, concentrated in vacuo, and purified by flash chromatography (gradient elution 30 to 50% ethyl acetate/hexanes) to yield acetic acid 2-(6-dimethylamino-1-oxo-3,4-dihydro-1H-isoquinolin-2-yl)-6-(4,4,5,5-tetramethyl-[1,3,2]dioxaborolan-2-yl)-benzyl ester (251 mg, 0.541 mmol). MS (ESI) 487.2 (M+Na)$^+$.

Example 32

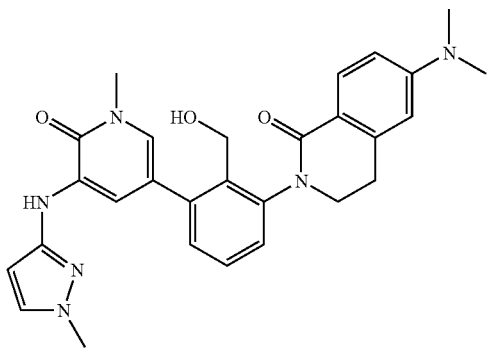

6-Dimethylamino-2-{2-hydroxymethyl-3-[1-methyl-5-(1-methyl-1H-pyrazol-3-ylamino)-6-oxo-1,6-dihydro-pyridin-3-yl]-phenyl}-3,4-dihydro-2H-isoquinolin-1-one 5-Bromo-1-methyl-3-(1-methyl-1H-pyrazol-3-ylamino)-1H-pyridin-2-one (35 mg, 0.13 mmol), acetic acid 2-(6-dimethylamino-1-oxo-3,4-dihydro-1H-isoquinolin-2-yl)-6-(4,4,5,5-tetramethyl-[1,3,2]dioxaborolan-2-yl)-benzyl ester (58 mg, 0.13 mmol), tetrakis(triphenylphosphine)palladium(0) (14 mg, 0.012 mmol), and sodium carbonate (40 mg, 0.38 mmol) were dissolved in 2 mL 1,2-dimethoxyethane and 1 mL water. This was microwaved at 120° C. for 30 minutes. This was partitioned between ethylacetate and water. The organic layer was washed with brine, dried over anhydrous magnesium sulfate, and concentrated in vacuo. This was dissolved in 3 mL tetrahydrofuran, 1.5 mL methanol, and 1.5 mL water. 1M aq. Lithium hydroxide solution (0.38 mL, 0.38 mmol) was added. This stirred for 3 hours. This was partitioned between ethylacetate and water. The organic layer was washed with brine, dried over anhydrous magnesium sulfate, concentrated in vacuo, and purified by preparative TLC (5% methanol/dichloromethane) to yield 6-Dimethylamino-2-{2- hydroxymethyl-3-[1-methyl-5-(1-methyl-1H-pyrazol-3-ylamino)-6-oxo-1,6-dihydro-pyridin-3-yl]-phenyl}-3,4-dihydro-2H-isoquinolin-1-one (39 mg, 0.078 mmol). MS (ESI) 499.2 (M+H)⁺.

Example 33

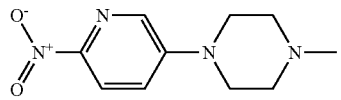

1-Methyl-4-(6-nitro-pyridin-3-yl)-piperazine

To 5-Bromo-2-nitro-pyridine (2.00 g, 9.85 mmol) in 10 mL dimethylsulfoxide was added potassium carbonate (2.72 g, 19.7 mmol), 1-methylpiperazine (1.64 mL, 14.8 mmol), and tetrabutylammonium iodide (36 mg, 0.097 mmol) and was heated at 120° C. for 18 hours. The mixture was made acidic with 1M aq. HCl and was partitioned between dichloromethane and water. The aqueous layer was made basic with 2M aq. sodium carbonate and was extracted with dichloromethane. The organic layer was dried over anhydrous magnesium sulfate, concentrated in vacuo, and was triturated with water to yield 1-Methyl-4-(6-nitro-pyridin-3-yl)-piperazine (1.82 g, 8.19 mmol). MS (ESI) 223.1 (M+H)⁺.

Example 34

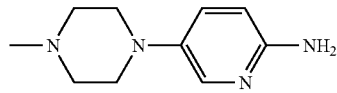

5-(4-Methyl-piperazin-1-yl)-pyridin-2-ylamine

1-Methyl-4-(6-nitro-pyridin-3-yl)-piperazine (1.748 g, 7.865 mmol) was stirred in 30 mL methanol with 175 mg 10% palladium on carbon under an atmosphere of hydrogen gas for 5 hours. This was filtered and concentrated in vacuo to yield 5-(4-Methyl-piperazin-1-yl)-pyridin-2-ylamine (1.485 g, 7.724 mmol). MS (ESI) 193.1 (M+H)⁺.

Example 35

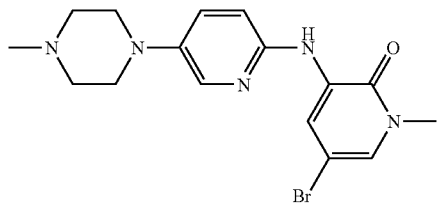

5-Bromo-1-methyl-3-[5-(4-methyl-piperazin-1-yl)-pyridin-2-ylamino]-1H-pyridin-2-one To 5-(4-Methyl-piperazin-1-yl)-pyridin-2-ylamine (1.06 g, 5.53 mmol), 3,5-Dibromo-1-methyl-1H-pyridin-2-one (1.23 g, 4.61 mmol), 4,5-bis(diphenylphosphino)-9,9-dimethylxanthene (400 mg, 0.691 mmol), and cesium carbonate (4.50 g, 13.8 mmol) was added 45 mL 1,4-dioxane and tris(dibenzylidineacetone)dipalladium(0) (422 mg, 0.461 mmol). This was heated in a a 120° C. oil bath for 6 hours under argon. This was partitioned between ethylacetate and dilute aqueous sodium bicarbonate. The organic layer was washed with brine, dried over anhydrous magnesium sulfate, concentrated in vacuo, and purified by flash chromatography (gradient elution with 2 to 5% methanol/dichloromethane) to yield 5-Bromo-1-methyl-3-[5-(4-methyl-piperazin-1-yl)-pyridin-2-ylamino]-1H-pyridin-2-one (484 mg, 1.28 mmol). MS (ESI) 380.0 (M+H)⁺.

Example 36

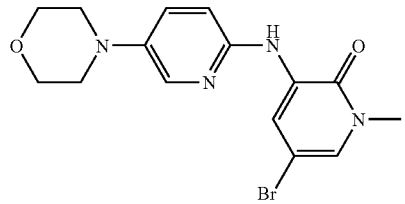

5-Bromo-1-methyl-3-(5-morpholin-4-yl-pyridin-2-ylamino)-1H-pyridin-2-one

This compound was made analogously to 5-Bromo-1-methyl-3-[5-(4-methyl-piperazin-1-yl)-pyridin-2-ylamino]-1H-pyridin-2-one. MS (ESI) 365.0 (M+H)⁺.

Example 37

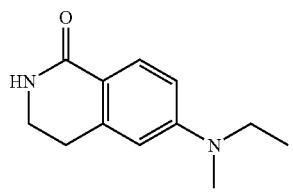

6-(Ethyl-methyl-amino)-3,4-dihydro-2H-isoquinolin-1-one

6-Fluoro-3,4-dihydro-2H-isoquinolin-1-one (2.00 g, 12.1 mmol) was deposited in a sealed tube with N-ethylmethylamine (4.0 mL, 47 mmol). This was heated at 150° C. for 24 hours. This was concentrated in vacuo and purified by flash chromatography (elution with ethylacetate) to yield 6-(Ethyl-methyl-amino)-3,4-dihydro-2H-isoquinolin-1-one (2.10 g, 10.3 mmol). MS (ESI) 205.1 (M+H)⁺.

Example 38

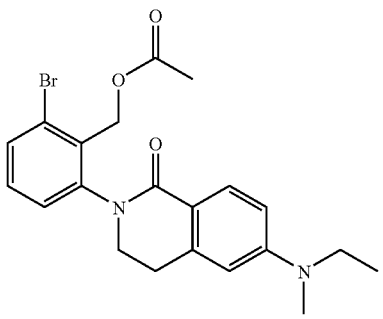

Acetic Acid 2-bromo-6-[6-(ethyl-methyl-amino)-1-oxo-3,4-dihydro-1H-isoquinolin-2-yl]-benzyl Ester 6-(Ethyl-methyl-amino)-3,4-dihydro-2H-isoquinolin-1-one (2.07 g, 10.1 mmol), acetic acid 2,6-dibromo-benzyl ester (6.25, 20.3 mmol), cuprous iodide (386 mg, 2.03 mmol) and potassium carbonate (1.40, 10.1 mmol) were deposited in a sealed vessel. 30 mL DMSO was added. Argon was bubbled through the mixture for 3 minutes and the lid was tightly closed. This was heated at 150° C. for 24 hours. Cuprous iodide (386 mg, 2.03 mmol) was added and the mixture was heated at 150° C. for an additional 24 hours. This was diluted with 300 mL ethyl acetate and 300 mL water. After stirring for 20 minutes, this was filtered through a pad of celite. The layers were separated. The ethylacetate layer was dried over anhydrous magnesium sulfate, concentrated in vacuo, and purified by flash chromatography (gradient elution 25 to 50% ethyl acetate/hexanes) to yield acetic acid 2-bromo-6-[6-(ethyl-methyl-amino)-1-oxo-3,4-dihydro-1H-isoquinolin-2-yl]-benzyl ester (1.21 g, 2.81 mmol). MS (ESI) 433.0 $(M+H)^+$.

Example 39

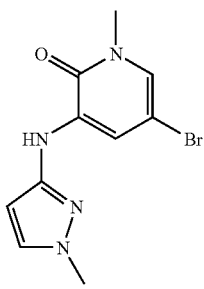

5-Bromo-1-methyl-3-(1-methyl-1H-pyrazol-3-ylamino)-1H-pyridin-2-one 3,5-Dibromo-1-methyl-1H-pyridin-2-one (469 mg, 1.76 mmol), 1-Methyl-1H-pyrazol-3-ylamine (205 mg, 2.1 mmol), tris(dibenzylidineacetone)dipalladium(0) (80 mg, 0.087 mmol), 2,2'-bis(diphenylphosphino-1,1'-binaphthalene (82 mg, 0.13 mmol), and cesium carbonate (801 mg, 2.46 mmol) were deposited in a sealed vial with 10 mL toluene. This was heated at 130° C. for 18 hours. The resulting mixture was poured into 50 mL water. This was extracted with ethylacetate. The ethylacetate layer was washed with brine, dried over anhydrous magnesium sulfate, filtered, concentrated in vacuo, and purified by flash chromatography (eluted with ethylacete/hexanes) to yield 5-Bromo-1-methyl-3-(1-methyl-1H-pyrazol-3-ylamino)-1H-pyridin-2-one (271 mg, 0.957 mmol). MS (ESI) 284.9 $(M+H)^+$.

Example 40

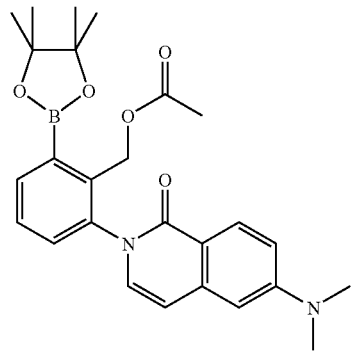

Acetic Acid 2-(6-dimethylamino-1-oxo-1H-isoquinolin-2-yl)-6-(4,4,5,5-tetramethyl-[1,3,2]dioxaborolan-2-yl)-benzyl Ester To Acetic acid 2-bromo-6-(6-dimethylamino-1-oxo-1H-isoquinolin-2-yl)-benzyl ester (420 mg, 1.01 mmol), bis(pinacolato)diboron (308 mg, 1.21 mmol), and potassium acetate (298 mg, 3.03 mmol) in a sealed tube was added 5 mL dimethylsulfoxide. Argon was bubbled through this mixture for 3 minutes. [1,1'-Bis(diphenylphosphino)ferrocene]dichloropalladium(II) complex with dichloromethane (25 mg, 0.030 mmol) was added. Argon was continued to bubble through the mixture for one more minute and the lid was tightly closed. This was heated at 80° C. for 18 hours. This was partitioned between ethyl acetate and water. The ethyl acetate layer was washed with brine, dried over anhydrous magnesium sulfate, concentrated in vacuo, and purified by flash chromatography (gradient elution 25 to 50% ethyl acetate/hexanes) to yield acetic acid Acetic acid 2-(6-dimethylamino-1-oxo-1H-isoquinolin-2-yl)-6-(4,4,5,5-tetramethyl-[1,3,2]dioxaborolan-2-yl)-benzyl ester (183 mg, 0.396 mmol). MS (ESI) 463.1 $(M+H)^+$.

Example 41

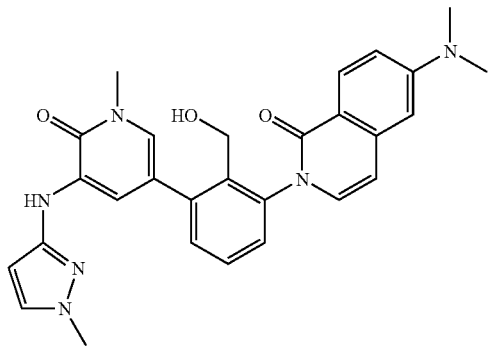

6-Dimethylamino-2-{2-hydroxymethyl-3-[1-methyl-5-(1-methyl-1H-pyrazol-3-ylamino)-6-oxo-1,6-dihydro-pyridin-3-yl]-phenyl}-2H-isoquinolin-1-one 5-Bromo-1-methyl-3-(1-methyl-1H-pyrazol-3-ylamino)-1H-pyridin-2-one (47 mg, 0.17 mmol), Acetic acid 2-(6-dimethylamino-1-oxo-1H-isoquinolin-2-yl)-6-(4,4,5,5-tetramethyl-[1,3,2]dioxaborolan-2-yl)-benzyl ester (77 mg, 0.17 mmol), tetrakis(triphenylphosphine)palladium(0) (19 mg, 0.016 mmol), and sodium carbonate (53 mg, 0.50 mmol) were dissolved in 2 mL 1,2-dimethoxyethane and 1 mL water. This was microwaved at 120° C. for 30 minutes. This was partitioned between ethylacetate and water. The organic layer was washed with brine, dried over anhydrous magnesium sulfate, and concentrated in vacuo. This was dissolved in 3 mL tetrahydrofuran, 1.5 mL methanol, and 1.5 mL water. 1M aq. Lithium hydroxide solution (0.5 mL, 0.5 mmol) was added. This stirred for 3 hours. This was partitioned between ethylacetate and water. The organic layer was washed with brine, dried over anhydrous magnesium sulfate, concentrated in vacuo, and purified by preparative TLC (elution with 5% methanol/dichloromethane) to yield 6-Dimethylamino-2-{2-hydroxymethyl-3-[1-methyl-5-(1-methyl-1H-pyrazol-3-ylamino)-6-oxo-1,6-dihydro-pyridin-3-yl]-phenyl}-2H-isoquinolin-1-one (37 mg, 0.075 mmol). MS (ESI) 497.1 (M+H)+.

Example 42

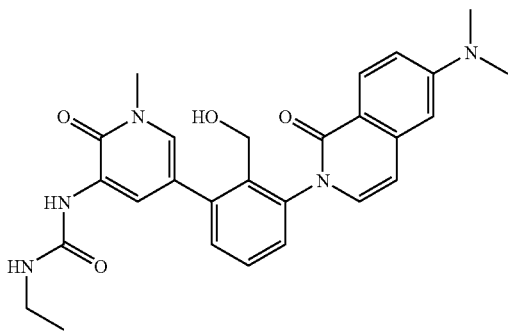

1-{5-[3-(6-Dimethylamino-1-oxo-1H-isoquinolin-2-yl)-2-hydroxymethyl-phenyl]-1-methyl-2-oxo-1,2-dihydro-pyridin-3-yl}-3-ethyl-urea To 1-Ethyl-3-[1-methyl-2-oxo-5-(4,4,5,5-tetramethyl-[1,3,2]dioxaborolan-2-yl)-1,2-dihydro-pyridin-3-yl]-urea (50 mg, 0.16 mmol), acetic acid 2-bromo-6-(6-dimethylamino-1-oxo-1H-isoquinolin-2-yl)-benzyl ester (65 mg, 0.16 mmol), potassium phosphate (66 mg, 0.31 mmol), 2-(dicyclohexylphoshphino)-2',4',6'-tri-i-propyl-1,1'-biphenyl (4.4 mg, 0.0092 mmol), and bis(dibenzylidineacetone)palladium (0) (2.6 mg, 0.0045 mmol) was added 4 mL of degassed 1:3 water/n-butanol. The headspace of the vessel was evacuated and backfilled with argon 4 times. This was heated at 100° C. for 2 hours. This was partitioned between ethyl acetate and water. The ethyl acetate layer was washed with brine, dried over anhydrous magnesium sulfate, and concentrated in vacuo. This was dissolved in 2 mL tetrahydrofuran, 1 mL methanol, and 1 mL water. 1M aq. lithium hydroxide solution (0.47 mL, 0.47 mmol) was added. After stirring for 3 hours, the resulting mixture was partitioned between ethyl acetate and water. The ethyl acetate layer was washed with brine, dried over anhydrous magnesium sulfate, concentrated in vacuo, and purified by preparative TLC (5% methanol/dichloromethane) to yield 1-{5-[3-(6-Dimethylamino-1-oxo-1H-isoquinolin-2-yl)-2-hydroxymethyl-phenyl]-1-methyl-2-oxo-1,2-dihydro-pyridin-3-yl}-3-ethyl-urea (33 mg, 0.068 mmol). MS (ESI) 488.1(M+H)+.

Example 43

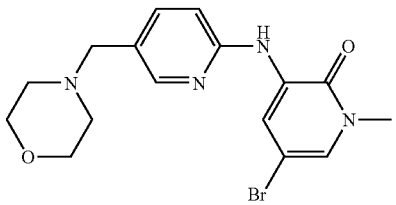

5-Bromo-1-methyl-3-(5-morpholin-4-ylmethyl-pyridin-2-ylamino)-1H-pyridin-2-one

5-Bromo-1-methyl-3-[5-(morpholine-4-carbonyl)-pyridin-2-ylamino]-1H-pyridin-2-one (2.3 g, 5.9 mmol) was dissolved in 30 mL tetrahydrofuran. Borane tetrahydrofuran complex (2.5 g, 29 mmol) was added. After stirring for 18 hours, this was concentrated in vacuo. Ethanol was added. This was refluxed for one hour. This was concentrated in vacuo and purified by flash chromatography to yield 5-Bromo-1-methyl-3-(5-morpholin-4-ylmethyl-pyridin-2-ylamino)-1H-pyridin-2-one (500 mg, 1.32 mmol). MS (ESI) 381.0 (M+H)+.

Example 44

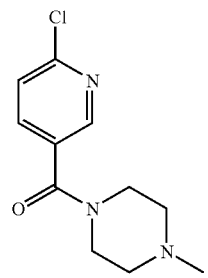

(6-Chloro-pyridin-3-yl)-(4-methyl-piperazin-1-yl)-methanone

To a solution of 6-Chloro-nicotinic acid (3.00 g, 19.0 mmol) in 30 mL dimethylformamide was added (benzotriazol-1-yloxy)tripyrrolidinophosphonium hexafluorophosphate (10.9 g, 20.9 mmol), 1-methylpiperazine (2.30 g, 22.1 mmol) and triethylamine (2.18 g, 21.5 mmol). After stirring for 18 hours, this was partitioned between ethyl acetate and water. The ethylacetate layer was dried over anhydrous sodium sulfate, concentrated in vacuo, and purified by flash chromatography (elution with 3% methanol/dichloromethane) to yield (6-Chloro-pyridin-3-yl)-(4-methyl-piperazin-1-yl)-methanone (2.50 g, 9.33 mmol).

Example 45

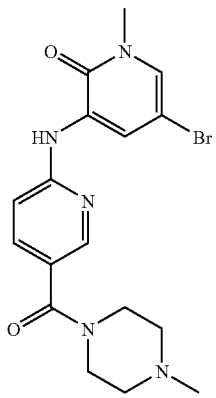

5-Bromo-1-methyl-3-[5-(4-methyl-piperazine-1-carbonyl)-pyridin-2-ylamino]-1H-pyridin-2-one To a solution of (6-Chloro-pyridin-3-yl)-(4-methyl-piperazin-1-yl)-methanone (2.00 g, 7.46 mmol) in 10 mL dimethylformamide was added 3-Amino-5-bromo-1-methyl-1H-pyridin-2-one (1.80 g, 8.95 mmol) and sodium hydride (537 mg, 22.4 mmol). After stirring for 18 hours, this was quenched with water. This was extracted with ethylacetate. The ethylacetate layer was dried over anhydrous sodium sulfate, concentrated in vacuo, and purified by flash chromatography (gradient elution 0 to 5% methanol/dichloromethane) to yield 5-Bromo-1-methyl-3-[5-(4-methyl-piperazine-1-carbonyl)-pyridin-2-ylamino]-1H-pyridin-2-one (900 mg, 1.94 mmol). MS (ESI) 406.0 (M+H)$^+$.

Example 46

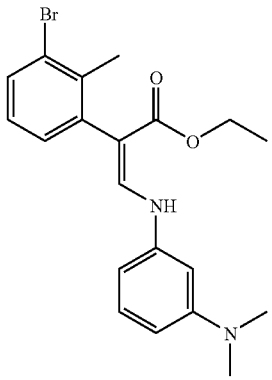

2-(3-Bromo-2-methyl-phenyl)-3-(3-dimethylamino-phenylamino)-acrylic Acid Ethyl Ester (3-Bromo-2-methyl-phenyl)-acetic acid benzyl ester (421 mg, 1.32 mmol) was dissolved in ethyl formate (2.5 mL, 31 mmol). Sodium hydride (95%, 67 mg, 2.6 mmol) was added. After stirring for 30 minutes, this was quenched with 1M aq. HCl. This was partitioned between ethyl acetate and water. The ethyl acetate layer was washed with water, washed with brine, dried over anhydrous magnesium sulfate, and concentrated in vacuo.

A portion of this material and N,N-Dimethyl-benzene-1,3-diamine (96 mg, 0.70 mmol) were stirred in 1 mL ethanol for 18 hours. This was concentrated in vacuo and purified by flash chromatography (gradient elution 5 to 20% ethyl acetate/hexanes) to yield 2-(3-Bromo-2-methyl-phenyl)-3-(3-dimethylamino-phenylamino)-acrylic acid ethyl ester (164 mg, 0.407 mmol). MS (ESI) 405.0 (M+H)$^+$.

Example 47

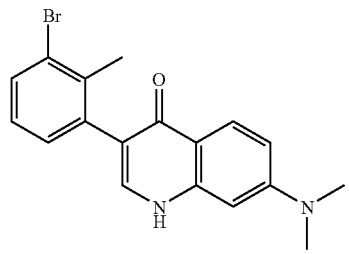

3-(3-Bromo-2-methyl-phenyl)-7-dimethylamino-1H-quinolin-4-one

To 2-(3-Bromo-2-methyl-phenyl)-3-(3-dimethylamino-phenylamino)-acrylic acid ethyl ester (100 mg, 0.248 mmol) was added 4 g polyphosphoric acid. This stirred at 140° C. for 10 minutes. 50 ml water was added and the mixture was stirred. The resulting precipitate was filtered and washed with water. The filtrate was extracted with 10% methanol/dichloromethane solution. The organic layer was dried over anhydrous magnesium sulfate and concentrated in vacuo. The resulting residue was combined with the precipitate and purified by flash chromatography (gradient elution 2 to 5% methanol/dichloromethane) to yield 3-(3-Bromo-2-methyl-phenyl)-7-dimethylamino-1H-quinolin-4-one (22 mg, 0.062 mmol). MS (ESI) 357.0 (M+H)$^+$.

Example 48

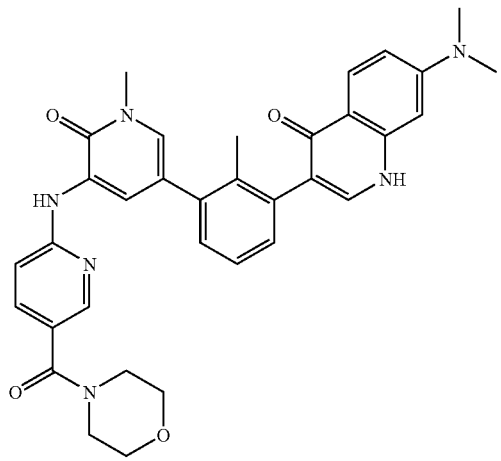

7-Dimethylamino-3-(2-methyl-3-{1-methyl-5-[5-(morpholine-4-carbonyl)-pyridin-2-ylamino]-6-oxo-1,6-dihydro-pyridin-3-yl}-phenyl)-1H-quinolin-4-one To Methyl-3-[5-(morpholine-4-carbonyl)-pyridin-2-ylamino]-5-(4,4,5,5-tetramethyl-[1,3,2]dioxaborolan-2-yl)-1H-pyridin-2-one (27 mg, 0.062 mmol), 3-(3-Bromo-2-methyl-phenyl)-7-dimethylamino-1H-quinolin-4-one (22 mg, 0.062 mmol), potassium phosphate (26 mg, 0.12 mmol), 2-(dicyclohexylphoshphino)-2',4',6'-tri-i-propyl-1,1'-biphenyl (1.7 mg, 0.0036 mmol), and bis(dibenzylidineacetone) palladium(0) (1.0 mg, 0.0018 mmol) was added 4 mL of degassed 1:3 water/n-butanol. The headspace of the vessel was evacuated and backfilled with argon 4 times. This was heated at 100° C. for 1 hour. This was partitioned between ethyl acetate and water. The ethyl acetate layer was washed with brine, dried over anhydrous magnesium sulfate, concentrated in vacuo, and purified by preparative TLC (5% methanol/dichloromethane) to yield 7-Dimethylamino-3-(2-methyl-3-{1-methyl-5-[5-(morpholine-4-carbonyl)-pyridin-2-ylamino]-6-oxo-1,6-dihydro-pyridin-3-yl}-phenyl)-1H-quinolin-4-one (14 mg, 0.024 mmol). MS (ESI) 591.1 (M+H)+.

Example 49

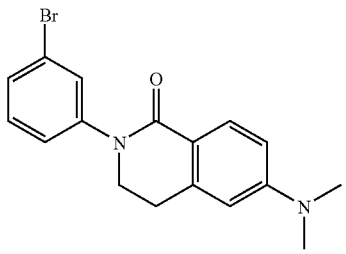

2-(3-Bromo-phenyl)-6-dimethylamino-3,4-dihydro-2H-isoquinolin-1-one

6-Dimethylamino-3,4-dihydro-2H-isoquinolin-1-one (762 mg, 4.01 mmol), cuprous iodide (153 mg, 0.802 mmol) and potassium carbonate (554 mg, 4.01 mmol) were deposited in a sealed type vessel. 6 mL DMSO and 1,3-dibromobenzene (1.89 g, 8.01 mmol) were added. Argon was bubbled through the mixture for 2 minutes and the lid was tightly closed. This was heated at 150° C. for 24 hours. Cuprous iodide (153 mg, 0.802 mmol) was added and the mixture was heated at 150° C. for an additional 24 hours. This was diluted with dichoromethane and filtered through a pad of celite. The filtrate was partitioned between dichloromethane and 5% aq. ammonium hydroxide. The dichloromethane layer was dried over anhydrous magnesium sulfate, concentrated in vacuo, and purified by flash chromatography (gradient elution 25 to 100% ethyl acetate/hexanes) to yield 2-(3-Bromo-phenyl)-6-dimethylamino-3,4-dihydro-2H-isoquinolin-1-one (939 mg, 2.72 mmol). MS (ESI) 345.0 (M+H)+.

Example 50

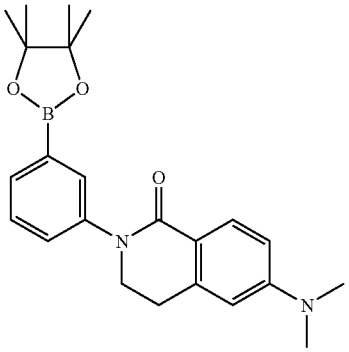

6-Dimethylamino-2-[3-(4,4,5,5-tetramethyl-[1,3,2]dioxaborolan-2-yl)-phenyl]-3,4-dihydro-2H-isoquinolin-1-one 2-(3-Bromo-phenyl)-6-dimethylamino-3,4-dihydro-2H-isoquinolin-1-one (163 mg, 0.472 mmol), bis(pinacolato)diboron (144 mg, 0.567 mmol), and potassium acetate (138 mg, 1.42 mmol) were deposited in a sealed vessel with 2 mL DMSO. Argon was bubbled through the mixture for 1 minute. [1,1'-Bis(diphenylphosphino)ferrocene]dichloropalladium (II) complex with dichloromethane (12 mg, 0.015 mmol) was added. Argon was continued to bubble through the mixture for one more minute and the lid was tightly closed. This was heated at 80° C. for 18 hours. This was partitioned between ethyl acetate and water. The ethyl acetate layer was washed with brine, dried over anhydrous magnesium sulfate, concentrated in vacuo, and purified by flash chromatography (30% ethyl acetate/hexanes) to yield 6-Dimethylamino-2-[3-(4,4,5,5-tetramethyl-[1,3,2]dioxaborolan-2-yl)-phenyl]-3,4-dihydro-2H-isoquinolin-1-one (137 mg, 0.349 mmol). MS (ESI) 393.2 (M+H)+.

Example 51

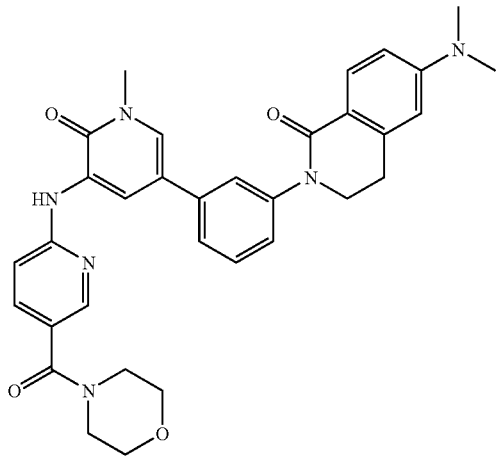

6-Dimethylamino-2-(3-{1-methyl-5-[5-(morpholine-4-carbonyl)-pyridin-2-ylamino]-6-oxo-1,6-dihydro-pyridin-3-yl}-phenyl)-3,4-dihydro-2H-isoquinolin-1-one 5-Bromo-1-methyl-3-[5-(morpholine-4-carbonyl)-pyridin-2-ylamino]-1H-pyridin-2-one (67 mg, 0.17 mmol), 6-Dimethylamino-2-[3-(4,4,5,5-tetramethyl-[1,3,2]dioxaborolan-2-yl)-phenyl]-3,4-dihydro-2H-isoquinolin-1-one (67 mg, 0.17 mmol), tetrakis(triphenylphosphine)palladium (0) (20 mg, 0.017 mmol), and sodium carbonate (54 mg, 0.51 mmol) in 2 mL 1,2-dimethoxyethane and 1 mL water was heated to 170° C. for 12.5 minutes in the microwave. The resulting mixture was partitioned between ethyl acetate and water. The ethyl acetate layer was washed with brine, dried over anhydrous magnesium sulfate, concentrated in vacuo, and purified by flash chromatography (gradient elution 2 to 5% methanol/dichloromethane) to yield 6-Dimethylamino-2-(3-{1-methyl-5-[5-(morpholine-4-carbonyl)-pyridin-2- ylamino]-6-oxo-1,6-dihydro-pyridin-3-yl}-phenyl)-3,4-dihydro-2H-isoquinolin-1-one (40 mg, 0.069 mmol). MS (ESI) 579.2 (M+H)⁺.

Example 52

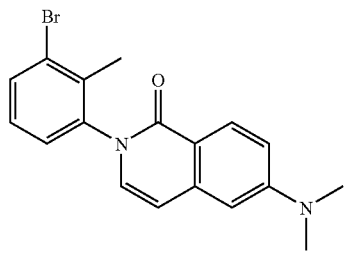

2-(3-Bromo-2-methyl-phenyl)-6-dimethylamino-2H-isoquinolin-1-one

6-Dimethylamino-2H-isoquinolin-1-one (50 mg, 0.27 mmol), cuprous iodide (10 mg, 0.053 mmol), and potassium carbonate (37 mg, 0.27 mmol) were deposited in sealed vessel. 3 mL DMSO and 2,6-dibromotoluene (133 mg, 0.532 mmol) were added. Argon was bubbled through the mixture for 2 minutes and the lid was tightly closed. This was heated at 150° C. for 5 hours. The resulting mixture was partitioned between ethyl acetate and water. The organic layer was washed with brine, dried over anhydrous magnesium sulfate, concentrated in vacuo, and purified by flash chromatography (30% ethyl acetate/hexanes) to yield 2-(3-Bromo-2-methyl-phenyl)-6-dimethylamino-2H-isoquinolin-1-one (43 mg, 0.12 mmol). MS (ESI) 357 (M+H)⁺.

Example 53

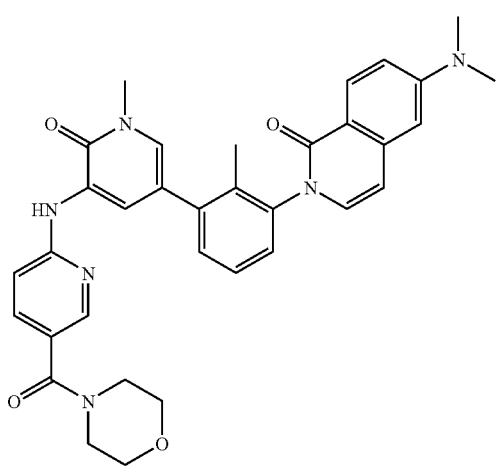

6-Dimethylamino-2-(2-methyl-3-{1-methyl-5-[5-(morpholine-4-carbonyl)-pyridin-2-ylamino]-6-oxo-1,6-dihydro-pyridin-3-yl}-phenyl)-2H-isoquinolin-1-one To 1-Methyl-3-[5-(morpholine-4-carbonyl)-pyridin-2-ylamino]-5-(4,4,5,5-tetramethyl-[1,3,2]dioxaborolan-2-yl)-1H-pyridin-2-one (69 mg, 0.16 mmol), 2-(3-Bromo-2-methyl-phenyl)-6-dimethylamino-2H-isoquinolin-1-one (36 mg, 0.100 mmol), potassium phosphate (43 mg, 0.20 mmol), 2-(dicyclohexylphoshphino)-2',4',6'-tri-i-propyl-1,1'-biphenyl (2.9 mg, 0.0061 mmol), and bis(dibenzylidineacetone) palladium(0) (1.7 mg, 0.0030 mmol) was added 4 mL of degassed 1:3 water/n-butanol. The headspace of the vessel was evacuated and backfilled with argon 4 times. This was heated at 100° C. for 110 minutes. This was partitioned between ethyl acetate and water. The ethyl acetate layer was washed with brine, dried over anhydrous magnesium sulfate, concentrated in vacuo, and purified by flash chromatography (gradient elution 2 to 10% methanol/dichloromethane) to yield 6-Dimethylamino-2-(2-methyl-3-{1-methyl-5-[5-(morpholine-4-carbonyl)-pyridin-2-ylamino]-6-oxo-1,6-dihydro-pyridin-3-yl}-phenyl)-2H-isoquinolin-1-one (46 mg, 0.078 mmol). MS (ESI) 591.1 (M+H)⁺.

Example 54

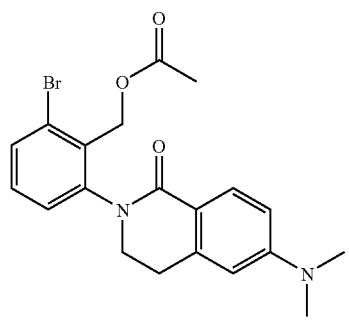

Acetic Acid 2-bromo-6-(6-dimethylamino-1-oxo-3,4-dihydro-1H-isoquinolin-2-yl)-benzyl Ester 6-Dimethylamino-3,4-dihydro-2H-isoquinolin-1-one (150 mg, 0.789 mmol), Acetic acid 2,6-dibromo-benzyl ester (487 mg, 1.58 mmol), cuprous iodide (30 mg, 0.16 mmol) and potassium carbonate (109 mg, 0.789 mmol) were deposited in a sealed vessel. 3 mL DMSO was added. Argon was bubbled through the mixture for 2 minutes and the lid was tightly closed. This was heated at 150° C. for 24 hours. Cuprous iodide (30 mg, 0.16 mmol) was added and the mixture was heated at 150° C. for an additional 24 hours. This was diluted with dichoromethane and filtered through a pad of celite. The filtrate was partitioned between dichloromethane and 5% aq. ammonium hydroxide. The dichloromethane layer was dried over anhydrous magnesium sulfate, concentrated in vacuo, and purified by flash chromatography (gradient elution 25 to 50% ethyl acetate/hexanes) to yield Acetic acid 2-bromo-6-(6-dimethylamino-1-oxo-3,4-dihydro-1H-isoquinolin-2-yl)-benzyl ester (93 mg, 0.22 mmol). MS (ESI) 417.1 (M+H)⁺.

Example 55

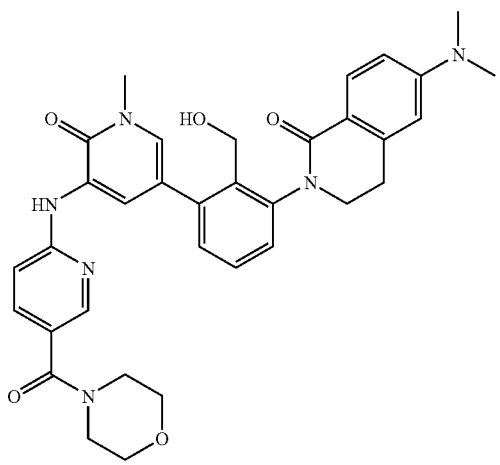

6-Dimethylamino-2-(2-hydroxymethyl-3-{1-methyl-5-[5-(morpholine-4-carbonyl)-pyridin-2-ylamino]-6-oxo-1,6-dihydro-pyridin-3-yl}-phenyl)-3,4-dihydro-2H-isoquinolin-1-one To 1-Methyl-3-[5-(morpholine-4-carbonyl)-pyridin-2-ylamino]-5-(4,4,5,5-tetramethyl-[1,3,2]dioxaborolan-2-yl)-1H-pyridin-2-one (60 mg, 0.14 mmol), Acetic acid 2-bromo-6-(6-dimethylamino-1-oxo-3,4-dihydro-1H-isoquinolin-2-yl)-benzyl ester (46 mg, 0.1 mmol), potassium phosphate (47 mg, 0.22 mmol), 2-(dicyclohexylphoshphino)-2',4',6'-tri-i-propyl-1,1'-biphenyl (3.1 mg, 0.0065 mmol), and bis(dibenzylidineacetone)palladium(0) (1.9 mg, 0033 mmol) was added 4 mL of degassed 1:3 water/n-butanol. The headspace of the vessel was evacuated and backfilled with argon 4 times. This was heated at 100° C. for 110 minutes. This was partitioned between ethyl acetate and water. The ethyl acetate layer was washed with brine, dried over anhydrous magnesium sulfate, and concentrated in vacuo. This was dissolved in 2 mL tetrahydrofuran, 1 mL methanol, and 1 mL water. 1M aq. lithium hydroxide solution (0.33 mL, 0.33 mmol) was added. After stirring for 18 hours, the resulting mixture was partitioned between ethyl acetate and water. The ethyl acetate layer was washed with brine, dried over anhydrous magnesium sulfate, concentrated in vacuo, and purified by flash chromatography (gradient elution 2 to 5% methanol/dichloromethane) to yield 6-Dimethylamino-2-(2-hydroxymethyl-3-{1-methyl-5-[5-(morpholine-4-carbonyl)-pyridin-2-ylamino]-6-oxo-1,6-dihydro-pyridin-3-yl}-phenyl)-3,4-dihydro-2H-isoquinolin-1-one (36 mg, 0.059 mmol). MS (ESI) 609.1 (M+H)⁺.

Example 56

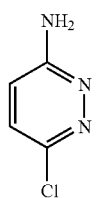

6-Chloro-pyridazin-3-ylamine 3,6-Dichloro-pyridazine (7.5 g, 50.35 mmol) was dissolved in ethanolic ammonia (100 mL) and heated at (130° C.) for overnight in pressure vessel. Then the ethanol was evaporated under reduced pressure and crude purified by silica gel (230-400 mesh) flash chromatography using EtOAc/Hexane (6:4) to afford the title compound (4 g, 61%) as a solid.

Example 57

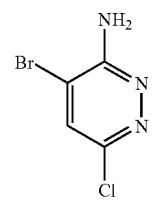

4-Bromo-6-chloro-pyridazin-3-ylamine

To a solution of 6-Chloro-pyridazin-3-ylamine (4 g, 31 mmol) in methanol (60 mL) was added NaHCO₃ (5.2 g, 62 mmol). The reaction mixture was stirred for 30 minutes at RT then Br₂ (4.9 g, 31 mmol) was added drop wise. Then the resulting reaction mixture was stirred additionally for 16 h at RT. After completion of reaction, the reaction mass concentrated under reduced pressure, crude purified by silica gel (100-200 mesh) chromatography using EtOAc/Hexane (8:2) to afford 4-Bromo-6-chloro-pyridazin-3-ylamine (2.3 g, 36%) as a solid.

Example 58

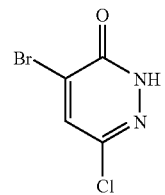

4-Bromo-6-chloro-2H-pyridazin-3-one

To a cooled solution (0-5° C.) of NaNO₂ (1 g, 13.20 mmol) in conc. H₂SO₄ (15 mL) was added 4-Bromo-6-chloro-pyridazin-3-ylamine (2.3 g, 11 mmol) in 50 mL of acetic acid. Then the reaction mixture was stirred for 1 h at 20° C. followed by addition of water (75 mL) and stirring continued for 5 h at RT. The reaction mixture extracted with EtOAc, dried over Na₂SO₄, concentrated under reduced pressure and crude purified by silica gel (100-200 mesh) chromatography using EtOAc/Hexane (8:2) to afford 4 (2.2 g, 95%) yellowish solid.

Example 59

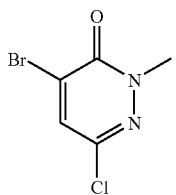

4-Bromo-6-chloro-2-methyl-2H-pyridazine-3-one

4-Bromo-6-chloro-2H-pyridazin-3-one (5.02 g, 23.97 mmol) was dissolved in 40 ml dimethylformamide. Cesium carbonate (9.37 g, 28.76 mmol) was added. After 5 min, iodomethane (5.103 g, 35.95 mmol) was added dropwise over 20 min. The reaction mixture was stirred 3 hours at room temperature. The precipitate was filtered off and concentrated and the resulting residue was treated with 20 ml dichloromethane. The insoluble material was filtered off again and washed with dichloromethane. The filtrate was concentrated in vacuo to yield 4-Bromo-6-chloro-2-methyl-2H-pyridazine-3-one (5.223 g, 23.37 mmol). MS (ESI) 224.9 $(M+H)^+$

Example 60

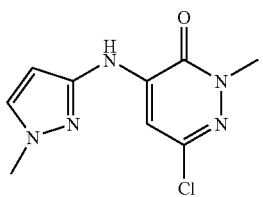

6-Chloro-2-methyl-4-(1-methyl-1H-pyrazol-3-ylamino)-2H-pyridazin-3-one

1-Methyl-1H-pyrazol-3-amine (806 mg, 8.3 mmol) was dissolved in 40 ml dioxane. Potassium tert-butoxide (1.793 g, 15.98 mmol) was added. Finally 4-Bromo-6-chloro-2-methyl-2H-pyridazine-3-one (1.7 g, 7.61 mmol) was added and the mixture was stirred for 3 hours at ambient temperature. The reaction mixture was transferred into an 150 ml Erlenmeyer flask and acidified with 15 ml 1 M aqueous hydrochloric solution, then treated with a saturated sodium bicarbonate solution until the ph reached about 8. It was extracted twice with each 100 ml of dichloromethane; and the organic phase was dried with sodium sulfate, filtered, and concentrated in vacuo to give 1.5 g of a light orange solid. This crude material was triturated with a mixture of dichloromethane and hexane. The suspension was filtered off and the resulting filter cake was dried under high vacuum to yield 6-Chloro-2-methyl-4-(1-methyl-1H-pyrazol-3-ylamino)-2H-pyridazin-3-one (967 mg, 4.03 mmol). MS (ESI) 240.0 $(M+H)^+$

Example 61

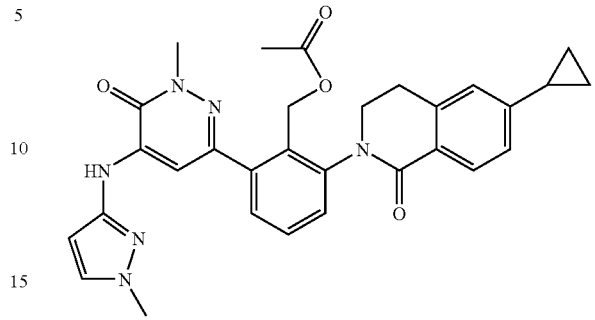

Acetic Acid 2-(6cyclopropyl-1-oxo-3,4-dihydro-1H-isoquinolin-2yl)-6-[1-methyl-5-(1-methyl-1H-pyrazol-3-ylamino)-6-oxo-1,6-dihydro-pyridazin-3-yl]-benzyl Ester 6-Chloro-2-methyl-4-(1-methyl-1H-pyrazol-3-ylamino)-2H-pyridazin-3-one (0.09 g, 0.376 mmol), acetic acid 2-(6cyclopropyl-1-oxo-3,4-dihydro-1H-isoquinolin-2yl)-6-(4,4,5,-tetramethyl-[1,3,2]dioxaborolan-2yl)-benzyl ester (0.191 g, 0.414 mmol) and cesium carbonate (0.428 g, 1.31 mmol) were treated with a degassed solution of 2 ml dioxane/0.2 ml water. After 5 min stirring [1,1'-bis(diphenylphosphino)ferrocene]dichloropalladium(II) complex (0.031 g, 0.038 mmol) was added and heated to 135° C. for 30 min in the microwave. The reaction mixture was filtered over cellulose, washed with 10 ml of dioxane and concentrated in vacuo. The residue was purified by silica gel chromatography (gradient elution 0-10% methanol in dichloromethane for 20 min) to yield a crude acetic acid 2-(6cyclopropyl-1-oxo-3,4-dihydro-1H-isoquinolin-2yl)-6-[1-methyl-5-(1-methyl-1H-pyrazol-3-ylamino)-6-oxo-1,6-dihydro-pyridazin-3-yl]-benzyl ester (0.200 g, 0.371 mmol). MS (ESI) 540.1 $(M+H)^+$

Example 62

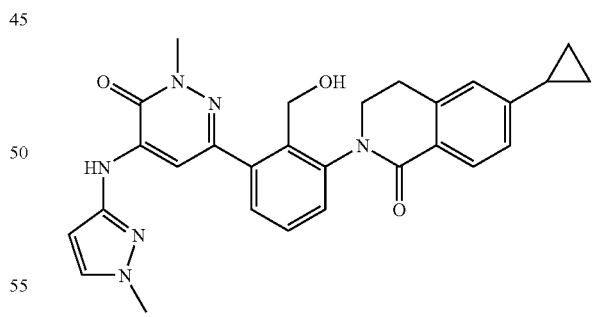

6-Cyclopropyl-2-{2-hydroxymethyl-3-[1-methyl-5-(1-methyl-1H-pyrazol-3-ylamino-6-oxo-1,6-dihydro-pyridazine-3-yl)-phenyl}-3,4-dihydro-2H-isoquinolin-1-one Acetic acid 2-(6cyclopropyl-1-oxo-3,4-dihydro-1H-isoquinolin-2yl)-6-[1-methyl-5-(1-methyl-1H-pyrazol-3-ylamino)-6-oxo-1,6-dihydro-pyridazin-3-yl]-benzyl ester (0.200 g, 0.371 mmol) was dissolved in 2 ml tetrahydrofuran, 1 ml water and 1 ml methanol. 1 M aqueous lithium hydroxide solution (1.1 ml, 1.11 mmol) was added and stirred for several hours at room temperature. It was extracted with dichloromethane/ammonium chloride solution and the organic phase was washed with brine, dried over sodium sulfate, filtered and concentrated. The residue was purified by silica gel chromatography (gradient elution 0-10% methanol in dichloromethane for 20 min) to yield 6-Cyclopropyl-2-{2-hydroxymethyl-3-[1-methyl-5-(1-methyl-1H-pyrazol-3-ylamino-6-oxo-1,6-dihydro-pyridazine-3-yl)-phenyl}-3,4-dihydro-2H-isoquinolin-1-one (0.087 g, 0.175 mmol). MS (ESI) 597.2 (M+H)$^+$

Example 63

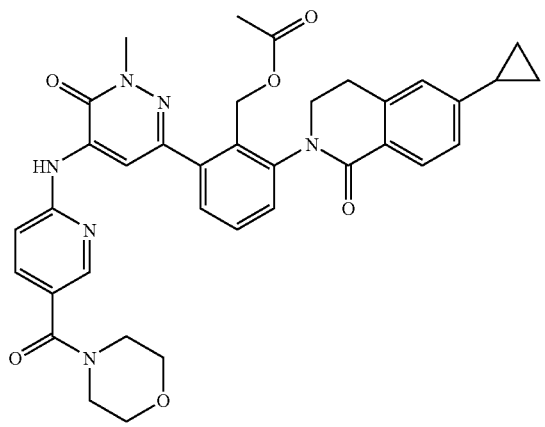

Acetic Acid 2-(6-cyclopropyl-1-oxo-3,4-dihydro-1H-isoquinolin-2yl)-6-{1-methyl-5-[5-(morpholine-4-carbonyl)-pyridin-2-ylamino]-6-oxo-1,6-dihydro-pyridazin-3-yl}-benzyl Ester 6-Chloro-2-methyl-4-[5-(morpholine-4-carbonyl)-pyridin-2-ylamino]-2H-pyridazin-3-one (0.070 g, 0.2 mmol), acetic acid 2-(6cyclopropyl-1-oxo-3,4-dihydro-1H-isoquinolin-2yl)-6-(4,4,5,-tetramethyl-[1,3,2]dioxaborolan-2yl)-benzyl ester (0.102 g, 0.221 mmol) and cesium carbonate (0.228 g, 0.7 mmol) were treated with a degassed solution of 1 ml dioxane/0.1 ml water. After 5 min stirring [1,1'-bis(diphenylphosphino)ferrocene]dichloropalladium(II) complex (0.016 g, 0.02 mmol) was added and the mixture heated to 135° C. for 30 min in the microwave. The reaction mixture was filtered over cellulose; washed with 5 ml of dioxane and concentrated in vacuo. The residue was purified by silica gel chromatography (gradient elution 0-10% methanol in dichloromethane for 20 min) to yield a crude acetic Acid 2-(6-cyclopropyl-1-oxo-3,4-dihydro-1H-isoquinolin-2yl)-6-{1-methyl-5-[5-(morpholine-4-carbonyl)-pyridin-2-ylamino]-6-oxo-1,6-dihydro-pyridazin-3-yl}-benzyl ester (0.121 g, 0.187 mmol). MS (ESI) 671.1 (M+Na)$^+$

Example 64

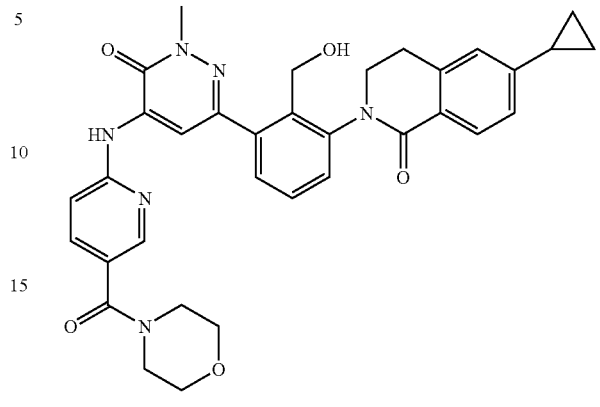

6-Cyclopropyl-2-(2-hydroxymethyl-3-{1-methyl-5-[5-(morpholine-4-carbonyl)-pyridin-2ylamino]-6-1,6-dihydro-pyridazin-3-yl}-phenyl)-3,4-dihydro-2H-isoquinolin-1-one Acetic Acid 2-(6-cyclopropyl-1-oxo-3,4-dihydro-1H-isoquinolin-2yl)-6-{1-methyl-5-[5-(morpholine-4-carbonyl)-pyridin-2-ylamino]-6-oxo-1,6-dihydro-pyridazin-3-yl}-benzyl ester (0.121 g, 0.187 mmol) was dissolved in 2 ml tetrahydrofuran, 1 ml water and 1 ml methanol. 1 M aqueous lithium hydroxide solution (0.560 ml, 0.561 mmol) was added and stirred for several hours at room temperature. It was extracted with dichloromethane/ammonium chloride solution and the organic phase was washed with brine, dried over sodium sulfate, filtered, and concentrated. The residue was purified by silica gel chromatography (gradient elution 0-10% methanol in dichloromethane for 20 min) to yield 6-Cyclopropyl-2-(2-hydroxymethyl-3-{1-methyl-5-[5-(morpholine-4-carbonyl)-pyridin-2ylamino]-6-1,6-dihydro-pyridazin-3-yl}-phenyl)-3,4-dihydro-2H-isoquinolin-1-one (0.070 g, 0.115 mmol). MS (ESI) 607.2 (M+H)$^+$

Example 65

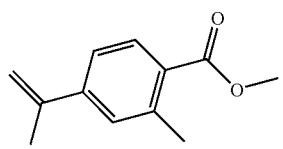

4-Isopropenyl-2-methyl-benzoic Acid Methyl Ester

4-Bromo-2-methyl-benzoic acid methyl ester (4 g, 17.46 mmol), isopropenylboronic acid pinacol ester (3.228 g, 19.21 mmol) and cesium carbonate (19.913 g, 61.11 mmol) were treated with a degassed solution of 15 ml dioxane/5 ml water. After 5 min stirring [1,1'-bis(diphenylphosphino)ferrocene] dichloropalladium(II) complex (0.718 g, 0.873 mmol) was added and heated to 120° C. for 40 min in the microwave. The reaction mixture was filtered over cellulose; washed with 20 ml dioxane and concentrated in vacuo. The residue was purified by 120 g silica gel chromatography (gradient elution 0-50% ethyl acetate in hexane during 50 min) to yield 4-Isopropenyl-2-methyl-benzoic acid methyl ester (2.94 g, 15.45 mmol). MS (ESI) 191.3 (M+H)+

Example 66

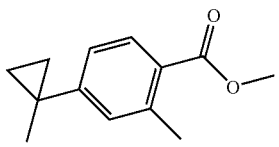

2-Methyl-4-(1-methyl-cyclopropyl)-benzoic Acid Methyl Ester

Formation of Diazomethane: N-Nitroso-N-methylurea (9.1 g, 61.8 mmol) was added under stirring in portions to a two phase mixture of 50 ml potassium hydroxide solution (23.9 g in 50 ml water) and 50 ml diethyl ether at 0° C. The color of the organic phase changed from colorless to yellow. The two phase mixture was vigorously stirred for 40 min at 0° C. The organic layer that contains diazomethane was separated. Cyclopropanation by adding diazomethane solution to methyl styrene: 4-Isopropenyl-2-methyl-benzoic acid methyl ester (2.94 g, 15.45 mmol) was dissolved in 15 ml diethyl ether and cooled to 0° C. Palladium (II) acetate (0.173 g, 0.773 mmol) was added. The yellow organic phase (containing diazomethane) was added dropwise. In total 20 ml of the organic phase (approximately 4 eq. of diazomethane) was added until the reaction was done. You observe releasing nitrogen by adding diazomethane to the methyl styrene intermediate. The reaction mixture was filtered over cellulose; washed with diethyl ether; concentrated; The residue (brown liquid) was purified by 40 g silica gel chromatography (gradient elution 0-100% ethyl acetate in hexane for 15 min) 2.9 g of a crude light yellow liquid was obtained. NMR shows 8% 2-methylbenzoic acid methyl ester. The crude residue was purified again by 110 g flash chromatography (gradient elution 0-20% EtOAc in Hex for 30 min) to give 2-Methyl-4-(1-methyl-cyclopropyl)-benzoic acid methyl ester (2.75 g, 13.46 mmol) MS (ESI) 268.9 (M+Na++ACN)

Example 67

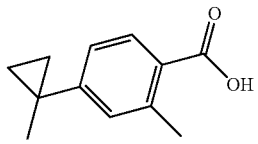

2-Methyl-4-(1-methyl-cyclopropyl)-benzoic Acid

2-Methyl-4-(1-methyl-cyclopropyl)-benzoic acid methyl ester (2.75 g, 13.46 mmol) was treated with methanol and 5 M aqueous sodium hydroxide solution (20.46 ml, 102.32 mmol). This solution was heated to 80° C. for 4 hours. The reaction mixture was concentrated until methanol was evaporated. A white solid was obtained. The solid was dissolved in 50 ml water under heating then cooled with an ice bath; acidified with 10 ml conc. hydrochloric acid. A white precipitate was formed; filtered; washed with water; dried under high vacuum over night to yield 2-Methyl-4-(1-methyl-cyclopropyl)-benzoic acid (2.18 g, 11.46 mmol) MS (ESI) 189.1 (M−H)−

Example 68

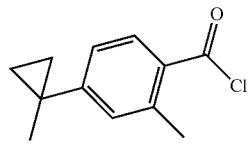

2-Methyl-4-(1-methyl-cyclopropyl)-benzoyl Chloride

2-Methyl-4-(1-methyl-cyclopropyl)-benzoic acid (2.139 g, 11.243 mmol) and phosphoruspentachloride (2.575 g, 12.37 mmol) were charged into a 50 ml flask under stirring. These both solids dissolved at 100° C. The reaction mixture was stirred 2 hours at 120° C. with an reflux condenser in a N2 atmosphere. After that the resulting phosphorus oxylchloride was distilled off at 140° C. from the reaction mixture. The whole reaction mixture was cooled to room temperature and the reaction mixture still remained as a solution. The desired product was distilled by Kugelrohr distillation (150° C./4 mbar) to give 2-Methyl-4-(1-methyl-cyclopropyl)-benzoyl chloride (1.92 g, 9.2 mmol)

Example 69

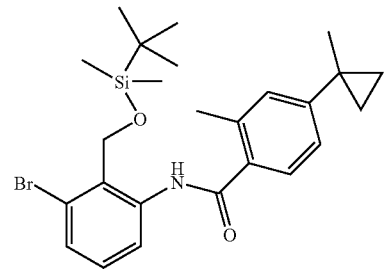

N-[3-Bromo-2-(tert-butyl-dimethyl-silanyloxymethyl)-phenyl]-2-methyl-4-(1-methyl-cyclopropyl)-benzamide 3-Bromo-2-(tert-butyl-dimethyl-silanyloxymethyl)-phenylamine (2.91 g, 9.2 mmol), 2-Methyl-4-(1-methyl-cyclopropyl)-benzoyl chloride (1.92 g, 9.2 mmol), N,N-diisopropylethylamine (2.41 ml, 13.8 mmol) and 4-dimethylaminopyridine (0.112 g, 0.92 mmol) were dissolved in 20 ml anhydrous tetrahydrofuran. The reaction mixture was refluxed over night; filtered off the precipitate; concentrated and extracted with ethyl acetate; washed with 2 M phosphate buffer pH 5.5, then with water and brine; dried over sodium sulfate; filtered; concentrated. 4.69 g of an oil was obtained. The crude was purified by 80 g silica gel chromatography (gradient elution 0-20% ethyl acetate in hexane for 25 min, then 20-100% ethyl acetate in hexane for 30 min) to give N-[3-Bromo-2-(tert-butyl-dimethyl-silanyloxymethyl)-phenyl]-2-methyl-4-(1-methyl-cyclopropyl)-benzamide (3.51 g, 7.185 mmol) MS (ESI) 510 (M+Na⁺)

Example 70

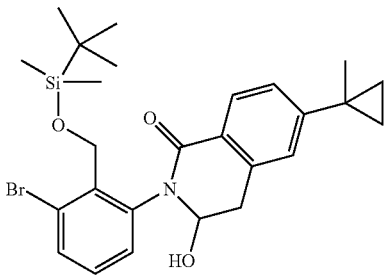

2-[3-Bromo-2-(tert-butyl-dimethyl-silanyloxymethyl)-phenyl]-3-hydroxy-7-(1-methyl-cyclopropyl)-3,4-dihydro-2H-isoquinolin-1-one 2,2,6,6-tetramethylpiperidine (2.28 g, 16.17 mmol) was dissolved in 13 ml anhydrous tetrahydrofuran under stirring; cooled by means of an ethylen glycol/ice bath mixture to −15° C. Buthyllithium, 2.5 M in hexanes (6.16 ml, 15.4 mmol) was added dropwise and the temperature was kept around −15° C. and stirred additionally 30 min at −15° C. A solution of N-[3-Bromo-2-(tert-butyl-dimethyl-silanyloxymethyl)-phenyl]-2-methyl-4-(1-methyl-cyclopropyl)-benzamide in 20 ml anhydrous tetrahydrofuran was added dropwise over a period of 10 minutes to the reaction mixture at −15° C. The reaction mixture was stirred for 2 hours. After that 3.55 ml of dimethylformamide was added in one portion. The reaction mixture was allowed to warm up to room temperature. It was stirred for 2 hours at room temperature, then cooled to 0° C., quenched with 25 ml of 1 M potassium hydrogen sulfate solution; extracted with ethyl acetate/water; organic phase was washed with brine; dried over sodium sulfate; filtered and concentrated. 2.71 g of a brown oil was obtained. Crystallization with dichloromethane and hexane gave 2-[3-Bromo-2-(tert-butyl-dimethyl-silanyloxymethyl)-phenyl]-3-hydroxy-7-(1-methyl-cyclopropyl)-3,4-dihydro-2H-isoquinolin-1-one (1.134 g, 2.2 mmol) MS (ESI) 516.0 (M−H)⁻

Example 71

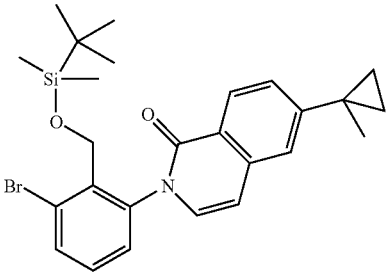

2-[3-Bromo-2-(tert-butyl-dimethyl-silanyloxymethyl)-phenyl]-7-(1-methyl-cyclopropyl)-2H-isoquinolin-1-one 2-[3-Bromo-2-(tert-butyl-dimethyl-silanyloxymethyl)-phenyl]-3-hydroxy-7-(1-methyl-cyclopropyl)-3,4-dihydro-2H-isoquinolin-1-one (1.134 g, 2.2 mmol) was dissolved in 13 ml dichloromethane at room temperature; triethylamine (1.31 ml, 9.44 mmol) followed by addition of methanesulfonyl chloride (0.478 g, 4.171 mmol) were added. It was stirred for 1.5 hours at room temperature but it's already done in 10 minutes according to LCMS. The reaction mixture was extracted with dichloromethane/water; organic phase was washed with brine; dried over sodium sulfate; filtered; concentrated to give 2-[3-Bromo-2-(tert-butyl-dimethyl-silanyloxymethyl)-phenyl]-7-(1-methyl-cyclopropyl)-2H-isoquinolin-1-one (1.094 g, 2.2 mmol) MS (ESI) 520.0 (M+Na⁺)

Example 72

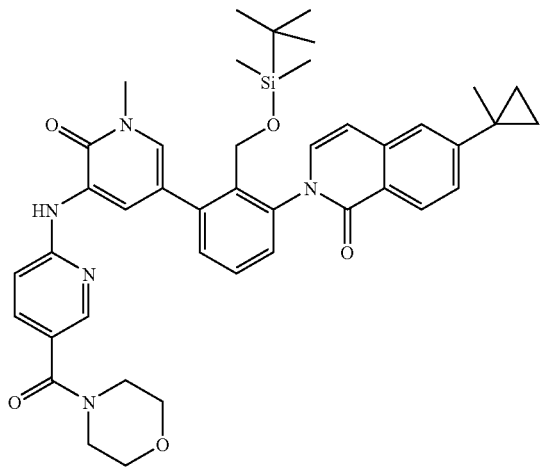

2-(2-tert-Butyl-dimethyl-silanyloxymethyl)-3-{1-methyl-5-[5-(morpholine-4-carbonyl)-pyridin-2-ylamino]-6-oxo-1,6-dihydro-pyridin-3-yl}-phenyl)-6-(1-methyl-cyclopropyl)-2H-isoquinolin-1-one 2-[3-Bromo-2-(tert-butyl-dimethyl-silanyloxymethyl)-phenyl]-7-(1-methyl-cyclopropyl)-2H-isoquinolin-1-one (0.102 g, 0.205 mmol) and 1-Methyl-3-[5-(morpholine-4-carbonyl)-pyridin-2-ylamino]-5-(4,4,5,5-tetramethyl-[1,3,2]dioxaborolan-2-yl)-1H-pyridin-2-one (0.1 g, 0.227 mmol) were dissolved in 2.5 ml dioxane under heating; 0.5 ml of water followed by cesium carbonate (0.259 g, 0.795 mmol) were added. After that [1,1'-bis(diphenylphosphino)ferrocene]dichloropalladium(II) complex (0.019 g, 0.023 mmol) was added and heated to 135° C. for 30 min by microwave. The reaction mixture was filtered over cellulose; washed with dioxane; concentrated; residue was purified by 24 g silica gel chromatography (gradient elution dichloromethane for 5 min, then 0-10% methanol in dichloromethane during in 25 min, then dichloromethane 9:1 methanol for 10 min) to yield 2-(2-tert-Butyl-dimethyl-silanyloxymethyl)-3-{1-methyl-5-[5-(morpholine-4-carbonyl)-pyridin-2-ylamino]-6-oxo-1,6-dihydro-pyridin-3-yl}-phenyl)-6-(1-methyl-cyclopropyl)-2H-isoquinolin-1-one (0.095 g, 0.13 mmol) MS (ESI) 732.2 (M+H)+

Example 73

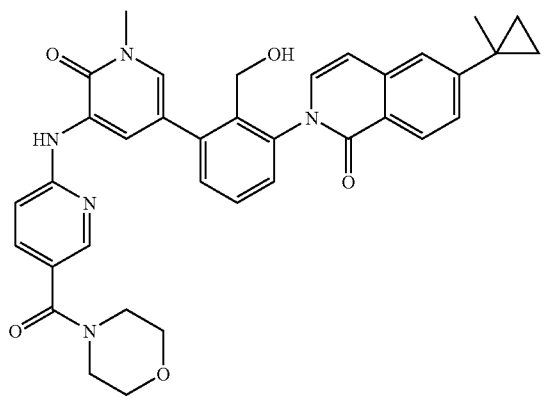

2-(2-Hydroxymethyl-3-{1-methyl-5-[5-(morpholine-4-carbonyl)-pyridin-2-ylamino]-6-oxo-1,6-dihydro-pyridin-3-yl}-phenyl)-6-(1-methyl-cyclopropyl)-2H-isoquinolin-1-one 2-(2-tert-Butyl-dimethyl-silanyloxymethyl)-3-{1-methyl-5-[5-(morpholine-4-carbonyl)-pyridin-2-ylamino]-6-oxo-1,6-dihydro-pyridin-3-yl}-phenyl)-6-(1-methyl-cyclopropyl)-2H-isoquinolin-1-one (0.095 g, 0.13 mmol) was dissolved in 3 ml dioxane. 3 M of aqueous hydrochloric acid solution (0.22 ml, 0.39 mmol) was added at room temperature. It was stirred for 30 min, then extracted with ethyl acetate/sodium bicarbonate solution; organic phase was washed with brine; dried over sodium sulfate; concentrated. The crude was purified by 12 g silica gel chromatography (gradient elution 0-10% methanol in dichloromethane during 30 min) to yield 2-(2-Hydroxymethyl-3-{1-methyl-5-[5-(morpholine-4-carbonyl)-pyridin-2-ylamino]-6-oxo-1,6-dihydro-pyridin-3-yl}-phenyl)-6-(1-methyl-cyclopropyl)-2H-isoquinolin-1-one (0.045 g, 0.0728 mmol) MS (ESI) 618.3 (M+H)+

Example 74

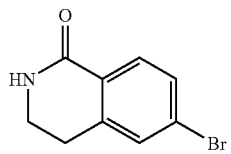

6-Bromo-3,4-dihydro-2H-isoquinolin-1-one

Methanesulfonic acid (100 mL) was added to a solution of 5-bromoindanone (25 g, 46 mmol) in $CH_2Cl_2$ (200 mL) at 0° C. Sodium azide 10.5 g, 162 mmol) was added slowly in portions to this mixture. After the sodium azide addition was complete, the mixture was stirred for an additional 30 min, and an aqueous mixture of NaOH (20 wt %) was added until the mixture was slightly basic. The mixture was extracted with methylene chloride, and the combined organic layers were evaporated under reduced pressure. Purification of the mixture by flash column chromatography on silica gel (0% to 50% EtOAc/Hexanes then 0% to 7% MeOH/CH2C12) provided 11.5 g of 6-Bromo-3,4-dihydro-2H-isoquinolin-1-one. MS (ESI) 226.1 (M+H)+.

Example 75

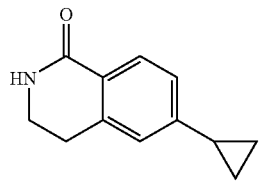

6-Cyclopropyl-3,4-dihydro-2H-isoquinolin-1-one

To a round bottomed flask charged with 6-Bromo-3,4-dihydro-2H-isoquinolin-1-one (16.9 g, 74.7 mmol), cyclopropylboronic acid (9.45 g, 1.5 equiv), tricyclohexylphosphine (1.04 mg, 0.025 equiv), and $K_3PO_4$ hexahydrate (50 g, 2 equiv) in toluene (210 mL) and H2O (15 mL) was added Pd(OAc)$_2$ (100 mg, 0.05 equiv). The combined mixture was heated for 4 h at 100° C. The reaction mixture was cooled, filtered and washed with toluene. The organic phase was partitioned and washed with water and brine, dried over $Na_2SO_4$, filtered and concentrated to an oil. Addition of hexanes produced 6-Cyclopropyl-3,4-dihydro-2H-isoquinolin-1-one as a tan solid (13.6 g). MS (ESI) 187.1 (M+H)+.

Example 76

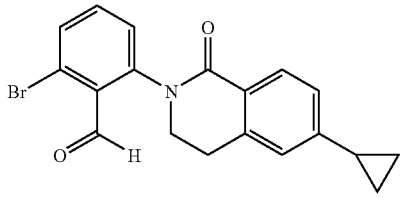

2-Bromo-6-(6-cyclopropyl-1-oxo-,4-dihydro-1H-isoquinolin-2-yl)-benzaldehyde

A round bottom flask was charged with 6-Cyclopropyl-3,4-dihydro-2H-isoquinolin-1-one (13.4 g, 5 mmol), 2,6-Dibromo-benzaldehyde (47.5 g, 72.0 mmol), Pd$_2$ (dba)$_3$.CHCl$_3$ (660 mg, 0.72 mmol), xanthphos (832 mg, 1.44 mmol), and cesium carbonate (46.8 g, 144 mmol). The vial was flushed with argon, 140 mL of dioxane was added, and the reaction mixture was heated at 110° C. for 4 h. The reaction mixture was cooled to rt and 30 mL of water and 60 mL of ethyl acetate were added before filtering over Solkaflok. The organic phase was separated and washed with brine followed by drying over $Na_2SO_4$. After filtration, the solvent was removed and the brown mass obtained was triturated with methylene chloride and diethyl ether to afford 6.5 grams of 2-Bromo-6-(6-cyclopropyl-1-oxo-,4-dihydro-1H-isoquinolin-2-yl)-benzaldehyde. A second crop of 7.5 grams of material was collected by addition of more diethyl ether. MS (ESI) 370.0 (M+H)+.

Example 77

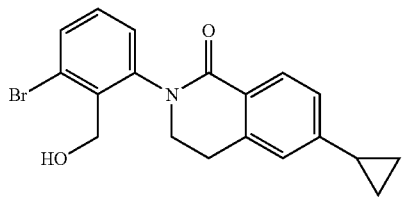

2-(3-bromo-2-hydroxymethyl-phenyl)-6-cyclopropyl-3,4-dihydro-2H-isoquinolin-1-one To a solution of 2-Bromo-6-(6-cyclopropyl-1-oxo-,4-dihydro-1H-isoquinolin-2-yl)-benzaldehyde (5.0 g, 13.5 mmol) in 60 mL of toluene and 10 mL of THF at −10° C. was added sodium borohydride (740 mg, 20 mmol) in portions. After 30 minutes the reaction mixture was quenched with water and partitioned into diethyl ether. The organic phase was washed with brine, dried over sodium sulfate and filtered. After concentrating under reduced pressure, purification by silica gel chromatography afforded 3.7 g of 2-(3-bromo-2-hydroxymethyl-phenyl)-6-cyclopropyl-3,4-dihydro-2H-isoquinolin-1-one as a colorless solid. MS (ESI) 372.0 (M+H)$^+$.

Example 78

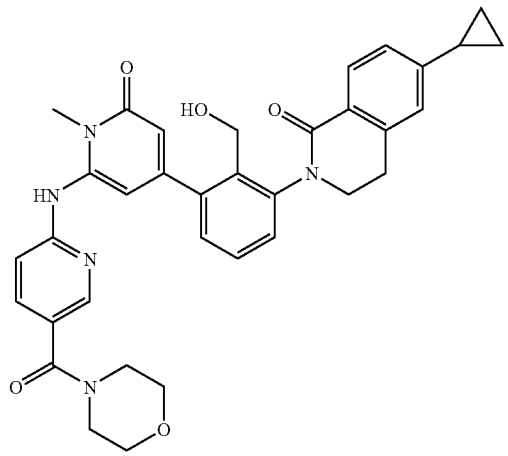

6-Cyclopropyl-2-(2-hydroxymethyl-3-{1-methyl-6-[5-(morpholine-4-carbonyl)-pyridin-2-ylamino]-2-oxo-1,2-dihydro-pyridin-4-yl}-phenyl)-3,4-dihydro-2H-isoquinolin-1-one To a flask charged with 2-(3-bromo-2-hydroxymethyl-phenyl)-6-cyclopropyl-3,4-dihydro-2H-isoquinolin-1-one (3.70 g, 9.9 mmol), 1-Methyl-6-[4-(morpholine-4-carbonyl)-phenylamino]-4-(4,4,5,5-tetramethyl-[1,3,2]dioxaborolan-2-yl)-1H-pyridin-2-one (4.38 g, 9.9 mmol), Pd$_2$(dba)$_3$·CHCl$_3$ (229 mg, 0.25 mmol), 2-Dicyclohexylphosphino-2',4',6'-Tri-i-Propyl-1,1'-Biphenyl (238 mg, 0.50 mmol), and K$_3$PO$_4$ hexahydrate (7.5 g, 20 mmol) was added 40 mL of 4:1 dioxane:water and the mixture heated to reflux for 4 h, cooled and filtered over Solka-Floc®, rinsing with ethyl acetate. Partitioned and washed the organic phase with water and brine. Dried over sodium sulfate, filtered and concentrated to afford a dark oil. Purification by silica gel chromatography (methylene chloride/methanol) afforded 3.2 g of 6-Cyclopropyl-2-(2-hydroxymethyl-3-{1-methyl-6-[4-(morpholine-4-carbonyl)-phenylamino]-2-oxo-1,2-dihydro-pyridin-4-yl}-phenyl)-3,4-dihydro-2H-isoquinolin-1-one as a colorless solid. MS (ESI) 606.1 (M+H)$^+$.

Example 79

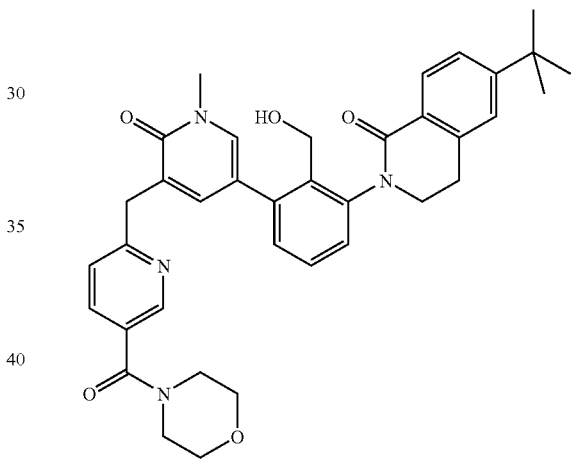

Preparation of 6-tert-Butyl-2-(2-hydroxymethyl-3-{1-methyl-5-[5-(morpholine-4carbonyl)-pyridin-2-ylamino]-6-oxo-1,6-dihydro-pyridin-3-yl}-phenyl)-3,4-dihydro-2H-isoquinolin-1-one Scheme 1

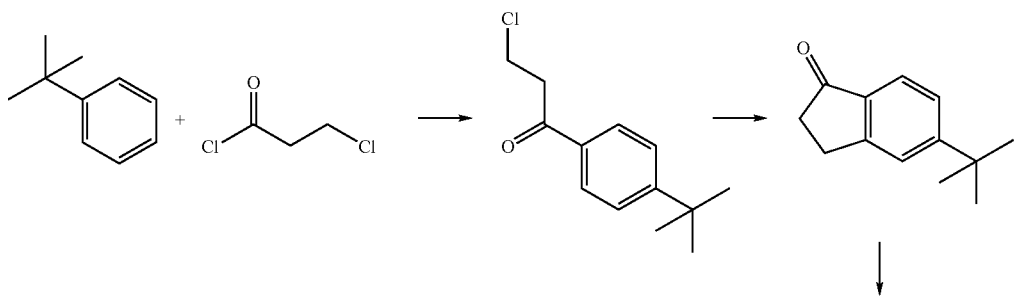

-continued

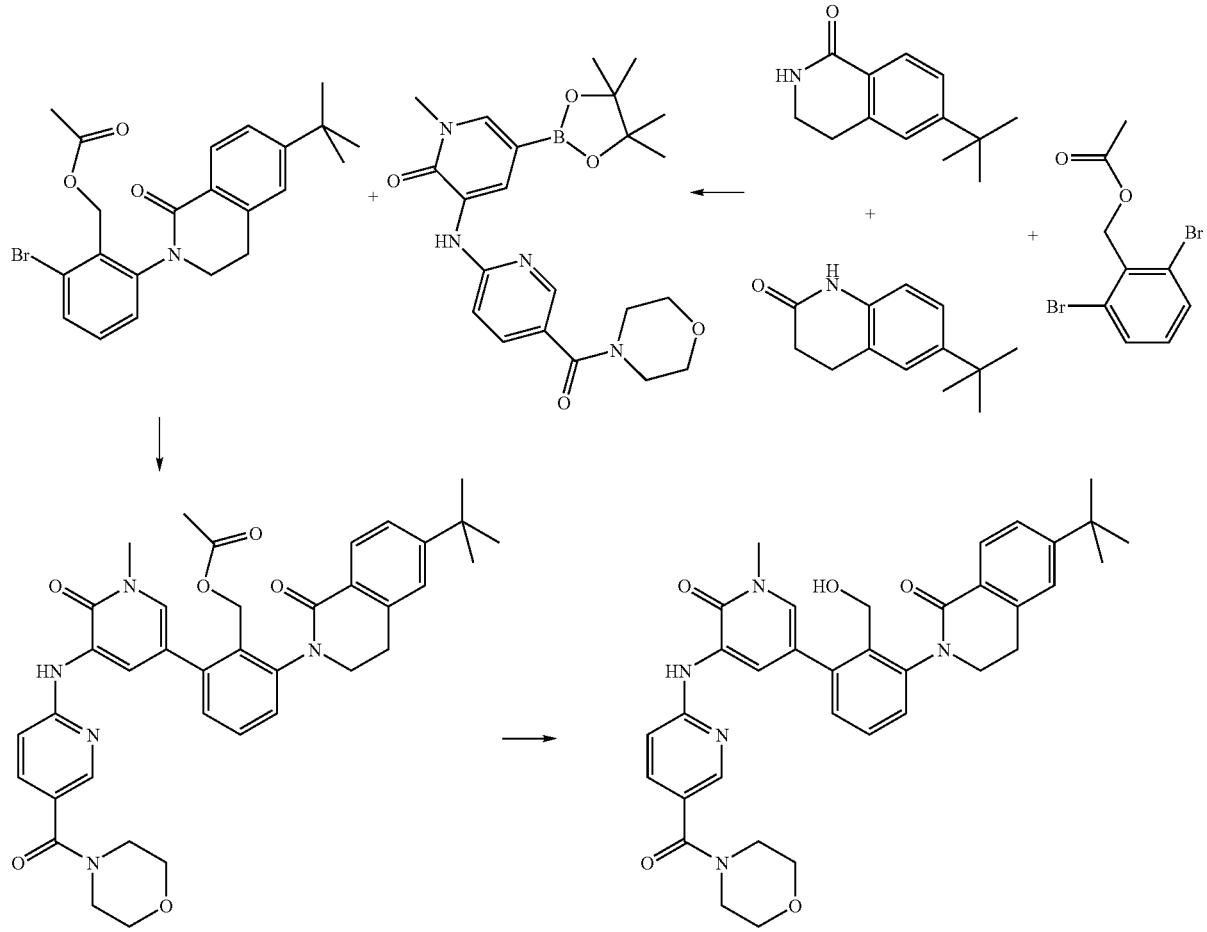

Example 80

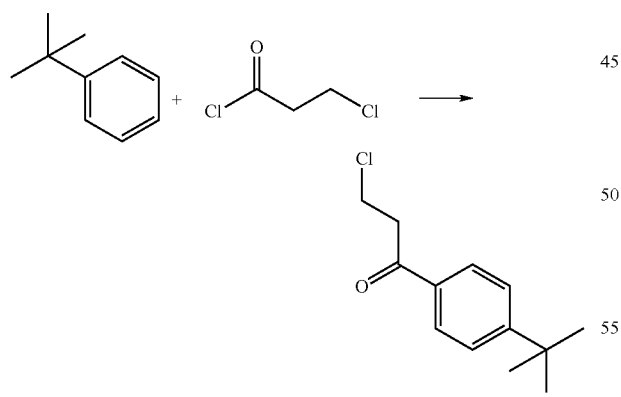

1-(4-tert-Butyl-phenyl)-3-chloro-propan-1-one

To aluminum chloride (29.33 g, 220 mmol) in dichloromethane (300 mL) at 0° C. with stirring was added dropwise a solution of t-butyl benzene (31 mL, 200 mmol) and 3-chloropropionyl chloride (19 mL, 200 mmol) in dichloromethane. After the addition was complete, the reaction mixture was stirred from 0° C. to room temperature overnight. Then next morning, TLC indicated that all of the t-butyl benzene was consumed, and the reaction mixture was cooled to 0° C. With stirring, water (about 120 mL) in a dropwise fashion until the effervescence ceased. Finally, the layers were separated, and the organic layer was washed with water (3×150 mL) and then brine (1×150 mL). The dichloromethane layer was dried over magnesium sulfate, filtered, concentrated and pumped to dryness to afford the title compound as a light tan powder (45.6 g).

Example 81

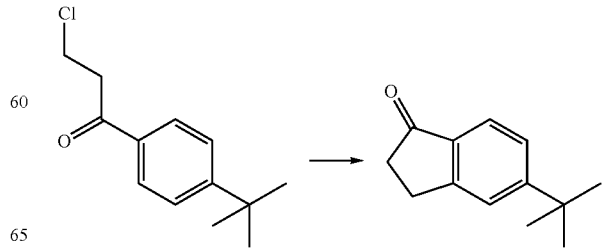

5-tert-Butyl-indan-1-one 1-(4-tert-Butyl-phenyl)-3-chloro-propan-1-one (45.6 g, 447 mmol) was taken up in concentrated sulfuric acid (200 mL) and the resulting mixture was heated to 100° C. with stirring for 2.5 hours. TLC indicated that all of the starting material had been consumed. After cooling to room temperature, the reaction mixture was very carefully poured onto about 1 Kg of crushed ice. Then some diethyl ether was added and the mixture was stirred carefully until it had cooled to about room temperature. Ethyl acetate (1200 mL) was added and after partitioning, the layers were separated. The acidic layer was then further extracted with ethyl acetate (2×200 mL). The combined ethyl acetate layers were washed with saturated sodium bicarbonate (5×300 mL). Finally the ethyl acetate layer was dried over magnesium sulfate, filtered, concentrated and pumped to dryness to afford the title compound as a colorless oil (15.764 g).

Example 82

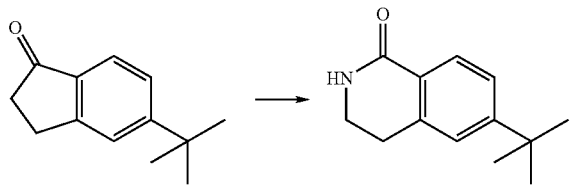

6-tert-Butyl-3,4-dihydro-2H-isoquinolin-1-one

To 5-tert-Butyl-indan-1-one (15.7 g, 83.4 mmol) in dichloromethane (150 mL) was added methanesulfonic acid (100 mL) and the resulting mixture was cooled to 0° C. Then sodium azide (10.83 g, 2 eq) was added carefully portionwise over 15 minutes. The resulting mixture was stirred at 0° C. for about 2.5 hours. TLC analysis confirmed that all of the 5-tert-Butyl-indan-1-one had been consumed. With stirring at 0° C. was added very carefully a solution of aqueous sodium hydroxide (20%) until pH=14. Then added dichloromethane (1000 mL) and water (500 mL) which results in a large emulsion. The layers were separated and the aqueous layer was further extracted with dicholormethane (2×200 mL). Finally the combined dichloromethane layers were washed with brine (9×200 mL), dried over magnesium sulfate and filtered through a bed of celite. After concentrating and pumping to dryness there was 13.5 g of crude product as a tan solid. Purification on a 400 g Analogix Column eluting with a gradient of 10% to 60% ethyl acetate in hexane provided the correct isomer as a white powder (7.22 g) ((M+H)$^+$=204) and the undesired isomer (1.555 g) as a white powder.

Example 83

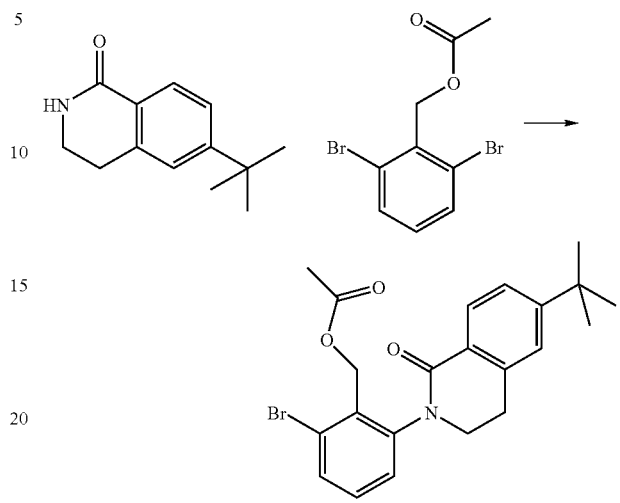

Acetic Acid 2-bromo-6-(6-tert-butyl-1-oxo-3,4-dihydro-1H-isoquinolin-2-yl)-benzyl Ester 6-tert-Butyl-3,4-dihydro-2H-isoquinolin-1-one (4 g, 19.67 mmol), Acetic acid 2,6-dibromo-benzyl ester (12.1 g, 2 eq), potassium phosphate tribasic (8.35 g, 2 eq) and copper iodide (787 mg, 0.2 eq) were taken up in dioxane (40 mL). Finally added N,N'-Dimethyl-cyclohexane-1,2-diamine (1.24 mL, 0.4 eq) and the resulting mixture was heated to reflux for 24 hours, after which time more copper iodide (394 mg, 0.1 eq) and N,N'-Dimethyl-cyclohexane-1,2-diamine (0.62 mL, 0.2 eq) were added. Stirred an additional 64 hours and then added more copper iodide (400 mg, 0.1 eq). Continued to stir at reflux for a total of 168 hours. Cooled to room temperature and then added ethylacetate (300 mL) and water (100 mL), partitioned and separated the layers. Washed with further water (2×100 mL) and then finally washed with brine (1×100 mL). The ethyl acetate layer was dried over magnesium sulfate, filtered and concentrated to give 4.45 g of crude product. Purification on a 240 g Analogix column afforded the title compound as a white foamy solid (516 mg) ((M+H)$^+$=431) and recovered 6-tert-Butyl-3,4-dihydro-2H-isoquinolin-1-one (2.188 g).

Example 84

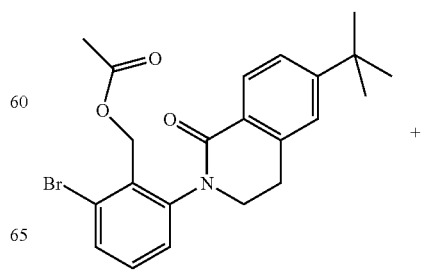

Example 85

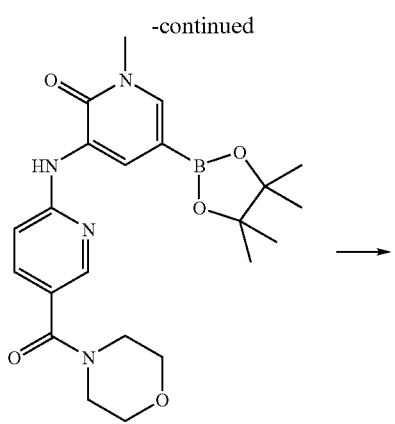

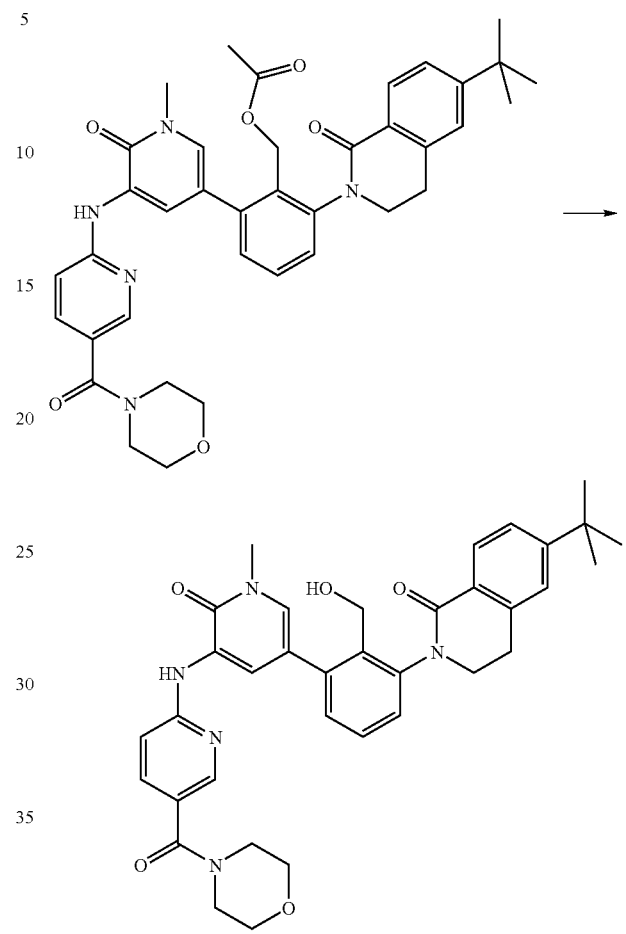

Acetic Acid 2-(6-tert-butyl-1-oxo-3,4-dihydro-1H-isoquinolin-2-yl)-6-{1-methyl-5-[5-(morpholine-4-carbonyl)-pyridin-2-ylamino]-6-oxo-1,6-dihydro-pyridin-3-yl}-benzyl Ester 1-Methyl-3-[5-(morpholine-4-carbonyl)-pyridin-2-ylamino]-5-(4,4,5,5-tetramethyl-[1,3,2]dioxaborolan-2-yl)-1H-pyridin-2-one (208 mg, 1 eq), Acetic acid 2-bromo-6-(6-tert-butyl-1-oxo-3,4-dihydro-1H-isoquinolin-2-yl)-benzyl ester (203 mg, 0.472 mmol), XPHOS (14 mg, 0.06 eq), potassium phosphate tribasic (200 mg, 2 eq), n-butanol (2.8 mL) and water (0.93 mL) were charged to a 50 mL round bottom flask, and then nitrogen gas was bubbled through the mixture for 10 minutes, before adding Pd(dba)$_2$ (8 mg, 0.03 eq). The resulting mixture was heated to 100° C. for 40 minutes, and by TLC analysis there was no starting material remaining. The reaction mixture was cooled to room temperature and then added ethyl acetate (150 mL) and water (40 mL). Partitioned and separated the layers and washed further with water (2×40 mL) and then brine (1×40 mL). Finally, the ethyl acetate layer was dried over magnesium sulfate, filtered and concentrated and pumped to dryness to afford the title compound which was used in the next step without any further purification ((M+H)$^+$=664).

6-tert-Butyl-2-(2-hydroxymethyl-3-{1-methyl-5-[5-(morpholine-4-carbonyl)-pyridin-2-ylamino]-6-oxo-1,6-dihydro-pyridin-3-yl}-phenyl)-3,4-dihydro-2H-isoquinolin-1-one Acetic acid 2-(6-tert-butyl-1-oxo-3,4-dihydro-1H-isoquinolin-2-yl)-6-{1-methyl-5-[5-(morpholine-4-carbonyl)-pyridin-2-ylamino]-6-oxo-1,6-dihydro-pyridin-3-yl}-benzyl ester (0.472 mmol) was taken up in THF (7 mL) and methanol (3 mL) and water (5 mL) and then added lithium hydroxide monohydrate (40 mg, 2 eq). The resulting mixture was stirred at room temperature overnight. The next morning the reaction was complete by TLC and most of the THF and methanol was removed under reduced pressure at 55° C. Then ethyl acetate (75 mL) and water (30 mL) were added and the layers were partitioned and then separated. Next, the ethyl acetate layer was washed with water (2×30 mL), brine (1×30 mL) and then dried over magnesium sulfate, filtered and concentrated to give 286 mg of crude product. Preparative Thin Layer Chromatography purification eluting on two 20×40 cm 1000 μM plates in 6% methanol in dicholomethane afforded the title compound (99 mg) as a white powder ((M+H)$^+$=622).

Example 86

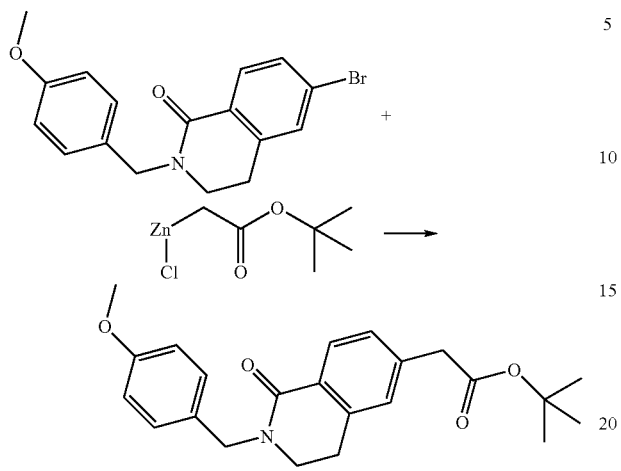

[2-(4-Methoxy-benzyl)-1-oxo-1,2,3,4-tetrahydro-isoquinolin-6-yl]-acetic Acid Tert-Butyl Ester (I)

6-Bromo-2-(4-methoxy-benzyl)-3,4-dihydro-2H-isoquinolin-1-one (1.9 g, 5.5 mmole), Q-phos (0.0632 g, 0.11 mmole) and Pd(dba)$_2$ (0.0781 g, 0.11 mmole) in 10 ml THF were added to 2-tert-butoxy-2-oxoethylzinc chloride 15 ml (0.55 M) under argon. The reaction mixture was stirred at room temperature for 16 hours. Next a third of the initial amount of Q-phos, Pd(dba)$_2$ and zinc enolate were added and the mixture heated for 1 hour at 70° C. to bring the reaction to completion. The desired product (2 g; 95.6% yield) was isolated by flash chromatography using silica gel column chromatography with 10%-40% ethylacetate in hexane as eluent.

Example 87

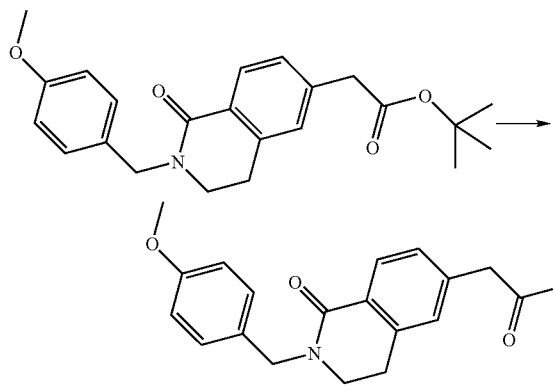

2-(4-Methoxy-benzyl)-1-oxo-1,2,3,4-tetrahydro-isoquinolin-6-yl]-acetic Acid (II)

The tert-butyl ester (I) (1 g, 5.7 mmole) was dissolved in 40 ml methanol and to this solution was added LiOH monohydrate (0.72 g, 17.3 mmole) in 6 ml water. The mixture was stirred at room temperature for 16 hours, then concentrated in vacuo, acidified with HCl 2N and extracted with ethylacetate. The organic layer was washed with brine, dried over sodium sulfate and concentrated in vacuo. The residue (1.8 g; 97% yield) was used in the next step without further purification.

Example 88

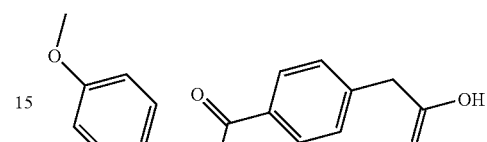

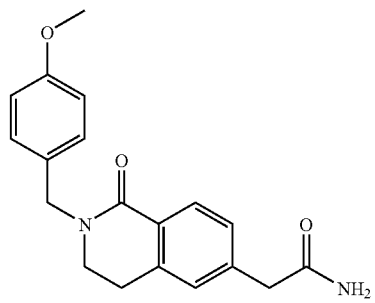

2-[2-(4-Methoxy-benzyl)-1-oxo-1,2,3,4-tetrahydro-isoquinolin-6-yl]-acetamide (III)

To the carboxylic acid (II) (2.3 g, 7 mmole) in 22 ml chloroform was added EEDQ (2.07 g, 8.4 mmole) and ammonium bicarbonate (1.66 g, 21 mmole). After stirring the mixture at room temperature for 16 hours, the amide was precipitated by addition of water (20 ml). The solid was filtered, washed with water and dried in vacuo. The residue was triturated with 50% ethylacetate in hexane, filtered and dried in vacuo to afford 1.4 g amide (III), 63% yield.

Example 89

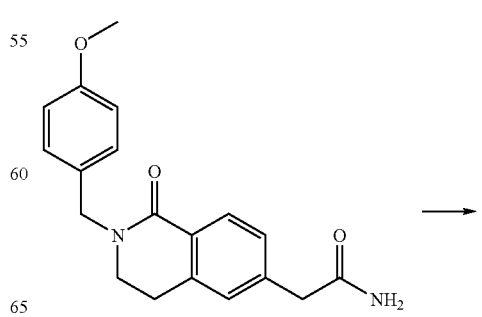

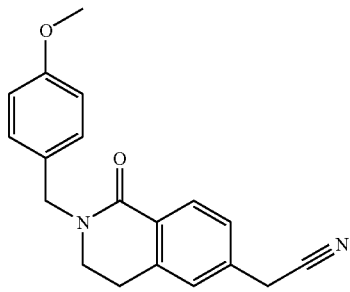

[2-(4-Methoxy-benzyl)-1-oxo-1,2,3,4-tetrahydro-isoquinolin-6-yl]-acetonitrile (IV)

The amide (III) (1.3 g, 4 mmole) was suspended in 5 ml THF and 10 ml DMF. To this mixture was added cyanuric chloride (0.370 g, 2 mmole) and after stirring at room temperature for 0.5 hour, the reaction mixture was partitioned between ethylacetate and brine; the organic layer was washed with 5% sodium bicarbonate, followed by brine and then dried over sodium sulfate. Purification by flash chromatograpy on silica gel column using 75% ethylacetate in hexane as eluent afforded 1.2 g (98% yield) of nitrile (IV).

Example 90

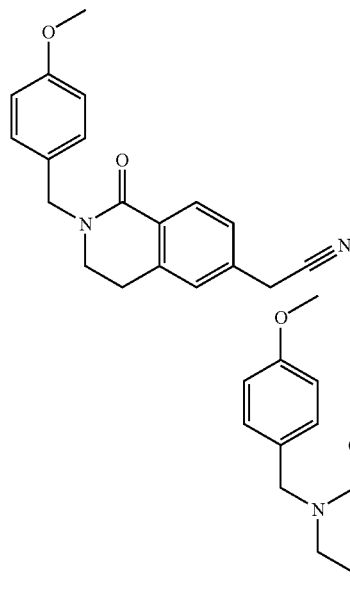

1-[2-(4-Methoxy-benzyl)-1-oxo-1,2,3,4-tetrahydro-isoquinolin-6-yl]-cyclopropanecarbonitrile (V)

To a suspension of sodium hydrate (0.228 g, 60%, 5.72 mmole) in 15 ml DMF was added nitrile (IV) (1.2 g, 3.9 mmole) and after stirring for 15 minutes at room temperature 1,2-dibromo-ethane (1.1 g, 5.8 mmole) in 1.5 ml DMF was added. The resulting mixture was stirred 0.5 hour at room temperature and then more sodium hydrate (0.114 g, 2.86 mmole) was added and the reaction mixture heated for about 10 minutes at 30-35° C. After cooling the mixture was partitioned between ethylacetate and brine, the organic layer was dried over sodium acetate and concentrated in vacuo. Purification by silica gel column chromatography with 30%-50% ethylacetate in hexane afforded compound (V) 1 g (77% yield).

Example 91

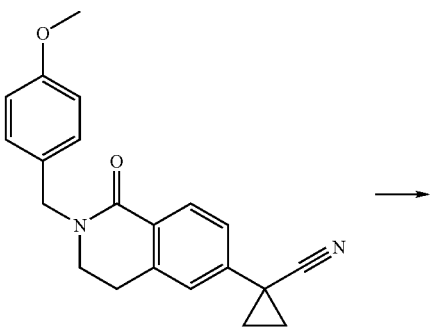

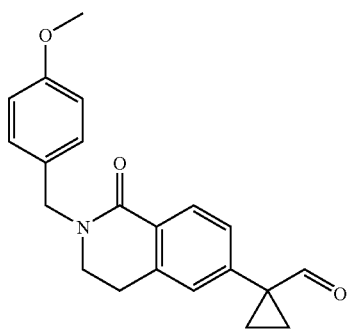

1-[2-(4-Methoxy-benzyl)-1-oxo-1,2,3,4-tetrahydro-isoquinolin-6-yl]-cyclopropanecarbaldehyde (VI)

To a solution of nitrile (V) (0.722 g, 2.17 mmole) in 3 ml dichloromethane and 9 ml toluene, cooled at −50° C. was added dropwise DIBAH (4.8 ml, 4.77 mmole). After stirring 1 hour at −50° C., the reaction was quenched with 5 ml HCl 1N, left to warm to room temperature and stirred 0.5 hour. Next the mixture was extracted with ethylacetate; the organic layer was washed with HCl 0.5N, sodium carbonate 5% solution, brine, next dried over sodium sulfate and concentrated in vacuo. The residue was purified by silica gel column chromatography using 30%-60% ethylacetate in hexane to provide aldehyde (VI) 0.075 g (10.3% yield).

Example 92

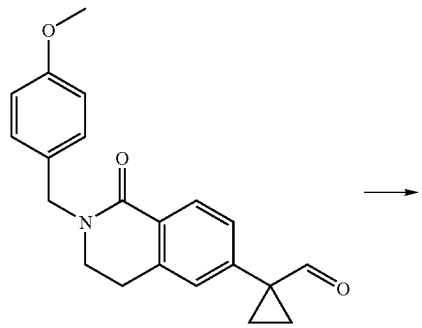

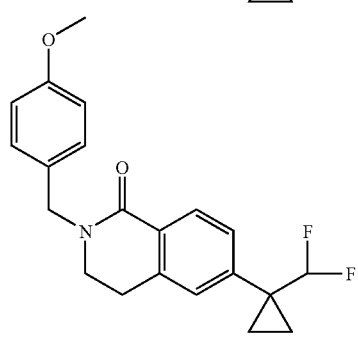

6-(1-Difluoromethyl-cyclopropyl)-2-(4-methoxy-benzyl)-3,4-dihydro-2H-isoquinolin-1-one (VII)

To a solution of DAST (0.042 g, 0.26 mmole) in 1.5 ml dichloromethylene was added aldehyde (VI) (0.075 g, 0.22 mmole) in 0.5 ml dichloromethylene. This mixture was stirred at room temperature for 16 hours. After cooling in an ice bath, water ml was added to the reaction mixture followed by ethylacetate. The organic layer was washed with 5% sodium bicarbonate solution and brine, then dried over sodium sulfate and concentrated in vacuo. The residue was purified silica gel prep TLC affording compound(VII) 0.068 g, 87% yield.

Example 93

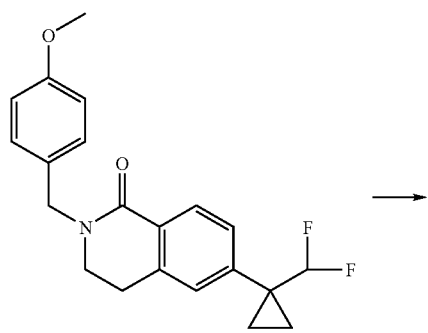

-continued

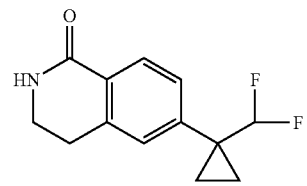

6-(1-Difluoromethyl-cyclopropyl)-3,4-dihydro-2H-isoquinolin-1-one (VIII)

Compound (VII) (0.068 g, 0.19 mmole) was dissolved in TFA 1 ml and heated to 70° C. for 1.5 hours. To the reaction mixture cooled to room temperature was added ethylacetate and the solution was washed with brine followed by sodium bicarbonate 5% solution, and again with brine. The organic layer was dried over sodium sulfate and concentrated in vacuo. The residue was purified by silica gel prep TLC with 5% methanol in dichloromethylene affording compound (VIII) 0.030 g, 66% yield.

Example 94

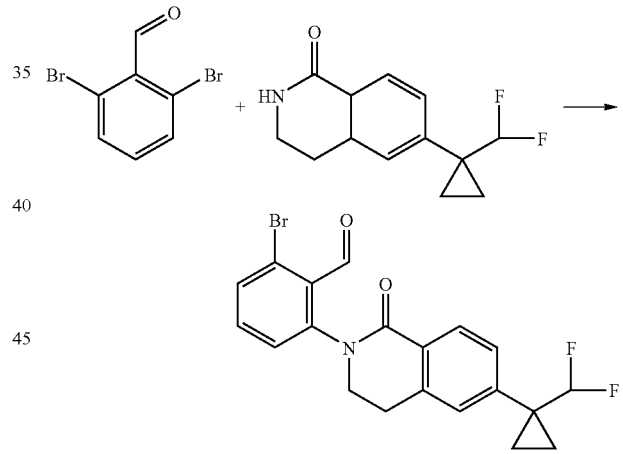

2-Bromo-6-[6-(1-difluoromethyl-cyclopropyl)-1-oxo-3,4-dihydro-1H-isoquinolin-benzaldehyde (IX)

To a mixture of compound (VIII) (0.030 g, 0.12 mmole), 2,6-dibromo-benzaldehyde (0.064 g, 0.25 mmole), cesium carbonate (0.054 g, 0.16 mmole) and Xantphos (0.002 G, 0.004 mmole) in a microwave tube under argon was added Pd(dba)$_2$ (0.0014 g, 0.0024 mmole). The tube was sealed and the reaction mixture was heated at 100° C. for 16 hours. After cooling the mixture was partitioned between ethylacetate and brine, the organic layer dried over sodium sulfate and concentrated in vacuo. The residue was purified by silica gel prep TLC with 40% ethylacetate in hexane as eluent affording 0.024 g, 48% yield.

Example 95

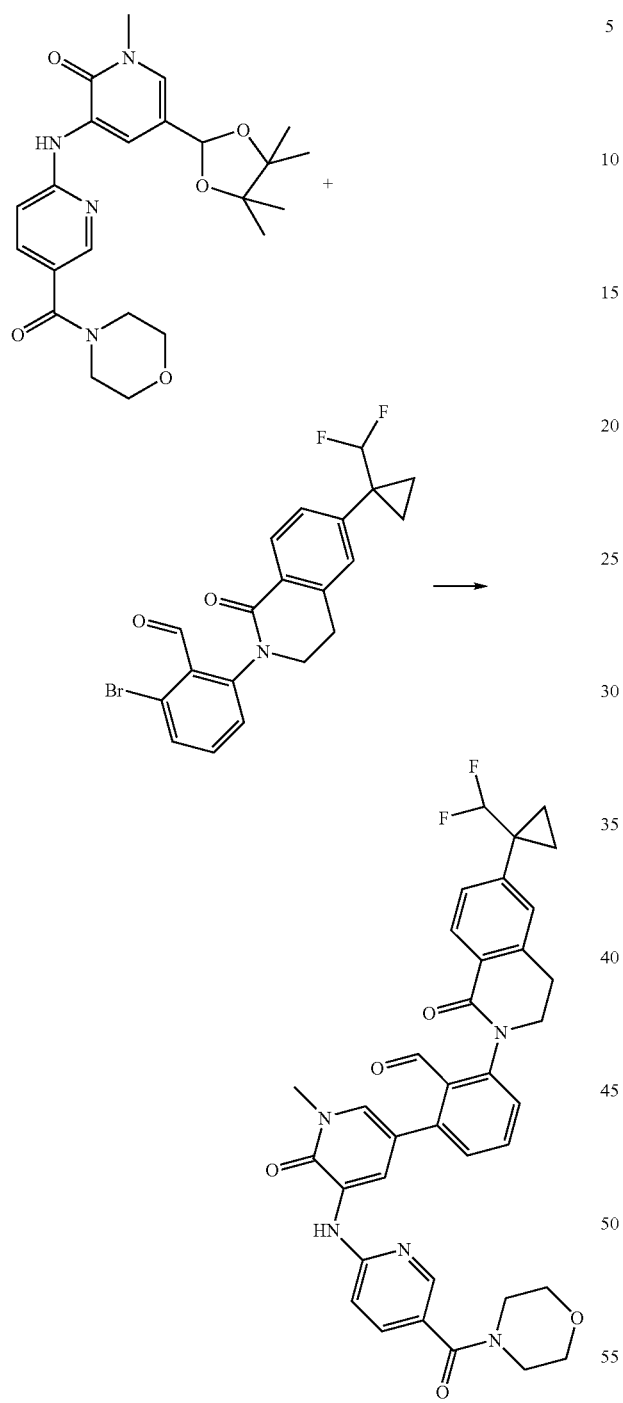

2-[6-(1-Difluoromethyl-cyclopropyl)-1-oxo-3,4-dihydro-1H-isoquinolin-2-yl]-6-{1-methyl-5-[5-(morpholine-4-carbonyl)-pyridin-2-ylamino]-6-oxo-1,6-dihydro-pyridin-3-yl}-benzaldehyde (X)

1-Methyl-3-[5-(morpholine-4-carbonyl)-pyridin-2-ylamino]-5-(4,4,5,5-tetramethyl-[1,3,2]dioxaborolan-2-yl)-1H-pyridin-2-one (0.025 g, 0.057 mmole) and benzaldehyde IX (0.024 g, 0.057 mmole) were dissolved in 0.5 ml n-butanol. To this solution under argon was added K₃PO₄ (0.024 g, 0.114 mmole), water 0.150 ml, Xphos (0.0027 g, 0.0057 mmole) and Pd(dba)₂ (0.0016 g, 0.0028 mmole). The mixture was heated 1 hour at 100° C. and after cooling partitioned between ethylacetate and brine. The organic layer was dried over sodium sulfate, concentrated in vacuo and the residue purified by silica gel prep TLC to afford 0.025 g (67% yield) of X.

Example 96

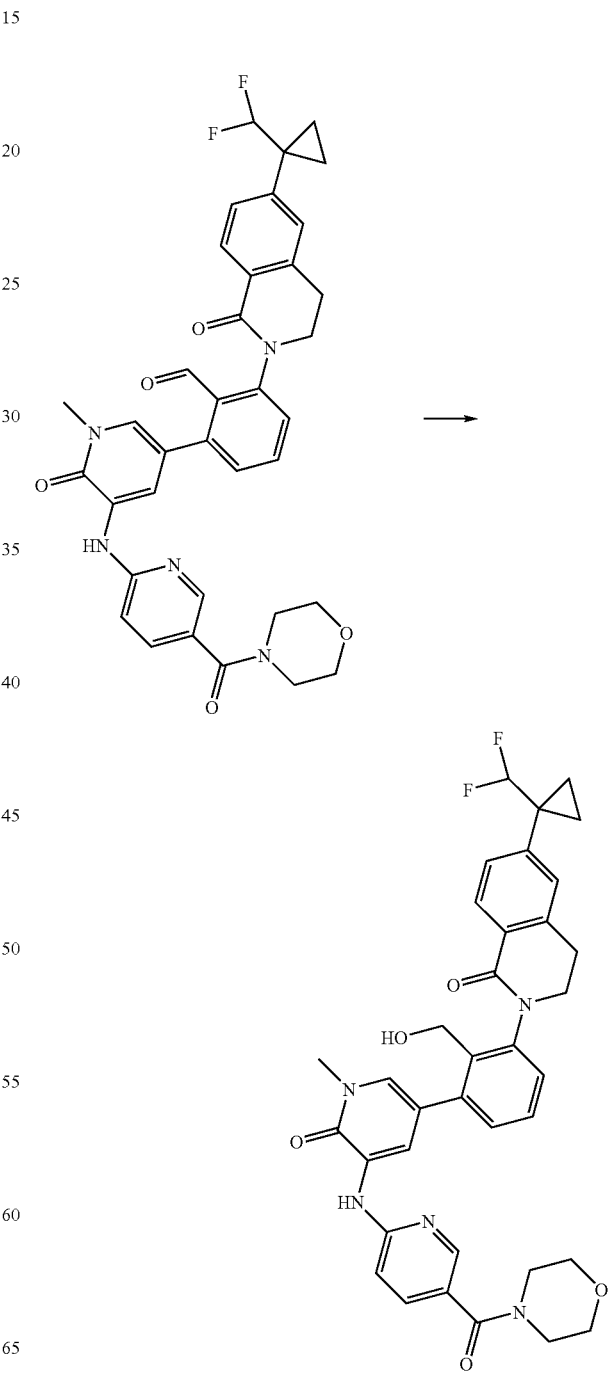

6-(1-Difluoromethyl-cyclopropyl)-2-(2-hydroxymethyl-3-{1-methyl-5-[5-(morpholine-4-carbonyl)-pyridin-2-ylamino]-6-oxo-1,6-dihydro-pyridin-3-yl}-phenyl)-3,4-dihydro-2H-isoquinolin-1-one (XI)

2-[6-(1-Difluoromethyl-cyclopropyl)-1-oxo-3,4-dihydro-1H-isoquinolin-2-yl]-6-{1-methyl-5-[5-(morpholine-4-carbonyl)-pyridin-2-ylamino]-6-oxo-1,6-dihydro-pyridin-3-yl}-benzaldehyde (0.025 g, 0.038 mmole) was dissolved into THF (2 ml). To this solution was added NaBH$_4$ (0.006 g, 0.015 mmole) and the mixture stirred at room temperature 0.5 hour after which it was quenched with ice water (4 ml) and extracted with ethylacetate. The organic layer was washed with brine, dried over sodium sulfate and concentrated in vacuo. The residue was purified by preparative TLC to afford 6-(1-Difluoromethyl-cyclopropyl)-2-(2-hydroxymethyl-3-{1-methyl-5-[5-(morpholine-4-carbonyl)-pyridin-2-ylamino]-6-oxo-1,6-dihydro-pyridin-3-yl}-phenyl)-3,4-dihydro-2H-isoquinolin-1-one (XI), 0.020 g (80% yield).

Example 97

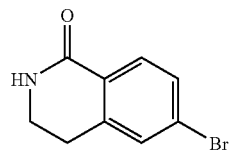

6-Bromo-3,4-dihydro-2H-isoquinolin-1-one

Methanesulfonic acid (100 mL) was added to a solution of 5-bromoindanone (25 g, 46 mmol) in CH$_2$Cl$_2$ (200 mL) at 0° C. Sodium azide 10.5 g, 162 mmol) was added slowly in portions to this mixture. After the sodium azide addition was complete, the mixture was stirred for an additional 30 min, and an aqueous mixture of NaOH (20 wt %) was added until the mixture was slightly basic. The mixture was extracted with methylene chloride, and the combined organic layers were evaporated under reduced pressure. Purification of the mixture by flash column chromatography on silica gel (0% to 50% EtOAc/Hexanes then 0% to 7% MeOH/CH2C12) provided 11.5 g of 6-Bromo-3,4-dihydro-2H-isoquinolin-1-one. MS (ESI) 226.1 (M+H)$^+$.

Example 98

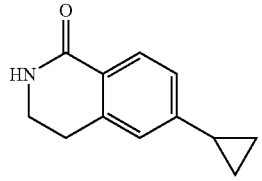

6-Cyclopropyl-3,4-dihydro-2H-isoquinolin-1-one

To a round bottomed flask charged with 6-Bromo-3,4-dihydro-2H-isoquinolin-1-one (16.9 g, 74.7 mmol), cyclopropylboronic acid (9.45 g, 1.5 equiv), tricyclohexylphosphine (1.04 mg, 0.025 equiv), and K$_3$PO$_4$ hexahydrate (50 g, 2 equiv) in toluene (210 mL) and H2O (15 mL) was added Pd(OAc)$_2$ (100 mg, 0.05 equiv). The combined mixture was heated for 4 h at 100° C. The reaction mixture was cooled, filtered and washed with toluene. The organic phase was partitioned and washed with water and brine, dried over Na$_2$SO$_4$, filtered and concentrated to an oil. Addition of hexanes produced 6-Cyclopropyl-3,4-dihydro-2H-isoquinolin-1-one as a tan solid (13.6 g). MS (ESI) 187.1 (M+H)$^+$.

Example 99

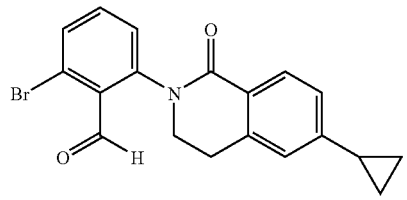

2-Bromo-6-(6-cyclopropyl-1-oxo-,4-dihydro-1H-isoquinolin-2-yl)-benzaldehyde

A round bottom flask was charged with 6-Cyclopropyl-3,4-dihydro-2H-isoquinolin-1-one (13.4 g, 5 mmol), 2,6-Dibromo-benzaldehyde (47.5 g, 72.0 mmol), Pd$_2$(dba)$_3$.CHCl$_3$ (660 mg, 0.72 mmol), xanthphos (832 mg, 1.44 mmol), and cesium carbonate (46.8 g, 144 mmol). The vial was flushed with argon, 140 mL of dioxane was added, and the reaction mixture was heated at 110° C. for 4 h. The reaction mixture was cooled to rt and 30 mL of water and 60 mL of ethyl acetate were added before filtering over Solkaflok. The organic phase was separated and washed with brine followed by drying over Na$_2$SO$_4$. After filtration, the solvent was removed and the brown mass obtained was triturated with methylene chloride and diethyl ether to afford 6.5 grams of 2-Bromo-6-(6-cyclopropyl-1-oxo-,4-dihydro-1H-isoquinolin-2-yl)-benzaldehyde. A second crop of 7.5 grams of material was collected by addition of more diethyl ether. MS (ESI) 370.0 (M+H)$^+$.

Example 100

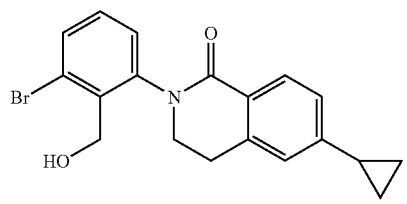

2-(3-bromo-2-hydroxymethyl-phenyl)-6-cyclopropyl-3,4-dihydro-2H-isoquinolin-1-one To a solution of 2-Bromo-6-(6-cyclopropyl-1-oxo-,4-dihydro-1H-isoquinolin-2-yl)-benzaldehyde (5.0 g, 13.5 mmol) in 60 mL of toluene and 10 mL of THF at −10° C. was added sodium borohydride (740 mg, 20 mmol) in portions. After 30 minutes the reaction mixture was quenched with water and partitioned into diethyl ether. The organic phase was washed with brine, dried over sodium sulfate and filtered.

After concentrating under reduced pressure, purification by silica gel chromatography afforded 3.7 g of 2-(3-bromo-2-hydroxymethyl-phenyl)-6-cyclopropyl-3,4-dihydro-2H-isoquinolin-1-one as a colorless solid. MS (ESI) 372.0 (M+H)+.

Example 101

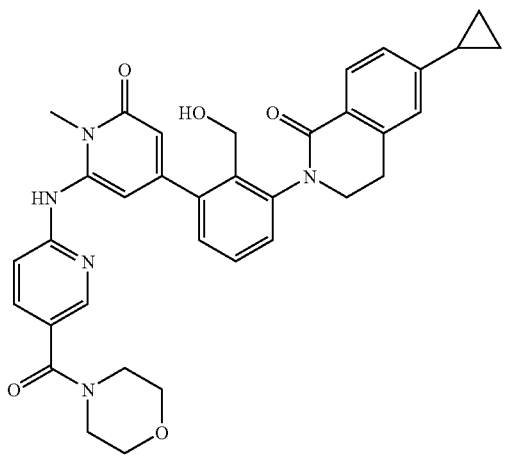

6-Cyclopropyl-2-(2-hydroxymethyl-3-{1-methyl-6-[5-(morpholine-4-carbonyl)-pyridin-2-ylamino]-2-oxo-1,2-dihydro-pyridin-4-yl}-phenyl)-3,4-dihydro-2H-isoquinolin-1-one: To a flask charged with 2-(3-bromo-2-hydroxymethyl-phenyl)-6-cyclopropyl-3,4-dihydro-2H-isoquinolin-1-one (3.70 g, 9.9 mmol), 1-Methyl-6-[4-(morpholine-4-carbonyl)-phenylamino]-4-(4,4,5,5-tetramethyl-[1,3,2]dioxaborolan-2-yl)-1H-pyridin-2-one (4.38 g, 9.9 mmol), Pd$_2$(dba)$_3$·CHCl$_3$ (229 mg, 0.25 mmol), 2-Dicyclohexylphosphino-2',4',6'-Tri-i-Propyl-1,1'-Biphenyl (238 mg, 0.50 mmol), and K$_3$PO$_4$ hexahydrate (7.5 g, 20 mmol) was added 40 mL of 4:1 dioxane:water and the mixture heated to reflux for 4 h, cooled and filtered over Solka-Floc®, rinsing with ethyl acetate. Partitioned and washed the organic phase with water and brine. Dried over sodium sulfate, filtered and concentrated to afford a dark oil. Purification by silica gel chromatography (methylene chloride/methanol) afforded 3.2 g of 6-Cyclopropyl-2-(2-hydroxymethyl-3-{1-methyl-6-[4-(morpholine-4-carbonyl)-phenylamino]-2-oxo-1,2-dihydro-pyridin-4-yl}-phenyl)-3,4-dihydro-2H-isoquinolin-1-one as a colorless solid. MS (ESI) 606.1 (M+H)+.

Example 102

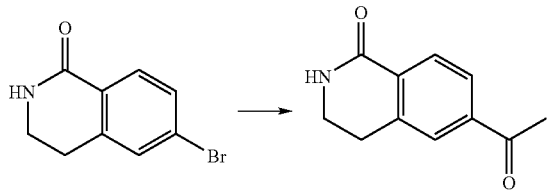

To a flask charged with 1.55 g of (PPh$_3$)$_2$PdCl$_2$ and 5.0 g of 6-Bromo-3,4-dihydro-2H-isoquinolin-1-one was added 25 mL of DMF. Then 9.58 g of Tributyl-(1-ethoxy-vinyl)-stannane was added and the reaction mixture was heated to 110° C. and stirred until completion of the reaction. The reaction mixture was filtered over celite and diluted with diethyl ether. After washing with saturated ammonium carbonate, water and brine, the solution was dried over sodium sulfate, filtered and concentrated in vacuo. The resulting mixture dissolved in THF and treated with 3.0 M aqueous HCl to effect hydrolysis. The mixture was then partitioned between water and diethyl ether. The organic phase was washed sequentially with saturated sodium bicarbonate, water, and brine and then dried over sodium sulfate. After filtration, the solution was concentrated and purified by flash chromatography to afford the 3.28 g of 6-Acetyl-3,4-dihydro-2H-isoquinolin-1-one.

Example 103

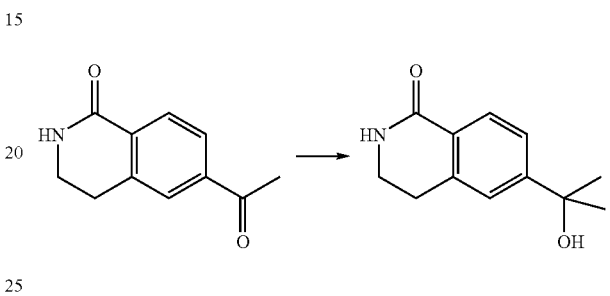

To a slurry of 680 mg of 6-Acetyl-3,4-dihydro-2H-isoquinolin-1-one in 25 mL of THF cooled to 0° C. was slowly added 3.6 mL of 3.0 M MeMgBr in THF. After 1 h the mixture was poured into a solution of ammonium chloride in ice water. Ethyl acetate was added and the organic phase was partitioned, dried over sodium sulfate, filtered, and concentrated. Purification by flash chromatography afforded 380 mg of 6-(1-Hydroxy-1-methyl-ethyl)-3,4-dihydro-2H-isoquinolin-1-one.

Example 104

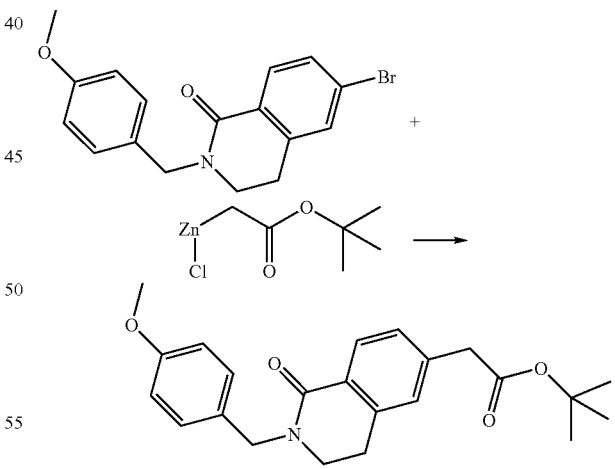

6-Bromo-2-(4-methoxy-benzyl)-3,4-dihydro-2H-isoquinolin-1-one (1.9 g, 5.5 mmole), Q-phos (0.0632 g, 0.11 mmole) and Pd(dba)$_2$ (0.0781 g, 0.11 mmole) in 10 ml THF were added to 2-tert-butoxy-2-oxoethylzinc chloride 15 ml (0.55 M) under argon. The reaction mixture was stirred at room temperature for 16 hours. Next a third of the initial amount of Q-phos, Pd(dba)$_2$ and zinc enolate were added and the mixture heated for 1 hour at 70° C. to bring the reaction to completion. 2 g of [2-(4-Methoxy-benzyl)-1-oxo-1,2,3,4-tetrahydro-isoquinolin-6-yl]-acetic acid tert-butyl ester was isolated by flash chromatography using silica gel column chromatography with 10%-40% ethyl acetate in hexane as eluent.

Example 105

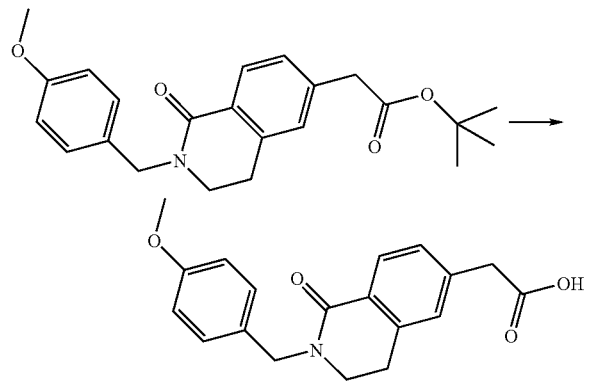

The [2-(4-Methoxy-benzyl)-1-oxo-1,2,3,4-tetrahydro-isoquinolin-6-yl]-acetic acid tert-butyl ester (1 g, 5.7 mmole) was dissolved in 40 ml methanol and to this solution was added LiOH monohydrate (0.72 g, 17.3 mmole) in 6 ml water. The mixture was stirred at room temperature for 16 hours, then concentrated in vacuo, acidified with HCl 2N and extracted with ethylacetate. The organic layer was washed with brine, dried over sodium sulfate and concentrated in vacuo. The resulting 1.8 g of 2-(4-Methoxy-benzyl)-1-oxo-1,2,3,4-tetrahydro-isoquinolin-6-yl]-acetic acid was used in the next step without further purification.

Example 106

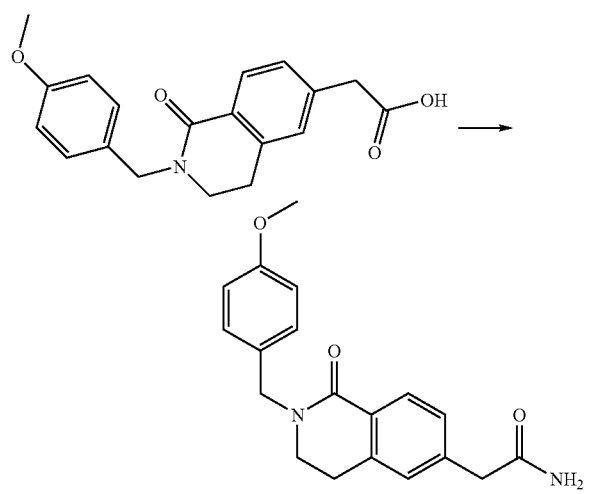

To a solution of 2.3 g of 2-(4-Methoxy-benzyl)-1-oxo-1,2,3,4-tetrahydro-isoquinolin-6-yl]-acetic acid in 22 ml of chloroform was added EEDQ (2.07 g, 8.4 mmole) and ammonium bicarbonate (1.66 g, 21 mmole). After stirring the mixture at room temperature for 16 hours, the amide was precipitated by addition of water (20 ml). The solid was filtered, washed with water and dried in vacuo. The residue was triturated with 50% ethylacetate in hexane, filtered and dried in vacuo to afford 1.4 g of 2-[2-(4-Methoxy-benzyl)-1-oxo-1,2,3,4-tetrahydro-isoquinolin-6-yl]-acetamide.

Example 107

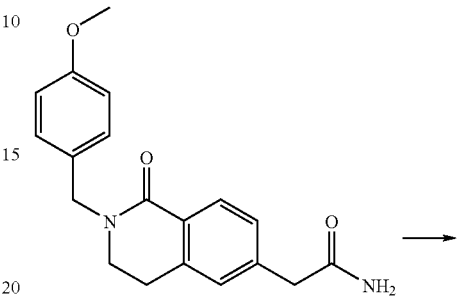

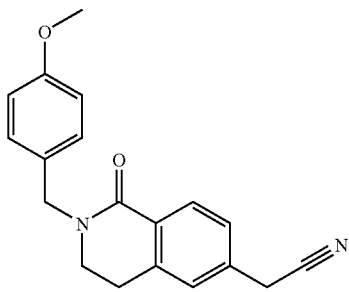

To a suspension of 1.3 g of 2-[2-(4-Methoxy-benzyl)-1-oxo-1,2,3,4-tetrahydro-isoquinolin-6-yl]-acetamide in 5 mL of THF and 10 mL of DMF was added 370 mg of cyanuric chloride and after stirring at room temperature for 0.5 hour, the reaction mixture was partitioned between ethyl acetate and brine. The organic layer was washed with 5% sodium bicarbonate, followed by brine and then dried over sodium sulfate. Purification by flash chromatograpy on silica gel column using 75% ethyl acetate in hexane as eluent afforded 1.2 g of [2-(4-Methoxy-benzyl)-1-oxo-1,2,3,4-tetrahydro-isoquinolin-6-yl]-acetonitrile.

Example 108

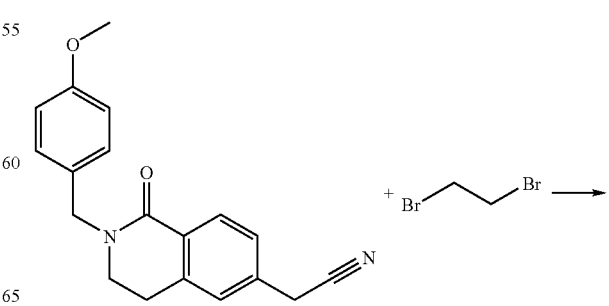

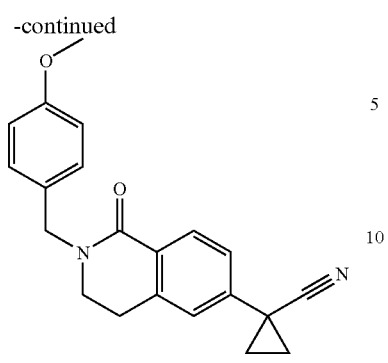

To a suspension of 228 mg of 60% sodium hydride in 15 ml DMF was added 1.2 g of [2-(4-Methoxy-benzyl)-1-oxo-1,2,3,4-tetrahydro-isoquinolin-6-yl]-acetonitrile and after stirring for 15 minutes at room temperature 1.1 g of 1,2-dibromoethane in 1.5 ml DMF was added. The resulting mixture was stirred 0.5 hour at room temperature and then more sodium hydride (0.114 g, 2.86 mmole) was added and the reaction mixture was heated for about 10 minutes at 30-35° C. After cooling, the mixture was partitioned between ethyl acetate and brine and the organic layer was dried over sodium acetate and concentrated in vacuo. Purification by silica gel column chromatography with 30%-50% ethylacetate in hexane afforded 1 g of 1-[2-(4-Methoxy-benzyl)-1-oxo-1,2,3,4-tetrahydro-isoquinolin-6-yl]-cyclopropanecarbonitrile.

Example 109

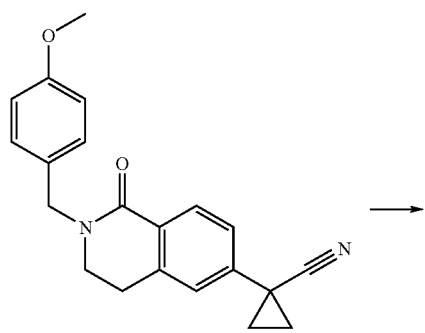

To a solution of 722 mg of 1-[2-(4-Methoxy-benzyl)-1-oxo-1,2,3,4-tetrahydro-isoquinolin-6-yl]-cyclopropanecarbonitrile in 3 ml of dichloromethane and 9 ml toluene, cooled at −50° C. was added dropwise 4.8 mL of 1.0 M DIBAL in THF. After stirring 1 hour at −50° C., the reaction was quenched with 5 ml of 1N HCl, left to warm to room temperature and stirred 0.5 hour. Next the mixture was extracted with ethyl acetate and the organic layer was washed with 0.5 N HCl, sodium carbonate 5% solution, and brine. After drying over sodium sulfate and removal of solvent in vacuo, the residue was purified by silica gel column chromatography using 30%-60% ethylacetate in hexane to provide 0.075 g of 1-[2-(4-Methoxy-benzyl)-1-oxo-1,2,3,4-tetrahydro-isoquinolin-6-yl]-cyclopropanecarbaldehyde.

Example 110

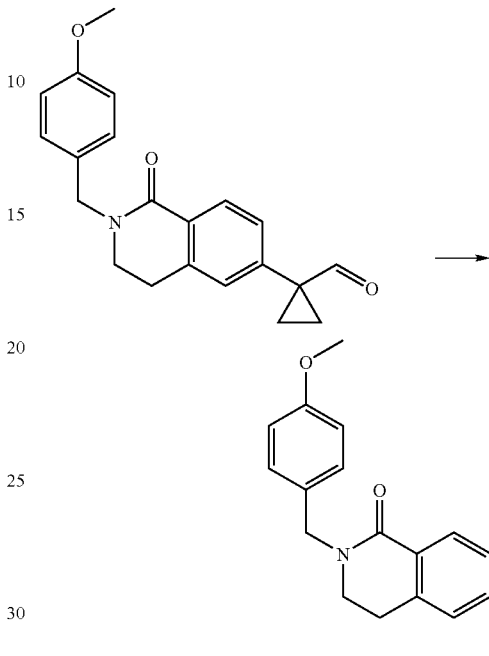

To a solution of DAST (0.042 g, 0.26 mmole) in 1.5 ml dichloromethylene was added 75 mg of 1-[2-(4-Methoxy-benzyl)-1-oxo-1,2,3,4-tetrahydro-isoquinolin-6-yl]-cyclopropanecarbaldehyde in 0.5 ml of dichloromethylene. This mixture was stirred at room temperature for 16 hours. After cooling in an ice bath, 5 ml of water was added to the reaction mixture followed by ethyl acetate. The organic layer was washed with 5% sodium bicarbonate solution and brine, then dried over sodium sulfate and concentrated in vacuo. The residue was purified silica gel prep TLC affording 0.068 g of 6-(1-difluoromethyl-cyclopropyl)-2-(4-methoxy-benzyl)-3,4-dihydro-2H-isoquinolin-1-one.

Example 111

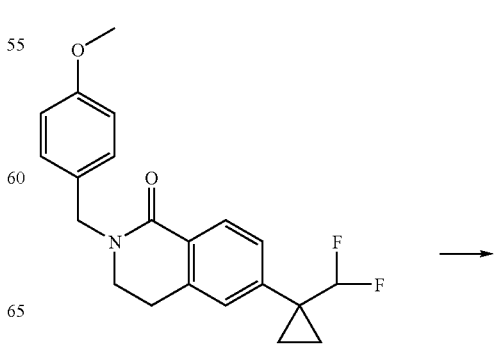

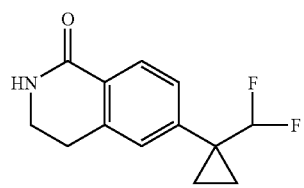

A solution of 68 mg of 6-(1-difluoromethyl-cyclopropyl)-2-(4-methoxy-benzyl)-3,4-dihydro-2H-isoquinolin-1-one in 1 mL of TFA was heated to 70° C. for 1.5 hours. After cooling the reaction mixture to room temperature ethyl acetate was added and the solution was washed with brine followed by sodium bicarbonate 5% solution, and again with brine. The organic layer was dried over sodium sulfate and concentrated in vacuo. The residue was purified by silica gel prep TLC with 5% methanol in dichloromethane affording 30 mg of 6-(1-Difluoromethyl-cyclopropyl)-3,4-dihidro-2H-isoquinolin-1-one.

Example 112

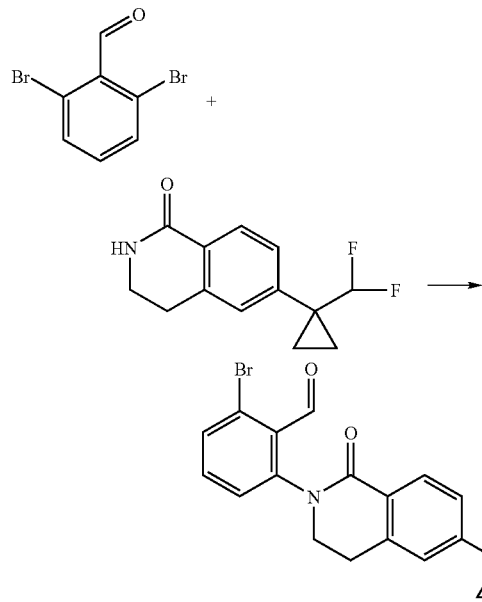

To a mixture of 30 mg of 6-(1-Difluoromethyl-cyclopropyl)-3,4-dihydro-2H-isoquinolin-1-one, 64 mg of 2,6-dibromo-benzaldehyde, 54 mg of cesium carbonate and 2 mg of Xantphos in a microwave tube under argon was added 14 mg of Pd(dba)$_2$. The tube was sealed and the reaction mixture was heated at 100° C. for 16 hours. After cooling the mixture was partitioned between ethyl acetate and brine, the organic layer dried over sodium sulfate and concentrated in vacuo. The residue was purified by silica gel prep TLC with 40% ethylacetate in hexane as eluent affording 0.024 g of 2-Bromo-6-[6-(1-difluoromethyl-cyclopropyl)-1-oxo-3,4-dihydro-1H-isoquinolin-benzaldehyde.

Example 113

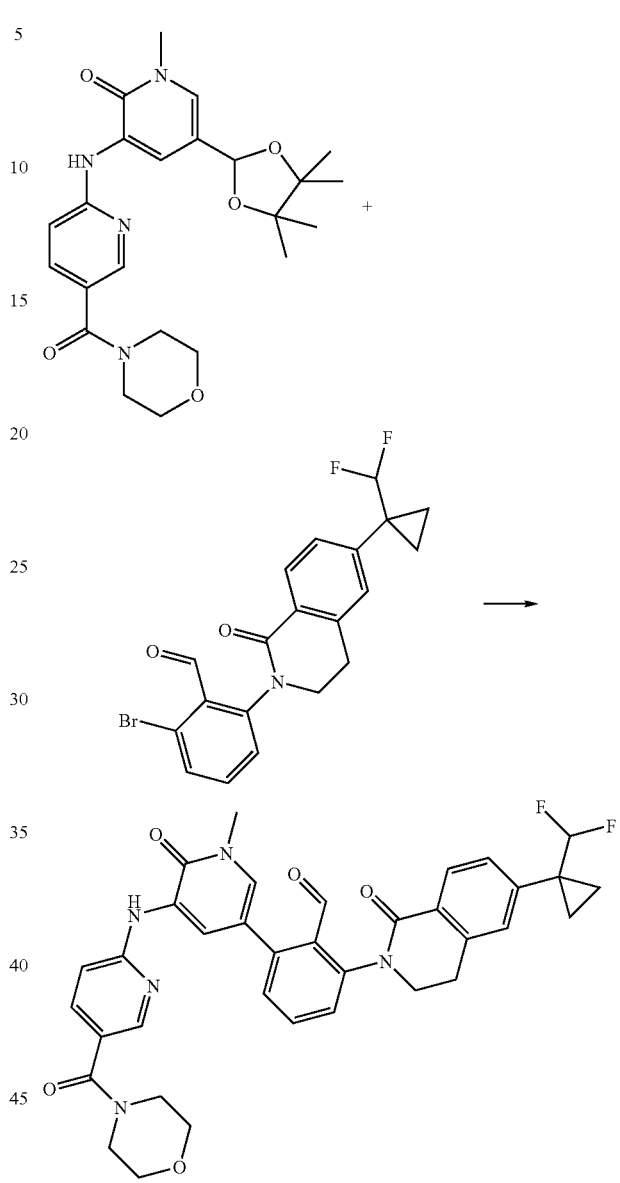

Methyl-3-[5-(morpholine-4-carbonyl)-pyridin-2-ylamino]-5-(4,4,5-tetramethyl-[1,3,2]dioxaborolan-2-yl)-1H-pyridin-2-one (0.025 g, 0.057 mmole) and 24 mg 2-Bromo-6-[6-(1-difluoromethyl-cyclopropyl)-1-oxo-3,4-dihydro-1H-isoquinolin-benzaldehyde were dissolved in 0.5 ml n-butanol. To this solution under argon was added K$_3$PO$_4$ (0.024 g, 0.114 mmole), water 0.150 ml, Xphos (0.0027 g, 0.0057 mmole) and Pd(dba)$_2$ (0.0016 g, 0.0028 mmole). The mixture was heated 1 hour at 100° C. and after cooling partitioned between ethylacetate and brine. The organic layer was dried over sodium sulfate, concentrated in vacuo and the residue purified by silica gel prep TLC to afford 0.025 g of 2-[6-(1-Difluoromethyl-cyclopropyl)-1-oxo-3,4-dihydro-1H-isoquinolin-2-yl]-6-{1-methyl-5-[5-(morpholine-4-carbonyl)-pyridin-2-ylamino]-6-oxo-1,6-dihydro-pyridin-3-yl}-benzaldehyde.

Example 114

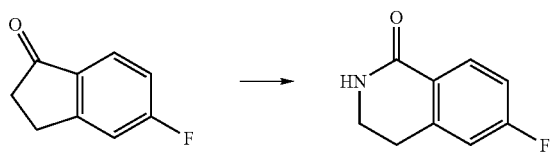

To 25.0 g (166.15 mmol) 5-fluoroindanone in a 3 L flask equipped with a mechanical stirrer was added 280 ml dichloromethane and 200 ml methanesulfonic acid. The mixture was cooled to 0° C. and 15.15 g (233.1 mmol) sodium azide was added in portions over 20 minutes. The mixture was stirred at 0° C. for 2 h, then 490 ml 20% aqueous sodium hydroxide was added dropwise over 30 minutes. The layers were separated and the organic phase dried over MgSO$_4$ and concentrated. Purification by column chromatography eluting with ethyl acetate/hexanes provided 16.76 g (61%) of the desired 6-fluoro-3,4-dihydroisoquinolinone isomer.

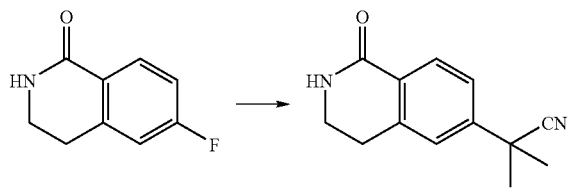

To 2.5 g (15.13 mmol) 6-fluoro-3,4-dihydroisoquinolinone and 5.5 ml (60.54 mmol) isobutyronitrile dissolved in 30 ml THF was added 91 ml (45.42 mmol) 0.5 M KHMDS in toluene. The mixture was heated to 70° C. and vigorously stirred 12 h. The mixture was cooled to room temperature, quenched with water, partitioned between ethyl acetate and brine and dried over MgSO$_4$. Purification by column chromatography eluting with ethyl acetate/hexanes provided 3.23 g (100%) of the product 2-methyl-2-(1-oxo-1,2,3,4-tetrahydroisoquinolin-6-yl)-propionitrile.

Example 116

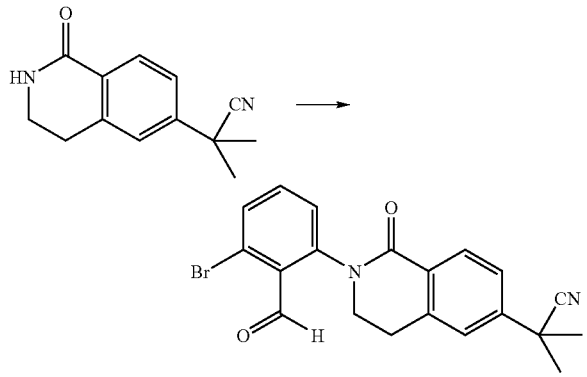

To 1.3 g (6.07 mmol) 2-methyl-2-(1-oxo-1,2,3,4-tetrahydroisoquinolin-6-yl)-propionitrile dissolved in 20 ml degassed dioxane was added 6.40 g (24.27 mmol) 2,6-dibromobenzaldehyde, 3.96 g (12.14 mmol) cesium carbonate, 70 mg (0.121 mmol) Pd(dba)$_2$, and 105 mg (0.182 mmol) xantphos. The mixture was heated to 110° C. for 3 h, cooled to room temperature, and filtered over Celite rinsing with dioxane. The mixture was then concentrated and purified by column chromatography, eluting with ethyl acetate/hexanes to provide 1.10 g (46%) 2-[2-(3-bromo-2-formylphenyl)-1-oxo-1,2,3,4-tetrahydroisoquinolin-6-yl]-2-methylpropionitrile.

Example 117

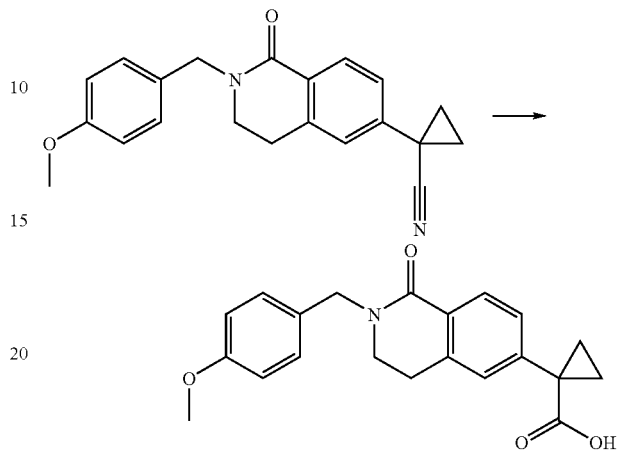

NaOH (5.4 g, 8 equiv) in H2O (16 mL) was added to a solution of the above cyanocyclopropane (5.6 g, 16.9 mmol) in EtOH (50 mL). This mixture was then heated to 100° C. for 9 h, after which it was cooled to rt, concentrated in vacuo to half the original volume, and neutralized with 1N HCl. The mixture was then extracted with CH2Cl2, washed with brine, dried over Na2SO$_4$, and concentrated in vacuo to provide cyclopropanecarboxylic acid product (5.9 g, 99%).

Example 118

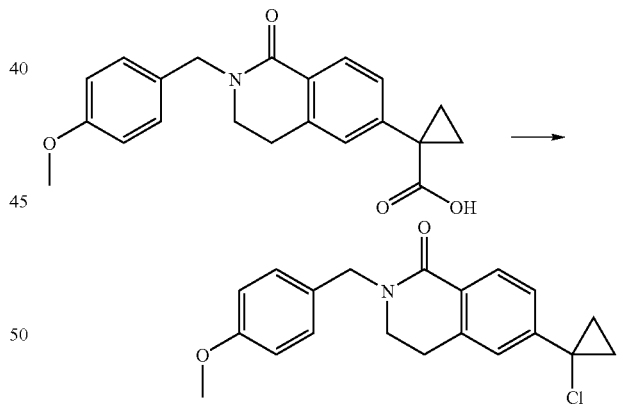

LiCl (2.5 g, 5 equiv) was added to a solution of the above cyclopropanecarboxylic acid (4.2 g, 12.0 mmol) in benzene (60 mL). The mixture was degassed for 30 min, after which Pb(OAc)$_4$ (6.6 g, 1.25 equiv) was added. The degassing was continued for an additional 45 min at rt, at which point the mixture was heated to 100° C. for 2 h. After cooling, the mixture was loaded onto silica gel, concentrated in vacuo, and chromatographed directly (SiO$_2$, 20% to 80% EtOAc/hexanes) to provide PMB-chlorocyclopropane product (1.11 g, 27%). Unreacted starting material (~2.2 g) can be recovered from the column by further elution with the following gradient 2% to 8% MeOH/DCM.

Example 119

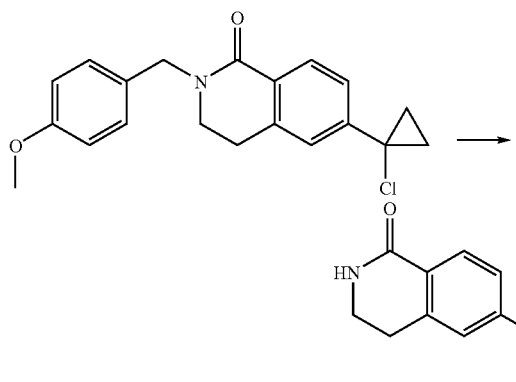

A solution of the above PMB-chlorocyclopropane (1.11 g, 3.3 mmol) in TFA (20 mL) was heated at 80° C. for 2 h. After which it was cooled to rt, and concentrated in vacuo. The residue obtained was redissolved in EtOAc and washed sequentially with sat. NaHCO3, H2O, and brine. The organic layer was then dried over Na2SO₄, and concentrated in vacuo to provide chlorocylopropane product (660 mg, 92%).

Example 120

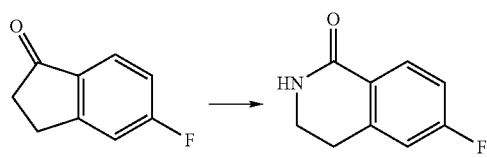

To 25.0 g (166.15 mmol) 5-fluoroindanone in a 3 L flask equipped with a mechanical stirrer was added 280 ml dichloromethane and 200 ml methanesulfonic acid. The mixture was cooled to 0° C. and 15.15 g (233.1 mmol) sodium azide was added in portions over 20 minutes. The mixture was stirred at 0° C. for 2 h, then 490 ml 20% aqueous sodium hydroxide was added dropwise over 30 minutes. The layers were separated and the organic phase dried over MgSO₄ and concentrated. Purification by column chromatography eluting with ethyl acetate/hexanes provided 16.76 g (61%) of the desired 6-fluoro-3,4-dihydroisoquinolinone isomer.

Example 121

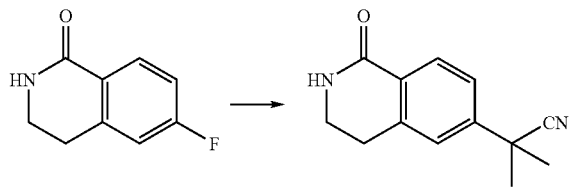

To 2.5 g (15.13 mmol) 6-fluoro-3,4-dihydroisoquinolinone and 5.5 ml (60.54 mmol) isobutyronitrile dissolved in 30 ml THF was added 91 ml (45.42 mmol) 0.5 M KHMDS in toluene. The mixture was heated to 70° C. and vigorously stirred 12 h. The mixture was cooled to room temperature, quenched with water, partitioned between ethyl acetate and brine and dried over MgSO₄. Purification by column chromatography eluting with ethyl acetate/hexanes provided 3.23 g (100%) of the product 2-methyl-2-(1-oxo-1,2,3,4-tetrahydroisoquinolin-6-yl)-propionitrile.

Example 122

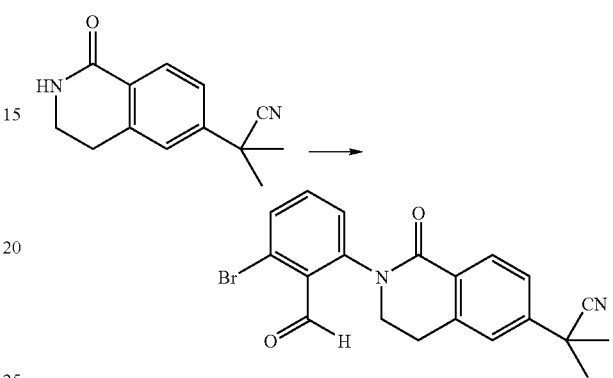

To 1.3 g (6.07 mmol) 2-methyl-2-(1-oxo-1,2,3,4-tetrahydroisoquinolin-6-yl)-propionitrile dissolved in 20 ml degassed dioxane was added 6.40 g (24.27 mmol) 2,6-dibromobenzaldehyde, 3.96 g (12.14 mmol) cesium carbonate, 70 mg (0.121 mmol) Pd(dba)₂, and 105 mg (0.182 mmol) xantphos. The mixture was heated to 110° C. for 3 h, cooled to room temperature, and filtered over Celite rinsing with dioxane. The mixture was then concentrated and purified by column chromatography, eluting with ethyl acetate/hexanes to provide 1.10 g (46%) 2-[2-(3-bromo-2-formylphenyl)-1-oxo-1,2,3,4-tetrahydroisoquinolin-6-yl]-2-methylpropionitrile.

Example 123

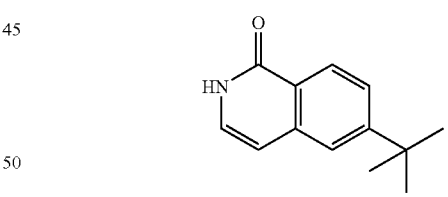

Preparation of 6-tert-Butyl-2H-isoquinolin-1-one: 6-tert-Butyl-3,4-dihydro-2H-isoquinolin-1-one (1.709 g, 8.4 mmol) and 2,3-5,6-dicyano-p-benzoquinone (DDQ) (3.85 g, 2 eq) were taken up in dioxane (130 mL) and the resulting mixture was heated to 100° C. for four days. After allowing to cool to room temperature, most of the dioxane was removed under reduced pressure at 55° C. Ethyl acetate (300 mL) and 2N NaOH (100 mL) were added to the residue and the mixture was partitioned and the layers were sepearated. Subsequently washed again with 2N NaOH (3×100 mL), water (1×125 mL) and finally with brine (1×125 mL). The ethyl acetate layer was dried over magnesium sulfate, filtered and concentrated to give the crude product (1.783 G). Purification on silica gel eluting with 30% ethyl acetate in hexanes afforded the title compound (779 mg) as a light tan powder. MS (ESI) 202.0 (M+H)$^+$.

Example 124

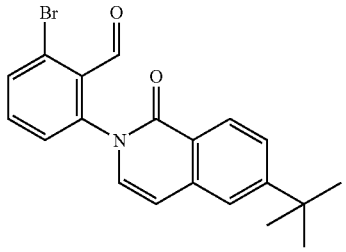

Preparation of 2-Bromo-6-(6-tert-butyl-1-oxo-1H-isoquinolin-2-yl)-benzaldehyde 6-tert-Butyl-2H-isoquinolin-1-one (272 mg, 1.35 mmol), 2,6-Dibromo-benzaldehyde (891 mg, 2.5 eq), xanthphos (35 mg, 0.045 eq) and cesium carbonate (616 mg, 1.4 eq) were taken up in dioxane (2.7 mL). Then nitrogen was bubbled through the solution for 10 minutes before adding bis(dibenzylideneacetone)palladium (23 mg, 0.03 eq). The resulting mixture was stirred at 100° C. overnight. By TLC and LC/MS there was no desired product observed. Next added copper iodide (55 mg, 0.02 eq) and cesium carbonate (320 mg, 0.73 eq) and more dioxane (4 mL). The resulting mixture was heated to 100° C. with stirring for 30 hours and by TLC the reaction was now complete. After cooling to room temperature, ethyl acetate (175 mL) and water (50 mL) were added. The layers were partitioned, and separated. The organice layer was then washed with water (3×50 mL) and finally with brine (1×50 mL) before drying over magnesium sulfate, filtering and concentrating. Purification on silica gel eluting with a step-wise gradient of 5% ethyl acetate to 20% ethyl acetate in hexanes gave the title compound as a light tan powder (215 mg). MS (ESI) 346.0 (M+H)$^+$.

Example 125

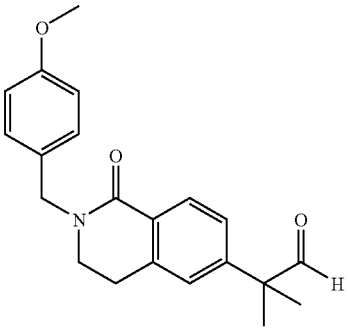

Preparation of 2-[2-(4-Methoxy-benzyl)-1-oxo-1,2,3,4-tetrahydro-isoquinolin-6-yl]-2-methyl-propionaldehyde: 6-Bromo-2-(4-methoxy-benzyl)-3,4-dihydro-2H-isoquinolin-1-one (5 g, 14.4 mmol), SPHOS (361 mg, 0.06 eq), cesium carbonate (5.65 g, 1.2 eq) and palladium acetate (130 mg, 0.04 eq) were placed in an open sealed tube and taken up in dioxane (58 mL). Argon was bubbled through the solution for about 15 minutes and then isobutyraldehyde (2.9 mL, 2 eq) was added and the mixture was capped and stirred at 80° C. overnight. The next day the reaction still was not complete, so additional palladium acetate (65 mg) and SPHOS (181 mg) and isobutyraldehyde (1.5 mL) were added and the reaction was stirred at 80° C. for another 24 hours. At this point the reaction still was not complete so additional palladium acetate (30 mg) and SPHOS (90 mg) were added and the reaction was stirred at 100° C. for another 24 hours. After 3 days, there was no starting material remaining and the reaction was cooled to room temperature. Added ethyl acetate (300 ml) and water 100 mL) and partitioned and separated the layers. The ethyl acetate layer was washed with brine (100 mL) and dried over magnesium sulfate, filtered and concentrated to give the crude product. Purification on silica gel eluting with 20% ethyl acetate in hexanes afforded the title compound as a thick colorless oil (428 mg). MS (ESI) 338.0 (M+H)$^+$.

Example 126

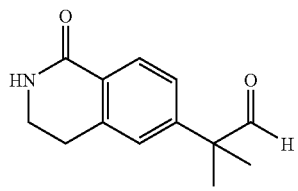

Preparation of 2-Methyl-2-(1-oxo-1,2,3,4-tetrahydro-isoquinolin-6-yl)-propionaldehyde: 2-[2-(4-Methoxy-benzyl)-1-oxo-1,2,3,4-tetrahydro-isoquinolin-6-yl]-2-methyl-propionaldehyde (420 mg, 1.25 mmol) was taken up in trifluoroacetic acid (5 mL) and the resulting mixture was stirred at 80° C. for 2.5 hours and then cooled to room temperature. The trifluoroacetic acid was removed under reduced pressure at 60° C., and then co-evaporated with ethyl acetate (5×). The residue was taken up in ethyl acetate (175 mL) and then washed with water (3×50 mL) and finally with brine (1×50 mL). The ethyl acetate layer was dried over magnesium sulfate, filtered and concentrated to give the crude product. Purification on silica gel eluting with a gradient of 50% ethyl acetate in hexanes to neat ethyl acetate gave the title compound as a white powder (228 mg). MS (ESI) 218.0 (M+H)$^+$.

Example 127

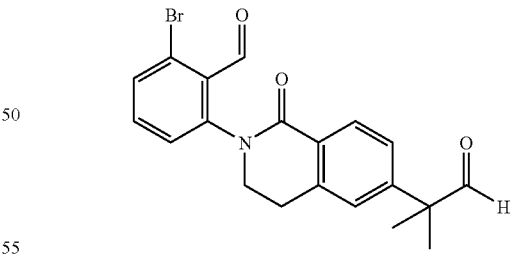

Preparation of 2-Bromo-6-[6-(1,1-dimethyl-2-oxo-ethyl)-1-oxo-3,4-dihydro-1H-isoquinolin-2-yl]-benzaldehyde: 2-Methyl-2-(1-oxo-1,2,3,4-tetrahydro-isoquinolin-6-yl)-propionaldehyde (224 mg, 1.03 mmol), 2,6-Dibromo-benzaldehyde (1.09 g, 4 eq), xanthphos (27 mg, 0.03 eq) and cesium carbonate (470 mg, 1.4 eq) were taken up in dioxane (2 mL) and argon was bubbled through the mixture for 10 minutes, before adding bis(dibenzylideneacetone)palladium (18 mg, 0.03 eq). The resulting mixture was placed under an argon atmosphere and heated to 100° C. with stirring for 2.5 hours by which time all of the starting material had been consumed by TLC and LC/MS analysis. After cooling to room temperature, ethyl acetate (175 mL) and water (50 mL) were added and the layers were partitioned and separated. The ethyl acetate layer was washed with brine (1×50 mL) and then dried over magnesium sulfate, filtered and concentrated to give the crude product. Purification on silica gel eluting with a gradient ranging from 5% ethyl acetate to 40% ethyl acetate in hexanes gave the title compound as a light yellow powder (302 mg). MS (ESI) 400.0 (M+H)$^+$.

Example 128

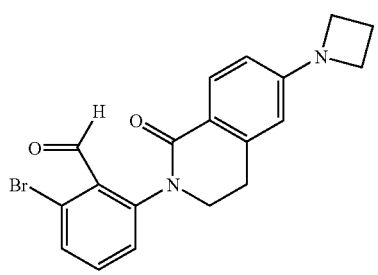

2-(6-Azetidin-1-yl-1-oxo-3,4-dihydro-1H-isoquinolin-2-yl)-6-bromo-benzaldehyde

5-Azetidin-1-yl-indan-1-one

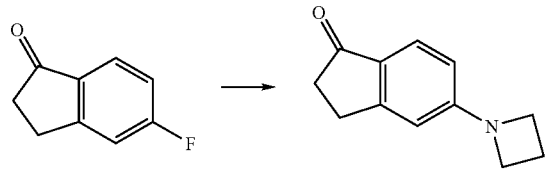

5-fluoro-1-indanone (7.44 g, 49.5 mmol), Azetidine HCl (5.1 g, 54.4 mmol) and K2CO3 (13.6 g, 99 mmol) were taken up in 60 ml of DMSO. The reaction mixture was heated at 100 C for 6 hours.

The mixture was partitioned between water and ethyl acetate. The aqueous layer was further extracted with 250 mL of ethyl acetate. The combined organic layers were washed with three 250 mL portions of water, dried over MgSO$_4$, filtered and concentrated. Column chromatography (0-40% EtOAc/Hexane) afforded 3.41 g of product.

Example 129

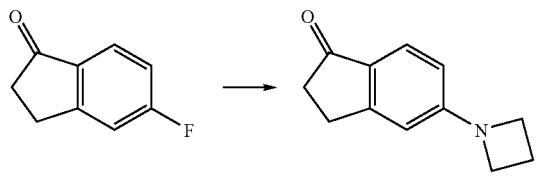

6-Azetidin-1-yl-3,4-dihydro-2H-isoquinolin-1-one. 5-azetidin-1-yl-indan-1-one (1.9 g, 10.14 mmol) and methane sulfonic acid (10.8 ml) were added to CH2C12 (100 ml). The reaction mixture was cooled to 0 C and sodium azide (1.32 g, 20.29 mmol) was carefully portion wise added over 30 min then reaction mixture was stirred at 0 C for 2 hours. After the reaction was done, it was slowly added 20% NaOH aq. at 0 C.

The mixture was partitioned between water and CH2C12. The aqueous layer was further extracted with 100 mL of CH2C12. The combined organic layers were washed with three 200 mL portions of water, dried over MgSO$_4$, filtered and concentrated. Column chromatography (0-60% EtOAc/Hexane) afforded 1.02 g of desired isomer.

Example 130

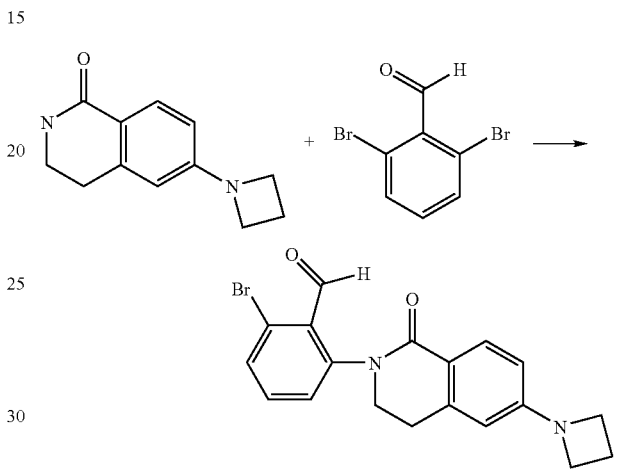

2-(6-Azetidin-1-yl-1-oxo-3,4-dihydro-1H-isoquinolin-2-yl)-6-bromo-benzaldehyde: 6-Azetidin-1-yl-3,4-dihydro-2H-isoquinolin-1-one (1.0 g, 4.94 mmol), 2-dicyclohexylphosphino-2',4', 6'-triisopropylbiphenyl (011 g, 0.22 mmol) and cesium carbonate (2.26 g, 6.92 mmol) were taken up in dioxane (50 ml) and then nitrogen was bubbled thorugh mixture for 10 min. Bis (dibenzylideneacetone) palladium(0) (0.085 g, 0.14 mmol) and Copper(1) iodide (0.93 g, 4.94 mmol) were added and then the reaction mixture was heated at 100 C for 82 hours.

The mixture was partitioned between water and ethyl acetate. The aqueous layer was further extracted with 100 mL of ethyl acetate. The combined organic layers were washed with three 100 mL portions of water, dried over MgSO$_4$, filtered and concentrated. Column chromatography (0-50% EtOAc/Hexane) afforded 0.74 g of product.

Example 131

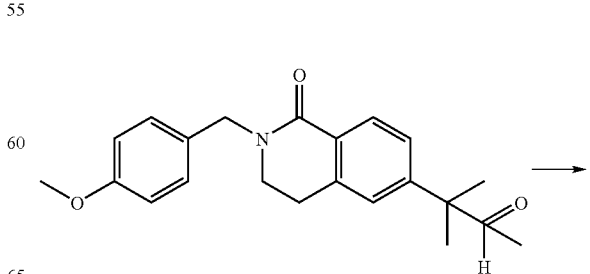

-continued

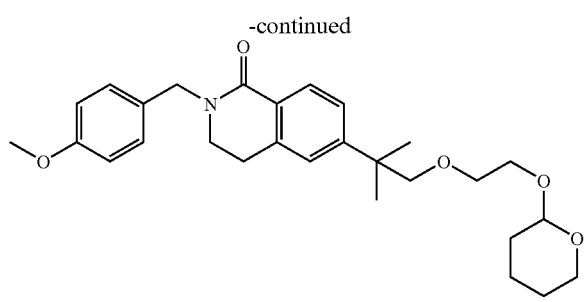

180 mg 2-[2-(4-Methoxy-benzyl)-1-oxo-1,2,3,4-tetrahydro-isoquinolin-6-yl]-2-methyl-propionaldehyde (0.54 mmol, 1 eq) was cooled to zero C in 20 ml of a 1:1 mixture of ethanol and THF. 20 mg sodium borohydride (0.54 mmol, 1 eq) was added and the mixture was stirred at 0 C for 1 hour. Quenched with water, then 2 drops glacial acetic acid, stirred for 5 minutes, and the mixture concentrated under vacuum to remove the majority of solvents, added saturated bicarb solution, extracted ethyl acetate 2×, dried ethyl acetate over MgSO4, and concentrated to give 180 mg 6-(2-Hydroxy-1,1-dimethyl-ethyl)-2-(4-methoxy-benzyl)-3,4-dihydro-2H-isoquinolin-1-one (M+H=340) which was used directly in the next reaction with no purification.

The residue from the previous reaction (180 mg, 0.53 mmol, 1 eq.) was dissolved in a 1:1 mixture of DMF and THF, and 0.2 ml 2-(2-Chloro-ethoxy)-tetrahydro-pyran (3.2 mmol, 6 eq) was added, followed by 80 mg sodium hydride (95% dry, 3.2 mmol, 6 eq) and the mixtured heated to 90 C overnight. Cooled, quenched 2 ml water, concentrated to dryness and loaded directly on a silica gel column, eluting with 50% ethyl acetate in hexanes to give 140 mg 6-{1,1-Dimethyl-2-[2-(tetrahydro-pyran-2-yloxy)-ethoxy]-ethyl}-2-(4-methoxy-benzyl)-3,4-dihydro-2H-isoquinolin-1-one. MS (ESI) 468.0 (M+H)⁺.

Example 132

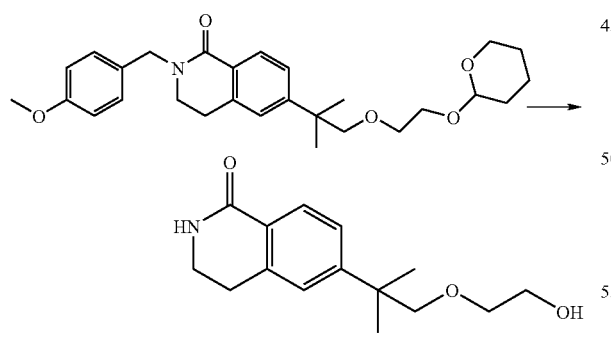

140 mg 6-{1,1-Dimethyl-2-[2-(tetrahydro-pyran-2-yloxy)-ethoxy]-ethyl}-2-(4-methoxy-benzyl)-3,4-dihydro-2H-isoquinolin-1-one (0.3 mmol, 1 eq) was dissolved in 5 ml trifluoroacetic acid, and the mixture heated to 80 C for 16 hours. The reaction was concentrated to dryness, partitioned between ethyl acetate and saturated sodium bicarbonate, separated layers and washed ethyl acetate with brine, dried MgSO4 and concentrated to give 75 mg 6-[2-(2-Hydroxy-ethoxy)-1,1-dimethyl-ethyl]-3,4-dihydro-2H-isoquinolin-1-one, M+H=264 which was used without purification in the next step.

Example 133

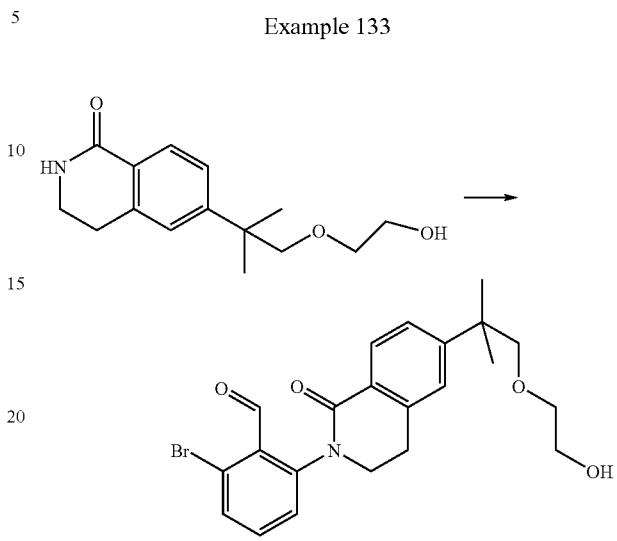

Combined 0.131 g (0.5 mmol, 1 eq) 6-(2-Hydroxy-1,1-dimethyl-ethyl)-2-(4-methoxy-benzyl)-3,4-dihydro-2H-isoquinolin-1-one, 0.528 g 2,6-dibromobenzaldehyde (2 mmol, 4 eq), 6 mg Xantphos (0.01 mmol, 0.02 eq), 9 mg bis(dibenzylideneacetone)palladium (0.015 mmol, 0.03 eq), and 0.326 g Cesium Carbonate (1 mmol, 2.0 eq) in 5 ml dioxane, bubbled argon gas through the mixture for 1 minute, sealed the reaction vessel and heated at 100 C for 13 hours, filtered through a sintered glass funnel while hot, concentrated and purified on a silica gel column eluting with 5% to 10% Methanol in CH₂Cl₂ to give 148 mg. Rotovaped, chromatographed (10% to 30% ea in hexanes) to give a solid, 325 mg 2-Bromo-6-{6-[2-(2-hydroxy-ethoxy)-1,1-dimethyl-ethyl]-1-oxo-3,4-dihydro-1H-isoquinolin-2-yl}-benzaldehyde. MS (ESI) 446.0 (M+H)⁺.

Example 134

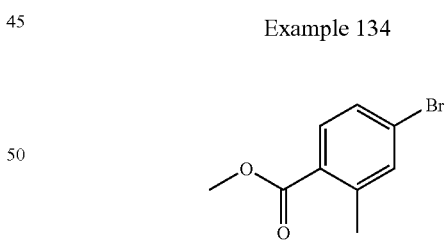

4-bromo-2-methylbenzoic acid (100.04 g, 465 mmol), 500 mL of anhydrous methanol, and 5 mL of concentrated sulfuric acid were stirred at reflux under nitrogen for 24 hr. Cooled to room temperature and concentrated in vacuo. Diluted the residue with 500 mL EtOAc and washed with 200 mL 1 M aqueous NaOH, 200 mL water, and 200 mL brine. Dried the solution over MgSO₄ and concentrated in vacuo to obtain methyl 4-bromo-2-methylbenzoate as a clear colorless liquid (100.06 g, 437 mmol). ¹H NMR (300 MHz, chloroform-d) ppm 2.59 (s, 3H) 3.89 (s, 3H) 7.39 (d, J=8.29 Hz, 1H) 7.42 (s, 1H) 7.79 (d, J=8.67 Hz, 1H).

Example 135

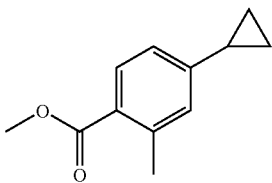

Cyclopropylboronic acid (25.08 g, 292 mmol), anhydrous tribasic potassium phosphate (178.12 g, 839 mmol), 2-dicyclohexylphosphino-2',4',6'-triisopropylbiphenyl (6.925 g, 14.5 mmol), methyl 4-bromo-2-methylbenzoate (55.93 g, 244 mmol), and 600 mL of toluene were charged into a 1000 mL round bottom flask fitted with a stir bar, septum, and nitrogen inlet. Stirred the mixture rapidly and added 65 mL of water. Sparged the mixture with nitrogen for 30 min. Added tris(dibenzylideneacetone)dipalladium(0) (3.321 g, 3.63 mmol). The reaction mixture was sparged with nitrogen for 15 min. Sealed the flask with a cap and stirred at 90° overnight. Added 150 mL water and allowed to cool to room temperature. Filtered the two phase system through diatomaceous earth to remove the solids and washed the filter cake with EtOAc. Separated the filtrate phases and washed the organic phase with 2×200 mL 5% $NaHCO_3$, 2×200 mL 10% $Na_2S_2O_3$, and 200 mL brine. Dried the solution over $MgSO_4$ and concentrated in vacuo. Vacuum distilled the residual liquid. Collected the fraction distilling at 108-111°/3 torr to obtain methyl 4-cyclopropyl-2-methylbenzoate as a clear colorless liquid (32.30 g, 170 mmol). $^1$H NMR (300 MHz, chloroform-d) ppm 0.71-0.80 (m, 2H) 0.98-1.07 (m, 2H) 1.83-1.95 (m, 1H) 2.58 (s, 3H) 3.87 (s, 3H) 6.87-6.96 (m, 2H) 7.83 (d, J=7.91 Hz, 1H).

Example 136

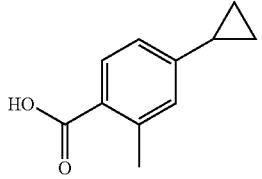

Methyl 4-cyclopropyl-2-methylbenzoate (32.00 g, 168 mmol), 250 mL of 5 M aqueous sodium hydroxide, and 150 mL of methanol were stirred at 85° for 18 hr. Cooled the reaction mixture to room temperature and concentrated in vacuo. Dissolved the white residue in 500 mL of water, cooled the solution in an ice bath, and added 120 mL of concentrated hydrochloric acid. A white precipitate formed. Extracted the aqueous mixture with 2×250 mL EtOAc. Combined the organic extracts and washed with 250 mL brine. Dried the solution over $MgSO_4$ and concentrated in vacuo to obtain 4-cyclopropyl-2-methylbenzoic acid as an off-white solid (29.52 g, 168 mmol). MS (ESI) MS (ESI) 175.0 (M–H)$^-$.

Example 137

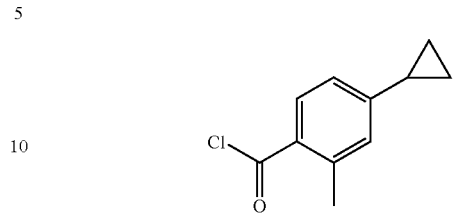

4-Cyclopropyl-2-methylbenzoic acid (25.01 g, 142 mmol) and phosphorus pentachloride (32.84 g, 158 mmol) were charged into a 100 mL round bottom flask fitted with a stir bar, reflux condenser, and calcium chloride drying tube exhausted through a dilute aqueous solution of NaOH as a gas trap. Refluxed the mixture at a bath temperature of 120° for 2 hr. Removed the $POCl_3$ byproduct by distillation at atmospheric pressure. Vacuum distilled the residue. Collected the fraction distilling at 116-118°/3 torr to obtain 4-cyclopropyl-2-methylbenzoyl chloride as a clear colorless liquid (26.39 g, 136 mmol). $^1$H NMR (300 MHz, chloroform-d) ppm 0.77-0.86 (m, 2H) 1.06-1.16 (m, 2H) 1.87-1.99 (m, 1H) 2.54 (s, 3H) 6.93-7.03 (m, 2H) 8.14 (d, J=8.29 Hz, 1H).

Example 138

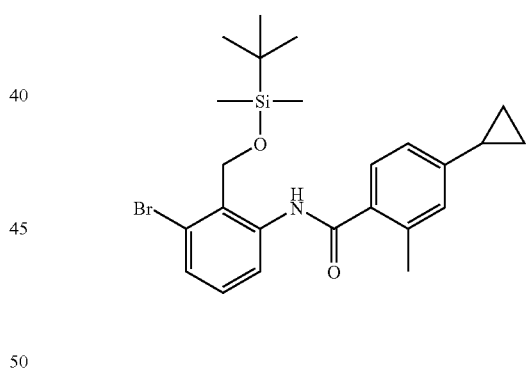

To a solution of [3-bromo-2-(tert-butyl-dimethyl-silanyloxymethyl)-phenylamine (21.28 g, 67.3 mmol) and anhydrous pyridine (6.5 mL, 80 mmol) in 50 mL of anhydrous toluene was added a solution of 4-cyclopropyl-2-methylbenzoyl chloride (13.25 g, 68.1 mmol) in 50 mL anhydrous toluene dropwise. A precipitate formed immediately upon addition. Stirred the mixture at ambient temperature under nitrogen overnight. Diluted the reaction mixture with 125 mL hexane and filtered off the precipitate. Washed the filtrate with 2×200 mL 1.0 M $KHSO_4$, 2×200 mL 5% $NaHCO_3$, and 250 mL water. Dried the solution over $MgSO_4$ and concentrated in vacuo to obtain N-[3-Bromo-2-(tert-butyl-dimethyl-silanyloxymethyl)-phenyl]-4-cyclopropyl-2-methyl-benzamide as a waxy light brown solid (31.54 g, 66.4 mmol). MS (ESI) 474, 476.0 (M+H)$^+$.

Example 139

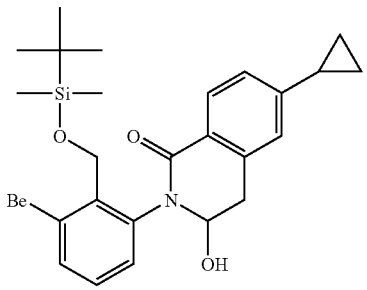

An oven dried 1000 mL round bottom flask was fitted with a stir bar, septum, and nitrogen inlet. Established and maintained $N_2$ atmosphere. Charged the flask with 2,2,6,6-tetramethylpiperidine (25 g, 180 mmol) and 300 mL anhydrous, inhibitor free THF. Cooled the solution in an ice/acetone bath to −15°. Stirred rapidly and added 58 mL of a 2.5 M solution of n-butyllithium (58 mL, 150 mmol) in hexane dropwise over 20 minutes using a syringe pump. Stirred the clear amber solution at −15° for 30 minutes. Added a solution of N-[3-bromo-2-(tert-butyl-dimethyl-silanyloxymethyl)-phenyl]-4-cyclopropyl-2-methyl-benzamide (16.65 g, 35.1 mmol) dissolved in 100 mL of anhydrous THF dropwise over 20 minutes using a syringe pump. Stirred the dark pomegranate colored solution at −15° for one hour. Added dimethylformamide (40 mL, 520 mmol) in one portion. The color changed tint from dark purple to dark amber and the solution warmed to −5°. Stirred the reaction 10 min at −5°, then removed the ice bath and allowed to stir at ambient temperature for 1 hr. [Removed a 55 mL aliquot for a separate experiment] Cooled the dark amber solution to 0° in an ice bath and quenched the reaction by addition of 125 mL of 3 N hydrochloric acid to give a solution pH of 2. Poured the reaction mixture into 1000 mL EtOAc and 500 mL water. Separated phases and washed the organic phase with 500 mL 5% aqueous $NaHCO_3$ and 500 mL brine. Dried the solution over $Na_2SO_4$ and concentrated in vacuo. Purified the residue by flash chromatography (gradient elution, 0 to 50% EtOAc/hexane) to obtain 2-[3-Bromo-2-(tert-butyl-dimethyl-silanyloxymethyl)-phenyl]-6-cyclopropyl-3-hydroxy-3,4-dihydro-2H-isoquinolin-1-one as a pale yellow solid (10.42 g, 20.7 mmol). MS (ESI) 500.0, 502.0 (M−H)⁻.

Example 140

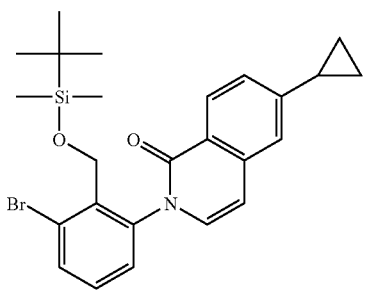

To a rapidly stirred solution of 2-[3-bromo-2-(tert-butyl-dimethyl-silanyloxymethyl)-phenyl]-6-cyclopropyl-3-hydroxy-3,4-dihydro-2H-isoquinolin-1-one (3.52 g, 7.00 mmol) and triethylamine (4.0 mL, 29 mmol) in 50 mL of anhydrous $CH_2Cl_2$ was added 0.85 mL of methanesulfonyl chloride. Purged the flask with nitrogen and stirred at room temperature overnight. Added 25 mL of $CH_2Cl_2$ and 50 mL of water and separated phases. Washed the organic phase with 50 ml brine. Dried the solution over $MgSO_4$ and concentrated in vacuo. Purified the residue by flash chromatography (gradient elution, 0 to 50% EtOAc/hexane) to obtain 2-[3-Bromo-2-(tert-butyl-dimethyl-silanyloxymethyl)-phenyl]-6-cyclopropyl-2H-isoquinolin-1-one as an amber resin (2.90 g, 5.99 mmol). MS (ESI) 484, 486 (M+H)⁺.

Example 141

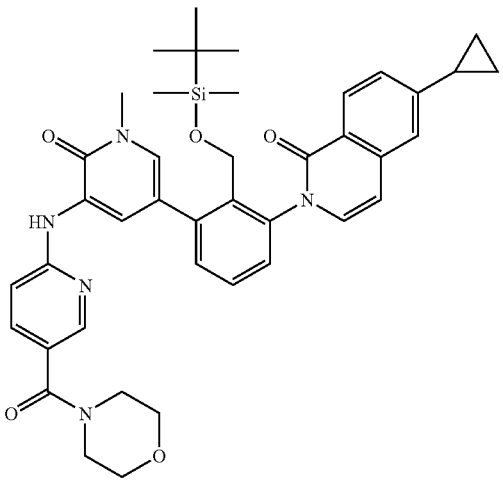

Methyl-3-[5-(morpholine-4-carbonyl)-pyridin-2-ylamino]-5-(4,4,5,5-tetramethyl-1,3,2-dioxaborolan-2-yl)-1H-pyridin-2-one (99 mg, 0.22 mmol), 2-[3-bromo-2-(tert-butyl-dimethyl-silanyloxymethyl)-phenyl]-6-cyclopropyl-2H-isoquinolin-1-one (120 mg, 0.248 mmol), 2 mL dioxane, and a solution of cesium carbonate in water (370 mg/420 µL) were charged into a 4 mL reaction vial fitted with a stir bar and septum. Sparged the mixture with nitrogen for 15 min. Added [1,1'-bis(diphenylphosphino)ferrocene]palladium(II) chloride 1:1 complex with dichloromethane (12 mg, 0.015 mmol). The reaction was sparged with nitrogen for 5 min. Sealed the vial and stirred at 90° 16 hr. Cooled to room temperature, partitioned the reaction mixture between 5 mL of 5% $NaHCO_3$ and 10 mL of EtOAc, and separated phases. Washed the organic phase with 5 mL of water and 5 mL of brine, dried over $Na_2SO_4$ and concentrated in vacuo. Purified by C18 reverse phase flash chromatography (gradient elution, 10 to 95% acetonitrile+0.1% TFA/water+0.1% TFA). Added 1 mL of saturated $NaHCO_3$ to the pooled product fractions and concentrated in vacuo. Extracted the remaining aqueous mixture with 2×10 mL $CH_2Cl_2$, dried over $Na_2SO_4$, and concentrated in vacuo to obtain 2-(2-(tert-Butyl-dimethyl-silanyloxymethyl)-3-{1-methyl-5-[5-(morpholine-4-carbonyl)-pyridin-2-ylamino]-6-oxo-1,6-dihydro-pyridin-3-yl}-phenyl)-6-cyclopropyl-2H-isoquinolin-1-one as a brittle amber foam. (70 mg, 0.097 mmol). MS (ESI) 718 (M+H)⁺.

Example 142

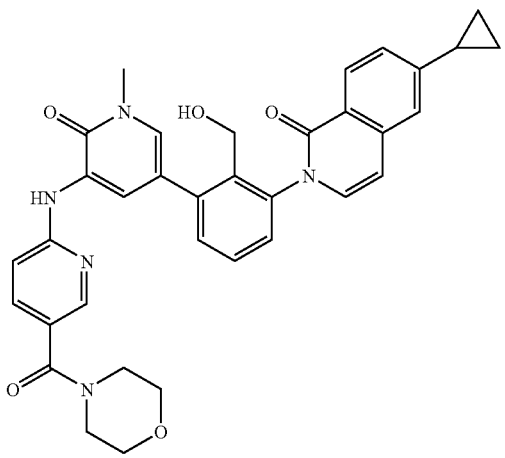

2-(2-(tert-Butyl-dimethyl-silanyloxymethyl)-3-{1-methyl-5-[5-(morpholine-4-carbonyl)-pyridin-2-ylamino]-6-oxo-1,6-dihydro-pyridin-3-yl}-phenyl)-6-cyclopropyl-2H-isoquinolin-1-one (56 mg, 0.078 mmol) was dissolved in 3 mL anhydrous THF. Added a 1.0 M solution of tetrabutylammonium fluoride (466 μL, 466 mmol) in THF and stirred at room temperature for 15 min. Partitioned the reaction mixture between 8 mL of water and 10 mL of $CH_2Cl_2$ and separated phases. Washed the organic phase with 8 mL of 1.0 M $KHSO_4$ and 8 mL of saturated aqueous $NaHCO_3$. Dried over $Na_2SO_4$ and concentrated in vacuo. Purified by C18 reverse phase flash chromatography (gradient elution, 10 to 95% acetonitrile+0.1% TFA/water+0.1% TFA). Added 1 mL of saturated $NaHCO_3$ to the pooled product fractions and concentrated in vacuo. Extracted the remaining aqueous mixture with 2×10 mL $CH_2Cl_2$, dried over $Na_2SO_4$, and concentrated in vacuo to obtain 6-Cyclopropyl-2-(2-hydroxymethyl-3-{1-methyl-5-[5-(morpholine-4-carbonyl)-pyridin-2-ylamino]-6-oxo-1,6-dihydro-pyridin-3-yl}-phenyl)-2H-isoquinolin-1-one as an off-white solid. (29 mg, 0.048 mmol). MS (ESI) 604 $(M+H)^+$.

Example 143

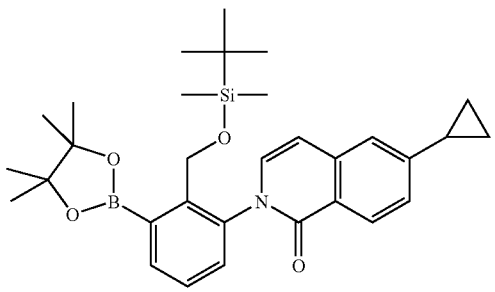

A catalyst solution was prepared by charging a 20 mL reaction vial fitted with a septum and nitrogen inlet with tris(dibenzylidineacetone)dipalladium(0) (168 mg, 0.183 mmol), tricyclohexylphosphine (253 mg, 0.902 mmol), and 10 mL of dioxane. Sparged the mixture for 15 min with nitrogen, then stirred at room temperature for 1 hr.

2-[3-Bromo-2-(tert-butyl-dimethyl-silanyloxymethyl)-phenyl]-6-cyclopropyl-2H-isoquinolin-1-one (2.85 g, 5.88 mmol), potassium acetate (1.17 g, 11.9 mmol), bis(pinacolato)diboron (3.01 g 11.9 mmol), and 20 mL of dioxane were charged into a 40 mL reaction vial fitted with a septum and nitrogen inlet. Heated and stirred until all the bis(pinacolato) diboron had dissolved. Sonicated the mixture for 5 min while it cooled down to room temperature. Sparged the mixture for 15 min with nitrogen. Added the catalyst solution prepared above via syringe. Stirred reaction mixture at 80° for 23 hr. Added 126 mg tris(dibenzylidineacetone)dipalladium(0) after 7 hr. Cooled the reaction mixture to room temp and filtered to remove solids. Removed the solvent from the filtrate in vacuo. Dissolved the residue in 100 mL $Et_2O$ and washed with 50 mL water and 50 mL brine. Dried the solution over $MgSO_4$ and concentrated in vacuo. Purified the residue by flash chromatography (gradient elution, 0 to 25% EtOAc/hexane). Recrystallized from hexane to obtain 2-[2-(tert-Butyl-dimethyl-silanyloxymethyl)-3-(4,4,5,5-tetramethyl-1,3,2-dioxaborolan-2-yl)-phenyl]-6-cyclopropyl-2H-isoquinolin-1-one as an off-white crystalline solid (1.16 g, 2.18 mmol). MS (ESI) 532 $(M+H)^+$.

Example 144

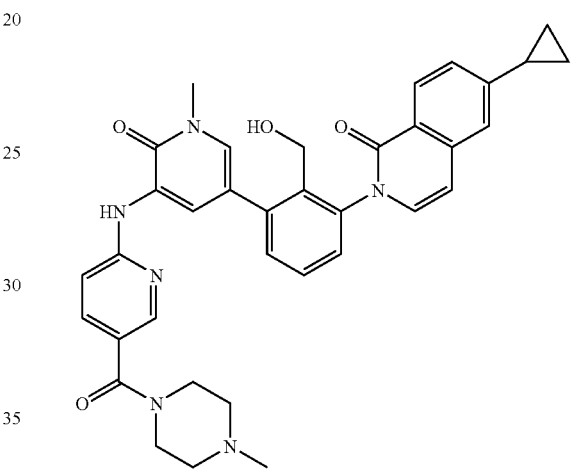

Methyl-3-[5-(4-methyl-piperazine-1-carbonyl)-pyridin-2-ylamino]-5-(4,4,5,5-tetramethyl-1,3,2-dioxaborolan-2-yl)-1H-pyridin-2-one (104 mg, 0.256 mmol), 2-[2-(tert-butyl-dimethyl-silanyloxymethyl)-3-(4,4,5,5-tetramethyl-1,3,2-dioxaborolan-2-yl)-phenyl]-6-cyclopropyl-2H-isoquinolin-1-one (124 mg, 0.233 mmol), 2 mL dioxane, 200 μL DMF, and a 0.86 mg/μL solution of cesium carbonate in water (450 μL, 1.2 mmol) were charged into a 4 mL reaction vial fitted with a stir bar and septum. Sparged mixture with nitrogen for 5 min. Added [1,1'-bis(diphenylphosphino)ferrocene]palladium(II) chloride 1:1 complex with dichloromethane (10 mg, 0.012 mmol). The reaction was sparged with nitrogen for 5 min. Sealed the vial and stirred at 90° 16 hr. Cooled to room temperature and filtered the reaction mixture through a 300 mg C18 cartridge. Washed the cartridge with 4 mL EtOAc, 4 mL water, and 4 mL EtOAc. Separated filtrate phases and washed the organic phase with 5 mL of water and 5 mL of brine. Dried the solution over $Na_2SO_4$ and concentrated in vacuo. Purified by C18 reverse phase flash chromatography (gradient elution, 10 to 95% acetonitrile+0.1% TFA/water+0.1% TFA). Added 1 mL of saturated $NaHCO_3$ to the pooled product fractions and concentrated in vacuo. Extracted the remaining aqueous mixture with 2×10 mL $CH_2Cl_2$, dried over $Na_2SO_4$, and concentrated in vacuo to obtain 6-cyclopropyl-2-(2-hydroxymethyl-3-{1-methyl-5-[5-(4-methyl-piperazine-1-carbonyl)-pyridin-2-ylamino]-6-oxo-1,6-dihydro-pyridin-3-yl}-phenyl)-2H-isoquinolin-1-one as an off-white solid. (80 mg, 0.13 mmol). MS (ESI) 617 $(M+H)^+$.

Example 145

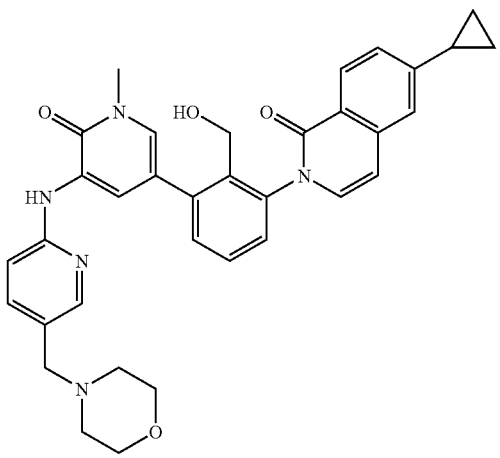

Methyl-3-(5-morpholin-4-ylmethyl-pyridin-2-ylamino)-5-(4,4,5,5-tetramethyl-1,3,2-dioxaborolan-2-yl)-1H-pyridin-2-one (96 mg, 0.25 mmol), 2-[2-(tert-butyl-dimethyl-silanyloxymethyl)-3-(4,4,5,5-tetramethyl-1,3,2-dioxaborolan-2-yl)-phenyl]-6-cyclopropyl-2H-isoquinolin-1-one (124 mg, 0.233 mmol), 2 mL dioxane, and a 0.86 mg/μL solution of cesium carbonate in water (450 μL, 1.2 mmol) were charged into a 4 mL reaction vial fitted with a stir bar and septum. Sparged mixture with nitrogen for 5 min. Added [1,1'-bis(diphenylphosphino)ferrocene]palladium(II) chloride 1:1 complex with dichloromethane (10 mg, 0.012 mmol). The reaction was sparged with nitrogen for 5 min. Sealed the vial and stirred at 90° 16 hr. Cooled to room temperature and filtered the reaction mixture through a 300 mg C18 cartridge. Washed the cartridge with 4 mL EtOAc, 4 mL water, and 4 mL EtOAc. Separated filtrate phases and washed the organic phase with 5 mL of water and 5 mL of brine. Dried the solution over $Na_2SO_4$ and concentrated in vacuo. Purified by C18 reverse phase flash chromatography (gradient elution, 10 to 95% acetonitrile+0.1% TFA/water+0.1% TFA). Added 1 mL of saturated $NaHCO_3$ to the pooled product fractions and concentrated in vacuo. Extracted the remaining aqueous mixture with 2×10 mL $CH_2Cl_2$, dried over $Na_2SO_4$, and concentrated in vacuo to obtain 6-Cyclopropyl-2-{2-hydroxymethyl-3-[1-methyl-5-(5-morpholin-4-ylmethyl-pyridin-2-ylamino)-6-oxo-1,6-dihydro-pyridin-3-yl]-phenyl}-2H-isoquinolin-1-one as an off-white solid. (73 mg, 0.12 mmol). MS (ESI) 590 (M+H)$^+$.

Example 146

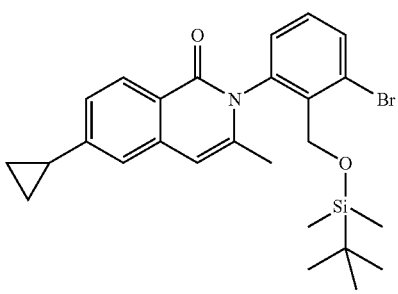

Fresh distilled 2,2,6,6-tetramethylpiperidine (0.476 g, 3.37 mmol) was dissolved under stirring in 10 ml anhydrous tetrahydrofuran and cooled by means of an ethylene lycol/dry ice bath mixture to −40° C. N-Buthyllithium, 2.5 M in hexane (1.26 ml, 3.16 mmol) was added dropwise and the temperature was kept around −40° C. and stirred additionally for 30 min at −40° C. A solution of N-[3-Bromo-2-(tert-butyl-dimethyl-silanyloxymethyl)-phenyl]-4-cyclopropyl-2-methyl-benzamide (0.200 g, 0.421 mmol) in 5 ml anhydrous tetrahydrofuran was added dropwise over a period of 10 minutes to the reaction mixture at −40° C. The reaction mixture was stirred additionally for 1 h. After that a solution of N-methoxy-N-methylacetamide 0.435 g, 33.7 mmol) in 2 ml anhydrous THF was added in a very short period of time at once. Afterward the reaction mixture was allowed to warm up to 0° C. It was stirred for 1 hour at 0° C. 5 ml of a 10% aqueous hydrochloric acid solution was added and stirred for 30 min at ambient temperature; extracted with ethyl acetate; washed with water and brine. The organic phase was dried over sodium sulfate, filtered, and concentrated. 0.223 g of a orange gum was obtained. The residue was purified by 24 g silica gel chromatography (gradient elution 0-10% methanol in dichloromethane for 30 min) to yield 2-[3-Bromo-2-(tert-butyl-dimethyl-silanyloxymethyl)-phenyl]-6-cyclopropyl-3-methyl-2H-isoquinolin-1-one (0.066 g, 0.132 mmol) MS (ESI) 522.0 (M+Na)$^+$.

Example 147

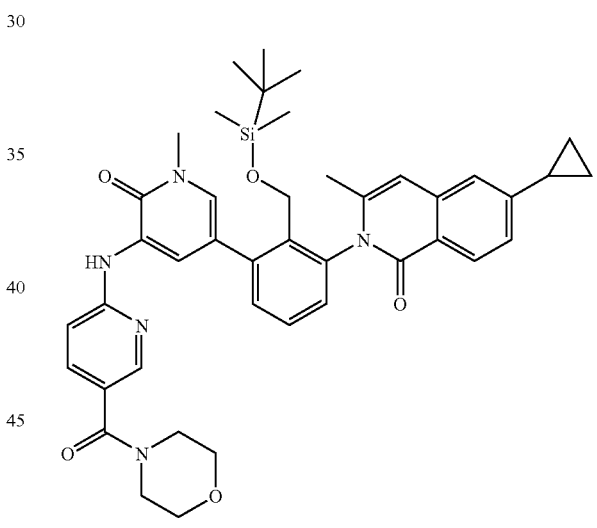

2-[3-Bromo-2-(tert-butyl-dimethyl-silanyloxymethyl)-phenyl]-6-cyclopropyl-3-methyl-2H-isoquinolin-1-one (0.045 g, 0.0903 mmol), 1-Methyl-3-[5-(morpholine-4-carbonyl)-pyridin-2-ylamino-5-(4,4,5,5-tetramethyl-[1,3,2]dioxaborolan-2-yl)-1H-pyridin-2-one (0.040 g, 0.0903 mmol) and cesium carbonate (0.089 g, 0.271 mmol) were treated with a degassed solution of 1.5 ml of dioxane/0.5 ml of water. After 5 min stirring [1,1'-bis(diphenylphosphino)ferrocene]dichloropalladium(II) complex (0.007 g, 0.009 mmol) was added and heated to 135° C. for 30 min in the microwave. The reaction mixture was filtered over cellulose, washed with 10 ml of dioxane, and concentrated in vacuo. The residue was purified silica gel chromatography (gradient elution 0-10% methanol in dichloromethane for 20 min) to yield a 2-(2-(tert-Butyl-dimethyl-silanyloxymethyl)-3-{1-methyl-5-[5-morpholine-4-carbonyl)-pyridin-2-ylamino]-6-oxo-1,6-dihydro-pyridin-3-yl}-phenyl)-6-cyclopropyl-3-methyl-2H-isoquinolin-1-one (0.043 mg, 0.0587 mmol) MS (ESI) 732.2 (M+H)+.

Example 148

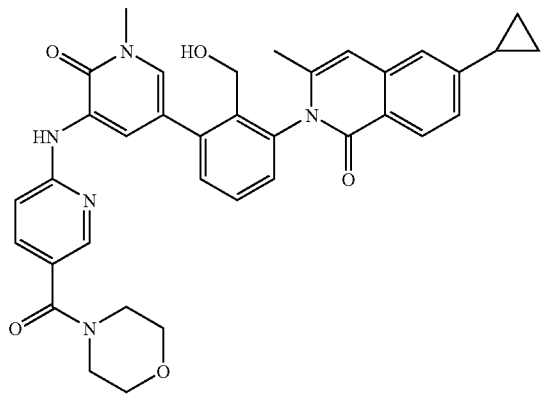

2-(2-(tert-Butyl-dimethyl-silanyloxymethyl)-3-{1-methyl-5-[5-morpholine-4-carbonyl)-pyridin-2-ylamino]-6-oxo-1,6-dihydro-pyridin-3-yl}-phenyl)-6-cyclopropyl-3-methyl-2H-isoquinolin-1-one (0.043 mg, 0.0587 mmol) was dissolved in 2 ml anhydrous tetrahydrofuran and cooled to 0° C. with an ice bath. Tetrabutylammonium fluoride, 1 M solution in THF (0.064 ml, 0.0646 mmol) was added and stirred for 1 hour at 0° C.

Afterward the reaction mixture was extracted with ethyl acetate/water. The organic phase was dried over sodium sulfate, filtered, and concentrated. The residue was purified by silica gel chromatography (gradient elution 0-10% methanol in dichloromethane for 20 min) to yield 6-Cyclopropyl-2-(2-hydroxymethyl-3-{1-methyl-5-[5-(morpholine-4-carbonyl)-pyridin-2-ylamino]-6-oxo-1,6-dihydro-pyridin-3-yl}-phenyl)-3-methyl-2H-isoquinolin-1-one (0.010 g, 0.0162 mmol) MS (ESI) 618.2 (M+H)+.

Example 149

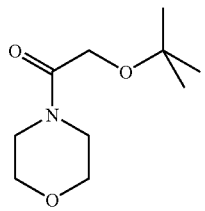

Morpholine (2.98 ml, 34.4 mmol), tert-Butoxy-acetic acid (4.485 g, 34.4 mmol) and HATU (13.093 g, 34.4 mmol) were dissolved in 15 ml dimethylformamide. The reaction mixture was stirred overnight at ambient temperature. It was extracted with ethyl acetate and the organic phase was washed with water, sodium bicarbonate solution, 1M HCl solution and finally with brine. The organic phase was dried over sodium sulfate, filtered, and concentrated to give 2-tert-Butoxy-1-morpholin-4-yl-ethanone (2.170 g, 10.78 mmol).

Example 150

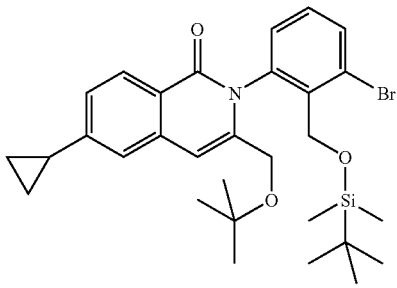

Freshly distilled 2,2,6,6-tetramethylpiperidine (1.3 g, 9.48 mmol) was dissolved in 8 ml anhydrous tetrahydrofuran and cooled by means of an ethylene glycol/dry ice bath mixture to −40° C. N-Buthyllithium, 2.5 M in hexane (2.7 ml, 8.43 mmol) was added dropwise and the temperature was kept around −40° C. and stirred additionally for 30 min at −40° C. A solution of N-[3-Bromo-2-(tert-butyl-dimethyl-silanyloxymethyl)-phenyl]-4-cyclopropyl-2-methyl-benzamide (1 g, 2.11 mmol) in 3 ml anhydrous tetrahydrofuran was added dropwise over a period of 10 minutes to the reaction mixture at −40° C. The reaction mixture was stirred additionally for 1 hour. After that a solution of 2-tert-Butoxy-1-morpholin-4-yl-ethanone (2.248 g, 11.17 mmol) in 4 ml anhydrous tetrahydrofuran was added in a very short period of time at once. Afterward the reaction mixture was allowed to warm up to 0° C. It was stirred for 1 hour at 0° C. 2.3 ml of an 10% aqueous hydrochloric acid solution was added and stirred for 30 min at ambient temperature; extracted with ethyl acetate; washed with water and brine. The organic phase was dried over sodium sulfate; filtered; concentrated; An orange gum was obtained. The residue was purified by 100 g silica gel chromatography (gradient elution 0-50% ethyl acetate in hexane for 30 min) to yield compound A: 2-[3-Bromo-2-(tert-butyl-dimethyl-silanyloxymethyl)-phenyl]-3-tert-butoxymethyl-6-cyclopropyl-2H-isoquinolin-1-one (0.485 g, 0.85 mmol) MS (ESI) 594.1 (M+Na)+.

Example 151

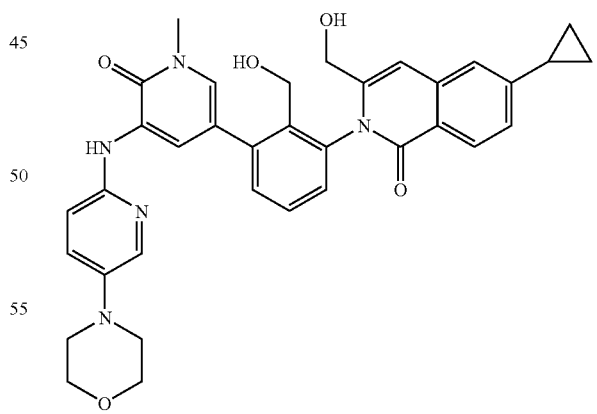

2-[3-Bromo-2-(tert-butyl-dimethyl-silanyloxymethyl)-phenyl]-3-tert-butoxymethyl-6-cyclopropyl-2H-isoquinolin-1-one (0.100 g, 0.175 mmol), 1-Methyl-3-(5-morpholin-4-yl-pyridin-2ylamino)-5-(4,4,5,5-tetramethyl-[1,3,2] dioxaborolan-2-yl)-1H-pyridin-2-one (0.079 g, 0.193 mmol), cesium carbonate (0.200 g, 0.613 mmol) were treated with 2 ml of dioxane and 0.5 ml of water. [1,1'-bis(diphenylphosphino)ferrocene]dichloropalladium(II) complex (0.014 g, 0.0175 mmol) was added and heated to 135° C. for 35 min at the microwave. The reaction mixture was filtered; washed with dichloromethane; concentrated; purification by 12 g silica gel column chromatography with 0-10% methanol in dichloromethane for 25 min; 124 mg of a brown gum was obtained.

The crude material was dissolved in 3 ml dioxane; treated with 0.4 ml 6 N HCl solution; heated with a heat gun in a sealed microwave vial for 30 seconds; extracted with ethyl acetate and sodium bicarbonate solution. Organic phase was concentrated and purified by 12 g silica gel chromatography with 0-30% methanol in dichloromethane for 25 min to yield 6-Cyclopropyl-3-hydroxymethyl-2-{2-hydroxymethyl-3-[1-methyl-5-(5-morpholin-4-yl-pyridin-2-ylamino)-6-oxo-1,6-dihydro-pyridin-3yl]-phenyl}-2H-isoquinolin-1-one (0.023 g, 0.038 mmol) MS (ESI) 606.1 (M+H)$^+$.

Example 152

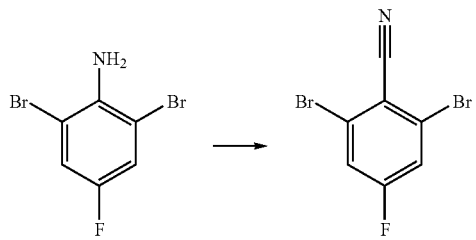

Dissolved copper (II) sulfate (3.56 g, 22 mmol, 1.2 eq) in 15 ml water, added about 10 g ice, stirred until homogeneous. Added KCN (6.05 g, 93 mmol, 5 eq), with internal thermometer, slowly, while keeping temp below 20 C by adding ice periodically. Precipitate dissolves at end of addition. Added NaHCO3 (12.5 g, 149 mmol, 8 eq), and benzene (20 ml). Heated this mixture to 50 C. In a separate flask, dissolved 2,6-dibromo4-fluoroaniline (Aldrich, 5.0 g, 19 mmol, 1 eq) in 8 ml water and 13 ml acetic acid. Added H2SO4, (5.6 g, 2.8 eq), dropwise. Mixture heats up and turns homogeneous. Cooled to 5 C, added NaNO2 (1.4 g, 20 mmol, 1.1 eq.) dissolved in 10 ml Water SLOWLY with rapid stirring, keeping temperature at 10 C (internal thermometer). Stirred 15 minutes and then added diazonium solution to CuCN solution while still heating CuCN solution at 50 with rapid stirring, dropwise over 20 minutes. Stirred 45 minutes more @ 50 C, cooled to room temp. in a water bath, extracted benzene 2×, washed benzene 1 N NaOH, back extracted aqueous with ether 1×, combined, washed brine, dried mgso4. Rotovaped, chromatographed (5% ea in hexanes) to give a pink solid, 2.22 g. M+H=278

Example 153

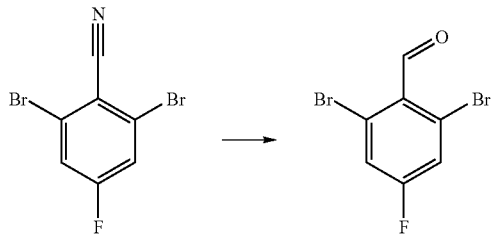

Cooled 2.2 g 2,6-Dibromo-4-fluoro-benzonitrile (8 mmol, 1 eq) to zero C in 10 ml CH2Cl2, added 8.7 ml of a 1 molar solution of Dibal in CH2Cl2 over 5 minutes. Allowed to warm to room temp. over 30 min. Added 20 ml ether, then quenched with 10 ml 3 N HCl. Stirred, heating at 40 C for 1 hour. Cooled, diluted ethyl acetate, washed water, brine, dried mgso4. Rotovaped, chromatogrpahed (eluting with 10% ethyl acetate/hexanes) to give 2.1 g solid. Dissolved solid in 10 ml THF, added 5 ml 1 N HCl. Stirred at room temperature 30 min, diluted ethyl acetate, washed water, brine, dried mgso4. Removed solvent at reduced pressure to give a solid, 1.68 g 2,6-Dibromo-4-fluoro-benzaldehyde. MS (ESI) 281.0 (M+H)$^+$.

Example 154

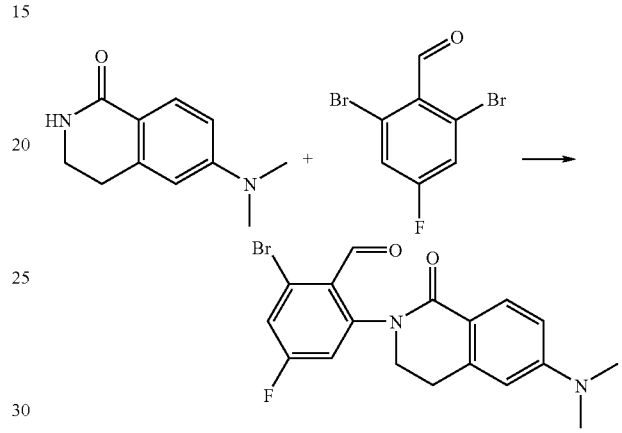

Combined 0.948 g (3.4 mmol, 2 eq) 2,6-Dibromo-4-fluoro-benzaldehyde, 0.320 g (1.7 mmol, 1 eq) 6-Dimethylamino-3,4-dihydro-2H-isoquinolin-1-one, 29 mg Xantphos (0.050 mmol, 0.03 eq), 19 mg bis(dibenzylideneacetone)palladium (0.033 mmol, 0.02 eq), and 1.09 g Cesium Carbonate (3 mmol, 2.0 eq) in 5 ml dioxane, bubbled argon gas through the mixture for 1 minute, sealed the reaction vessel and heated at 100 C for 3 hours, then cooled to 80 C and heated for 14 hours. Cooled, diluted ethyl acetate, washed water 2×, brine, dried mgso4. Rotovaped, chromatographed (10% to 30% ea in hexanes) to give a solid, 325 mg 2-Bromo-6-(6-dimethylamino-1-oxo-3,4-dihydro-1H-isoquinolin-2-yl)-4-fluoro-benzaldehyde. MS (ESI) 391.0 (M+H)$^+$.

Example 155

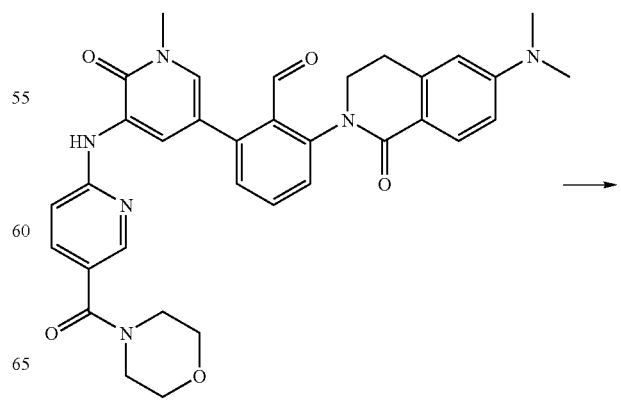

-continued

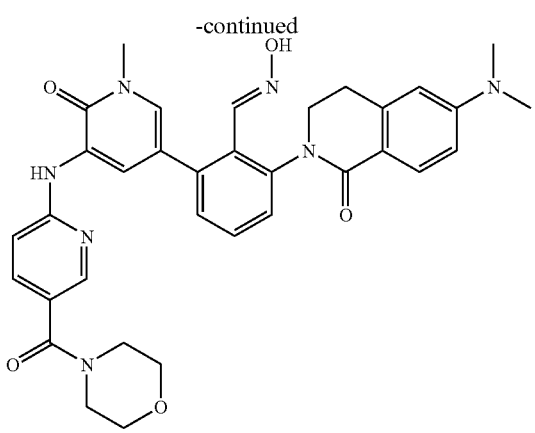

To a mixture of hydroxylamine hydrochloride (18.4 mg, 0.26 mmol) and NaOMe (14 mg, 0.26 mmol) in MeOH (2 mL) was added the aldehyde (100 mg, 0.18 mmol) in THF (2 mL). The reaction mixture was stirred at 60° C. overnight and then cooled to room temperature. The solvent was evaporated under reduced pressure and the residue was purified with flash chromatography (0-10% MeOH/DCM) to give 64 mg (57%) of the desired oxime as a brown solid. MS (ESI) 623.0 (M+H)$^+$.

Example 156

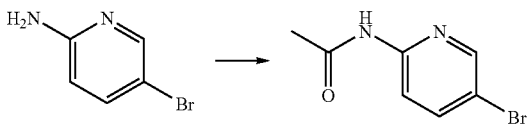

To a stirred solution of 5-Bromo-pyridin-2-ylamine (100 mg, 0.578 mmol) in dry THF was added acetic anhydride (70.25 mg, 0.693 mmol). The reaction mixture was stirred at 20° C. for 12 hrs. THF was distilled out and to it was added ethyl acetate. The organic layer was washed with saturated NaHCO3 solution and dried over anhy sodium sulphate. Removal of the solvent afforded N-(5-Bromo-pyridin-2-yl)-acetamide (100 mg, 80%). This was carried to next step without further purification.

Example 157

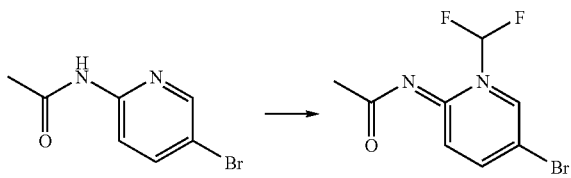

To a stirred solution of N-(5-Bromo-pyridin-2-yl)-acetamide (1 g, 4.6 mmol) in 30 ml CH3CN was added ClCF2COONa (848 mg, 5.58 mmol), followed by 18-Crown-6 (244 mg, 0.93 mmol). The reaction mixture was heated to reflux for 12 hrs. Then the reaction mixture was cooled down and the solvent was removed under reduced pressure. To this was added methylene dichloride and washed with water. Organic layer was dried over any sodium sulphate and concentrated under reduced pressure to furnish the crude N-[5-Bromo-1-difluoromethyl-1H-pyridin-(2E)-ylidene]-acetamide. This was carried to the next step without purification.

Example 158

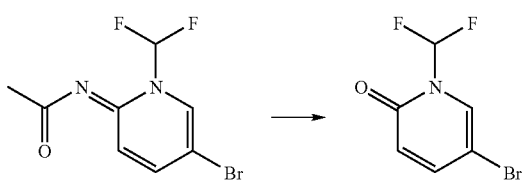

To a stirred solution of the crude N-[5-Bromo-1-difluoromethyl-1H-pyridin-(2E)-ylidene]-acetamide (1 g) in 10 ml CH3CN was added 1% KHSO4 in water (10 ml). The reaction mixture was heated at reflux for 3 hrs. The reaction mixture was cooled down and the solvent was removed under reduced pressure. Without any workup this crude was purified by column chromatography using 10% ethyl acetate in hexane to get 5-Bromo-1-difluoromethyl-1H-pyridin-2-one (550 mg, 52%).

Example 159

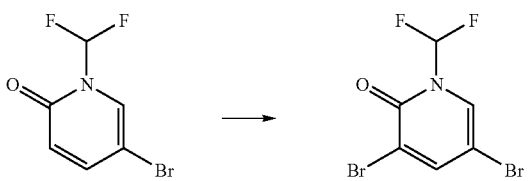

To a stirred solution of 5-Bromo-1-difluoromethyl-1H-pyridin-2-one (1 g, 4.46 mmol) in 7 ml acetic acid was added bromine (0.24 ml, 4.46 mmol) drop wise at 0° C. and then the reaction mixture was stirred at rt for 12 hrs. Acetic acid was removed under reduced pressure. To this was added ethylacetate and washed with aq NaHCO3 solution. Organic layer was dried over any sodium sulphate and concentrated under reduced pressure. It was purified by column chromatography using 5% ethyl acetate in hexane to afford 3,5-Dibromo-1-difluoromethyl-1H-pyridin-2-one (900 mg, 66.5%).

Example 160

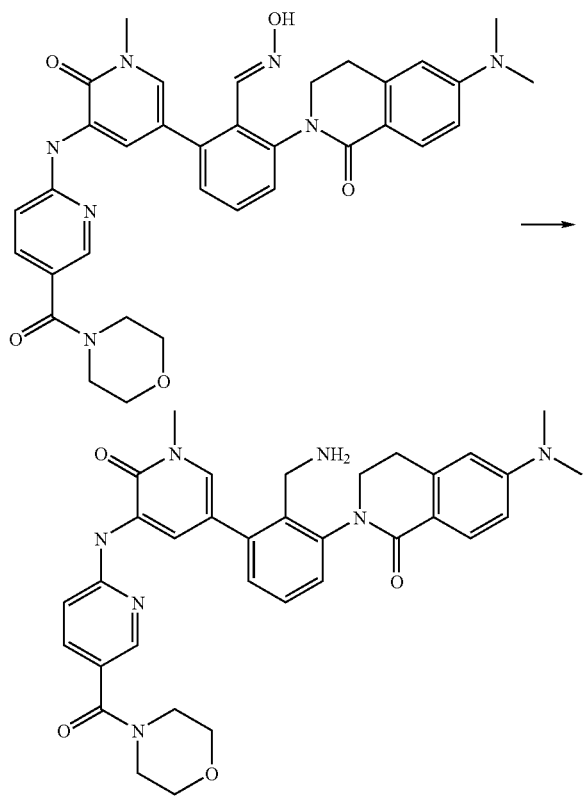

Solid NaBH₄ (44 mg, 1.16 mmol) was added in four portions to a solution of the oxime (120 mg, 0.19 mmol) and NiCl₂.6H₂O (276 mg, 1.16 mmol) in MeOH (2 mL) at 0° C. After gas evolution ceased, the solution was allowed to warm to rt and was maintained at rt for 30 min. Aqueous HCl (2 mL) was added dropwise (gas evolution) and the resulting suspension was stirred vigorously at rt for 30 min. The mixture was brought to pH~7 with the addition of saturated aqueous NaHCO₃, extracted with EtOAc (3☐15 mL), and concentrated in vacuo. The residue was purified with SiO₂ gel chromatography (0-15% MeOH/CH₂Cl₂) to give 40 mg (34%) of the desired amine as an off-white foam.

Example 161

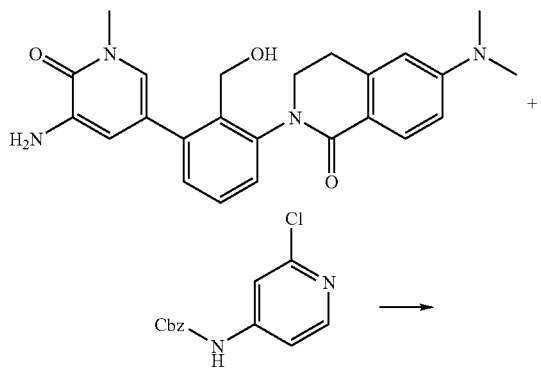

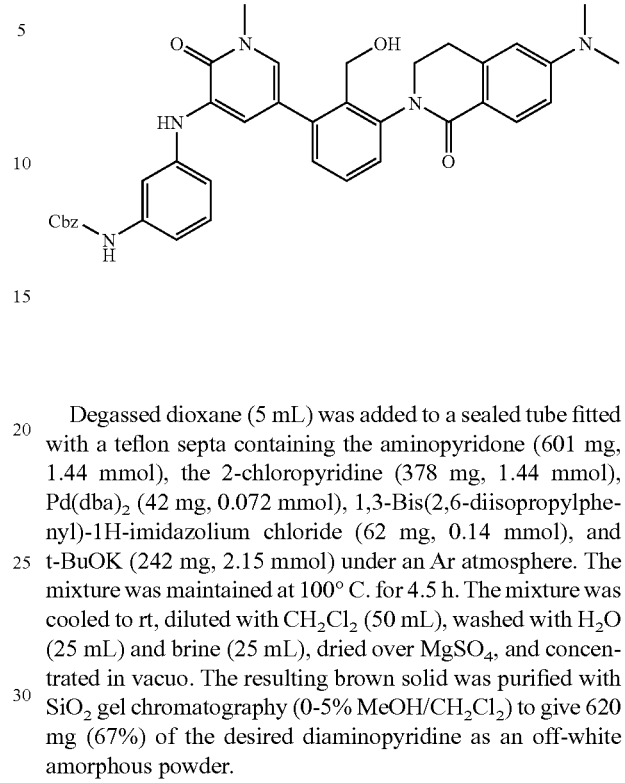

Degassed dioxane (5 mL) was added to a sealed tube fitted with a teflon septa containing the aminopyridone (601 mg, 1.44 mmol), the 2-chloropyridine (378 mg, 1.44 mmol), Pd(dba)₂ (42 mg, 0.072 mmol), 1,3-Bis(2,6-diisopropylphenyl)-1H-imidazolium chloride (62 mg, 0.14 mmol), and t-BuOK (242 mg, 2.15 mmol) under an Ar atmosphere. The mixture was maintained at 100° C. for 4.5 h. The mixture was cooled to rt, diluted with CH₂Cl₂ (50 mL), washed with H₂O (25 mL) and brine (25 mL), dried over MgSO₄, and concentrated in vacuo. The resulting brown solid was purified with SiO₂ gel chromatography (0-5% MeOH/CH₂Cl₂) to give 620 mg (67%) of the desired diaminopyridine as an off-white amorphous powder.

Example 162

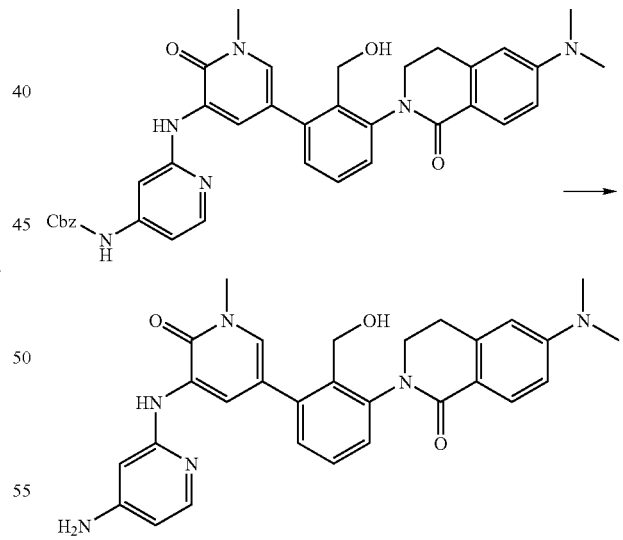

A slurry of Pd/C (10%, 30 mg) in H₂O (2 mL) was added via pipet to a suspension of the carbamate (601 mg, 0.93 mmol) in degassed MeOH (50 mL). The suspension was fitted with a H₂ balloon and stirred vigorously at rt for 18 h. The suspension was filtered through Celite® and concentrated in vacuo. The brown residue was further purified with SiO₂ gel chromatography (0-15% MeOH/CH₂Cl₂) to give 342 mg (72%) of the desired diaminopyridine as a clear foam.

Example 163

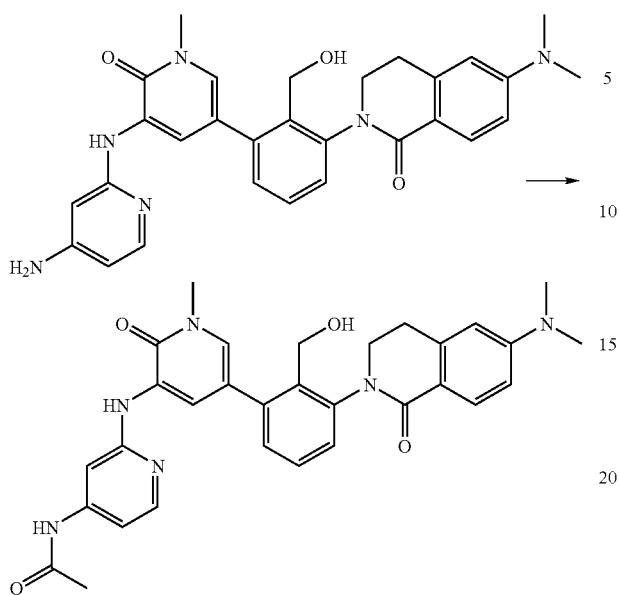

Acetyl chloride (9 μL, 0.12 mmol) was added dropwise to a solution of the diaminopyridine (58 mg, 0.11 mmol) in CH$_2$Cl$_2$ (1.0 mL) at 0° C. The solution was allowed to warm to rt and was maintained at rt for 1.0 h. The solution was diluted with CH$_2$Cl$_2$ (10 mL), washed with saturated NaHCO$_3$ (2×10 mL) and brine (10 mL), dried over Na$_2$SO$_4$, and concentrated in vacuo. The brown residue was further purified with SiO$_2$ gel chromatography (0-12% MeOH/CH$_2$Cl$_2$) to give 32 mg (52%) of the desired acetamide as a clear foam.

Example 164

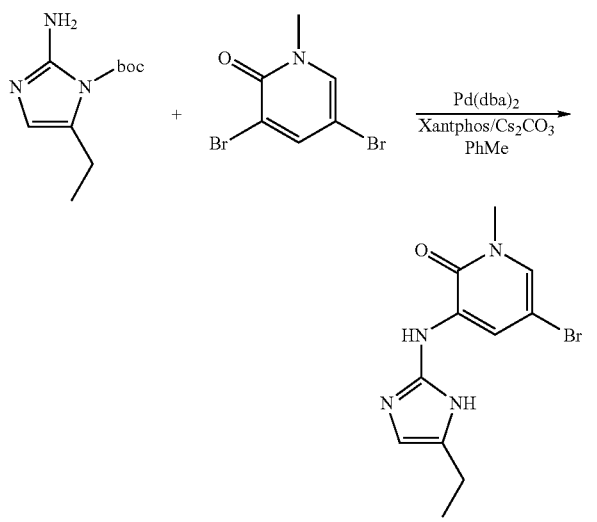

Degassed toluene (5 mL) was added to a sealed tube fitted with a teflon septa containing the aminoimidazole (117 mg, 0.56 mmol), the dibromopyridone (167 mg, 0.67 mmol), Pd(dba)$_2$ (29 mg, 0.03 mmol), Xantphos ligand 935 mg, 0.06 mmol), and Cs$_2$CO$_3$ (550 mg, 1.68 mmol) under an Ar atmosphere, and the resulting mixture was maintained at 100° C. overnight. Solvent was removed in vacuo, and the brown residue was further purified with SiO$_2$ gel chromatography (0-4% MeOH/CH$_2$Cl$_2$) to give 75 mg (30%) of the desired product as a white solid. (M+H)$^+$=297.

Example 165

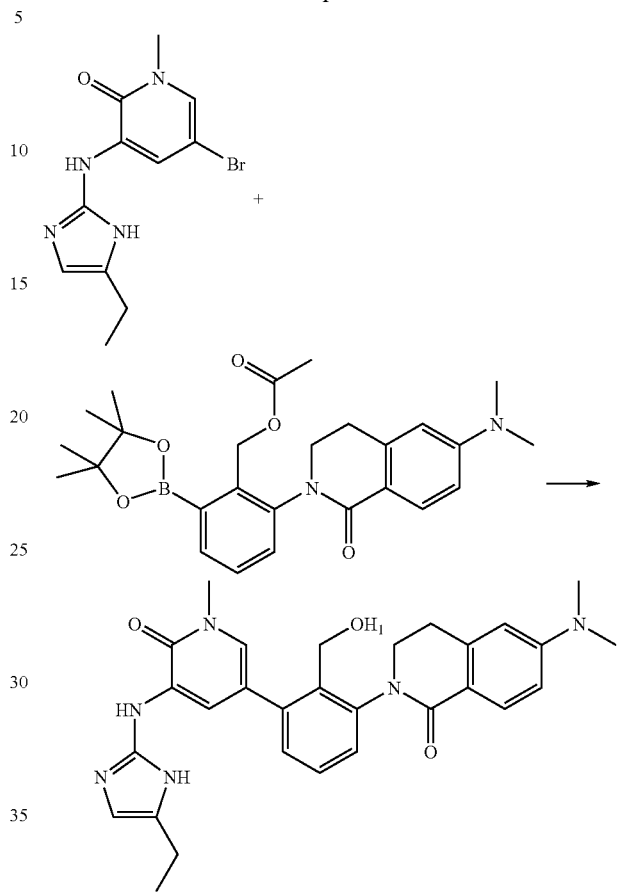

A mixture of the bromopyridone (60 mg, 0.15 mmol), the boronate (75 mg, 0.15 mmol), Pd(dba)$_2$ (4 mg, 0.0075 mmol), XPhos ligand (7 mg, 0.015 mmol), K$_3$PO$_4$ (63 mg, 0.3 mmol) in t-BuOH (3.0 mL) and H$_2$O (0.3 mL) was maintained at 100° C. in a microwave reactor for three hours. After removal of solvent, the residue was purified with flash chromatography (0-8% MeOH/DCM) followed by preparative TLC (5% MeOH/DCM) to give 7 mg (10%) of the desired product as a yellow film (M+1)$^+$=513.

Example 166

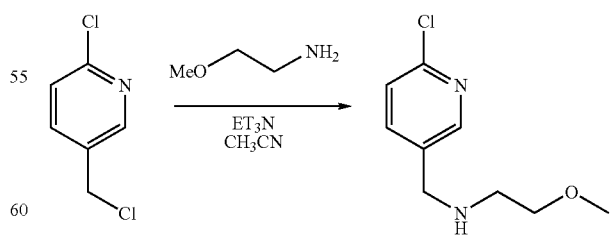

A mixture of 2-Chloro-5-chloromethyl-pyridine (486 mg, 3 mmol), 2-methoxy ethylamine (310 ul, 3.6 mmol) and triethylamine (300 uL) in 10 ml acetonitril was heated to 60° C. overnight. The solvent was removed in vacuo. The residue was partitioned between EtOAc and water. The organic phase was washed with brine, dried with MgSO$_4$. The residue was purified by flash chromatography (0-8% MeOH/DCM) to afford 287 mg (48%) of the desired amine as a colorless liquid. MS (ESI) 201.0 (M+H)$^+$.

Example 167

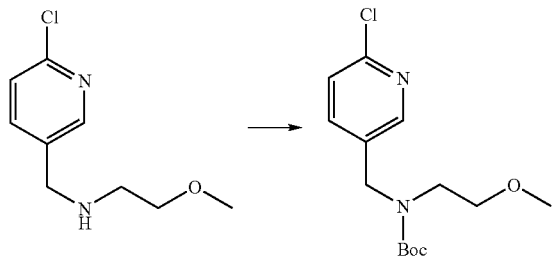

A mixture of the chloropyridine (160 mg, 0.8 mmol), Di-tert-butyl dicarbonate (210 mg, 096 mmol) and diiopropyl ethylamine (210 ul, 1.2 mmol) in 10 ml DCM was maintained at rt overnight. The solvent was removed in vacuo. The residue was purified with flash chromatography (0-25% EtOAc/Hexane) to give 215 mg (90%) of the desired carbamate as a colorless liquid.

Example 168

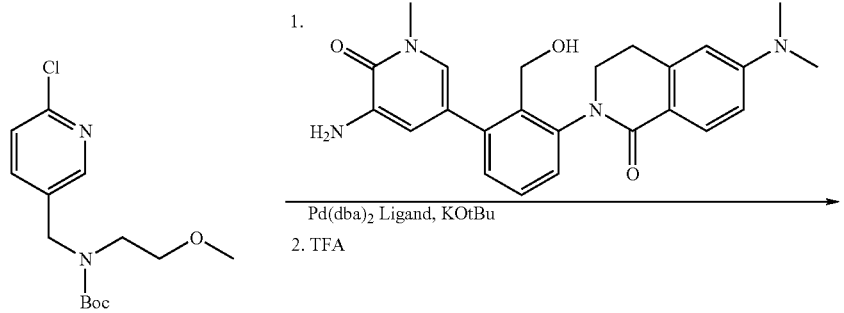

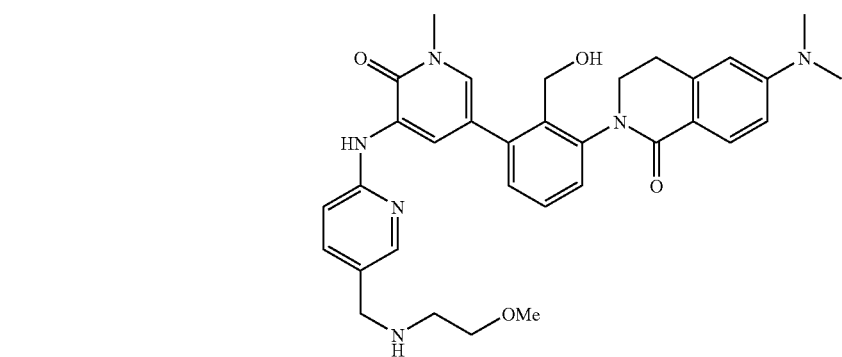

A mixture of the chloropyridine (42 mg, 0.14 mmol), the aminopyridine (58 mg, 0.14 mmol), Pd(dba)$_2$ (4 mg, 0.0075 mmol), 1,3-Bis(2,6-diisopropylphenyl)-1H-imidazolium chloride (6 mg, 0.014 mmol), KOtBu (24 mg, 0.21 mmol) in dioxane (5.0 mL) was reacted using the method described in Procedure 3. The product mixture was then concentrated and redissolved in TFA:DCM (1:1, 5 mL) and maintained at rt for 2 h. The reaction mixture was concentrated and the residue was purified with flash chromatography (0-10% MeOH/DCM) to give 28 mg (35%) of the desired secondary amine as a light yellow film. MS (ESI) 583.0 (M+H)$^+$.

Example 169

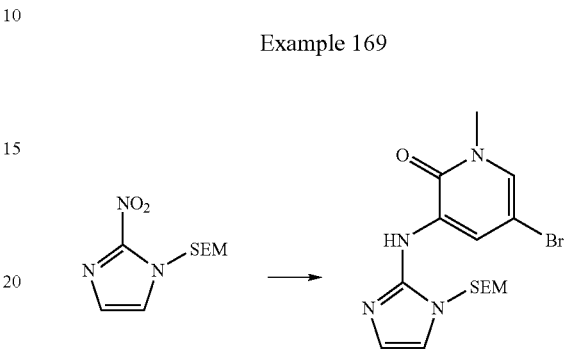

A slurry of Pd/C (10%, 40 mg) in H$_2$O (2 mL) was added via pipet to a solution of the nitroimidazole (300 mg, 0.1.23 mmol) in degassed EtOH (10 mL). The reaction was fitted with a H$_2$ balloon and stirred vigorously at rt for 18 h. The suspension was filtered through Celite® and concentrated in vacuo to give 271 mg of an air sensitive 2-aminoimidazole which was directly reacted with N-methyl-3,5-dibromopyridone (260 mg, 1.0 mmol), Pd(dba)$_2$ (52 mg, 0.05 mmol), Xantphos ligand (58 mg, 0.10 mmol), and Cs$_2$CO$_3$ (577 mg, 3.0 mmol) in PhMe (5 mL) according to the conditions described in Procedure 6 to give 100 mg (25%) of the desired product as a brown foam.

Example 170

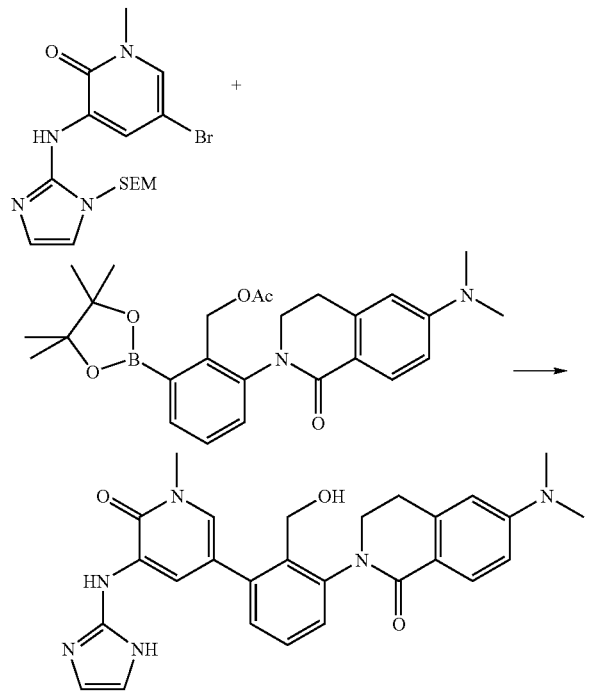

The bromopyridone (60 mg, 0.15 mmol) and the boronate (70 mg, 0.15 mmol) underwent Suzuki coupling and acetate saponification using the conditions described in Procedure 7. After removal of solvents, the unpurified residue (30 mg) was treated with TFA:DCM (1:1, 5 mL) and maintained at rt for 2 h to remove the SEM protecting group. The reaction mixture was concentrated and the residue was purified with preparative thin layer chromatography (5% MeOH/DCM) to give 15 mg (30%) of the desired 2-aminoimidazole as a light yellow film. MS (ESI) 485.0 (M+H)$^+$.

Example 171

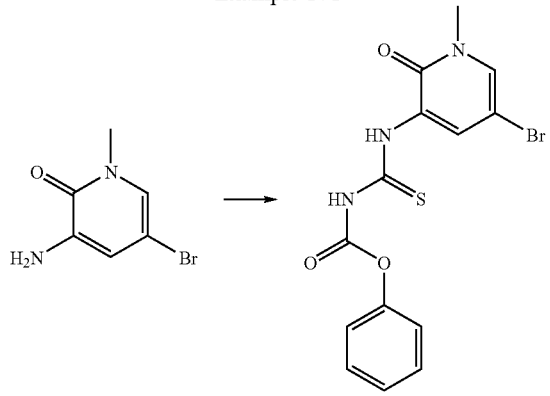

Phenyl chloroformate (2.32 mL, 3 equiv) in acetone (3 mL) is added dropwise to a suspension of potassium thiocyanate (1.79 g, 3 equiv) in acetone (12 mL) over 5 min. After stirring for 10 min, the slurry is heated to 60° C. for 10 min after which it is cooled to ambient temperature. To this slurry is added aminopyridone (1.25 g, 6.15 mmol) in acetone (5 mL) and the mixture is stirred overnight. The mixture is then filtered, washed with dichloromethane, concentrated in vacuo, and chromatograhed (50% to 100% EtOAc/Hexanes) to give slightly impure bromo phenyl carbamate (1.80 g, ~77%)

Example 172

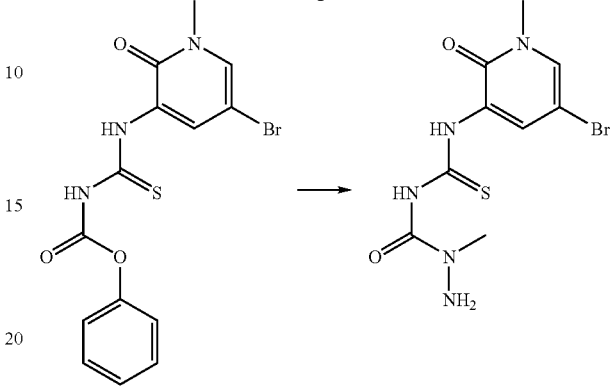

Methyl hydrazine (500 □L, 2 equiv) is added dropwise to a solution of bromo phenyl carbamate (1.80 g, ~4.70 mmol) in THF (30 mL). After stirring 1 h, the slurry is diluted with Et$_2$O (30 mL), filtered, and washed with more Et$_2$O (30 mL) to give bromo hydrazide (800 mg, 51%)

Example 173

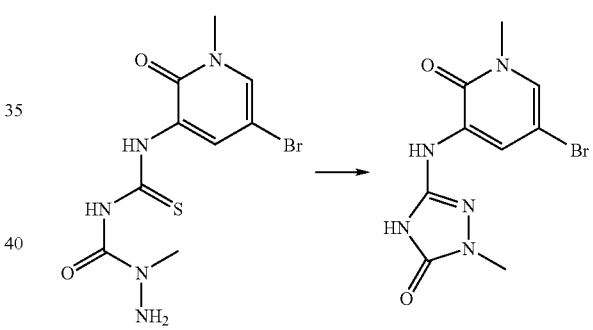

Bromo hydrazide (800 mg, 2.39 mmol) suspended in EtOH (50 mL) is refluxed for 48 h. Upon completion, as determined by LC/MS, the slurry is diluted with Et$_2$O (50 mL), filtered, and washed with more Et$_2$O (25 mL) to give bromo triazolinone (575 mg, 80%).

Example 174

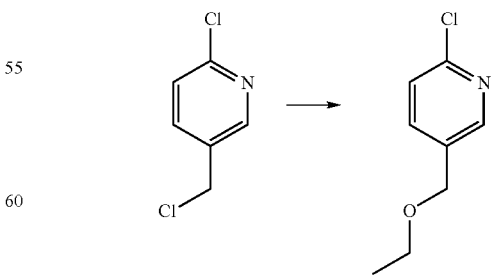

2-Chloro-5-chloromethyl-pyridine (1 g, 6.2 mmol) was dissolved in 15 ml dry ethanol. After cooling in an ice bath NaH (248 mg 60%, 6.2 mmol) was added to this solution. The reaction was warmed to rt and stirred for 16 hours. After this time the reaction was quenched with 15 ml ice-water and extracted with ethyl acetate (2×50 ml). The combined organic layers were washed with brine, dried over sodium sulfate and concentrated in vacuo. The residue was purified by column chromatography using 5%-10% ethyl acetate in hexane to afford 400 mg of 2-Chloro-5-ethoxymethyl-pyridine (yield 37%).

Example 175

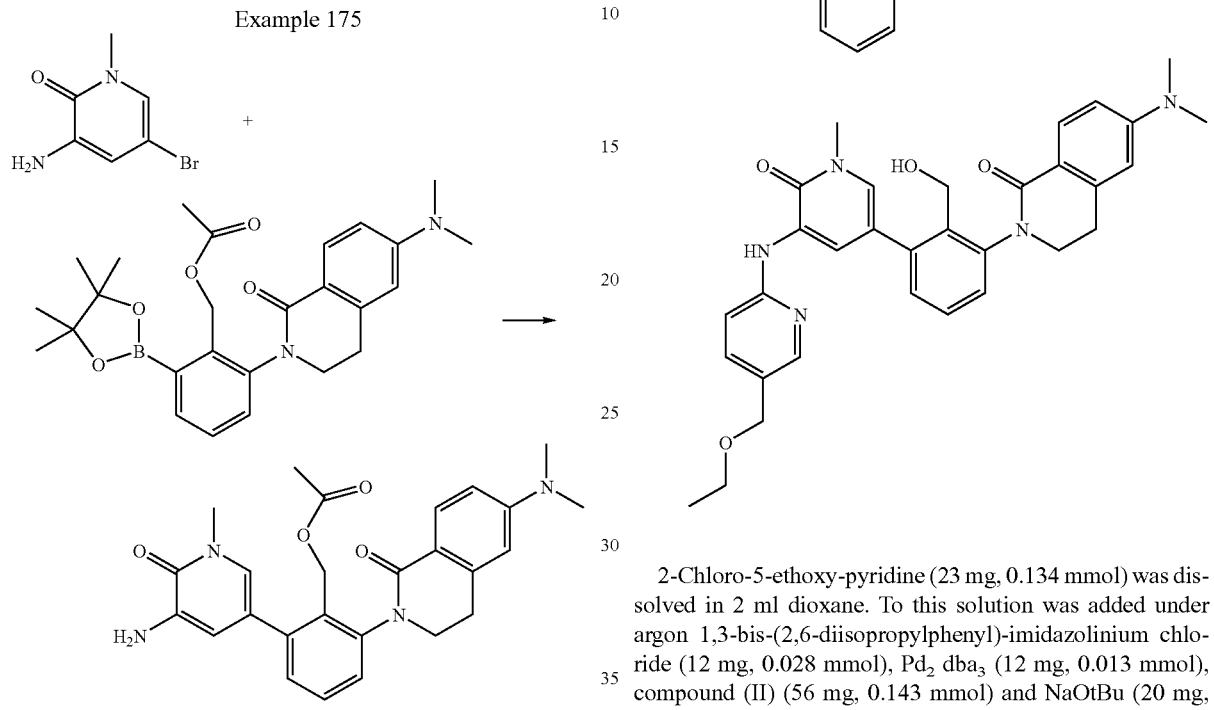

3-Amino-5-bromo-1-methyl-1H-pyridin-2-one (392 mg, 1.93 mmol) was placed into 13 ml n-butanol. To this mixture under argon was added: Pddba$_2$ (55.2 mg, 0.096 mmol), XPhos (91.2 mg, 0.191 mmol), acetic acid 2-(6-dimethylamino-1-oxo-3,4-dihydro-1H-isoquinolin-2-yl)-6-(4,4,5,5-tetramethyl-[1,3,2]dioxaborolan-2-yl)-benzyl ester (900 mg, 1.93 mmol), potassium phosphate (814 mg, 3.84 mmol) and 4 ml water. The mixture was heated under argon in a sealed flask for 45 minutes at 100-110° C. After cooling, the mixture was diluted with ethylacetate, washed with brine, dried over sodium sulfate and concentrated in vacuo. The residue was purified by column chromatography using 5% methanol in dichloromethylene to afford 450 mg of Acetic acid 2-(5-amino-1-methyl-6-oxo-1,6-dihydro-pyridin-3-yl)-6-(6-dimethylamino-1-oxo-3,4-dihydro-1H-isoquinolin-2-yl)-benzyl ester (49% yield).

Example 176

2-Chloro-5-ethoxy-pyridine (23 mg, 0.134 mmol) was dissolved in 2 ml dioxane. To this solution was added under argon 1,3-bis-(2,6-diisopropylphenyl)-imidazolinium chloride (12 mg, 0.028 mmol), Pd$_2$dba$_3$ (12 mg, 0.013 mmol), compound (II) (56 mg, 0.143 mmol) and NaOtBu (20 mg, 0.21 mmol). The mixture was heated under argon at 100° C. for 6 hours. After cooling, the reaction was diluted with ethylacetate, washed with brine, dried over sodium sulfate and concentrated in vacuo. The residue was purified by Prep TLC using 5% methanol in dichloromethylene to afford 23 mg of 6-Dimethylamino-2-{3-[5-(5-ethoxymethyl-pyridin-2-ylamino)-1-methyl-6-oxo-1,6-dihydro-pyridin-3-yl]-2-hydroxymethyl-phenyl}-3,4-dihydro-2H-isoquinolin-1-one (31% yield).

Example 177

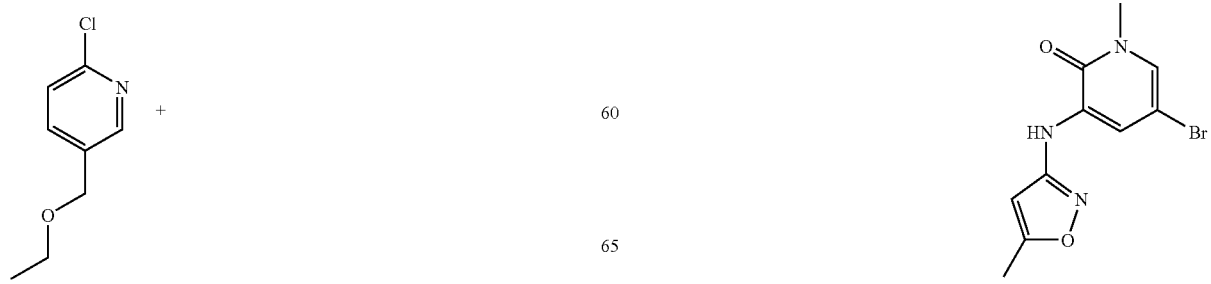

A solution of 3,5-dibromo-1-methyl-1H-pyridin-2-one (200 mg, 0.75 mmol) in 4 ml dioxane was placed in a microwave tube filled with argon. To this solution was added Xantphos (13 mg, 0.022 mmol), Pd$_2$dba$_3$ (16.8 mg, 18.3 mmol), 5-methyl-isoxazole-3-ylamine (73.6 mg, 0.75 mmol) and sodium phenoxide (127.6 mg, 1.1 mmol). The tube was sealed and heated at 150° C. using microwave irradiation. After cooling the reaction mixture was diluted with ethylacetate, washed with brine, dried over sodium sulfate and concentrated in vacuo. The residue was triturated with ethylacetate. The resulting mixture was filtered affording 100 mg (47% yield) of 5-Bromo-1-methyl-3-(5-methyl-isoxazol-3-ylamino)-1H-pyridin-2-one which was used in the next step without additional purification.

Example 178

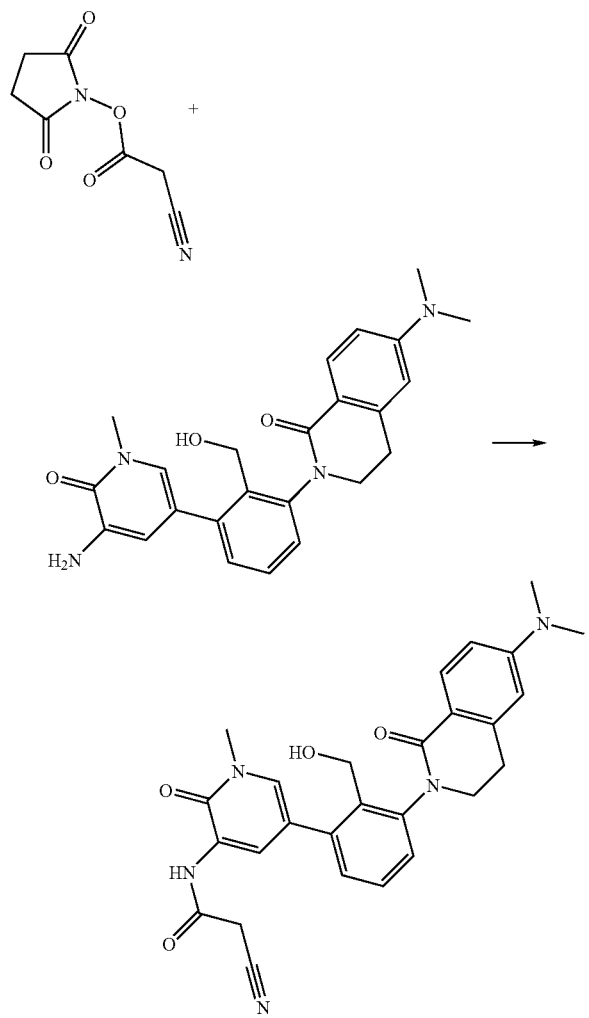

2-[3-(5-Amino-1-methyl-6-oxo-1,6-dihydro-pyridin-3-yl)-2-hydroxymethyl-phenyl]-6-dimethylamino-3,4-dihydro-2H-isoquinolin-1-one (40 mg, 0.095 mmol) was placed in a mixture of 1.5 ml dioxane and 0.5 ml of ethanol. To this mixture was added cyano-acetic acid 2,5-dioxo-pyrrolidin-1-yl ester, at first 1 equivalent (17.4 mg, 0.095 mmol), and then over a period of 3 days 5 more equivalents of this reagent at 2-4 hours intervals. During this time the reaction mixture was heated at 50-60° C. After cooling, the reaction mixture was diluted with ethylacetate, washed with brine, dried over sodium sulfate and concentrated in vacuo. The residue was purified by Prep TLC with 5% methanol in dichloromethylene to afford 12 mg (26% yield) of 2-Cyano-N-{5-[3-(6-dimethylamino-1-oxo-3,4-dihydro-1H-isoquinolin-2-yl)-2-hydroxymethyl-phenyl]-1-methyl-2-oxo-1,2-dihydro-pyridin-3-yl}-acetamide.

Example 179

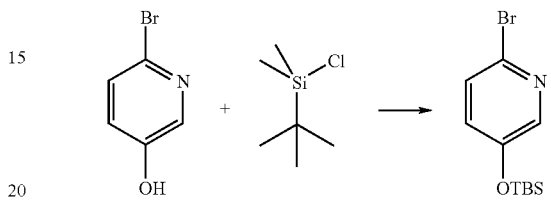

To a solution of 2-bromo-5-hydroxy pyridine (1.0 g, 5.75 mmol) and imidazole (0.59 g, 8.63 mmol) in 50 mL of dry dichloromethane was added tert-Butyl-chloro-dimethyl-silane. The resultant suspension was stirred over night at room temperature. The mixture was washed with 2×50 mL portions of water, dried over Mg$_2$SO$_4$ and concentrated onto granular silica. The mixture was purified by flash chromatography on a silica gel column with 1:1 ethyl acetate/hexanes to give a clear yellow oil (1.1 g, 3.8 mmol).

Example 180

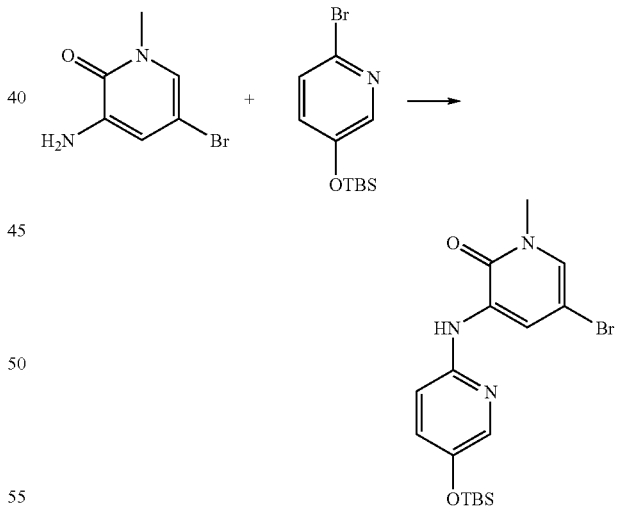

Combined in a sealable tube was 3-Amino-5-bromo-1-methyl-1H-pyridin-2-one (0.38 g, 1.9 mmol), 2-bromo-5-(tert-butyl-dimethyl-silanyloxy)-pyridine (0.54 g, 1.9 mmol), and Cs$_2$CO$_3$ (0.85 g, 2.6 mmol) in 5 mL of dry 1,4-dioxane. The mixture was bubbled with argon for 10 minutes. To the suspension was added Pd$_2$(dba)$_3$ (0.12 g, 0.13 mmol) and xantphos (0.15 g, 0.26 mmol). The vessel was sealed and heated over night at 85° C. The cooled mixture was filtered over celite, concentrated and purified on a prep plate with 1:1

Example 181

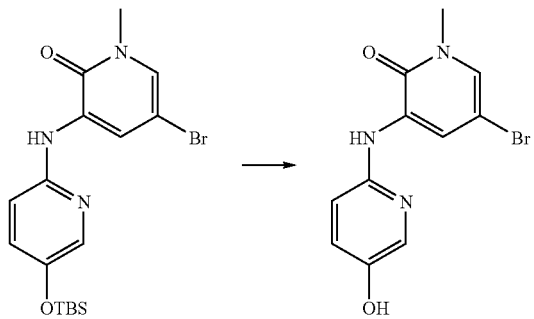

To a solution of 5-bromo-3-(5-hydroxy-pyridin-2-ylamino)-1-methyl-1H-pyridin-2-one in 35 mL of dry THF was added 1M TBAF in THF (2.59 mL, 2.59 mmol) at 0° C. The reaction stirred for 20 minutes and was quenched with 10 mL of water. The reaction was partitioned between water and ethyl acetate, dried over Mg$_2$SO$_4$ and concentrated to give 0.78 g as a white solid of the desired phenol.

Example 182

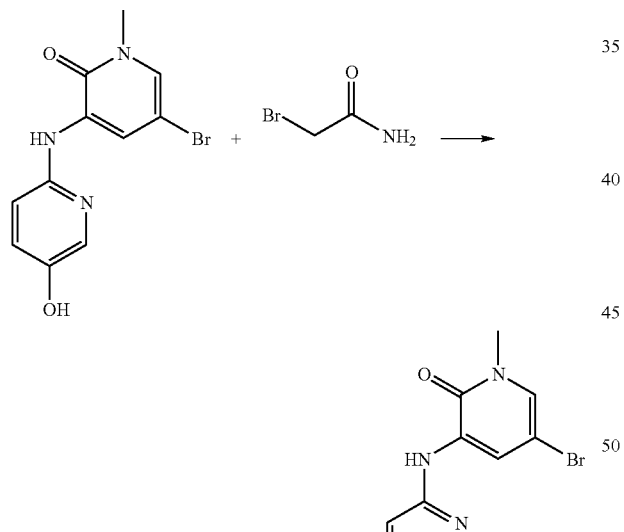

In 4 mL of dry DMF was combined 5-bromo-3-(5-hydroxy-pyridin-2-ylamino)-1-methyl-1H-pyridin-2-one (0.1 g, 0.34 mmol), 2-bromo-acetamide (0.05 g, 0.37 mmol) and K$_2$CO$_3$ (0.09 g, 0.68 mmol) at room temperature. The suspension was stirred for two hours at 60° C. and over night at room temperature. The mixture was partitioned between ethyl acetate and water, dried over Mg$_2$SO$_4$ and concentrated to give 0.08 g of the desired product as a dark green solid.

Example 183

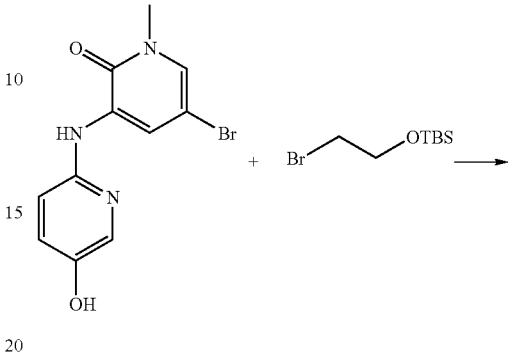

Combined in a sealed vial was 5-bromo-3-(5-hydroxy-pyridin-2-ylamino)-1-methyl-1H-pyridin-2-one (0.1 g, 0.34 mmol), (2-bromo-ethoxy)-tert-butyl-dimethyl-silane (0.155 g, 0.34 mmol) and K$_2$CO$_3$ (0.09 g, 0.68 mmol) in 3 mL of dry DMF. The mixture stirred over night at room temperature. The reaction was partitioned between ethyl acetate and water, dried over Mg$_2$SO$_4$, concentrated and was purified on a prep plate with 3:1 ethyl acetate/hexanes. The desired protected alcohol was obtained as a waxy solid (45 mg, 0.1 mmol).

Example 184

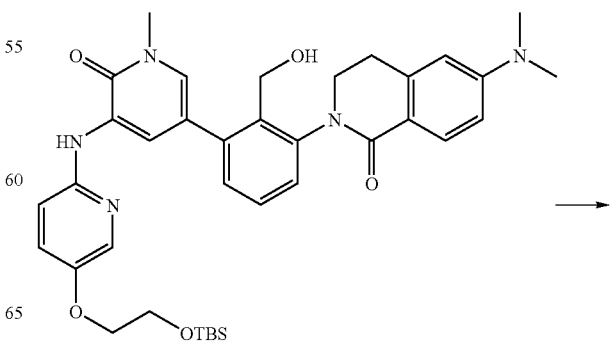

-continued

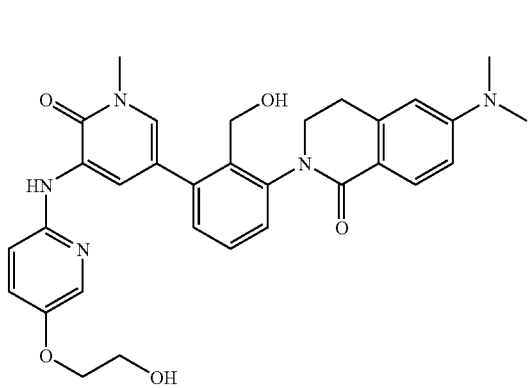

To a solution of the TBS protected alcohol (80 mg, 0.13 mmol) in 1.5 mL of 1:2 methylene chloride/methanol was added 3 drops of concentrated HCl. The solution stirred in a sealed vial for three hours at room temperature. The reaction was neutralized with 6 equivalents of MP-carbonate resin and filtered, concentrated, and purified on a prep plate with 5% methanol in methylene chloride to afford 13 mg of the desired product as a light brown solid.

Example 185

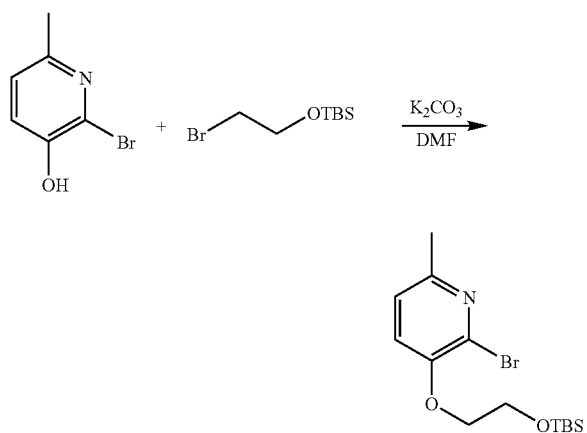

Sealed in a tube was 2-Bromo-6-iodo-pyridin-3-ol (6.0 g, 20 mmol), 2-Bromo-ethoxy)-tert-butyl-dimethyl-silane (5.3 g, 22 mmol), and $K_2CO_3$ (5.6 g, 40 mmol) in 10 mL of dry DMF. The heterogeneous mixture was heated to 50° C. overnight. A 200 mL portion of water was added to the stirred reaction. A white precipitous solid formed, was filtered under vacuum, washed with several small portions of water, and dried in a vacuum oven at 60° C. to give 8.62 g (18.9 mmol) of a slightly light pink solid.

Example 186

In 4 mL of dry DMF was suspended 86 mg (3.4 mmol) of NaH (95% in mineral oil) at room temperature. To this suspension was added 2-methoxy-ethanol (0.37 g, 4.9 mmol) and the mixture stirred one hour. A solution of 2-bromo-3-[2-(tert-butyl-dimethyl-silanyloxy)-ethoxy]-6-iodo-pyridine (1.5 g, 3.3 mmol) in 2.5 mL of dry DMF was added to the reaction and the combined suspension heated to 100° C. for two hours and cooled to room temperature overnight. The reaction was quenched with 100 mL of water and extracted with diethyl ether. The combined organic material was concentrated and purified by silica gel chromatography with a gradient of 10-20% ethyl acetate/hexanes. The desired product was isolated as a clear oil (0.47 g, 1.04 mmol).

Example 187

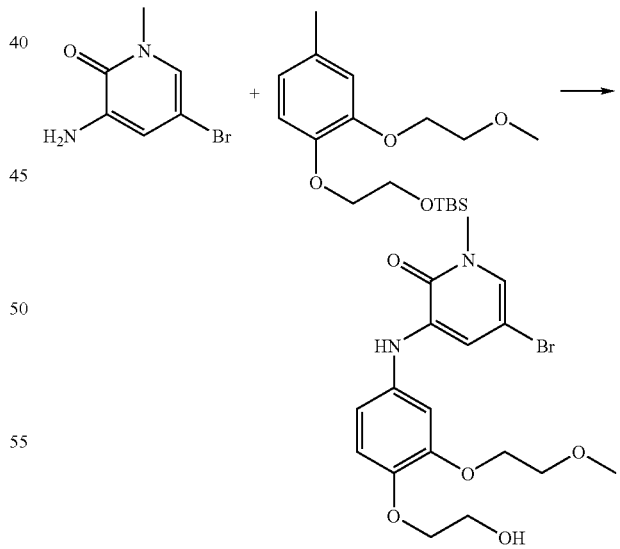

Combined in a sealable vial was 3-amino-5-bromo-1-methyl-1H-pyridin-2-one (0.18 g, 0.86 mmol), tert-Butyl-{2-[4-iodo-2-(2-methoxy-ethoxy)-phenoxy]-ethoxy}-dimethyl-silane (0.47 g, 1.04 mmol), and $Cs_2CO_3$ (0.42 g, 1.3 mmol) in 10 mL of dry 1,4-dioxane. The mixture was bubbled with argon for 10 minutes. Added to this mixture was Pd(OAc)$_2$ (19 mg, 0.09 mmol) and xantphos (10 mg, 0.17 mmol). The reaction was sealed and heated to 100° C. for 3 hrs. Material was filtered over celite, dry loaded onto granular silica, and chromatographed with a gradient of 30-75% ethyl acetate/hexanes to give 0.19 g (0.35 mmol) of the desired product.

Example 188

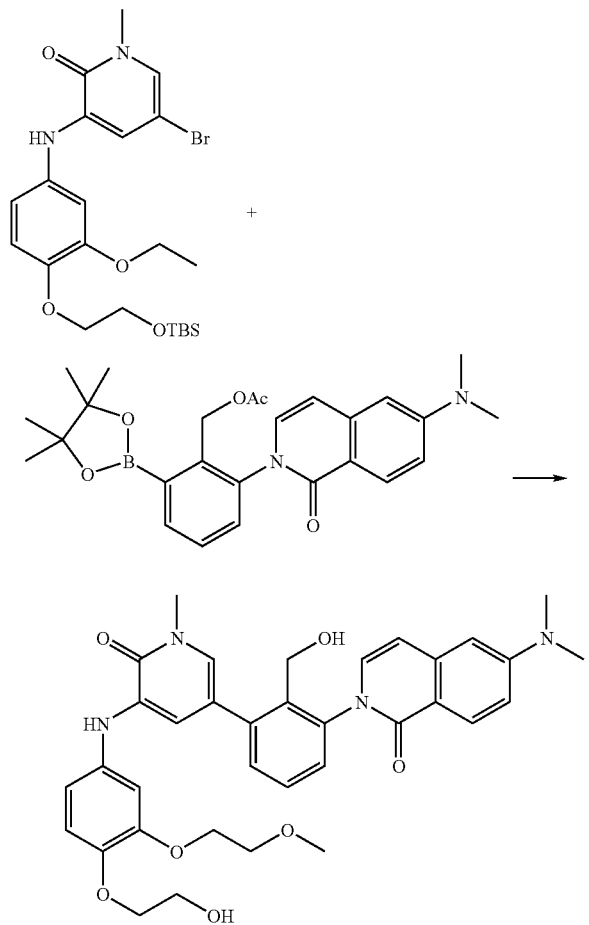

Combined in a 25 mL round bottom flask was the bromo pyridine (0.18 g, 0.35 mmol), the boronate (0.14 g, 0.29 mmol), and Cs$_2$CO$_3$ (0.24 g, 0.73 mmol) in 3 mL of 1,4-dioxane and 0.75 mL water. Argon was bubbled through the stirred solution for ten minutes. To this solution was added PdCl$_2$(dppf) (12 mg, 0.015 mmol) and the reaction heated for 3 hours at 100° C. The cooled mixture was diluted with 2 mL methanol and 0.75 mL of 1 M NaOH was added. The mixture stirred an additional 2 hours followed by an aqueous work up with water and CHCl$_3$. The crude concentrated material was diluted with 2 mL of dry THF and a solution of 1 M TBAF in THF (0.15 mL, 0.15 mmol) was added drop wise and the reaction stirred at room temperature for 30 minutes. A portion of 10 mL of water was added to quench the reaction followed by an aqueous work up with CHCl$_3$. The material was purified on a prep plate with 5% methanol/methylene chloride to give 13.1 mg (0.02 mmol) of the desired product as a light brown solid.

Example 189

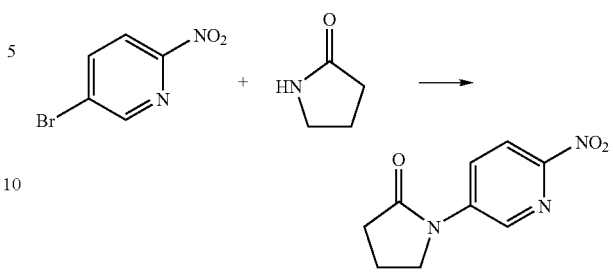

A mixture of 5-bromo-2-nitro-pyridine (1.0 g, 4.93 mmol), pyrrolidin-2-one (0.42 g, 4.93 mmol), and Cs$_2$CO$_3$ (2.25 g, 6.9 mmol) in 15 mL of dry toluene was stirred for 10 minutes while argon was bubbled through. To the stirred suspension was added Pd$_2$(dba)$_3$ (0.81 g, 0.2 mmol) and Binap (0.25 g, 0.4 mmol). The reaction was heated to 80° C. overnight. The cooled mixture was filtered over celite, concentrated and dry loaded onto granular silica. The reaction was purified with flash chromatography on a silica gel column eluting with 80% ethyl acetate/hexane to give the desired product as a light brown solid (0.821 g, 3.9 mmol).

Example 190

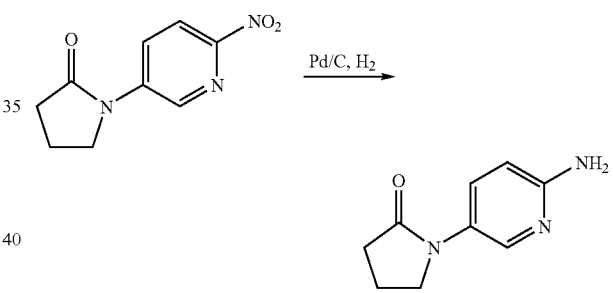

To a dry argon filled flask was added Pd/C. The catalyst was carefully wet with 10 mL of dry methanol. 1-(6-Methyl-pyridin-3-yl)-pyrrolidin-2-one (0.82 g, 4.0 mmol) was diluted with 10 mL dry dichloromethane and 20 mL dry methanol and added to the suspension of catalyst. Three consecutive balloons of H$_2$ was bubbled through the reaction mixture. Reaction stirred under H$_2$ atmosphere for 4 hours at room temperature. The suspension was filtered over Solka-Floc and rinsed with methanol and ethyl acetate. The concentrated filtrate afforded a white solid of the desired amino pyridine (0.69 g, 3.9 mmol).

Example 191

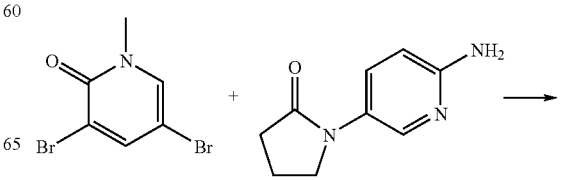

-continued

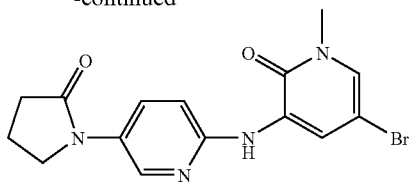

Combined in a sealable tube was 3,5-Dibromo-1-methyl-1H-pyridin-2-one (0.17 g, 0.94 mmol), 1-(6-Amino-pyridin-3-yl)-pyrrolidin-2-one (0.25 g, 0.94 mmol), and $Cs_2CO_3$ (0.43 g, 1.3 mmol) in 5 mL of dry 1,4-dioxane. The mixture was bubbled with argon for 10 minutes. To the suspension was added $Pd_2(dba)_3$ (0.06 g, 0.07 mmol) and xantphos (0.08 g, 0.13 mmol). The vessel was sealed and heated over night at 80° C. The cooled mixture was filtered over celite, concentrated and purified on a prep plate with 2% MeOH/DCM to give 0.08 g (0.2 mmol) of a light green solid.

Assay Data

Bruton's Tyrosine Kinase (Btk) Inhibition Assay

The assay is a capture of radioactive $^{33}P$ phosphorylated product through filtration. The interactions of Btk, biotinylated $SH_2$ peptide substrate (Src homology), and ATP lead to phosphorylation of the peptide substrate. Biotinylated product is bound streptavidin sepharose beads. All bound, radiolabeled products are detected by scintillation counter.

Plates assayed are 96-well polypropylene (Greiner) and 96-well 1.2 μm hydrophilic PVDF filter plates (Millipore). Concentrations reported here are final assay concentrations: 10-100 μM compounds in DMSO (Burdick and Jackson), 5-10 nM Btk enzyme (His-tagged, full-length), 30 μM peptide substrate (Biotin-Aca-AAAEEIYGEI-$NH_2$), 100 μM ATP (Sigma), 8 mM imidazole (Sigma, pH 7.2), 8 mM glycerol-2-phosphate (Sigma), 200 μM EGTA (Roche Diagnostics), 1 mM $MnCl_2$ (Sigma), 20 mM $MgCl_2$ (Sigma), 0.1 mg/ml BSA (Sigma), 2 mM DTT (Sigma), 1 μCi $^{33}P$ ATP (Amersham), 20% streptavidin sepharose beads (Amersham), 50 mM EDTA (Gibco), 2 M NaCl (Gibco), 2 M NaCl w/1% phosphoric acid (Gibco), microscint-20 (Perkin Elmer).

$IC_{50}$ determinations are calculated from 10 data points per compound utilizing data produced from a standard 96-well plate assay template. One control compound and seven unknown inhibitors were tested on each plate and each plate was run twice. Typically, compounds were diluted in half-log starting at 100 μM and ending at 3 nM. The control compound was staurosporine. Background was counted in the absence of peptide substrate. Total activity was determined in the presence of peptide substrate. The following protocol was used to determine Btk inhibition.

1) Sample preparation: The test compounds were diluted at half-log increments in assay buffer (imidazole, glycerol-2-phosphate, EGTA, $MnCl_2$, $MgCl_2$, BSA).

2) Bead preparation
   a.) rinse beads by centrifuging at 500 g
   b.) reconstitute the beads with PBS and EDTA to produce a 20% bead slurry 3) Pre-incubate reaction mix without substrate (assay buffer, DTT, ATP, $^{33}P$ ATP) and mix with substrate (assay buffer, DTT, ATP, $^{33}P$ ATP, peptide substrate) 30° C. for 15 min.

4) To start assay, pre-incubate 10 μL Btk in enzyme buffer (imidazole, glycerol-2-phos-phate, BSA) and 10 μL of test compounds for 10 min at RT.

5) Add 30 μL reaction mixture without or with substrate to Btk and compounds.

6) Incubate 50 μL total assay mix for 30 min at 30° C.

7) Transfer 40 μL of assay to 150 μL bead slurry in filter plate to stop reaction.

8) Wash filter plate after 30 min, with following steps
   a. 3×250 μL NaCl
   b. 3×250 μL NaCl containing 1% phosphoric acid
   c. 1×250 μL $H_2O$ 9) Dry plate for 1 h at 65° C. or overnight at RT 10) Add 50 μL microscint-20 and count $^{33}P$ cpm on scintillation counter.

Calculate percent activity from raw data in cpm percent activity=(sample–bkg)/(total activity–bkg)×100

Calculate $IC_{50}$ from percent activity, using one-site dose response sigmoidal model $y=A+((B-A)/(1+((x/C)^D)))$ x=cmpd conc,y=% activity,A=min,B=max,C=$IC_{50}$, D=1 (hill slope)

Representative results are in Table II below:

TABLE II

| Compound | Btk inhibition $IC_{50}$ (μM) |
| --- | --- |
| I-1 | 0.42 |
| I-2 | 0.04 |
| II-2 | 0.37 |
| III-1 | 1.08 |
| III-2 | 2.76 |

Inhibition of B-Cell Activation—B Cell FLIPR Assay in Ramos Cells

Inhibition of B-cell activation by compounds of the present invention is demonstrated by determining the effect of the test compounds on anti-IgM stimulated B cell responses.

The B cell FLIPR assay is a cell based functional method of determining the effect of potential inhibitors of the intracellular calcium increase from stimulation by an anti-IgM antibody. Ramos cells (human Burkitt's lymphoma cell line. ATCC-No. CRL-1596) were cultivated in Growth Media (described below). One day prior to assay, Ramos cells were resuspended in fresh growth media (same as above) and set at a concentration of $0.5 \times 10^6$/mL in tissue culture flasks. On day of assay, cells are counted and set at a concentration of $1 \times 10^6$/mL1 in growth media supplemented with 1 μM FLUO-3AM (TeELabs Cat-No. 0116, prepared in anhydrous DMSO and 10% Pluronic acid) in a tissue culture flask, and incubated at 37° C. (4% $CO_2$) for one h. To remove extracellular dye, cells were collected by centrifugation (5 min, 1000 rpm), resuspended in FLIPR buffer (described below) at $1 \times 10^6$ cells/mL and then dispensed into 96-well poly-D-lysine coated black/clear plates (BD Cat-No. 356692) at $1 \times 10^5$ cells per well. Test compounds were added at various concentrations ranging from 100 μM to 0.03 μM (7 concentrations, details below), and allowed to incubate with cells for 30 min at RT. Ramos cell Ca$^{2+}$ signaling was stimulated by the addition of 10 μg/mL anti-IgM (Southern Biotech, Cat-No. 2020-01) and measured on a FLIPR (Molecular Devices, captures images of 96 well plates using a CCD camera with an argon laser at 480 nM excitation).

Media/Buffers:

Growth Medium: RPMI 1640 medium with L-glutamine (Invitrogen, Cat-No. 61870-010), 10% Fetal Bovine Serum (FBS, Summit Biotechnology Cat-No. FP-100-05); 1 mM Sodium Pyruvate (Invitrogen Cat. No. 11360-070).

FLIPR buffer: HBSS (Invitrogen, Cat-No. 141175-079), 2 mM CaCl$_2$ (Sigma Cat-No. C-4901), HEPES (Invitrogen, Cat-No. 15630-080), 2.5 mM Probenecid (Sigma, Cat-No. P-8761), 0.1% BSA (Sigma, Cat-No. A-7906), 11 mM Glucose (Sigma, Cat-No. G-7528)

Compound Dilution Details:

In order to achieve the highest final assay concentration of 100 μM, 24 μL of 10 mM compound stock solution (made in DMSO) is added directly to 576 μL of FLIPR buffer. The test compounds are diluted in FLIPR Buffer (using Biomek 2000 robotic pipettor) resulting in the following dilution scheme: vehicle, $1.00 \times 10^{4}$ M, $1.00 \times 10^{-5}$, $3.16 \times 10^{-6}$, $1.00 \times 10^{-6}$, $3.16 \times 10^{-7}$, $1.00 \times 10^{-7}$, $3.16 \times 10^{-8}$.

Assay and Analysis:

Intracellular increases in calcium were reported using a max-min statistic (subtracting the resting baseline from the peak caused by addition of the stimulatory antibody using a Molecular Devices FLIPR control and statistic exporting software. The IC$_{50}$ was determined using a non-linear curve fit (GraphPad Prism software).

Pharmaceutical compositions of the subject Compounds for administration via several routes were prepared as described in this Example.

| Composition for Oral Administration (A) | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration (B) | |
|---|---|
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration (C) | |
|---|---|
| Ingredient | % wt./wt. |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

| Parenteral Formulation (D) | |
|---|---|
| Ingredient | % wt./wt. |
| Active ingredient | 0.25 g |
| Sodium Chloride | qs to make isotonic |
| Water for injection to | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

| Suppository Formulation (E) | |
|---|---|
| Ingredient | % wt./wt. |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

| Topical Formulation (F) | |
|---|---|
| Ingredients | grams |
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

Mouse Collagen-Induced Arthritis (mCIA)

On day 0 mice are injected at the base of the tail or several spots on the back with an emulsion of Type II Collagen (i.d.) in Complete Freund's adjuvant (CFA). Following collagen immunization, animals will develop arthritis at around 21 to 35 days. The onset of arthritis is synchronized (boosted) by systemic administration of collagen in Incomplete Freund's adjuvant (IFA; i.d.) at day 21. Animals are examined daily after day 20 for any onset of mild arthritis (score of 1 or 2; see score description below) which is the signal to boost. Following boost, mice are scored and dosed with candidate therapeutic agents for the prescribed time (typically 2-3 weeks) and dosing frequency, daily (QD) or twice-daily (BID).

Rat Collagen-Induced Arthritis (rCIA)

On day 0, rats are injected with an emulsion of Bovine Type II Collagen in Incomplete Freund's adjuvant (IFA) is injected intradermally (i.d.) on several locations on the back. A booster injection of collagen emulsion is given around day 7, (i.d.) at the base of the tail or alternative sites on the back. Arthritis is generally observed 12-14 days after the initial collagen injection. Animals may be evaluated for the development of arthritis as described below (Evaluation of arthritis) from day 14 onwards. Animals are dosed with candidate therapeutic agents in a preventive fashion starting at the time of secondary challenge and for the prescribed time (typically 2-3 weeks) and dosing frequency, daily (QD) or twice-daily (BID).

Evaluation of Arthritis:

In both models, developing inflammation of the paws and limb joints is quantified using a scoring system that involves the assessment of the 4 paws following the criteria described below:

| Scoring: | |
|---|---|
| 1 | = swelling and/or redness of paw or one digit. |
| 2 | = swelling in two or more joints. |
| 3 | = gross swelling of the paw with more than two joints involved. |
| 4 | = severe arthritis of the entire paw and digits. |

Evaluations are made on day 0 for baseline measurement and starting again at the first signs or swelling for up to three times per week until the end of the experiment. The arthritic index for each mouse is obtained by adding the four scores of the individual paws, giving a maximum score of 16 per animal.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

What is claimed:

1. A compound of Formula I,

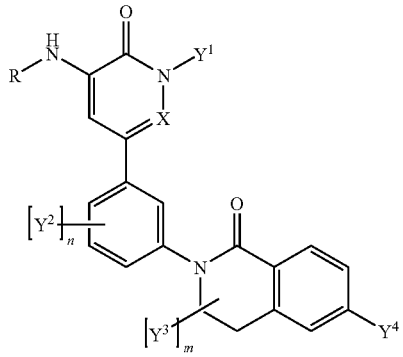

wherein:

R is H, $-R^1$, $-R^1-R^2-R^3$, $-R^1-R^3$, or $-R^2-R^3$;
  $R^1$ is aryl, heteroaryl, cycloalkyl, or heterocycloalkyl, and is optionally substituted with one or more lower alkyl, hydroxy, hydroxy lower alkyl, lower alkoxy, halo, nitro, amino, amido, cyano, oxo, or halo-lower alkyl;
  $R^2$ is $-C(=O)$, $-C(=O)O$, $-C(=O)NR^2$, $-NHC(=O)O$, [[,]]$-C(=NH)NR^2$, or $-S(=O)_2$;
  $R^{2'}$ is H or lower alkyl;
  $R^3$ is H or $R^4$;
  $R^4$ is lower alkyl, amino, aryl, arylalkyl, alkylaryl, heteroaryl, allyl heteroaryl, heteroaryl alkyl, cycloalkyl, alkyl cycloalkyl, cycloalkyl alkyl, heterocycloalkyl, alkyl heterocycloalkyl, or heterocycloalkyl alkyl, and is optionally substituted with one or more lower alkyl, hydroxy, lower alkoxy, hydroxy lower alkyl, hydroxy lower alkoxy, lower alkyl sulfonyl, lower alkyl sulfonamido, carbamate, carboxy, ester, amido, acyl, halo, nitro, amino, cyano, oxo, or halo-lower alkyl;
X is CH or N;
$Y^1$ is H, lower alkyl, or lower haloalkyl;
each $Y^2$ is independently halogen, oxime, or lower alkyl, wherein lower alkyl is optionally substituted with one or more substituents selected from the group consisting of hydroxy, lower alkoxy, lower haloalkoxy, lower haloalkyl, carboxy, amino, and halogen;
n is 0, 1, 2, or 3;
$Y^3$ is halogen or lower alkyl, wherein lower alkyl is optionally substituted with one or more substituents selected from the group consisting of hydroxy, lower alkoxy, amino, and halogen;
m is 0 or 1;
$Y^4$ is $Y^{4a}$, $Y^{4b}$, $Y^{4c}$, or $Y^{4d}$;
  $Y^{4a}$ is H or halogen;
  $Y^{4b}$ is lower alkyl, optionally substituted with one or more substituents selected from the group consisting of lower haloalkyl, halogen, hydroxy, amino, cyano, and lower alkoxy;
  $Y^{4c}$ is lower cycloalkyl, optionally substituted with one or more substituents selected from the group consisting of lower alkyl, lower haloalkyl, halogen, hydroxy, amino, cyano, and lower alkoxy; and
  $Y^{4d}$ is amino, optionally substituted with one or more lower alkyl, alkoxy lower alkyl, or hydroxy lower alkyl;

or a pharmaceutically acceptable salt thereof.

2. The compound of claim 1, wherein $Y^1$ is methyl.
3. The compound of claim 2, wherein X is CH.
4. The compound of claim 3, wherein n is 1 and m is 0.
5. The compound of claim 4, wherein $Y^2$ is methyl.
6. The compound of claim 4, wherein $Y^2$ is hydroxymethyl.
7. The compound of claim 4, wherein $Y^2$ is hydroxyethyl.
8. The compound of claim 4, wherein $Y^2$ is halogen.
9. The compound of claim 6, wherein $Y^4$ is

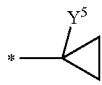

wherein, $Y^5$ is halogen, lower alkyl, or lower haloalkyl.

10. The compound of claim 6, wherein $Y^4$ is

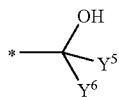

wherein, $Y^5$ and $Y^6$ are independently H, lower alkyl, or lower haloalkyl.

11. The compound of claim 6, wherein $Y^4$ is

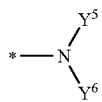

wherein, $Y^5$ and $Y^6$ are independently H or lower alkyl.

12. The compound of claim 6, wherein $Y^4$ is

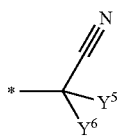

wherein, $Y^5$ and $Y^6$ are independently H, lower alkyl, or lower haloalkyl.

13. The compound of claim 9, wherein
R is -$R^1$-$R^2$-$R^3$;
$R_1$ is phenyl or pyridyl;
$R^2$ is —C(=O);
$R^3$ is $R^4$; and
$R^4$ is morpholine or piperazine, optionally substituted with one or more lower alkyl.

14. The compound of claim 10, wherein
$R_1$ is -$R^1$-$R^2$-$R^3$;
$R_1$ is phenyl or pyridyl;
$R^2$ is —C(=O);
$R^3$ is $R^4$; and
$R^4$ is morpholine or piperazine, optionally substituted with one or more lower alkyl.

15. The compound of claim 12, wherein
R is -$R^1$-$R^2$-$R^3$;
$R^1$ is phenyl or pyridyl;
$R^2$ is —C(=O);
$R^3$ is $R^4$; and
$R^4$ is morpholine or piperazine, optionally substituted with one or more lower alkyl.

16. The compound of claim 12, wherein
R is -$R^1$-$R^2$-$R^3$;
$R^1$ is phenyl or pyridyl;
$R^2$ is —C(=O);
$R^3$ is $R^4$; and
$R^4$ is morpholine or piperazine, optionally substituted with one or more lower alkyl.

17. The compound of claim 1, wherein Formula I is selected from the group consisting of:

6-Dimethylamino-2-(3-{1-methyl-5-[5-(morpholine-4-carbonyl)-pyridin-2-ylamino]-6-oxo-1,6-dihydro-pyridin-3-yl}-phenyl)-3,4-dihydro-2H-isoquinolin-1-one;

6-Dimethylamino-2-(2-hydroxymethyl-3-{1-methyl-5-[5-(morpholine-4-carbonyl)-pyridin-2-ylamino]-6-oxo-1,6-dihydro-pyridin-3-yl}-phenyl)-3,4-dihydro-2H-isoquinolin-1-one;

6-Dimethylamino-2-(2-methyl-3-{1-methyl-5-[5-(morpholine-4-carbonyl)-pyridin-2-ylamino]-6-oxo-1,6-dihydro-pyridin-3-yl}-phenyl)-3,4-dihydro-2H-isoquinolin-1-one;

1-{5-[3-(6-Dimethylamino-1-oxo-3,4-dihydro-1H-isoquinolin-2-yl)-2-hydroxymethyl-phenyl]-1-methyl-2-oxo-1,2-dihydro-pyridin-3-yl}-3-ethyl-urea;

6-Dimethylamino-2-{2-hydroxymethyl-3-[1-methyl-5-(1-methyl-1H-pyrazol-3-ylamino)-6-oxo-1,6-dihydro-pyridin-3-yl]-phenyl}-3,4-dihydro-2H-isoquinolin-1-one;

6-Cyclopropyl-2-(2-hydroxymethyl-3-{1-methyl-5-[5-(morpholine-4-carbonyl)-pyridin-2-ylamino]-6-oxo-1,6-dihydro-pyridin-3-yl}-phenyl)-3,4-dihydro-2H-isoquinolin-1-one;

2-(2-Difluoromethoxy-3-{1-methyl-5-[5-(morpholine-4-carbonyl)-pyridin-2-ylamino]-6-oxo-1,6-dihydro-pyridin-3-yl}-phenyl)-6-dimethylamino-3,4-dihydro-2H-isoquinolin-1-one;

6-Dimethylamino-2-{2-hydroxymethyl-3-[1-methyl-5-(5-morpholin-4-ylmethyl-pyridin-2-ylamino)-6-oxo-1,6-dihydro-pyridin-3-yl]-phenyl}-3,4-dihydro-2H-isoquinolin-1-one;

6-Dimethylamino-2-(2-hydroxymethyl-3-{1-methyl-5-[5-(4-methyl-piperazine-1-carbonyl)-pyridin-2-ylamino]-6-oxo-1,6-dihydro-pyridin-3-yl}-phenyl)-3,4-dihydro-2H-isoquinolin-1-one;

2-(2-Hydroxymethyl-3-{1-methyl-5-[5-(morpholine-4-carbonyl)-pyridin-2-ylamino]-6-oxo-1,6-dihydro-pyridin-3-yl}-phenyl)-6-methylamino-3,4-dihydro-2H-isoquinolin-1-one;

2-{3-[5-(1-tert-Butyl-1H-pyrazol-3-ylamino)-1-methyl-6-oxo-1,6-dihydro-pyridin-3-yl]-2-hydroxymethyl-phenyl}-6-cyclopropyl-3,4-dihydro-2H-isoquinolin-1-one;

6-Cyclopropyl-2-{3-[5-(1-ethyl-1H-pyrazol-3-ylamino)-1-methyl-6-oxo-1,6-dihydro-pyridin-3-yl]-2-hydroxymethyl-phenyl}-3,4-dihydro-2H-isoquinolin-1-one;

2-{3-[5-(1-Cyclohexyl-1H-pyrazol-3-ylamino)-1-methyl-6-oxo-1,6-dihydro-pyridin-3-yl]-2-hydroxymethyl-phenyl}-6-cyclopropyl-3,4-dihydro-2H-isoquinolin-1-one;

6-Cyclopropyl-2-(2-hydroxymethyl-3-{1-methyl-6-oxo-5-[1-(2,2,2-trifluoro-ethyl)-1H-pyrazol-3-ylamino]-1,6-dihydro-pyridin-3-yl}-phenyl)-3,4-dihydro-2H-isoquinolin-1-one;

6-Cyclopropyl-2-{3-[5-(1-cyclopropyl-1H-pyrazol-3-ylamino)-1-methyl-6-oxo-1,6-dihydro-pyridin-3-yl]-2-hydroxymethyl-phenyl}-3,4-dihydro-2H-isoquinolin-1-one;

6-Dimethylamino-2-(2-hydroxymethyl-3-{1-methyl-5-[5-(4-methyl-piperazin-1-yl)-pyridin-2-ylamino]-6-oxo-1,6-dihydro-pyridin-3-yl}-phenyl)-3,4-dihydro-2H-isoquinolin-1-one;

6-Cyclopropyl-2-{2-hydroxymethyl-3-[1-methyl-5-(1-methyl-1H-pyrazol-3-ylamino)-6-oxo-1,6-dihydro-pyridin-3-yl]-phenyl}-3,4-dihydro-2H-isoquinolin-1-one;

6-Cyclopropyl-2-{2-hydroxymethyl-3-[5-(2-isopropyl-2H-[1,2,3]triazol-4-ylamino)-1-methyl-6-oxo-1,6-dihydro-pyridin-3-yl]-phenyl}-3,4-dihydro-2H-isoquinolin-1-one;

6-Cyclopropyl-2-{2-hydroxymethyl-3-[5-(1-isopropyl-1H-pyrazol-3-ylamino)-1-methyl-6-oxo-1,6-dihydro-pyridin-3-yl]-phenyl}-3,4-dihydro-2H-isoquinolin-1-one;

6-(1-Fluoro-cyclopropyl)-2-(2-hydroxymethyl-3-{1-methyl-5-[5-(morpholine-4-carbonyl)-pyridin-2-ylamino]-6-oxo-1,6-dihydro-pyridin-3-yl}-phenyl)-3,4-dihydro-2H-isoquinolin-1-one;

6-Dimethylamino-2-{2-hydroxymethyl-3-[1-methyl-5-(5-morpholin-4-yl-pyridin-2-ylamino)-6-oxo-1,6-dihydro-pyridin-3-yl]-phenyl}-3,4-dihydro-2H-isoquinolin-1-one;

6-(Ethyl-methyl-amino)-2-(2-hydroxymethyl-3-{1-methyl-5-[5-(morpholine-4-carbonyl)-pyridin-2-ylamino]-6-oxo-1,6-dihydro-pyridin-3-yl}-phenyl)-3,4-dihydro-2H-isoquinolin-1-one;

6-tert-Butyl-2-(2-hydroxymethyl-3-{1-methyl-5-[5-(morpholine-4-carbonyl)-pyridin-2-ylamino]-6-oxo-1,6-dihydro-pyridin-3-yl}-phenyl)-3,4-dihydro-2H-isoquinolin-1-one;

6-(1-Difluoromethyl-cyclopropyl)-2-(2-hydroxymethyl-3-{1-methyl-5-[5-(morpholine-4-carbonyl)-pyridin-2-ylamino]-6-oxo-1,6-dihydro-pyridin-3-yl}-phenyl)-3,4-dihydro-2H-isoquinolin-1-one;

6-Cyclopropyl-2-(2-hydroxymethyl-3-{1-methyl-5-[5-(4-methyl-piperazin-1-yl)-pyridin-2-ylamino]-6-oxo-1,6-dihydro-pyridin-3-yl}-phenyl)-3,4-dihydro-2H-isoquinolin-1-one;

6-Fluoro-2-(2-hydroxymethyl-3-{1-methyl-5-[5-(morpholine-4-carbonyl)-pyridin-2-ylamino]-6-oxo-1,6-dihydro-pyridin-3-yl}-phenyl)-3,4-dihydro-2H-isoquinolin-1-one;

6-tert-Butyl-2-(2-hydroxymethyl-3-{1-methyl-5-[5-(4-methyl-piperazin-1-yl)-pyridin-2-ylamino]-6-oxo-1,6-dihydro-pyridin-3-yl}-phenyl)-3,4-dihydro-2H-isoquinolin-1-one;

6-Cyclopropyl-2-(2-hydroxymethyl-3-{1-methyl-5-[6-(4-methyl-piperazin-1-yl)-pyridazin-3-ylamino]-6-oxo-1,6-dihydro-pyridin-3-yl}-phenyl)-3,4-dihydro-2H-isoquinolin-1-one;

2-(3-{5-[5-(4,4-Difluoro-piperidine-1-carbonyl)-pyridin-2-ylamino]-1-methyl-6-oxo-1,6-dihydro-pyridin-3-yl}-2-hydroxymethyl-phenyl)-6-dimethylamino-3,4-dihydro-2H-isoquinolin-1-one;

6-Dimethylamino-2-{2-hydroxymethyl-3-[1-methyl-5-(1-methyl-5-oxo-4,5-dihydro-1H-[1,2,4]triazol-3-ylamino)-6-oxo-1,6-dihydro-pyridin-3-yl]-phenyl}-3,4-dihydro-2H-isoquinolin-1-one;

6-Dimethylamino-2-(2-hydroxymethyl-3-{1-methyl-5-[5-(2-oxa-6-aza-spiro[3.3]heptane-6-carbonyl)-pyridin-2-ylamino]-6-oxo-1,6-dihydro-pyridin-3-yl}-phenyl)-3,4-dihydro-2H-isoquinolin-1-one;

6-Dimethylamino-2-(2-hydroxymethyl-3-{1-methyl-5-[6-(4-methyl-piperazin-1-yl)-pyridazin-3-ylamino]-6-oxo-1,6-dihydro-pyridin-3-yl}-phenyl)-3,4-dihydro-2H-isoquinolin-1-one;

6-Dimethylamino-2-(3-{5-[5-(1,1-dioxo-1$\lambda^6$-thiomorpholine-4-carbonyl)-pyridin-2-ylamino]-1-methyl-6-oxo-1,6-dihydro-pyridin-3-yl}-2-hydroxymethyl-phenyl)-3,4-dihydro-2H-isoquinolin-1-one;

6-Cyclopropyl-2-(2-hydroxymethyl-3-{5-[1-(2-hydroxy-2-methyl-propyl)-1H-pyrazol-3-ylamino]-1-methyl-6-oxo-1,6-dihydro-pyridin-3-yl}-phenyl)-3,4-dihydro-2H-isoquinolin-1-one;

6-Dimethylamino-2-{3-[5-(5-ethoxymethyl-pyridin-2-ylamino)-1-methyl-6-oxo-1,6-dihydro-pyridin-3-yl]-2-hydroxymethyl-phenyl}-3,4-dihydro-2H-isoquinolin-1-one;

6-Dimethylamino-2-(2-hydroxymethyl-3-{5-[5-(2-methoxy-ethoxymethyl)-pyridin-2-ylamino]-1-methyl-6-oxo-1,6-dihydro-pyridin-3-yl}-phenyl)-3,4-dihydro-2H-isoquinolin-1-one;

6-Dimethylamino-2-(3-{5-[5-(2-hydroxy-ethoxymethyl)-pyridin-2-ylamino]-1-methyl-6-oxo-1,6-dihydro-pyridin-3-yl}-2-hydroxymethyl-phenyl)-3,4-dihydro-2H-isoquinolin-1-one;

6-Cyclopropyl-2-(3-{5-[1-(2-hydroxy-ethyl)-1H-pyrazol-3-ylamino]-1-methyl-6-oxo-1,6-dihydro-pyridin-3-yl}-2-hydroxymethyl-phenyl)-3,4-dihydro-2H-isoquinolin-1-one;

6-Dimethylamino-2-{2-hydroxymethyl-3-[5-(5-methanesulfonylmethyl-pyridin-2-ylamino)-1-methyl-6-oxo-1,6-dihydro-pyridin-3-yl]-phenyl}-3,4-dihydro-2H-isoquinolin-1-one;

6-Dimethylamino-2-(2-hydroxymethyl-3-{1-methyl-6-oxo-5-[5-(2-oxo-pyrrolidin-1-ylmethyl)-pyridin-2-ylamino]-1,6-dihydro-pyridin-3-yl}-phenyl)-3,4-dihydro-2H-isoquinolin-1-one;

6-{5-[3-(6-Dimethylamino-1-oxo-3,4-dihydro-1H-isoquinolin-2-yl)-2-hydroxymethyl-phenyl]-1-methyl-2-oxo-1,2-dihydro-pyridin-3-ylamino}-N-(2-methoxyethyl)-N-methyl-nicotinamide;

2-(3-{5-[5-(4,4-Difluoro-piperidin-1-ylmethyl)-pyridin-2-ylamino]-1-methyl-6-oxo-1,6-dihydro-pyridin-3-yl}-2-hydroxymethyl-phenyl)-6-dimethylamino-3,4-dihydro-2H-isoquinolin-1-one;

6-Cyclopropyl-2-(3-{5-[1-(2-hydroxy-3-methoxy-propyl)-1H-pyrazol-3-ylamino]-1-methyl-6-oxo-1,6-dihydro-pyridin-3-yl}-2-hydroxymethyl-phenyl)-3,4-dihydro-2H-isoquinolin-1-one;

6-Cyclopropyl-2-(2-hydroxymethyl-3-{1-methyl-5-[1-(2-morpholin-4-yl-ethyl)-1H-pyrazol-3-ylamino]-6-oxo-1,6-dihydro-pyridin-3-yl}-phenyl)-3,4-dihydro-2H-isoquinolin-1-one;

6-Dimethylamino-2-[3-(5-{5-[4-(2-hydroxy-ethyl)-piperazin-1-yl]-pyridin-2-ylamino}-1-methlyl-6-oxo-1,6-dihydro-pyridin-3-yl)-2-hydroxymethyl-phenyl]-3,4-dihydro-2H-isoquinolin-1-one;

2-(2-Hydroxymethyl-3-{1-methyl-5-[5-(morpholine-4-carbonyl)-pyridin-2-ylamino]-6-oxo-1,6-dihydro-pyridin-3-yl}-phenyl)-6-(1-methyl-cyclopropyl)-3,4-dihydro-2H-isoquinolin-1-one;

6-Dimethylamino-2-(3-{5-[5-(4-ethoxy-piperidine-1-carbonyl)-pyridin-2-ylamino]-1-methyl-6-oxo-1,6-dihydro-pyridin-3-yl}-2-hydroxymethyl-phenyl)-3,4-dihydro-2H-isoquinolin-1-one;

6-Dimethylamino-2-(2-hydroxymethyl-3-{5-[5-(4-methoxymethyl-piperidine-1-carbonyl)-pyridin-2-ylamino]-1-methyl-6-oxo-1,6-dihydro-pyridin-3-yl}-phenyl)-3,4-dihydro-2H-isoquinolin-1-one;

2-(3-{5-[5-(Azetidine-1-carbonyl)-pyridin-2-ylamino]-1-methyl-6-oxo-1,6-dihydro-pyridin-3-yl}-2-hydroxymethyl-phenyl)-6-dimethylamino-3,4-dihydro-2H-isoquinolin-1-one;

2-(3-{5-[5-(3,3-Difluoro-azetidine-1-carbonyl)-pyridin-2-ylamino]-1-methyl-6-oxo-1,6-dihydro-pyridin-3-yl}-2-hydroxymethyl-phenyl)-6-dimethylamino-3,4-dihydro-2H-isoquinolin-1-one;

6-Dimethylamino-2-(3-{5-[5-(1,1-dioxo-1λ⁶-isothiazolidin-2-ylmethyl)-pyridin-2-ylamino]-1-methyl-6-oxo-1,6-dihydro-pyridin-3-yl}-2-hydroxymethyl-phenyl)-3,4-dihydro-2H-isoquinolin-1-one;

6-tert-Butyl-2-{2-hydroxymethyl-3-[1-methyl-5-(5-morpholin-4-yl-pyridin-2-ylamino)-6-oxo-1,6-dihydro-pyridin-3-yl]-phenyl}-3,4-dihydro-2H-isoquinolin-1-one;

6-tert-Butyl-2-(2-hydroxymethyl-3-{1-methyl-5-[5-(2-oxa-6-aza-spiro[3.3]heptane-6-carbonyl)-pyridin-2-ylamino]-6-oxo-1,6-dihydro-pyridin-3-yl}-phenyl)-3,4-dihydro-2H-isoquinolin-1-one;

6-Dimethylamino-2-(3-{5-[5-(4-ethyl-piperazin-1-yl)-pyridin-2-ylamino]-1-methyl-6-oxo-1,6-dihydro-pyridin-3-yl}-2-hydroxymethyl-phenyl)-3,4-dihydro-2H-isoquinolin-1-one;

6-Dimethylamino-2-(3-{5-[5-(4-ethyl-piperazin-1-yl)-pyridin-2-ylamino]-1-methyl-6-oxo-1,6-dihydro-pyridin-3-yl}-2-hydroxymethyl-phenyl)-3,4-dihydro-2H-isoquinolin-1-one;

6-Dimethylamino-2-(2-hydroxymethyl-3-{5-[5-(4-hydroxy-4-methyl-piperidine-1-carbonyl)-pyridin-2-ylamino]-1-methyl-6-oxo-1,6-dihydro-pyridin-3-yl}-phenyl)-3,4-dihydro-2H-isoquinolin-1-one;

N-(6-{5-[3-(6-Dimethylamino-1-oxo-3,4-dihydro-1H-isoquinolin-2-yl)-2-hydroxymethyl-phenyl]-1-methyl-2-oxo-1,2-dihydro-pyridin-3-ylamino}-pyridin-3-ylmethyl)-methanesulfonamide;

(6-{5-[3-(6-Dimethylamino-1-oxo-3,4-dihydro-1H-isoquinolin-2-yl)-2-hydroxymethyl-phenyl]-1-methyl-2-oxo-1,2-dihydro-pyridin-3-ylamino}-pyridin-3-ylmethyl)-carbamic acid methyl ester;

6-Cyclopropyl-2-(2-hydroxymethyl-3-{1-methyl-5-[5-(2-oxa-6-aza-spiro[3.3]heptane-6-carbonyl)-pyridin-2-ylamino]-6-oxo-1,6-dihydro-pyridin-3-yl}-phenyl)-3,4-dihydro-2H-isoquinolin-1-one;

6-Cyclopropyl-2-(3-{5-[5-(1,1-dioxo-1λ⁶-thiomorpholine-4-carbonyl)-pyridin-2-ylamino]-1-methyl-6-oxo-1,6-dihydro-pyridin-3-yl}-2-hydroxymethyl-phenyl)-3,4-dihydro-2H-isoquinolin-1-one;

6-(Ethyl-methyl-amino)-2-{2-hydroxymethyl-3-[1-methyl-5-(5-morpholin-4-yl-pyridin-2-ylamino)-6-oxo-1,6-dihydro-pyridin-3-yl]-phenyl}-3,4-dihydro-2H-isoquinolin-1-one;

6-Cyclopropyl-2-(3-{5-[1-(2-dimethylamino-ethyl)-1H-pyrazol-3-ylamino]-1-methyl-6-oxo-1,6-dihydro-pyridin-3-yl}-2-hydroxymethyl-phenyl)-3,4-dihydro-2H-isoquinolin-1-one;

6-(1-Hydroxy-1-methyl-ethyl)-2-(2-hydroxymethyl-3-{1-methyl-5-[5-(morpholine-4-carbonyl)-pyridin-2-ylamino]-6-oxo-1,6-dihydro-pyridin-3-yl}-phenyl)-3,4-dihydro-2H-isoquinolin-1-one;

6-[(2-Hydroxy-ethyl)-methyl-amino]-2-(2-hydroxymethyl-3-{1-methyl-5-[5-(morpholine-4-carbonyl)-pyridin-2-ylamino]-6-oxo-1,6-dihydro-pyridin-3-yl}-phenyl)-3,4-dihydro-2H-isoquinolin-1-one;

6-Dimethylamino-2-[3-(5-{5-[(2-hydroxy-ethyl)-methyl-amino]-pyridin-2-ylamino}-1-methyl-6-oxo-1,6-dihydro-pyridin-3-yl)-2-hydroxymethyl-phenyl]-3,4-dihydro-2H-isoquinolin-1-one;

6-Dimethylamino-2-{2-hydroxymethyl-3-[5-(4-hydroxy-3,4,5,6-tetrahydro-2H-[1,3']bipyridinyl-6'-ylamino)-1-methyl-6-oxo-1,6-dihydro-pyridin-3-yl]-phenyl}-3,4-dihydro-2H-isoquinolin-1-one;

6-Dimethylamino-2-(3-{5-[5-(1,1-dioxo-1λ⁶-thiomorpholin-4-yl)-pyridin-2-ylamino]-1-methyl-6-oxo-1,6-dihydro-pyridin-3-yl}-2-hydroxymethyl-phenyl)-3,4-dihydro-2H-isoquinolin-1-one;

2-(3-{5-[5-(3,3-Difluoro-azetidin-1-yl)-pyridin-2-ylamino]-1-methyl-6-oxo-1,6-dihydro-pyridin-3-yl}-2-hydroxymethyl-phenyl)-6-dimethylamino-3,4-dihydro-2H-isoquinolin-1-one;

6-Dimethylamino-2-(3-{5-[5-(3-hydroxy-azetidin-1-yl)-pyridin-2-ylamino]-1-methyl-6-oxo-1,6-dihydro-pyridin-3-yl}-2-hydroxymethyl-phenyl)-3,4-dihydro-2H-isoquinolin-1-one;

2-{3-[5-(5-Diethylamino-pyridin-2-ylamino)-1-methyl-6-oxo-1,6-dihydro-pyridin-3-yl]-2-hydroxymethyl-phenyl}-6-dimethylamino-3,4-dihydro-2H-isoquinolin-1-one;

2-{2-Hydroxymethyl-3-[1-methyl-5-(5-morpholin-4-yl-pyridin-2-ylamino)-6-oxo-1,6-dihydro-pyridin-3-yl]-phenyl}-6-(1-methyl-cyclopropyl)-3,4-dihydro-2H-isoquinolin-1-one;

2-{3-[5-(4,4-Difluoro-3,4,5,6-tetrahydro-2H-[1,3']bipyridinyl-6'-ylamino)-1-methyl-6-oxo-1,6-dihydro-pyridin-3-yl]-2-hydroxymethyl-phenyl}-6-dimethylamino-3,4-dihydro-2H-isoquinolin-1-one;

6-Dimethylamino-2-{2-hydroxymethyl-3-[5-(1-methanesulfonylmethyl-1H-pyrazol-3-ylamino)-1-methyl-6-oxo-1,6-dihydro-pyridin-3-yl]-phenyl}-3,4-dihydro-2H-isoquinolin-1-one;

6-Dimethylamino-2-{2-hydroxymethyl-3-[1-methyl-6-oxo-5-(2-propyl-2H-[1,2,3]triazol-4-ylamino)-1,6-dihydro-pyridin-3-yl]-phenyl}-3,4-dihydro-2H-isoquinolin-1-one;

6-Dimethylamino-2-(2-hydroxymethyl-3-{1-methyl-6-oxo-5-[5-(2-oxo-pyrrolidin-1-yl)-pyridin-2-ylamino]-1,6-dihydro-pyridin-3-yl}-phenyl)-3,4-dihydro-2H-isoquinolin-1-one;

6'-{5-[3-(6-Dimethylamino-1-oxo-3,4-dihydro-1H-isoquinolin-2-yl)-2-hydroxymethyl-phenyl]-1-methyl-2-oxo-1,2-dihydro-pyridin-3-ylamino}-3,4,5,6-tetrahydro-[1,3']bipyridinyl-2-one;

6-Dimethylamino-2-(3-{5-[5-(1,1-dioxo-1λ⁶-[1,2]thiazinan-2-yl)-pyridin-2-ylamino]-1-methyl-6-oxo-1,6-dihydro-pyridin-3-yl}-2-hydroxymethyl-phenyl)-3,4-dihydro-2H-isoquinolin-1-one;

6-Dimethylamino-2-(3-{5-[5-(1,1-dioxo-1λ⁶-isothiazolidin-2-yl)-pyridin-2-ylamino]-1-methyl-6-oxo-1,6-dihydro-pyridin-3-yl}-2-hydroxymethyl-phenyl)-3,4-dihydro-2H-isoquinolin-1-one;

2-(6-{5-[3-(6-Dimethylamino-1-oxo-3,4-dihydro-1H-isoquinolin-2-yl)-2-hydroxymethyl-phenyl]-1-methyl-2-oxo-1,2-dihydro-pyridin-3-ylamino}-pyridin-3-yloxy)-acetamide;

6-Cyclopropyl-2-(2-hydroxymethyl-3-{1-methyl-5-[5-(2-oxa-6-aza-spiro[3.3]hept-6-yl)-pyridin-2-ylamino]-6-oxo-1,6-dihydro-pyridin-3-yl}-phenyl)-3,4-dihydro-2H-isoquinolin-1-one;

1-(6-{5-[3-(6-Cyclopropyl-1-oxo-3,4-dihydro-1H-isoquinolin-2-yl)-2-hydroxymethyl-phenyl]-1-methyl-2-oxo-1,2-dihydro-pyridin-3-ylamino}-pyridine-3-carbonyl)-piperidine-4-carbonitrile;

6-Cyclopropyl-2-(3-{5-[5-(3-ethoxy-pyrrolidine-1-carbonyl)-pyridin-2-ylamino]-1-methyl-6-oxo-1,6-dihydro-pyridin-3-yl}-2-hydroxymethyl-phenyl)-3,4-dihydro-2H-isoquinolin-1-one;

6-Dimethylamino-2-(2-hydroxymethyl-3-{5-[5-(3-methanesulfonyl-propoxy)-pyridin-2-ylamino]-1-methyl-6-oxo-1,6-dihydro-pyridin-3-yl}-phenyl)-3,4-dihydro-2H-isoquinolin-1-one;

6-Dimethylamino-2-(3-{5-[5-(2-hydroxy-ethoxy)-pyridin-2-ylamino]-1-methyl-6-oxo-1,6-dihydro-pyridin-3-yl}-2-hydroxymethyl-phenyl)-3,4-dihydro-2H-isoquinolin-1-one;

2-(3-{5-[5-(4-Acetyl-piperazin-1-yl)-pyridin-2-ylamino]-1-methyl-6-oxo-1,6-dihydro-pyridin-3-yl}-2-hydroxymethyl-phenyl)-6-dimethylamino-3,4-dihydro-2H-isoquinolin-1-one;

1-(6-{5-[3-(6-Cyclopropyl-1-oxo-3,4-dihydro-1H-isoquinolin-2-yl)-2-hydroxymethyl-phenyl]-1-methyl-2-oxo-1,2-dihydro-pyridin-3-ylamino}-pyridine-3-carbonyl)-piperidine-3-carbonitrile;

2-(2-acetaldehyde oxime-3-{1-methyl-5-[5-(morpholine-4-carbonyl)-pyridin-2-ylamino]-6-oxo-1,6-dihydro-pyridin-3-yl}-phenyl)-6-dimethylamino-3,4-dihydro-2H-isoquinolin-1-one 2-[6-(1-Chloro-cyclopropyl)-1-oxo-3,4-dihydro-1H-isoquinolin-2-yl]-6-{1-methyl-5-[5-(morpholine-4-carbonyl)-pyridin-2-ylamino]-6-oxo-1,6-dihydro-pyridin-3-yl}-benzaldehyde;

6-(1-Chloro-cyclopropyl)-2-(2-hydroxymethyl-3-{1-methyl-5-[5-(morpholine-4-carbonyl)-pyridin-2-ylamino]-6-oxo-1,6-dihydro-pyridin-3-yl}-phenyl)-3,4-dihydro-2H-isoquinolin-1-one;

6-Dimethylamino-2-{2-hydroxymethyl-3-[5-(4-hydroxy-4-methyl-3,4,5,6-tetrahydro-2H-[1,3']bipyridinyl-6'-ylamino)-1-methyl-6-oxo-1,6-dihydro-pyridin-3-yl]-phenyl}-3,4-dihydro-2H-isoquinolin-1-one;

2-[2-(2-Hydroxymethyl-3-{1-methyl-5-[5-(morpholine-4-carbonyl)-pyridin-2-ylamino]-6-oxo-1,6-dihydro-pyridin-3-yl}-phenyl)-1-oxo-1,2,3,4-tetrahydro-isoquinolin-6-yl]-2-methyl-propionitrile;

6-(1-Chloro-cyclopropyl)-2-{2-hydroxymethyl-3-[1-methyl-5-(5-morpholin-4-yl-pyridin-2-ylamino)-6-oxo-1,6-dihydro-pyridin-3-yl]-phenyl}-3,4-dihydro-2H-isoquinolin-1-one 6-Dimethylamino-2-(2-hydroxymethyl-3-{1-methyl-5-[5-(2-oxa-6-aza-spiro[3.3]hept-6-yl)-pyridin-2-ylamino]-6-oxo-1,6-dihydro-pyridin-3-yl}-phenyl)-3,4-dihydro-2H-isoquinolin-1-one;

1-(2-{2-Hydroxymethyl-3-[1-methyl-5-(5-morpholin-4-yl-pyridin-2-ylamino)-6-oxo-1,6-dihydro-pyridin-3-yl]-phenyl}-1-oxo-1,2,3,4-tetrahydro-isoquinolin-6-yl)-cyclopropanecarbonitrile;

2-(2-{2-Hydroxymethyl-3-[1-methyl-5-(5-morpholin-4-yl-pyridin-2-ylamino)-6-oxo-1,6-dihydro-pyridin-3-yl]-phenyl}-1-oxo-1,2,3,4-tetrahydro-isoquinolin-6-yl)-2-methyl-propionitrile;

6-Dimethylamino-2-{2-hydroxymethyl-3-[1-methyl-6-oxo-5-(5-piperazin-1-yl-pyridin-2-ylamino)-1,6-dihydro-pyridin-3-yl]-phenyl}-3,4-dihydro-2H-isoquinolin-1-one;

6-Dimethylamino-2-{2-hydroxymethyl-3-[5-(5-hydroxymethyl-pyridin-2-ylamino)-1-methyl-6-oxo-1,6-dihydro-pyridin-3-yl]-phenyl}-3,4-dihydro-2H-isoquinolin-1-one;

6-Dimethylamino-2-{2-hydroxymethyl-3-[1-methyl-5-(6-morpholin-4-yl-pyrimidin-4-ylamino)-6-oxo-1,6-dihydro-pyridin-3-yl]-phenyl}-3,4-dihydro-2H-isoquinolin-1-one;

6-Dimethylamino-2-{2-hydroxymethyl-3-[1-methyl-5-(5-methyl-isoxazol-3-ylamino)-6-oxo-1,6-dihydro-pyridin-3-yl]-phenyl}-3,4-dihydro-2H-isoquinolin-1-one;

6-Dimethylamino-2-{2-hydroxymethyl-3-[5-(isoxazol-3-ylamino)-1-methyl-6-oxo-1,6-dihydro-pyridin-3-yl]-phenyl}-3,4-dihydro-2H-isoquinolin-1-one;

6-(1-Chloro-cyclopropyl)-2-[3-(5-{5-[4-(2-hydroxy-ethyl)-piperazin-1-yl]-pyridin-2-ylamino}-1-methyl-6-oxo-1,6-dihydro-pyridin-3-yl)-2-hydroxymethyl-phenyl]-3,4-dihydro-2H-isoquinolin-1-one;

1-[2-(2-Hydroxymethyl-3-{1-methyl-5-[5-(morpholine-4-carbonyl)-pyridin-2-ylamino]-6-oxo-1,6-dihydro-pyridin-3-yl}-phenyl)-1-oxo-1,2,3,4-tetrahydro-isoquinolin-6-yl]-cyclopropanecarbonitrile;

2-(6-{5-[3-(6-Dimethylamino-1-oxo-3,4-dihydro-1H-isoquinolin-2-yl)-2-hydroxymethyl-phenyl]-1-methyl-2-oxo-1,2-dihydro-pyridin-3-ylamino}-pyridin-3-yloxy)-N,N-dimethyl-acetamide;

6-(1-Hydroxy-1-methyl-ethyl)-2-{2-hydroxymethyl-3-[1-methyl-5-(5-morpholin-4-yl-pyridin-2-ylamino)-6-oxo-1,6-dihydro-pyridin-3-yl]-phenyl}-3,4-dihydro-2H-isoquinolin-1-one;

6-Dimethylamino-2-(2-hydroxymethyl-3-{5-[5-(2-hydroxy-propoxymethyl)-pyridin-2-ylamino]-1-methyl-6-oxo-1,6-dihydro-pyridin-3-yl}-phenyl)-3,4-dihydro-2H-isoquinolin-1-one;

(2-{5-[3-(6-Dimethylamino-1-oxo-3,4-dihydro-1H-isoquinolin-2-yl)-2-hydroxymethyl-phenyl]-1-methyl-2-oxo-1,2-dihydro-pyridin-3-ylamino}-pyridin-4-yl)-carbamic acid benzyl ester;

2-{3-[5-(4-Amino-pyridin-2-ylamino)-1-methyl-6-oxo-1,6-dihydro-pyridin-3-yl]-2-hydroxymethyl-phenyl}-6-dimethylamino-3,4-dihydro-2H-isoquinolin-1-one;

N-(2-{5-[3-(6-Dimethylamino-1-oxo-3,4-dihydro-1H-isoquinolin-2-yl)-2-hydroxymethyl-phenyl]-1-methyl-2-oxo-1,2-dihydro-pyridin-3-ylamino}-pyridin-4-yl)-acetamide;

6-Dimethylamino-2-(2-hydroxymethyl-3-{1-methyl-5-[6-(4-methyl-piperazin-1-yl)-pyrimidin-4-ylamino]-6-oxo-1,6-dihydro-pyridin-3-yl}-phenyl)-3,4-dihydro-2H-isoquinolin-1-one;

6-[(2-Hydroxy-ethyl)-methyl-amino]-2-{2-hydroxymethyl-3-[1-methyl-5-(5-morpholin-4-yl-pyridin-2-ylamino)-6-oxo-1,6-dihydro-pyridin-3-yl]-phenyl}-3,4-dihydro-2H-isoquinolin-1-one;

2-(3-{1-Difluoromethyl-5-[5-(morpholine-4-carbonyl)-pyridin-2-ylamino]-6-oxo-1,6-dihydro-pyridin-3-yl}-2-hydroxymethyl-phenyl)-6-dimethylamino-3,4-dihydro-2H-isoquinolin-1-one;

6-Dimethylamino-2-(2-hydroxymethyl-3-{5-[5-(2-methoxy-ethoxy)-pyridin-2-ylamino]-1-methyl-6-oxo-1,6-dihydro-pyridin-3-yl}-phenyl)-3,4-dihydro-2H-isoquinolin-1-one;

2-(3-{5-[5-(3,3-Difluoro-azetidin-1-ylmethyl)-pyridin-2-ylamino]-1-methyl-6-oxo-1,6-dihydro-pyridin-3-yl}-2-hydroxymethyl-phenyl)-6-dimethylamino-3,4-dihydro-2H-isoquinolin-1-one;

6-Dimethylamino-2-(3-{5-[5-(1,1-dioxo-1$\lambda^6$-thiomorpholin-4-ylmethyl)-pyridin-2-ylamino]-1-methyl-6-oxo-1,6-dihydro-pyridin-3-yl}-2-hydroxymethyl-phenyl)-3,4-dihydro-2H-isoquinolin-1-one;

1-(5-{3-[6-(1-Chloro-cyclopropyl)-1-oxo-3,4-dihydro-1H-isoquinolin-2-yl]-2-hydroxymethyl-phenyl}-1-methyl-2-oxo-1,2-dihydro-pyridin-3-yl)-3-ethyl-urea;

6-Dimethylamino-2-{2-hydroxymethyl-3-[1-methyl-6-oxo-5-(5-trifluoromethyl-isoxazol-3-ylamino)-1,6-dihydro-pyridin-3-yl]-phenyl}-3,4-dihydro-2H-isoquinolin-1-one;

1-{5-[3-(6-tert-Butyl-1-oxo-3,4-dihydro-1H-isoquinolin-2-yl)-2-hydroxymethyl-phenyl]-1-methyl-2-oxo-1,2-dihydro-pyridin-3-yl}-3-methyl-urea;

6-Dimethylamino-2-(2-hydroxymethyl-3-{5-[5-(3-hydroxy-3-methyl-azetidin-1-yl)-pyridin-2-ylamino]-1-methyl-6-oxo-1,6-dihydro-pyridin-3-yl}-phenyl)-3,4-dihydro-2H-isoquinolin-1-one;

6-(1-Chloro-cyclopropyl)-2-{2-hydroxymethyl-3-[5-(4-hydroxy-4-methyl-3,4,5,6-tetrahydro-2H-[1,3']bipyridinyl-6'-ylamino)-1-methyl-6-oxo-1,6-dihydro-pyridin-3-yl]-phenyl}-3,4-dihydro-2H-isoquinolin-1-one;

2-(3-{5-[5-(4-Acetyl-piperazin-1-yl)-pyridin-2-ylamino]-1-methyl-6-oxo-1,6-dihydro-pyridin-3-yl}-2-hydroxymethyl-phenyl)-6-(1-chloro-cyclopropyl)-3,4-dihydro-2H-isoquinolin-1-one;

6-(1-Chloro-cyclopropyl)-2-{2-hydroxymethyl-3-[1-methyl-6-oxo-5-(5-piperazin-1-yl-pyridin-2-ylamino)-1,6-dihydro-pyridin-3-yl]-phenyl}-3,4-dihydro-2H-isoquinolin-1-one;

1-{5-[3-(6-tert-Butyl-1-oxo-3,4-dihydro-1H-isoquinolin-2-yl)-2-hydroxymethyl-phenyl]-1-methyl-2-oxo-1,2-dihydro-pyridin-3-yl}-3-ethyl-urea;

6-[Bis-(2-hydroxy-ethyl)-amino]-2-{2-hydroxymethyl-3-[1-methyl-5-(5-morpholin-4-yl-pyridin-2-ylamino)-6-oxo-1,6-dihydro-pyridin-3-yl]-phenyl}-3,4-dihydro-2H-isoquinolin-1-one;

2-(6-Dimethylamino-1-oxo-3,4-dihydro-1H-isoquinolin-2-yl)-6-{1-methyl-5-[5-(morpholine-4-carbonyl)-pyridin-2-ylamino]-6-oxo-1,6-dihydro-pyridin-3-yl}-benzoic acid;

6-Dimethylamino-2-{5-fluoro-2-hydroxymethyl-3-[1-methyl-5-(5-morpholin-4-yl-pyridin-2-ylamino)-6-oxo-1,6-dihydro-pyridin-3-yl]-phenyl}-3,4-dihydro-2H-isoquinolin-1-one;

1-(6-{5-[3-(6-Dimethylamino-1-oxo-3,4-dihydro-1H-isoquinolin-2-yl)-2-hydroxymethyl-phenyl]-1-methyl-2-oxo-1,2-dihydro-pyridin-3-ylamino}-pyridin-3-yl)-pyrrolidine-3-carboxylic acid methyl ester;

1-(6-{5-[3-(6-Dimethylamino-1-oxo-3,4-dihydro-1H-isoquinolin-2-yl)-2-hydroxymethyl-phenyl]-1-methyl-2-oxo-1,2-dihydro-pyridin-3-ylamino}-pyridin-3-yl)-pyrrolidine-3-carboxylic acid;

6-Dimethylamino-2-(2-hydroxymethyl-3-{5-[6-(2-methoxy-1-methyl-ethylamino)-pyridin-2-ylamino]-1-methyl-6-oxo-1,6-dihydro-pyridin-3-yl}-phenyl)-3,4-dihydro-2H-isoquinolin-1-one;

6-Dimethylamino-2-{2-hydroxymethyl-3-[5-(1H-imidazol-2-ylamino)-1-methyl-6-oxo-1,6-dihydro-pyridin-3-yl]-phenyl}-3,4-dihydro-2H-isoquinolin-1-one;

N-{5-[3-(6-Dimethylamino-1-oxo-3,4-dihydro-1H-isoquinolin-2-yl)-2-hydroxymethyl-phenyl]-1-methyl-2-oxo-1,2-dihydro-pyridin-3-yl}-N'-carboxylic acid butyl ester-guanidine N-{5-[3-(6-Dimethylamino-1-oxo-3,4-dihydro-1H-isoquinolin-2-yl)-2-hydroxymethyl-phenyl]-1-methyl-2-oxo-1,2-dihydro-pyridin-3-yl}-guanidine;

2-(2-Aminomethyl-3-{1-methyl-5-[5-(morpholine-4-carbonyl)-pyridin-2-ylamino]-6-oxo-1,6-dihydro-pyridin-3-yl}-phenyl)-6-dimethylamino-3,4-dihydro-2H-isoquinolin-1-one;

6-Dimethylamino-2-(2-dimethylaminomethyl-3-{1-methyl-5-[5-(morpholine-4-carbonyl)-pyridin-2-ylamino]-6-oxo-1,6-dihydro-pyridin-3-yl}-phenyl)-3,4-dihydro-2H-isoquinolin-1-one;

1-(5-{2-Hydroxymethyl-3-[6-(1-hydroxy-1-methyl-ethyl)-1-oxo-3,4-dihydro-1H-isoquinolin-2-yl]-phenyl}-1-methyl-2-oxo-1,2-dihydro-pyridin-3-yl)-3-methyl-urea;

1-(5-{3-[6-(2-Cyano-1,1-dimethyl-ethyl)-1-oxo-3,4-dihydro-1H-isoquinolin-2-yl]-2-hydroxymethyl-phenyl}-1-methyl-2-oxo-1,2-dihydro-pyridin-3-yl)-3-methyl-urea;

2-[2-Hydroxymethyl-3-(5-{5-[4-(2-methoxy-ethyl)-piperazin-1-yl]-pyridin-2-ylamino}-1-methyl-6-oxo-1,6-dihydro-pyridin-3-yl)-phenyl]-6-(1-methyl-cyclopropyl)-3,4-dihydro-2H-isoquinolin-1-one;

6-Dimethylamino-2-(2-hydroxymethyl-3-{5-[6-((R)-3-hydroxy-pyrrolidin-1-yl)-pyridin-2-ylamino]-1-methyl-6-oxo-1,6-dihydro-pyridin-3-yl}-phenyl)-3,4-dihydro-2H-isoquinolin-1-one;

6-Dimethylamino-2-{3-[5-(5-ethyl-isoxazol-3-ylamino)-1-methyl-6-oxo-1,6-dihydro-pyridin-3-yl]-2-hydroxymethyl-phenyl}-3,4-dihydro-2H-isoquinolin-1-one;

6-Cyclopropyl-2-{2-hydroxymethyl-3-[1-methyl-5-(5-morpholin-4-yl-pyridin-2-ylamino)-6-oxo-1,6-dihydro-pyridin-3-yl]-phenyl}-3,4-dihydro-2H-isoquinolin-1-one;

6-Azetidin-1-yl-2-(2-hydroxymethyl-3-{1-methyl-5-[5-(morpholine-4-carbonyl)-pyridin-2-ylamino]-6-oxo-1,6-dihydro-pyridin-3-yl}-phenyl)-3,4-dihydro-2H-isoquinolin-1-one;

1-{5-[3-(6-Dimethylamino-1-oxo-3,4-dihydro-1H-isoquinolin-2-yl)-4-fluoro-2-hydroxymethyl-phenyl]-1-methyl-2-oxo-1,2-dihydro-pyridin-3-yl}-3-methyl-urea;

6-tert-Butyl-2-{2-hydroxymethyl-3-[1-methyl-6-oxo-5-(5-piperazin-1-yl-pyridin-2-ylamino)-1,6-dihydro-pyridin-3-yl]-phenyl}-3,4-dihydro-2H-isoquinolin-1-one;

2-Cyano-N-{5-[3-(6-dimethylamino-1-oxo-3,4-dihydro-1H-isoquinolin-2-yl)-2-hydroxymethyl-phenyl]-1-methyl-2-oxo-1,2-dihydro-pyridin-3-yl}-acetamide;

6-[2-(2-Hydroxy-ethoxy)-1,1-dimethyl-ethyl]-2-{2-hydroxymethyl-3-[1-methyl-5-(5-morpholin-4-yl-pyridin-2-ylamino)-6-oxo-1,6-dihydro-pyridin-3-yl]-phenyl}-3,4-dihydro-2H-isoquinolin-1-one;

6-(1-Chloro-cyclopropyl)-2-(2-hydroxymethyl-3-{1-methyl-5-[5-(4-methyl-piperazin-1-yl)-pyridin-2-ylamino]-6-oxo-1,6-dihydro-pyridin-3-yl}-phenyl)-3,4-dihydro-2H-isoquinolin-1-one 6-(1-Hydroxy-1-methyl-ethyl)-2-(2-hydroxymethyl-3-{1-methyl-5-[5-(4-methyl-piperazin-1-yl)-pyridin-2-ylamino]-6-oxo-1,6-dihydro-pyridin-3-yl}-phenyl)-3,4-dihydro-2H-isoquinolin-1-one;

6-(2-Hydroxy-1,1-dimethyl-ethyl)-2-(2-hydroxymethyl-3-{1-methyl-5-[5-(morpholine-4-carbonyl)-pyridin-2-ylamino]-6-oxo-1,6-dihydro-pyridin-3-yl}-phenyl)-3,4-dihydro-2H-isoquinolin-1-one;

2-[2-(2-Hydroxymethyl-3-{1-methyl-5-[5-(4-methyl-piperazin-1-yl)-pyridin-2-ylamino]-6-oxo-1,6-dihydro-pyridin-3-yl}-phenyl)-1-oxo-1,2,3,4-tetrahydro-isoquinolin-6-yl]-2-methyl-propionitrile N-{5-[3-(6-Dimethylamino-1-oxo-3,4-dihydro-1H-isoquinolin-2-yl)-2-hydroxymethyl-phenyl]-1-methyl-2-oxo-1,2-dihydro-pyridin-3-yl}-3-oxo-butyramide;

6-Dimethylamino-2-[2-hydroxymethyl-3-(5-{5-[(2-methoxy-ethylamino)-methyl]-pyridin-2-ylamino}-1- methyl-6-oxo-1,6-dihydro-pyridin-3-yl)-phenyl]-3,4-dihydro-2H-isoquinolin-1-one;

6-Dimethylamino-2-{3-[5-(5-ethyl-4-oxo-4,5-dihydro-1H-imidazol-2-ylamino)-1-methyl-6-oxo-1,6-dihydro-pyridin-3-yl]-2-hydroxymethyl-phenyl}-3,4-dihydro-2H-isoquinolin-1-one;

1-{5-[3-(6-tert-Butyl-1-oxo-3,4-dihydro-1H-isoquinolin-2-yl)-2-hydroxymethyl-phenyl]-1-methyl-2-oxo-1,2-dihydro-pyridin-3-yl}-3-(3-dimethylamino-propyl)-urea;

6-Dimethylamino-2-{3-[5-(5-ethyl-1H-imidazol-2-ylamino)-1-methyl-6-oxo-1,6-dihydro-pyridin-3-yl]-2-hydroxymethyl-phenyl}-3,4-dihydro-2H-isoquinolin-1-one;

6-Cyclopropyl-2-(2-hydroxymethyl-3-{1-methyl-5-[5-(morpholine-4-carbonyl)-pyridin-2-ylamino]-6-oxo-1,6-dihydro-pyridazin-3-yl}-phenyl)-3,4-dihydro-2H-isoquinolin-1-one; and 6-Cyclopropyl-2-{2-hydroxymethyl-3-[1-methyl-5-(1-methyl-1H-pyrazol-3-ylamino)-6-oxo-1,6-dihydro-pyridazin-3-yl]-phenyl}-3,4-dihydro-2H-isoquinolin-1-one.

18. A method for treating an arthritis comprising administering to a patient in need thereof a therapeutically effective amount of the compound of claim 1.

19. A pharmaceutical composition comprising the compound of claim 1 admixed with at least one pharmaceutically acceptable carrier, excipient or diluent.

* * * * *

UNITED STATES PATENT AND TRADEMARK OFFICE
CERTIFICATE OF CORRECTION

PATENT NO. : 7,683,064 B2
APPLICATION NO. : 12/322870
DATED : March 23, 2010
INVENTOR(S) : Joshua Kennedy-Smith It is certified that error appears in the above-identified patent and that said Letters Patent is hereby corrected as shown below:

Claim 1, column 284, line 27, delete "$NR^2$," and insert -- $NR^{2'}$, --.

Claim 1, column 284, delete line 28 and insert -- $(=O)O$, $-C(=NH)NR^{2'}$, or $-S(=O)_2$; --.

Claim 13, column 285, beginning of line 49, delete "$R_1$" and insert -- $R^1$ --.

Claim 14, column 285, beginning of line 55, delete "$R_1$" and insert -- R --.

Claim 14, column 285, beginning of line 56, delete "$R_1$" and insert -- $R^1$ --.

Signed and Sealed this

Eighth Day of June, 2010

David J. Kappos
*Director of the United States Patent and Trademark Office*